US009776987B2

(12) United States Patent
Kim et al.

(10) Patent No.: US 9,776,987 B2
(45) Date of Patent: *Oct. 3, 2017

(54) AMIDE DERIVATIVES FOR GPR119 AGONIST

(71) Applicant: CHONG KUN DANG PHARMACEUTICAL CORP., Seoul (KR)

(72) Inventors: Yuntae Kim, Yongin-si (KR); ChangSik Lee, Yongin-si (KR); DaeKyu Choi, Yongin-si (KR); MooSung Ko, Yongin-si (KR); Younghue Han, Yongin-si (KR); SoYoung Kim, Yongin-si (KR); JaeKi Min, Yongin-si (KR); DoHoon Kim, Yongin-si (KR)

(73) Assignee: CHONG KUN DANG PHARMACEUTICAL CORP, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/039,226

(22) PCT Filed: Nov. 25, 2014

(86) PCT No.: PCT/KR2014/011356
§ 371 (c)(1),
(2) Date: May 25, 2016

(87) PCT Pub. No.: WO2015/080446
PCT Pub. Date: Jun. 4, 2015

(65) Prior Publication Data
US 2017/0129875 A1   May 11, 2017

(30) Foreign Application Priority Data

Nov. 26, 2013  (KR) ........................ 10-2013-0144601

(51) Int. Cl.
*C07D 401/12* (2006.01)
*C07D 401/14* (2006.01)

(52) U.S. Cl.
CPC ......... *C07D 401/12* (2013.01); *C07D 401/14* (2013.01)

(58) Field of Classification Search
None
See application file for complete search history.

(56) References Cited

U.S. PATENT DOCUMENTS

| 8,101,634 | B2 | 1/2012 | Fang et al. |
| 8,258,156 | B2 | 9/2012 | Alper et al. |
| 8,334,288 | B2 | 12/2012 | Epple et al. |
| 2012/0077812 | A1 | 3/2012 | Fang et al. |
| 2015/0166480 | A1 | 6/2015 | Lee et al. |

FOREIGN PATENT DOCUMENTS

| CN | 101657471 A | 2/2010 |
| CN | 102137844 A | 7/2011 |
| CN | 104364246 A | 2/2015 |
| DE | 102004037515 A1 | 3/2005 |
| EA | 201100138 A1 | 8/2011 |
| EA | 015835 B1 | 12/2011 |
| JP | 2010501629 A | 1/2010 |
| JP | 2010501630 A | 1/2010 |
| JP | 2010512334 A | 4/2010 |
| JP | 2011527701 A | 11/2011 |
| JP | 2012533546 A | 12/2012 |
| JP | 2015522559 A | 8/2015 |
| KR | 10-2009-0097184 A | 9/2009 |
| KR | 10-2012-0024964 A | 3/2012 |
| RU | 2443699 C2 | 2/2012 |
| WO | 9103243 A1 | 3/1991 |
| WO | 0206191 A1 | 1/2002 |
| WO | 0206196 A1 | 1/2002 |
| WO | 0234739 A1 | 5/2002 |
| WO | 2008025798 A1 | 3/2008 |
| WO | 2008025799 A1 | 3/2008 |
| WO | 2008025800 A1 | 3/2008 |
| WO | 2008-070692 A2 | 6/2008 |
| WO | 2008081204 A1 | 7/2008 |
| WO | 2009014910 A2 | 1/2009 |
| WO | 2009-106561 A1 | 9/2009 |
| WO | 2009106565 A1 | 9/2009 |
| WO | 2010-006191 A1 | 1/2010 |
| WO | 2010048149 A2 | 4/2010 |
| WO | 2011005929 A1 | 1/2011 |
| WO | 2011008663 A1 | 1/2011 |
| WO | 2011148922 A | 1/2011 |
| WO | 2011127051 A1 | 10/2011 |
| WO | 2011145718 A | 11/2011 |
| WO | 2012041158 A1 | 4/2012 |
| WO | 2012069917 A1 | 5/2012 |
| WO | 2012077655 A | 6/2012 |
| WO | 2012173174 A | 12/2012 |
| WO | 2013/187646 A1 | 12/2013 |

OTHER PUBLICATIONS

Faghih, et al., "Synthesis and SAR of Aminoalkoxy-biaryl-4-carboxamides: Novel and Selective Histamine $H_3$ Receptor Antagonists," Bioorganic & Medicinal Chemistry Letters 13 (2003), pp. 1325-1328.

Witte, et al., "Detection of multiple $H_3$ receptor affinity states utilizing [$^3$H]A-349821, a novel, selective, non-imidazole histamine $H_3$ receptor inverse agonist radioligand," British Journal of Pharmacology (2006), vol. 148 (5), pp. 657-670.

Pourcet, et al., "Selective PPAR modulators, dual and pan PPAR agonists: multimodal drugs for the treatment of Type 2 diabetes and atherosclerosis," Expert Opinion Emerging Drugs, 2006, vol. 11(3), pp. 379-401.

(Continued)

*Primary Examiner* — Timothy R Rozof
(74) *Attorney, Agent, or Firm* — Heslin Rothenberg Farley & Mesiti P.C.

(57) ABSTRACT

The present invention relates to novel amide derivatives, stereoisomers thereof or pharmaceutically acceptable salts thereof; methods for preparing the compound; and pharmaceutical compositions comprising the compound. The novel amide derivatives, according to the present invention, having an effect as GPR119 agonist can be used for treatment of metabolic disorders, including diabetes mellitus (especially type II) and related disorders.

11 Claims, No Drawings

(56) References Cited

OTHER PUBLICATIONS

Holman, "Long-term efficacy of sulfonylureas: a United Kingdom Prospective Diabetes Study perspective," Metabolism Clinical and Experimental, 2006, vol. 55 (Suppl. 1), pp. S2-S5.
Chu, et al., "A Role for β-Cell-Expressed G Protein-Coupled Receptor 119 in Glycemic Control by Enhancing Glucose-Dependent Insulin Release," Endocrinology, 2007, vol. 148(6), pp. 2601-2609.
Overton, et al., "GPR119, a novel G protein-coupled receptor target for the treatment of type 2 diabetes and obesity," British Journal of Pharmacology, 2008, vol. 153, pp. S76-S81.
Soga, et al., "Lysophosphatidylcholine enhances glucose-dependent insulin secretion via an orphan G-protein-coupled receptor," Biochemical and Biophysical Research Communications, 2005, vol. 326, pp. 744-751.
Chu, et al., "A Role for Intestinal Endocrine Cell Expressed G Protein-Couple Receptor 119 in Glycemic Control by Enhancing Glucagon-Like Peptide-1 and Glucose Dependent Insulinotropic Peptide Release," Endocrinology, (2008), vol. 149, Issue 5, pp. 2038-2047.
Extended European Search Report for EP14866648.0 dated Mar. 22, 2017, 7 pages.
Wu, et al., "2,5-Disubstituted pyridines as potent GPR119 agonists," Bioorganic & Medicinal Chemistry Letters, 513, 20, 2577-2581 (2010).
Chinese Search Report for 2013800307723 dated Jul. 28, 2015.
Russian Search Report for Russian Patent Application No. 2014142328 based on PCT/KR2013/005096 dated Feb. 12, 2016.
Ritter et al., "G Protein-Coupled Receptor 119 (CPR119) Agonists for the Treatment of Diabetes: Recent Progress and Prevailing Challenges," 2015, 14 pages, Journal of Medicinal Chemistry.
Patent Cooperation Treaty, International Search Report for PCT/KR2013/005096 mailed Oct. 24, 2013, 5 pages.
International Search Report for International Application No. PCT/KR2014/011356, dated Mar. 9, 2015.
International Search Report dated Jun. 1, 2017 of the corresponding Chinese Patent Application No. 201480064763.0.

AMIDE DERIVATIVES FOR GPR119 AGONIST

TECHNICAL FIELD

The present invention relates to novel compounds that are useful in the treatment of metabolic disorders, including diabetes mellitus (types I and II) and related disorders, pharmaceutical compositions comprising the compounds, and therapeutic uses for the compounds.

BACKGROUND ART

Diabetes mellitus is a severe disorder that affects more and more human in the world. The forecast of International Diabetes Federation alludes that the total worldwide number of human with diabetes mellitus will be 380,000,000 (three hundred eighty million) until 2025. The attack rate of diabetes mellitus is increasing along with a growing tendency of obesity in many countries. The severe effect of diabetes mellitus includes the increased risk of stroke, heart disease, kidney failure, blindness and amputation. Cardiovascular disorders are more than 70% leading cause of all death in human with Type II diabetes (T2DM) [B. Pourcet et al. Expert Opin. Emerging Drugs 2006, 11, 379-401].

Diabetes mellitus is characterized in the insulin secretion and/or the disturbance of insulin signal reaction in peripheral tissues. There are two types' diabetes mellitus, that is, insulin-dependent diabetes mellitus and non-insulin-dependent diabetes mellitus. Most of the patients with diabetes mellitus are suffering from non-insulin-dependent diabetes mellitus, which is known as Type II diabetes or NIDDM. Because of the severe consequence of diabetes mellitus, the control of diabetes mellitus is necessary desperately.

The treatment of NIDDM generally begins weight loss, healthy diet and exercise program. Although these factors are important especially to dissolve the increased risk of cardiovascular disorders related to diabetes mellitus, they are not effective generally for the control of diabetes mellitus itself. There are many drugs useful for the treatment of diabetes mellitus, including insulin, metformin, sulfonylureas, acarbose, thiazolidinedione, GLP-1 analogue and DPP IV inhibitor. However, some of such treatment agents have a problem including more than one disadvantage of hypoglycemic episodes, weight gain, gastrointestinal problems and loss in responsiveness to therapy over time.

Although many medicines for the treatment of diabetes mellitus through the various mechanisms are approved, lots of medicines still are under clinical appraisal, and there still is need to develop novel compound for the treatment of diabetes mellitus. Recently, the research result showing the observation that beta-cell function of diabetes patient declines over time regardless of success or failure of treatment with diet, sulfonylureas, metformin or insulin has been published [R. R. Holman Metabolism 2006, 55, S2-S5].

GPR119 is a protein consisted of 335 amino acids expressed in beta-cell of pancreatic islet [Z.-L. Chu et al., Endocrinol. 2007, J 48, 2601-2609] and gastro-intestinal tract [Z.-L. Chu et. al., Endocrinol. 2008, 149, 2038-2047]. Said protein belongs to the receptor family coupled to G-protein, and some candidates including oleoylethanolamide (OEA), N-oleoyldopamine and olvanil are suggested as intrinsic ligand [H. A. Overton et al. Brit. J. Pharmacol. 2008, 153, S76-81].

It is supported from many research using cell line and animal that GPR119 may perform a certain function in glucose-dependent secretion of insulin, and targeting to GPR119 receptor may be effective to the treatment of diabetes mellitus. Activation of GPR119 receptor by lisophosphatidilcholine forces up the glucose-dependent secretion in the pancreas beta-cell line of mice, and the insulin secretion can be blocked by GPR119-specific siRNA [T. Soga et al. Biochem. Biophys. Res. Commun. 2005, 326]

Therefore, GPR119 receptor activator is needed for the treatment of disorders, such as diabetes mellitus.

DISCLOSURE

Technical Problem

The object of this invention is to provide a novel amide derivative, stereoisomers thereof, pharmaceutically acceptable salts thereof, and a preparing method thereof.

The other object of this invention is to provide a novel amide derivative being able to control GPR119 activity with low adverse effect, stereoisomers thereof, pharmaceutically acceptable salts thereof, and a preparing method thereof.

Technical Solution

To achieve the above objects, the present invention provides a novel amide derivative of the following formula 1, stereoisomers thereof, or pharmaceutically acceptable salts thereof:

[Formula 1]

$$R_1 \underset{R_2\ R_3}{\overset{R_4}{\diagdown}} \underset{R_5}{N} - O - \underset{X_4 \mid X_3}{\overset{X_1=X_2}{\diagdown}} - \underset{R_6}{\overset{}{\diagdown}} - \underset{X_8 \mid X_7}{\overset{X_5=X_6}{\diagdown}} - \underset{R_7}{\overset{O}{\diagdown}} N \underset{R_9}{\overset{R_8}{\diagdown}} \underset{m}{\overset{O}{\diagdown}} NH_2$$

wherein $X_1, X_2, X_3, X_4, X_5, X_6, X_7$ and $X_8$ are each independently C or N;

$R_1$ is —F or —$C_{1-3}$perfluorinated alkyl;

$R_2$ and $R_3$ are each independently selected from the group consisting of halogen, —$C_{1-5}$alkyl and $C_{3-6}$cycloalkyl, wherein —$C_{1-5}$alkyl and $C_{3-6}$cycloalkyl may be each independently non-substituted, or substituted with halogen, —CN, —$C_{1-5}$alkyl or —$C_{1-5}$alkyl, or $R_2$ and $R_3$, taken together with the carbon atom to which they are attached, may form $C_{3-6}$cycloalkyl (wherein $C_{3-6}$cycloalkyl may be non-substituted, or substituted with halogen, —$OC_{1-5}$alkyl or —$C_{1-5}$alkyl);

$R_4$ and $R_5$ are each independently H, halogen or —$C_{1-5}$alkyl;

$R_6$ and $R_7$ are each independently H, halogen, —$C_{1-5}$alkyl or —CN;

$R_8$ is H, —$C_{1-5}$alkyl or —$C_{1-5}$alkylOCH$_3$;

$R_9$ is H, halogen or OH; and m is 1 or 2.

Preferably, the present invention provides a novel amide derivative of the above formula 1, stereoisomers thereof, or pharmaceutically acceptable salts thereof:

wherein $R_1$ is —F or —$C_{1-3}$perfluorinated alkyl;

$R_2$ and $R_3$ are each independently selected from the group consisting of halogen and —$C_{1-5}$alkyl, or $R_2$ and $R_3$, taken together with the carbon atom to which they are attached, may form $C_{3-6}$cycloalkyl (wherein $C_{3-6}$cycloalkyl may be non-substituted, or substituted with halogen, —$OC_{1-5}$alkyl or —$C_{1-5}$alkyl);

$R_4$ and $R_5$ are each independently H;

$R_6$ and $R_7$ are each independently H, halogen or —CN;

$R_8$ is H or —$C_{1-5}$alkyl;

$R_9$ is H or OH; and m is 1.

More preferably, the present invention provides a novel amide derivative of the above formula 1, stereoisomers thereof, or pharmaceutically acceptable salts thereof:

wherein

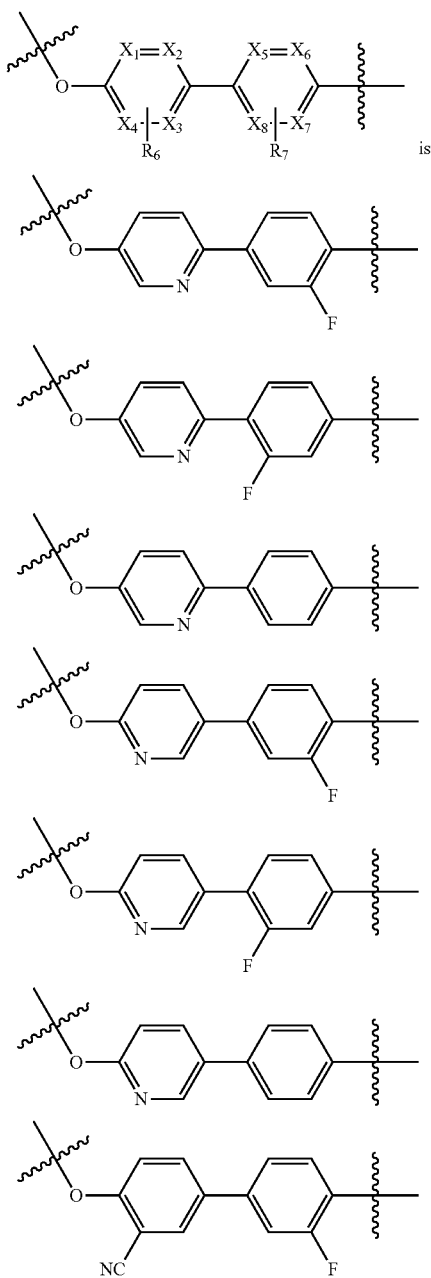

is

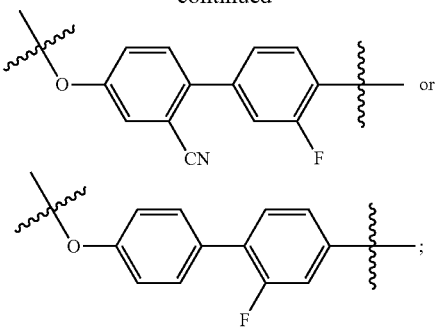

$R_1$ is —F or —$C_{1-3}$perfluorinated alkyl;

$R_2$ and $R_3$ are each independently selected from the group consisting of halogen and —$C_{1-5}$alkyl, or $R_2$ and $R_3$, taken together with the carbon atom to which they are attached, may form $C_{3-6}$cycloalkyl (wherein $C_{3-6}$cycloalkyl may be non-substituted, or substituted with halogen, —$OC_{1-5}$alkyl or —$C_{1-5}$alkyl);

$R_4$ and $R_5$ are each independently H;

$R_8$ is H or —$C_{1-5}$alkyl;

$R_9$ is H or OH; and m is 1.

The compound of formula 1 may be used generally as a form of pharmaceutically acceptable salt thereof. The pharmaceutically acceptable salts thereof include pharmaceutically acceptable base addition salts and acid addition salts, for example, metal salts, such as alkali and alkaline earth metal salts, ammonium salt, organic amine addition salt, amino acid addition salt and sulfonate salt. Acid addition salts include inorganic acid addition salts, such as hydrogen chloride salt, sulfonic acid salt and phosphoric acid salt; and organic acid addition salts, such as alkyl sulfonate, aryl sulfonate, acetate, malate, fumarate, tartrate, citrate and lactate. Examples of metal salts include alkali metal salt, such as lithium salt, sodium salt and potassium salt; alkaline earth metal salts, such as magnesium salt, calcium salt, aluminium salt and zinc salt. Examples of ammonium salt include ammonium salt and tetramethylammonium salt. Examples of organic amine addition salts include salts with morpholine and piperidine. Examples of amino acid addition salts include salts with glycine, phenylalanine, glutamic acid and lysine. Examples of sulfonate salt include mesylate, tosylate and benzenesulfonic acid salts.

Specific examples of preferred compounds of formula 1 according to the present invention include:

Compound 1148: (S)-1-(2'-cyano-3-fluoro-4'-((1-(2-fluoro-2-methylpropyl)piperidin-4-yl)methoxy)biphenyl-carbonyl)-2-methylpyrrolidin-2-carboxamide;

Compound 1191: (2S,4R)-1-(2'-cyano-3-fluoro-4'-((1-(2-fluoro-2-methylpropyl)piperidin-4-yl)methoxy)biphenyl-carbonyl)-4-hydroxypyrrolidin-2-carboxamide;

Compound 1192: (2S,4S)-1-(2'-cyano-3-fluoro-4'-((1-(2-fluoro-2-methylpropyl)piperidin-4-yl)methoxy)biphenyl-carbonyl)-4-fluoropyrrolidin-2-carboxamide;

Compound 1198: (2S,4S)-4-fluoro-1-(4'-((1-((1-(trifluoromethyl)cyclobutyl)methyl)piperidin-4-yl)methoxy)biphenylcarbonyl)pyrrolidin-2-carboxamide;

Compound 1199: (2S,4R)-4-hydroxy-1-(4'-((1-((1-(trifluoromethyl)cyclobutyl)methyl)piperidin-4-yl)methoxy)biphenylcarbonyl)pyrrolidin-2-carboxamide;

Compound 1200: (2S,4R)-1-(2-fluoro-4-(5-((1-((1-(trifluoromethyl)cyclobutyl)methyl)piperidin-4-yl)methoxy)pyrazin-2-yl)benzoyl)-4-hydroxypyrrolidin-2-carboxamide;

Compound 1204: (2S,4R)-1-(4'-((1-(2-ethyl-2-fluorobutyl)piperidin-4-yl)methoxy)biphenylcarbonyl)-4-hydroxypyrrolidin-2-carboxamide;

Compound 1205: (2S,4R)-1-(4'-((1-(2-ethyl-2-fluorobutyl)piperidin-4-yl)methoxy)-2-fluorobiphenylcarbonyl)-4-hydroxypyrrolidin-2-carboxamide;

Compound 1206: (S)-1-(2-fluoro-4-(5-((1-(2-fluoro-2-methylpropyl)piperidin-4-yl)methoxy)pyrimidin-2-yl)benzoyl)-2-methylpyrrolidin-2-carboxamide;

Compound 1207: (S)-1-(2-fluoro-4-(5-((1-(2-fluoro-2-methylpropyl)piperidin-4-yl)methoxy)pyridin-2-yl)benzoyl)-2-methylpyrrolidin-2-carboxamide;

Compound 1208: (2S,4R)-1-(2-fluoro-4-(6-((1-(3,3,3-trifluoro-2,2-dimethylpropyl)piperidin-4-yl)methoxy)pyridin-3-yl)benzoyl)-4-hydroxypyrrolidin-2-carboxamide;

Compound 1209: (2S,4S)-4-fluoro-1-(4-(5-((1-((1-(trifluoromethyl)cyclobutyl)methyl)piperidin-4-yl)methoxy)pyrazin-2-yl)benzoyl)pyrrolidin-2-carboxamide;

Compound 1210: (2S,4S)-1-(4'-((1-(2-ethyl-2-fluorobutyl)piperidin-4-yl)methoxy)-2-fluorobiphenylcarbonyl)-4-fluoropyrrolidin-2-carboxamide;

Compound 1211: (2S,4S)-1-(4'-((1-(2-ethyl-2-fluorobutyl)piperidin-4-yl)methoxy)-3-fluorobiphenylcarbonyl)-4-fluoropyrrolidin-2-carboxamide;

Compound 1220: (2S,3S)-1-(2-fluoro-4'-((1-((1-(trifluoromethyl)cyclobutyl)methyl)piperidin-4-yl)methoxy)biphenylcarbonyl)-3-hydroxypyrrolidin-2-carboxamide;

Compound 1229: (2S,3S)-1-(2'-cyano-4'-((1-(2-ethyl-2-fluorobutyl)piperidin-4-yl)methoxy)-3-fluorobiphenylcarbonyl)-3-hydroxypyrrolidin-2-carboxamide;

Compound 1235: (2S,3S)-1-(3-fluoro-4-(6-((1-((1-(trifluoromethyl)cyclobutyl)methyl)piperidin-4-yl)methoxy)pyridin-3-yl)benzoyl)-3-hydroxypyrrolidin-2-carboxamide;

Compound 1238: (S)-1-(4-(6-((1-(2,2-difluorobutyl)piperidin-4-yl)methoxy)pyridin-3-yl)-2-fluorobenzoyl)pyrrolidin-2-carboxamide;

Compound 1239: (S)-1-(3-fluoro-4'-((1-(2,2,3,3,3-pentafluoropropyl)piperidin-4-yl)methoxy)biphenylcarbonyl)pyrrolidin-2-carboxamide;

Compound 1240: (2S,4R)-1-(2',3-difluoro-4'-((1-(3,3,3-trifluoro-2,2-dimethylpropyl)piperidin-4-yl)methoxy)biphenylcarbonyl)-4-hydroxypyrrolidin-2-carboxamide;

Compound 1241: (2S,4R)-1-(4-(6-((1-(2,2-difluorobutyl)piperidin-4-yl)methoxy)pyridin-3-yl)-2-fluorobenzoyl)-4-hydroxypyrrolidin-2-carboxamide;

Compound 1244: (2S,3S)-1-(4'-((1-(2-ethyl-2-fluorobutyl)piperidin-4-yl)methoxy)-3,3'-difluorobiphenylcarbonyl)-3-hydroxypyrrolidin-2-carboxamide;

Compound 1245: (2S,3S)-1-(4'-((1-(2-ethyl-2-fluorobutyl)piperidin-4-yl)methoxy)-2'-fluorobiphenylcarbonyl)-3-hydroxypyrrolidin-2-carboxamide;

Compound 1249: (2S,3S)-1-(2-fluoro-4-(5-((1-((1-(trifluoromethyl)cyclobutyl)methyl)piperidin-4-yl)methoxy)pyrazin-2-yl)benzoyl)-3-hydroxypyrrolidin-2-carboxamide;

Compound 1253: (2S,3S)-1-(3-fluoro-4-(5-((1-((1-(trifluoromethyl)cyclobutyl)methyl)piperidin-4-yl)methoxy)pyrazin-2-yl)benzoyl)-3-hydroxypyrrolidin-2-carboxamide;

Compound 1255: (2S,4R)-1-(2-fluoro-4'-((1-(1-trifluoromethyl)cyclobutyl)methyl)piperidin-4-yl)methoxy)biphenylcarbonyl)-4-hydroxypyrrolidin-2-carboxamide;

Compound 1256: (2S,4R)-1-(3-fluoro-4'-((1-(2,2,3,3,3-pentafluoropropyl)piperidin-4-yl)methoxy)biphenylcarbonyl)-4-hydroxypyrrolidin-2-carboxamide;

Compound 1257: (2S,4R)-1-(4-(5-((1-(2-ethyl-2-fluorobutyl)piperidin-4-yl)methoxy)pyrimidin-2-yl)-2-fluorobenzoyl)-4-hydroxypyrrolidin-2-carboxamide;

Compound 1258: (2S,4R)-1-(2-fluoro-4'-((1-((1-(trifluoromethyl)cyclobutyl)methyl)piperidin-4-yl)methoxy)biphenylcarbonyl)-4-hydroxy-2-methylpyrrolidin-2-carboxamide;

Compound 1259: (S)-1-(3'-cyano-3-fluoro-4'-((1-(2-fluoro-2-methylpropyl)piperidin-4-yl)methoxy)biphenylcarbonyl)-2-methylpyrrolidin-2-carboxamide;

Compound 1261: (2S,4R)-1-(3'-cyano-3-fluoro-4'-((1-(2-fluoro-2-methylpropyl)piperidin-4-yl)methoxy)biphenylcarbonyl)-4-hydroxypyrrolidin-2-carboxamide;

Compound 1262: 1-(2-fluoro-4-(5-((1-((1-(trifluoromethyl)cyclobutyl)methyl)piperidin-4-yl)methoxy)pyrazin-2-yl)benzoyl)-4-hydroxypiperidin-2-carboxamide;

Compound 1263: (S)-1-(2-fluoro-4-(5-((1-((1-(trifluoromethyl)cyclobutyl)methyl)piperidin-4-yl)methoxy)pyrazin-2-yl)benzoyl)-2-methylpyrrolidin-2-carboxamide;

Compound 1264: (S)-1-(2-fluoro-4-(5-((1-(2,2,3,3,3-pentafluoropropyl)piperidin-4-yl)methoxy)pyridin-2-yl)benzoyl)pyrrolidin-2-carboxamide;

Compound 1265: (2S,4R)-1-(2-fluoro-4-(5-((1-(2,2,3,3,3-pentafluoropropyl)piperidin-4-yl)methoxy)pyridin-2-yl)benzoyl)-4-hydroxypyrrolidin-2-carboxamide;

Compound 1266: (S)-1-(2-fluoro-4-(5-((1-(2,2,3,3,3-pentafluoropropyl)piperidin-4-yl)methoxy)pyridin-2-yl)benzoyl)-2-methylpyrrolidin-2-carboxamide;

Compound 1267: (S)-1-(2-fluoro-4-(5-((1-(3,3,3-trifluoro-2,2-dimethylpropyl)piperidin-4-yl)methoxy)pyridin-2-yl)benzoyl)pyrrolidin-2-carboxamide;

Compound 1268: (2S,4R)-1-(2-fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxamide;

Compound 1269: (S)-1-(2-fluoro-4-(5-((1-(3,3,3-trifluoro-2,2-dimethylpropyl)piperidin-4-yl)methoxy)pyridin-2-yl)benzoyl)-2-methylpyrrolidin-2-carboxamide;

Compound 1271: (2S,4R)-1-(2-fluoro-4-(5-((1-(2-fluoro-2-methylpropyl)piperidin-4-yl)methoxy)pyridin-2-yl)benzoyl)-4-hydroxy-2-methylpyrrolidin-2-carboxamide;

Compound 1272: (2S,4R)-1-(3'-cyano-4'-((1-(2-ethyl-2-fluorobutyl)piperidin-4-yl)methoxy)-3-fluorobiphenylcarbonyl)-4-hydroxypyrrolidin-2-carboxamide;

Compound 1276: (2S,4R)-1-(3'-cyano-3-fluoro-4'-((1-(2-fluoro-2-methylpropyl)piperidin-4-yl)methoxy)biphenylcarbonyl)-4-hydroxy-2-methylpyrrolidin-2-carboxamide;

Compound 1277: (2R,4R)-1-(3'-cyano-3-fluoro-4'-((1-(2-fluoro-2-methylpropyl)piperidin-4-yl)methoxy)biphenylcarbonyl)-4-hydroxy-2-methylpyrrolidin-2-carboxamide;

Compound 1278: (2S,4R)-1-(2'-cyano-3-fluoro-4'-((1-(2-fluoro-2-methylpropyl)piperidin-4-yl)methoxy)biphenylcarbonyl)-4-hydroxy-2-methylpyrrolidin-2-carboxamide;

Compound 1279: (2S,4R)-1-(4-(5-((1-(2-ethyl-2-fluorobutyl)piperidin-4-yl)methoxy)pyridin-2-yl)-2-fluorobenzoyl)-4-hydroxypyrrolidin-2-carboxamide;

Compound 1280: (2S,4R)-1-(2-fluoro-4-(5-((1-((1-(trifluoromethyl)cyclobutyl)methyl)piperidin-4-yl)methoxy)pyridin-2-yl)benzoyl)-4-hydroxypyrrolidin-2-carboxamide;

Compound 1281: (2S,4R)-4-hydroxy-1-(4-(5-((1-(2,2,3,3,3-pentafluoropropyl)piperidin-4-yl)methoxy)pyrazin-2-yl)benzoyl)pyrrolidin-2-carboxamide;

Compound 1286: (2S,4R)-1-(3-fluoro-4-(5-((1-((1-(trifluoromethyl)cyclobutyl)methyl)piperidin-4-yl)methoxy)pyridin-2-yl)benzoyl)-4-hydroxypyrrolidin-2-carboxamide;

Compound 1287: (2S,4R)-1-(4-(5-((1-(2-ethyl-2-fluorobutyl)piperidin-4-yl)methoxy)pyridin-2-yl)-3-fluorobenzoyl)-4-hydroxypyrrolidin-2-carboxamide;

Compound 1288: (2S,4R)-1-(3'-cyano-4'-((1-(2-fluoro-2-methylpropyl)piperidin-4-yl)methoxy)biphenylcarbonyl)-4-hydroxypyrrolidin-2-carboxamide;

Compound 1290: (2S,4R)-1-(2-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxamide;

Compound 1291: (2S,4R)-1-(4-(5-((1-(2-ethyl-2-fluorobutyl)piperidin-4-yl)methoxy)pyridin-2-yl)-2-fluorobenzoyl)-4-hydroxy-2-methylpyrrolidin-2-carboxamide;

Compound 1292: (2S,4R)-1-(4-(5-((1-(2-ethyl-2-fluorobutyl)piperidin-4-yl)methoxy)pyridin-2-yl)-3-fluorobenzoyl)-4-hydroxy-2-methylpyrrolidin-2-carboxamide;

Compound 1294: (2S,4R)-1-(2-fluoro-4-(5-((1-(3,3,3-trifluoro-2,2-dimethylpropyl)piperidin-4-yl)methoxy)pyridin-2-yl)benzoyl)-4-hydroxy-2-methylpyrrolidin-2-carboxamide;

Compound 1295: (2S,4R)-1-(2-fluoro-4-(6-((1-(3,3,3-trifluoro-2,2-dimethylpropyl)piperidin-4-yl)methoxy)pyridin-3-yl)benzoyl)-4-hydroxy-2-methylpyrrolidin-2-carboxamide;

Compound 1297: (S)-1-(2-fluoro-4-(5-((1-((1-(trifluoromethyl)cyclobutyl)methyl)piperidin-4-yl)methoxy)pyridin-2-yl)benzoyl)-2-methylpyrrolidin-2-carboxamide;

Compound 1299: (S)-1-(4-(5-((1-(2-ethyl-2-fluorobutyl)piperidin-4-yl)methoxy)pyridin-2-yl)-2-fluorobenzoyl)-2-methylpyrrolidin-2-carboxamide;

Compound 1300: (S)-1-(2-fluoro-4-(5-((1-((1-(trifluoromethyl)cyclobutyl)methyl)piperidin-4-yl)methoxy)pyridin-2-yl)benzoyl)pyrrolidin-2-carboxamide;

Compound 1301: (S)-2-methyl-1-(4-(5-((1-(2,2,3,3,3-pentafluoropropyl)piperidin-4-yl)methoxy)pyrazin-2-yl)benzoyl)pyrrolidin-2-carboxamide;

Compound 1305: (2S,4R)-1-(4-(5-((1-(2-ethyl-2-fluorobutyl)piperidin-4-yl)methoxy)pyridin-2-yl)benzoyl)-4-hydroxypyrrolidin-2-carboxamide;

Compound 1306: (2S,4R)-1-(4-(6-((1-(2-ethyl-2-fluorobutyl)piperidin-4-yl)methoxy)pyridin-3-yl)benzoyl)-4-hydroxypyrrolidin-2-carboxamide;

Compound 1307: (2S,4R)-1-(4-(6-((1-(2-ethyl-2-fluorobutyl)piperidin-4-yl)methoxy)pyridin-3-yl)-3-fluorobenzoyl)-4-hydroxypyrrolidin-2-carboxamide;

Compound 1308: (2S,4R)-1-(4-(6-((1-(2-ethyl-2-fluorobutyl)piperidin-4-yl)methoxy)pyridin-3-yl)-2-fluorobenzoyl)-4-hydroxypyrrolidin-2-carboxamide;

Compound 1309: (2S,4R)-1-(4-(5-((1-(2-ethyl-2-fluorobutyl)piperidin-4-yl)methoxy)pyridin-2-yl)benzoyl)-4-hydroxy-2-methylpyrrolidin-2-carboxamide;

Compound 1311: (2S,4R)-1-(3-fluoro-4-(5-((1-(2,2,3,3,3-pentafluoropropyl)piperidin-4-yl)methoxy)pyridin-2-yl)benzoyl)-4-hydroxypyrrolidin-2-carboxamide;

Compound 1312: (S)-1-(3-fluoro-4-(5-((1-(2,2,3,3,3-pentafluoropropyl)piperidin-4-yl)methoxy)pyridin-2-yl)benzoyl)pyrrolidin-2-carboxamide;

Compound 1313: (S)-1-(3-fluoro-4-(5-((1-(2,2,3,3,3-pentafluoropropyl)piperidin-4-yl)methoxy)pyridin-2-yl)benzoyl)-2-methylpyrrolidin-2-carboxamide;

Compound 1314: (S)-1-(3-fluoro-4-(5-((1-((1-(trifluoromethyl)cyclobutyl)methyl)piperidin-4-yl)methoxy)pyridin-2-yl)benzoyl)pyrrolidin-2-carboxamide;

Compound 1315: (S)-1-(3-fluoro-4-(5-((1-((1-(trifluoromethyl)cyclobutyl)methyl)piperidin-4-yl)methoxy)pyridin-2-yl)benzoyl)-2-methylpyrrolidin-2-carboxamide;

Compound 1316: (2S,4R)-1-(3-fluoro-4-(6-((1-((1-(trifluoromethyl)cyclobutyl)methyl)piperidin-4-yl)methoxy)pyridin-3-yl)benzoyl)-4-hydroxypyrrolidin-2-carboxamide;

Compound 1317: (2S,4R)-1-(2-fluoro-4-(6-((1-((1-(trifluoromethyl)cyclobutyl)methyl)piperidin-4-yl)methoxy)pyridin-3-yl)benzoyl)-4-hydroxypyrrolidin-2-carboxamide;

Compound 1318: (S)-1-(3-fluoro-4-(6-((1-((1-(trifluoromethyl)cyclobutyl)methyl)piperidin-4-yl)methoxy)pyridin-3-yl)benzoyl)-2-methylpyrrolidin-2-carboxamide;

Compound 1319: (S)-1-(2-fluoro-4-(6-((1-((1-(trifluoromethyl)cyclobutyl)methyl)piperidin-4-yl)methoxy)pyridin-3-yl)benzoyl)-2-methylpyrrolidin-2-carboxamide;

Compound 1320: (S)-2-methyl-1-(4-(6-((1-((1-(trifluoromethyl)cyclobutyl)methyl)piperidin-4-yl)methoxy)pyridin-3-yl)benzoyl)pyrrolidin-2-carboxamide;

Compound 1321: (2R,4R)-1-(4'-((1-(2-ethyl-2-fluorobutyl)piperidin-4-yl)methoxy)-2-fluorobiphenylcarbonyl)-4-hydroxypyrrolidin-2-carboxamide;

Compound 1322: (2S,4R)-4-hydroxy-1-(4-(5-((1-(3,3,3-trifluoro-2,2-dimethylpropyl)piperidin-4-yl)methoxy)pyridin-2-yl)benzoyl)pyrrolidin-2-carboxamide;

Compound 1323: (2S,4R)-1-(3-fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxamide;

Compound 1325: (2S,4R)-1-(3-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxamide;

Compound 1326: (2S,4R)-1-(2-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxamide;

Compound 1327: (2S,4R)-4-hydroxy-2-methyl-1-(4-(6-((1-((1-(trifluoromethyl)cyclobutyl)methyl)piperidin-4-yl)methoxy)pyridin-3-yl)benzoyl)pyrrolidin-2-carboxamide;

Compound 1328: (2S,4R)-1-(4-(6-((1-(2-ethyl-2-fluorobutyl)piperidin-4-yl)methoxy)pyridin-3-yl)benzoyl)-4-hydroxy-2-methylpyrrolidin-2-carboxamide; and Compound 1329: (2S,4R)-1-(3-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxamide.

Specific examples of more preferred compounds of formula 1 according to the present invention include:

Compound 1205: (2S,4R)-1-(4'-((1-(2-ethyl-2-fluorobutyl)piperidin-4-yl)methoxy)-2-fluorobiphenylcarbonyl)-4-hydroxypyrrolidin-2-carboxamide;

Compound 1207: (S)-1-(2-fluoro-4-(5-((1-(2-fluoro-2-methylpropyl)piperidin-4-yl)methoxy)pyridin-2-yl)benzoyl)-2-methylpyrrolidin-2-carboxamide;

Compound 1279: (2S,4R)-1-(4-(5-((1-(2-ethyl-2-fluorobutyl)piperidin-4-yl)methoxy)pyridin-2-yl)-2-fluorobenzoyl)-4-hydroxypyrrolidin-2-carboxamide;

Compound 1280: (2S,4R)-1-(2-fluoro-4-(5-((1-((1-(trifluoromethyl)cyclobutyl)methyl)piperidin-4-yl)methoxy)pyridin-2-yl)benzoyl)-4-hydroxypyrrolidin-2-carboxamide;

Compound 1290: (2S,4R)-1-(2-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxamide;

Compound 1291: (2S,4R)-1-(4-(5-((1-(2-ethyl-2-fluorobutyl)piperidin-4-yl)methoxy)pyridin-2-yl)-2-fluorobenzoyl)-4-hydroxy-2-methylpyrrolidin-2-carboxamide;

Compound 1323: (2S,4R)-1-(3-fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxamide; and Compound 1329 (2S,4R)-1-(3-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxamide.

The present invention also provides pharmaceutical composition comprising the amide derivative of the formula 1, stereoisomers thereof, or pharmaceutically acceptable salts thereof; and pharmaceutically acceptable carriers thereof.

Preferably, the composition is used for treatment of a disease associated with GPR119 agonist.

Preferably, said disease associated with GPR119 agonist is diabetes mellitus, and more preferably, Type II diabetes mellitus.

Advantageous Effects

The present invention can provide a novel amide derivative, stereoisomers thereof, or pharmaceutically acceptable salts thereof.

In addition, the present invention can provide a novel amide derivative being able to control GPR119 activity with low adverse effect, stereoisomers thereof, or pharmaceutically acceptable salts thereof.

The compounds of the present invention showed excellent solubility in water and excellent antidiabetic activity with compared to MBX-2982 of Metabolex Inc. (WO2009014910) and GSK1292263 of GSK Inc. (WO2008070692), which are in Phase II of clinical trial as an activator for GPR119 receptor, but have disadvantage of their low solubility in water, Synthetic Schemes

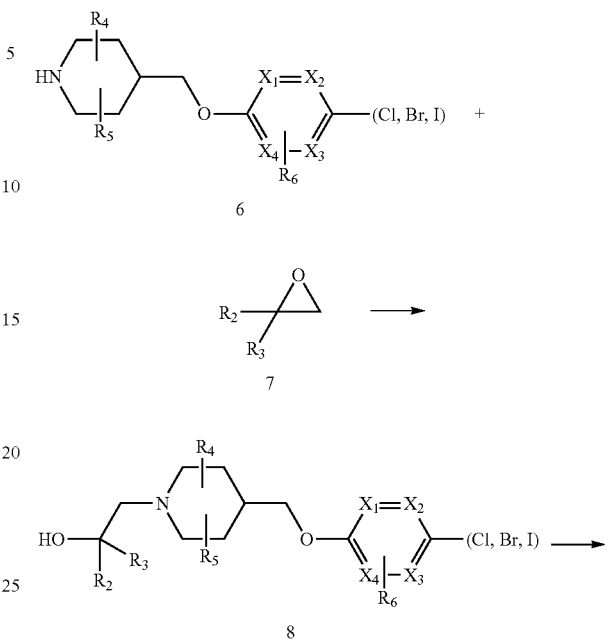

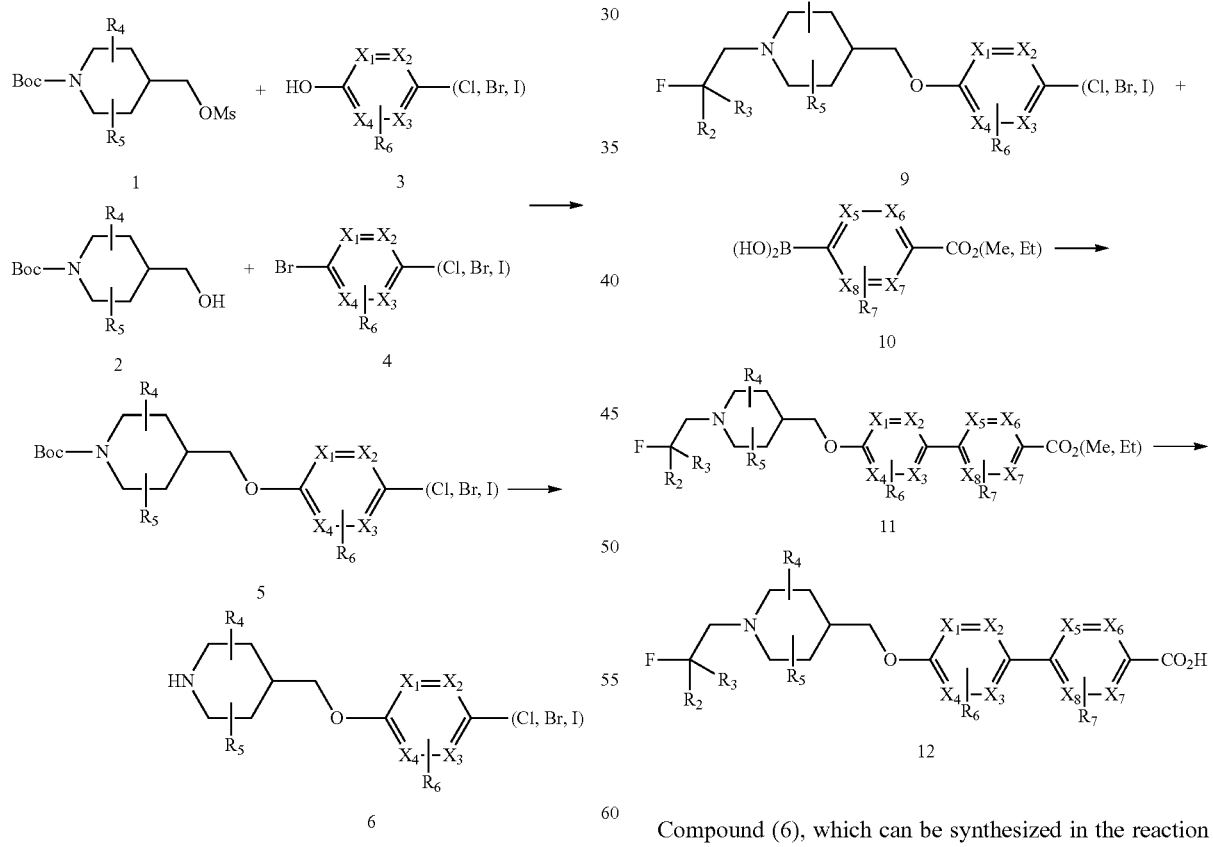

Compound (5) can be synthesized by substitution reaction of compound (1) with compound (3) or by substitution reaction of compound (2) with compound (4). And then, through removing of protection group of compound (5), compound (6) can be synthesized.

Compound (6), which can be synthesized in the reaction scheme 1, is reacted with oxirane compound (7) to afford compound (8), of which hydroxyl group is substituted with fluoride to afford compound (9). Compound (9) and boron compound (10) are subjected to Suzuki coupling reaction to afford compound (11), which is hydrolyzed to afford compound (12).

[Reaction Scheme 3]

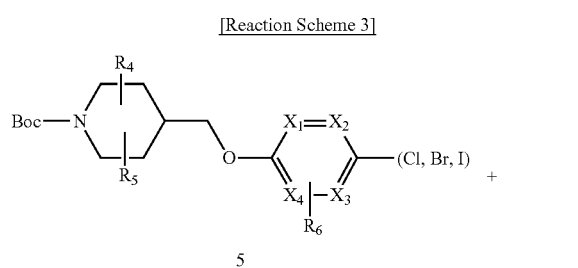

5

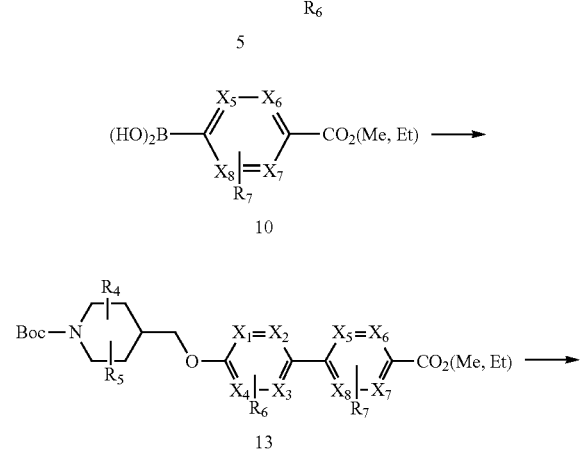

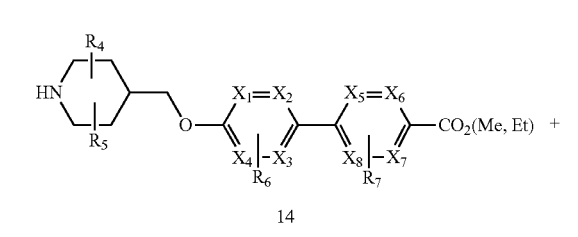

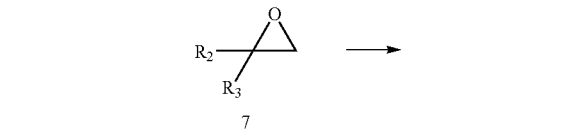

7

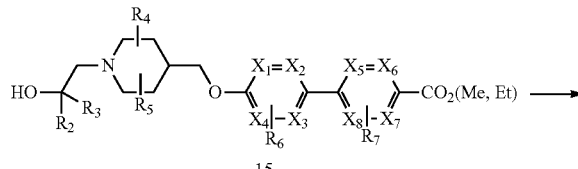

15

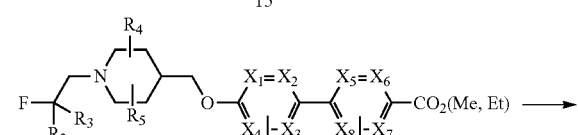

11

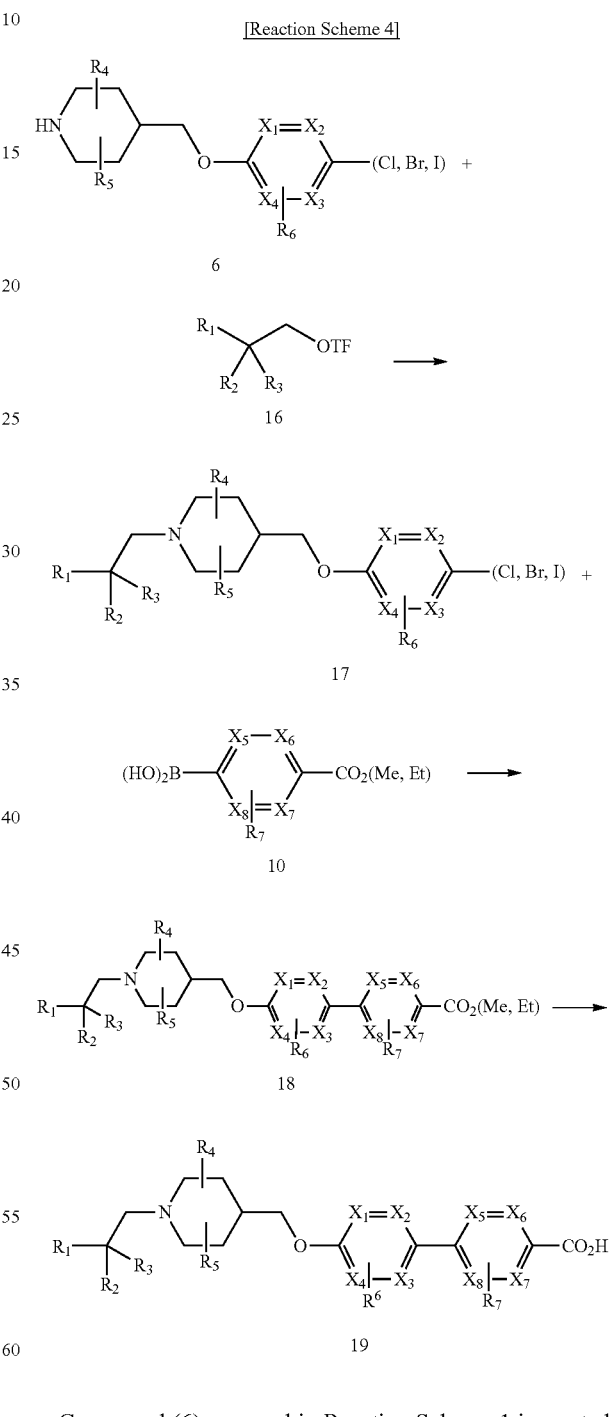

boron compound (10) to afford compound (13). Through removing of protection group of compound (13), compound (14) can be synthesized. compound (14) is reacted with compound (7) to afford compound (15), of which hydroxyl group is substituted with fluoride to afford compound (11). Lastly, compound (11) is hydrolyzed to afford compound (12).

[Reaction Scheme 4]

Compound (6) prepared in Reaction Scheme 1 is reacted with triplate compound (16), thereby to afford compound (17). Compound (17) is subjected to Suzuki coupling reaction with boronic acid compound (10) to afford compound (18), which is hydrolyzed to afford compound (19).

Compound (5), which can be synthesized in the reaction scheme 1, is subjected to Suzuki coupling reaction with

[Reaction Scheme 5]

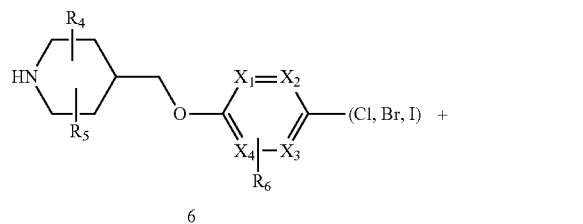

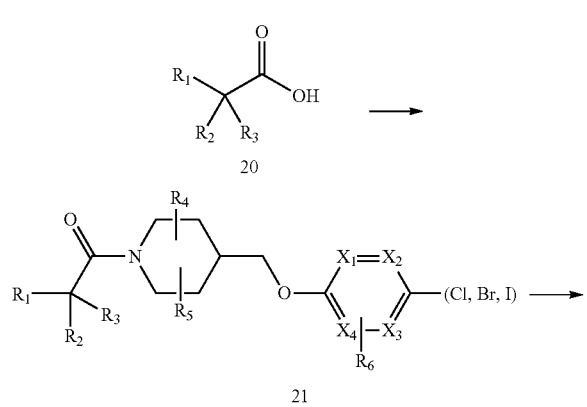

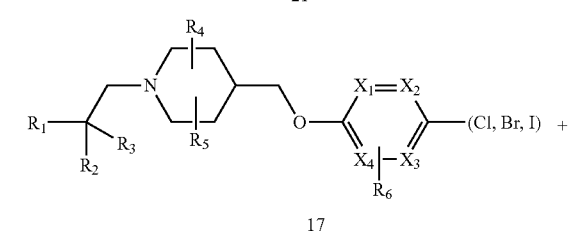

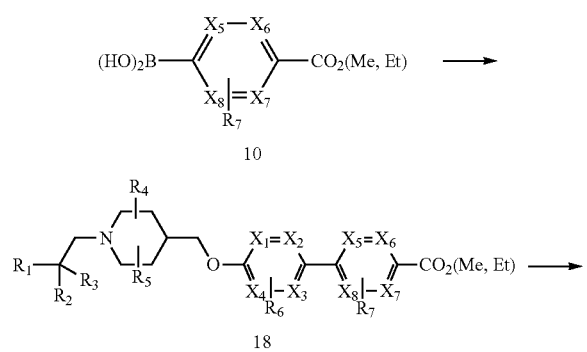

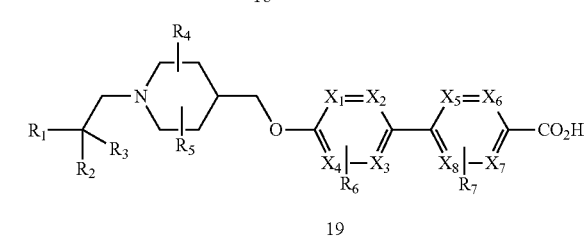

Compound (6) prepared in Reaction Scheme 1 is reacted with compound (20) to form an amide bond, thereby to afford compound (21). Then, compound (21) is reduced to afford compound (17). Compound (17) is subjected to Suzuki coupling reaction with boronic acid compound (10) to afford compound (18), which is hydrolyzed to afford compound (19).

[Reaction Scheme 6]

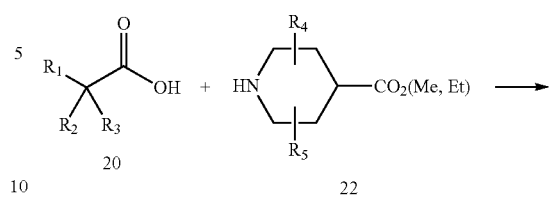

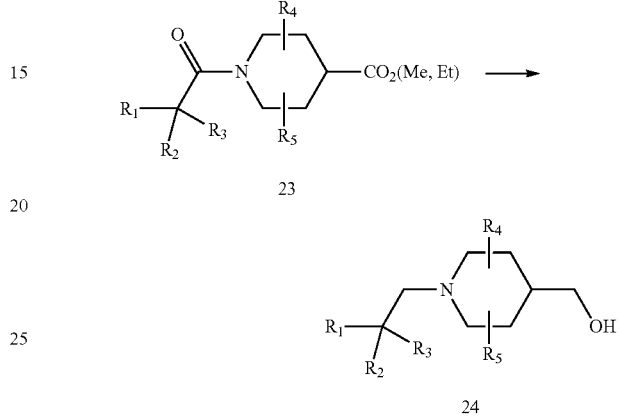

Compound (20) is reacted with compound (22) to form an amide bond, and then subjected to reduction thereby to afford compound (24).

[Reaction Scheme 7]

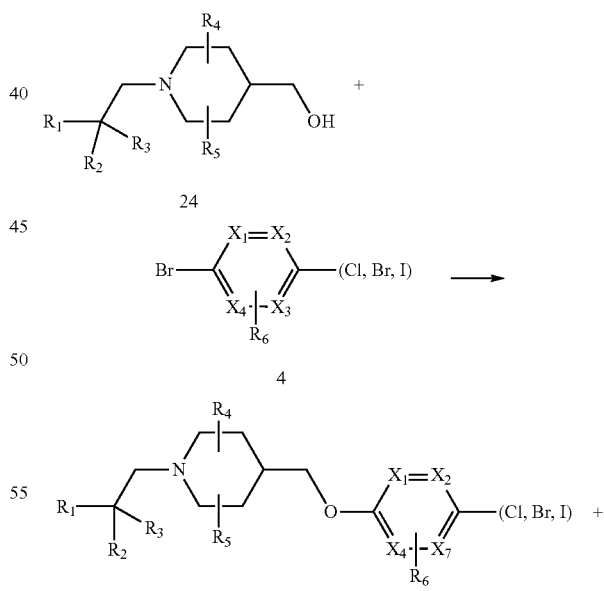

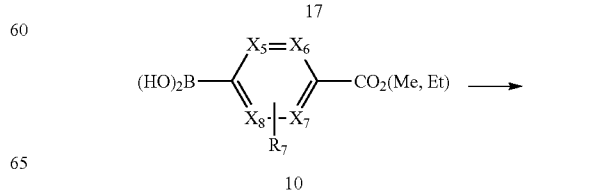

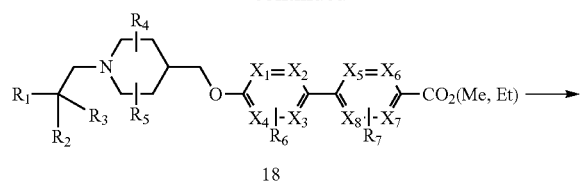

18

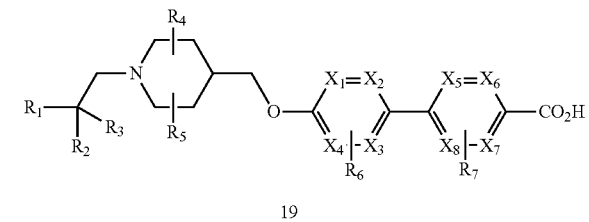

19

Compound (24) prepared in Reaction Scheme 6 is subjected to substitution reaction with compound (4) to afford compound (17). Compound (17) is subjected to Suzuki coupling reaction with boronic acid compound (10) to afford compound (18), which is hydrolyzed to afford compound (19).

[Reaction Scheme 8]

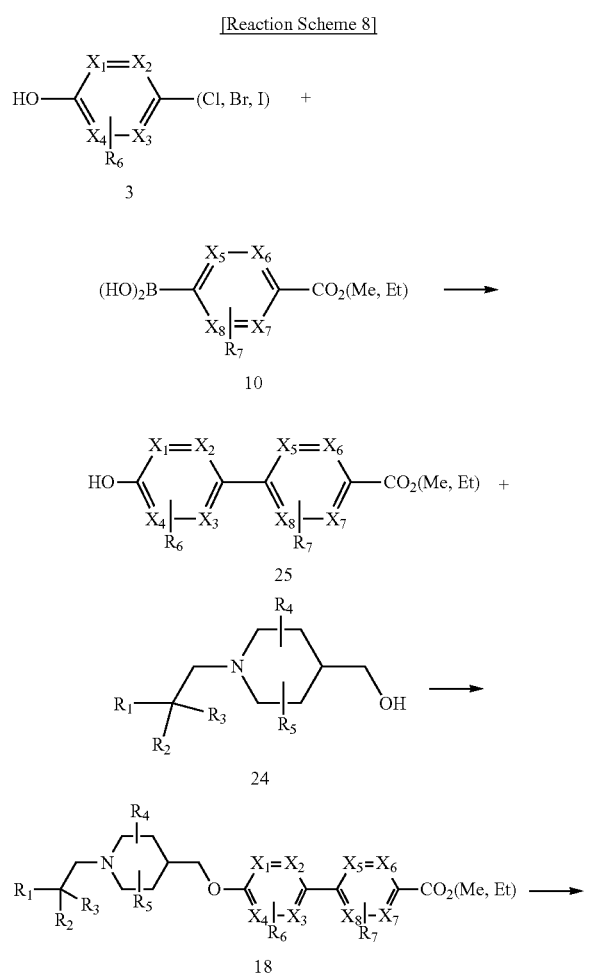

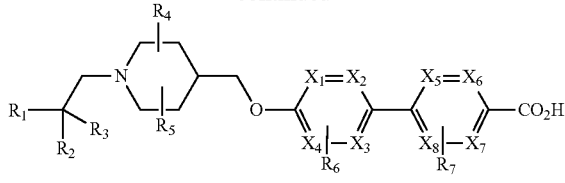

19

Compound (3) is subjected to Suzuki coupling reaction with boronic acid compound (10) to afford compound (25). Compound (25) is subjected to Mizunobu reaction with compound (24) to afford compound (18), which is hydrolyzed to afford compound (19).

[Reaction Scheme 9]

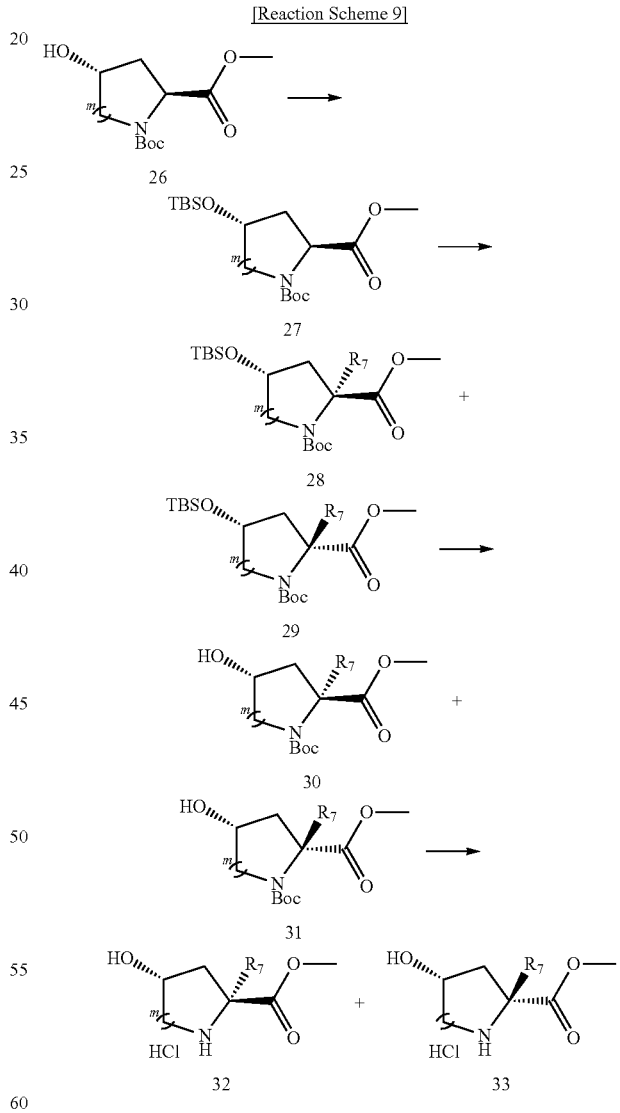

Into the hydroxyl group of compound (26), a protection group is introduced to form compound (27), to which R7 is introduced in the strong alkaline condition to afford compounds (28) and (29). The protection groups of hydroxyl group and secondary amine are removed to afford compounds (32) and (33).

[Reaction Scheme 10]
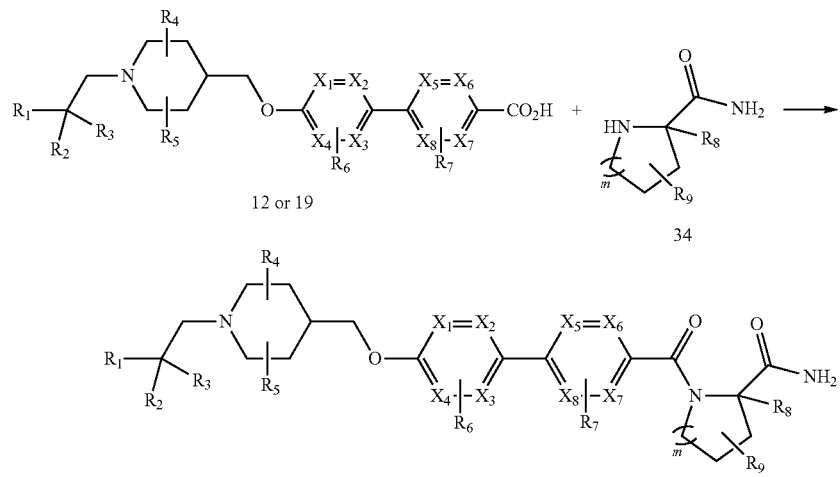
Formula 1
Compound (12) prepared in Reaction Scheme 2 or 3, or compound (19) prepared in Reaction Scheme 4, 5, 7 or 8 is reacted with compound (34) to form an amide bond thereby to afford the compound of formula 1. Through the above Reaction Scheme, compounds 1220, 1229, 1235, 1238, 1239, 1244, 1245, 1249, 1253, 1264, 1267, 1272, 1279, 1280, 1281, 1286, 1287, 1288, 1300, 1305, 1306, 1307, 1308, 1311, 1312, 1314, 1316, 1317, 1321, 1322 and 1323 can be synthesized.
[Reaction Scheme 11]
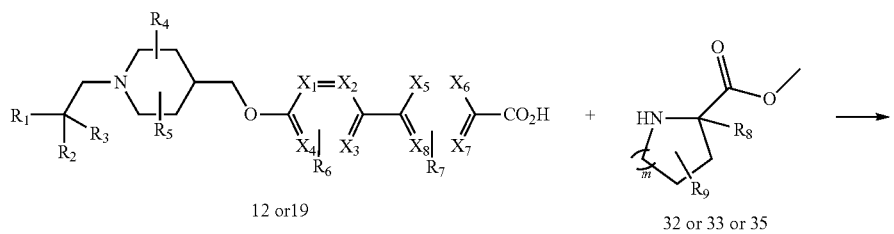
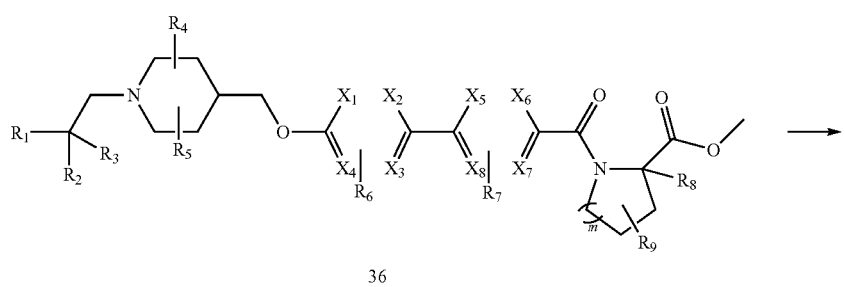
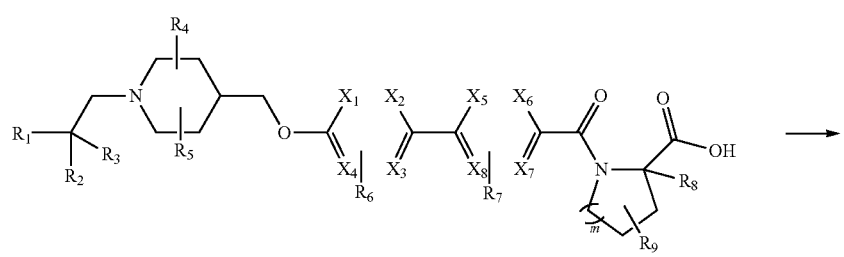

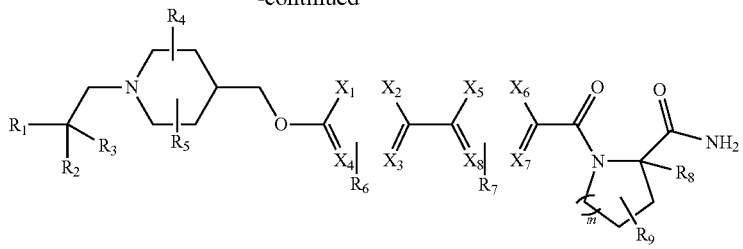

Formula 1

Compound (12) prepared in Reaction Scheme 2 or 3, or compound (19) prepared in Reaction Scheme 4, 5, 7 or 8 is reacted with compound (32), (33) or (35) prepared in Reaction Scheme 9 to form an amide bond thereby to afford compound (36). Through the hydrolysis reaction of compound (36), compound (37) is synthesized, and then made to form an amide bond thereby to afford the compound of formula 1. Through the above Reaction Scheme, compounds 1148, 1191, 1192, 1198, 1199, 1200, 1204, 1205, 1206, 1207, 1208, 1209, 1210, 1211, 1240, 1241, 1255, 1256, 1257, 1258, 1259, 1261, 1262, 1263, 1265, 1266, 1268, 1269, 1271, 1276, 1277, 1278, 1290, 1291, 1292, 1294, 1295, 1297, 1299, 1301, 1309, 1313, 1315, 1318, 1319, 1320, 1325, 1326, 1327, 1328 and 1329 can be synthesized.

Abbreviations

The following abbreviations and terms have the indicated meanings throughout:
Ac=acetyl
Boc=t-butoxycarbonyl
Bu=butyl
DAST=diethylaminosulfur trifluoride
DCM=MC=CH$_2$Cl$_2$=dichloromethane=methylene chloride
DIAD=diisopropyl azodicarboxylate
DIPEA=N,N-diisopropylethylamine
DME=dimethoxyethane
DMF=N,N-dimethylformamide
DMSO=dimethyl sulfoxide
dppp=1,3-Bis(diphenylphosphino)propane
EDC=1-ethyl-3-(3-dimethylaminopropyl) carbodiimide=EDCI
Et=ethyl
EtOAc=ethyl acetate=EA
EtOH=ethanol
HATU=1-[bis(dimethylamino)methylene]-1H-1,2,3-triazolo[4,5-b]pyridinium 3-oxide hexafluorophosphate
HOBt=1-hydroxybenzotriazole
HX=Hx=hexane
LAH=lithium aluminium hydride
m-CPBA=meta-chloroperoxybenzoic acid
Me=methyl
MeCN=methyl cyanide=acetonitrile=ACN
MeOH=methanol
MsCl=methanesulfonyl chloride
Pd(dbpf)Cl$_2$=[1,1'-Bis(di-tert-butylphosphino)ferrocene]dichloropalladium(II)
Pd(dppf)Cl$_2$=[1,1'-Bis(diphenylphosphino)ferrocene]dichloropalladium(II)
PPh$_3$=triphenylphosphine
t- or tert-=tertiary
TBAF=tetra-n-butylammonium fluoride
TEA=triethylamine
TFA=trifluoroacetic acid
THF=tetrahydrofuran

BEST MODE FOR CARRYING OUT THE INVENTION

The compound of formula 1 can be prepared by the method known from various references. Hereinafter, the preparing method for compound of formula 1 will be described in further detail with reaction scheme.

Synthesis of Intermediates

Synthesis of Intermediate 1: 4'-((1-((1-(trifluoromethyl)cyclobutyl)methyl)piperidin-4-yl)methoxy)biphenyl-4-carboxylic acid

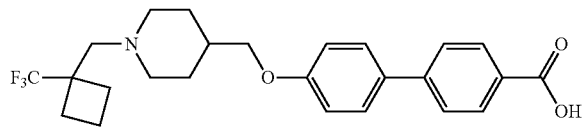

Step 1. Synthesis of tert-butyl 4-(hydroxymethyl)piperidin-1-carboxylate: 4-Piperidinemethanol (5.00 g, 43.41 mmol), (Boc)$_2$O (10.97 mL, 47.75 mmol) and TEA (7.22 mL, 52.09 mmol) were dissolved in DCM (50 mL) at room temperature. The solution was stirred at the same temperature for 1 h. To the reaction mixture, saturated NH$_4$Cl aqueous solution was added, and the mixture was extracted with dichloromethane. The organic layer was washed with water, dried with anhydrous MgSO$_4$, and then concentrated under reduced pressure. The obtained product was used without further purification (9.30 g, 99%, yellow oil).

Step 2. Synthesis of tert-butyl 4-((methylsulfonyloxy)methyl)piperidin-1-carboxylate: tert-Butyl 4-(hydroxymethyl)piperidin-1-carboxylate (9.30 g, 43.19 mmol), MsCl (3.70 mL, 47.51 mmol) and TEA (7.18 mL, 51.83 mmol) were dissolved in DCM (50 mL) at 0° C. The solution was stirred at room temperature for 2 h. To the reaction mixture, saturated NH$_4$Cl aqueous solution was added, and the mixture was extracted with ethyl acetate. The organic layer was washed with saturated NH$_4$Cl aqueous solution, dried with anhydrous MgSO$_4$, and then concentrated under reduced pressure. The concentrate was purified by column chromatography (SiO$_2$, ethyl acetate/hexane=5% to 10%), and concentrated to obtain the desired compound (11.80 g, 93%) as white solid.

Step 3. Synthesis of tert-butyl 4-((4-bromophenoxy)methyl)piperidin-1-carboxylate: tert-Butyl 4-((methylsulfonyloxy)methyl)piperidin-1-carboxylate (6.60 g, 22.49 mmol), 4-bromophenol (3.89 g, 22.49 mmol) and Cs$_2$CO$_3$ (10.99 g, 33.74 mmol) were dissolved in acetonitrile (50 mL) at 65° C. The solution was stirred at the same temperature for 5 h. To the reaction mixture, saturated NH$_4$Cl aqueous solution was added, and the mixture was extracted with ethyl acetate. The organic layer was washed with water, dried with anhydrous MgSO$_4$, and then concentrated under reduced pressure. The concentrate was purified by column chromatography (SiO$_2$, ethyl acetate/hexane=5% to 10%), and concentrated to obtain the desired compound (7.88 g, 94%) as yellow oil.

Step 4. Synthesis of 4-((4-bromophenoxy)methyl)piperidine hydrochloride: tert-Butyl 4-((4-bromophenoxy)methyl)piperidin-1-carboxylate (7.88 g, 21.28 mmol) and HCl (4.00M solution in 1,4-dioxane, 21.28 mL, 85.12 mmol) were dissolved in DCM (50 mL) at room temperature. The solution was stirred at the same temperature for 1 h. The precipitated solid was collected by filtration, and dried to obtain the desired compound (6.34 g, 97%) as white solid.

Step 5. Synthesis of (4-((4-bromophenoxy)methyl)piperidin-1-yl)(1-(trifluoromethyl)cyclobutyl)methanone: 4-((4-Bromophenoxy)methyl)piperidine hydrochloride (2.00 g, 6.52 mmol) was dissolved in CH$_2$Cl$_2$ (40 mL), and then EDC (2.50 g, 13.05 mmol), HOBt (1.76 g, 13.05 mmol), DIPEA (2.31 mL, 13.05 mmol), 1-(trifluoromethyl)cyclobutane carboxylic acid (1.09 g, 6.52 mmol) was added thereto. The mixture was stirred at the room temperature for 12 hours. From the reaction mixture, the solvent was removed under reduced pressure. To the obtained concentrate, water was added, and the mixture was extracted with dichloromethane. The organic layer was washed with saturated NaHCO$_3$ aqueous solution, dried with anhydrous MgSO$_4$, and then concentrated under reduced pressure. The concentrate was purified by silica gel column chromatography (EtOAc/hexane=1/4) to obtain white solid (2.10 g, 76%).

Step 6. Synthesis of 4-((4-bromophenoxy)methyl)-1-((1-(trifluoromethyl)cyclobutyl)methyl)piperidine: (4-((4-Bromophenoxy)methyl)piperidin-1-yl)(1-(trifluoromethyl)cyclobutyl)methanone (0.81 g, 1.93 mmol) was dissolved in THF (10 mL). 2.00 M Borane dimethyl sulfide complex solution (4.83 mL, 9.66 mmol) in THF was added thereto, and then stirred for 2 hours at room temperature. To the reaction mixture, water was added, and the mixture was extracted with EtOAc. The organic layer was washed with saturated NaHCO$_3$ aqueous solution, dried with anhydrous MgSO$_4$, and then concentrated under reduced pressure. The concentrate was purified by silica gel column chromatography (EtOAc/hexane=1/8) to obtain yellow solid (0.48 g, 61%).

Step 7. Synthesis of methyl 4'-((1-((1-(trifluoromethyl)cyclobutyl)methyl)piperidin-4-yl)methoxy)biphenyl-4-carboxylate: To 4-((4-bromophenoxy)methyl)-1-((1-(trifluoromethyl)cyclobutyl)methyl)piperidine (0.40 g, 0.98 mmol), 4-(methoxycarbonyl)phenylboronic acid (0.17 g, 0.98 mmol), Pd(dbpf)Cl$_2$ (0.03 g, 0.04 mmol) and Cs$_2$CO$_3$ (0.64 g, 1.96 mmol), 1,4-dioxane (4 mL)/water (1 mL) were added. With a microwave radiation, the mixture was heated at 120° C. for 20 minutes, and then cooled to room temperature. To the reaction mixture, water was added, and the mixture was extracted with dichloromethane. The organic layer was washed with saturated NaCl aqueous solution, dried with anhydrous MgSO$_4$, and then concentrated under reduced pressure. The concentrate was purified by column chromatography (SiO$_2$, 12 g cartridge; ethyl acetate/hexane=0% to 20%), and concentrated to obtain the desired compound (0.35 g, 77%) as pale yellow solid.

Step 8. Synthesis of Intermediate 1: Methyl 4'-((1-((1-(trifluoromethyl)cyclobutyl)methyl)piperidin-4-yl)methoxy)biphenyl-4-carboxylate (0.35 g, 0.75 mmol) and LiOH (0.15 g, 3.79 mmol) were mixed in THF (3 mL)/methanol (1 mL)/H$_2$O (1 mL) at room temperature. The mixture was added with LiOH.H$_2$O (excess amount) and stirred at 80° C. for 5 h. The reaction mixture was concentrated under reduced pressure. To the concentrate, water (20 mL) was added. After stirring, the precipitated solid was collected by filtration, and dried to obtain the desired compound (0.31 g, 91%) as white solid.

Synthesis of Intermediate 2: 2-fluoro-4'-((1-((1-(trifluoromethyl)cyclobutyl)methyl)piperidin-4-yl)methoxy)biphenyl-4-carboxylic acid

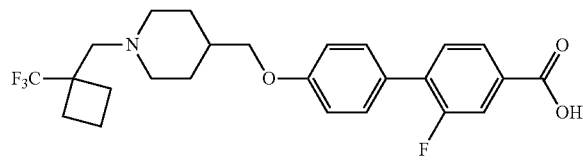 [SMILES: O=C(O)c1ccc(-c2ccc(OCC3CCN(CC4(C(F)(F)F)CCC4)CC3)cc2)c(F)c1]

Step 1. Synthesis of methyl 2-fluoro-4'-((1-((1-(trifluoromethyl)cyclobutyl)methyl)piperidin-4-yl)methoxy)biphenyl-4-carboxylate: To 4-((4-bromophenoxy)methyl)-1-((1-(trifluoromethyl)cyclobutyl)methyl)piperidine (Step 6 of Intermediate 1, 0.78 g, 1.92 mmol), 4-bromo-3-fluorobenzoic acid (0.45 g, 2.30 mmol), Pd(dppf)Cl$_2$ (0.07 g, 0.09 mmol) and Cs$_2$CO$_3$ (1.25 g, 3.84 mmol), DME (9 mL)/H$_2$O (3 mL) were added. With a microwave radiation, the mixture was heated at 110° C. for 20 minutes, and then cooled to room temperature. To the reaction mixture, water was added, and the mixture was extracted with EtOAc. The organic layer was washed with saturated NH$_4$Cl aqueous solution, dried with anhydrous MgSO$_4$, and then concentrated under reduced pressure. The concentrate was purified by column chromatography (SiO$_2$, EtOAc/hexane=0% to 100%), and concentrated to obtain the desired compound (0.54 g, 59%) as white solid.

Step 2. Synthesis of Intermediate 2: Methyl 2-fluoro-4'-((1-((1-(trifluoromethyl)cyclobutyl)methyl)piperidin-4-yl)methoxy)biphenyl-4-carboxylate (0.54 g, 1.13 mmol) and LiOH.H$_2$O (0.23 g, 5.68 mmol) were dissolved in THF (8 mL)/MeOH (8 mL)/H$_2$O (4 mL) at room temperature. The solution was stirred at the same temperature for 1 h. The precipitated solid was collected by filtration, and dried to obtain the desired compound (0.50 g, 94%) as white solid.

Synthesis of Intermediate 3: 4-(5-((1-((1-(Trifluoromethyl)cyclobutyl)methyl)piperidin-4-yl)methoxy)pyrazin-2-yl)benzoic acid

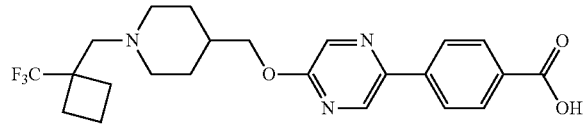

Step 1. Synthesis of ethyl 1-(1-(trifluoromethyl)cyclobutanecarbonyl)piperidin-4-carboxylate: 1-(Trifluoromethyl)cyclobutanecarboxylic acid (0.50 g, 2.97 mmol), ethyl piperidin-4-carboxylate (0.51 g, 3.27 mmol), EDC (1.14 g, 5.94 mmol), and HOBt (0.80 mg, 5.95 mmol) were dissolved in CH$_2$Cl$_2$ (10 mL). DIPEA (1.05 mL, 5.95 mmol) was added thereto. They are reacted at room temperature for 8 hours. To the reaction mixture, saturated NH$_4$Cl aqueous solution and EtOAc were added, And then, the organic layer was extracted from there. The extracted organic lay was dried with MgSO$_4$, and filtered. The obtained filtrate was purified by silica gel column chromatography (10-70% EtOAc/hexane) to obtain the desired compound (0.75 g, 82%) as colorless oil.

Step 2. Synthesis of (1-((1-(trifluoromethyl)cyclobutyl)methyl)piperidin-4-yl)methanol: Ethyl 1-(1-(trifluoromethyl)cyclobutanecarbonyl)piperidin-4-carboxylate (0.76 g, 2.47 mmol) was dissolved in anhydrous THF (20 mL). At 0° C., LAH (1.00 M in THF, 12.34 mL, 12.34 mmol) was added slowly thereto. They are reacted at 50° C. for 10 hours. At 0° C., MeOH was added thereto slowly thereby to make the reaction completed. To the reaction mixture, water and EtOAc were added, And then, the organic layer was extracted from there. The extracted organic lay was dried with MgSO$_4$, filtered, and dried sufficiently, thereby to obtain the desired compound (0.58 g, 94%) as colorless oil.

Step 3. Synthesis of 2-iodo-5-((1-((1-(trifluoromethyl)cyclobutyl)methyl)piperidin-4-yl)methoxy)pyrazine: (1-((1-(Trifluoromethyl)cyclobutyl)methyl)piperidin-4-yl)methanol (0.88 g, 3.50 mmol) was dissolved in THF (30 mL). At 0° C., NaH (0.13 g, 5.25 mmol) was added thereto. The mixture was stirred for 30 minutes. 2-bromo-5-iodopyrazine (1.09 g, 3.85 mmol) was added thereto, followed by stirring at 55° C. for 10 h. To the reaction mixture, water was added, and the mixture was extracted with EtOAc. The organic layer was washed with saturated brine aqueous solution, dried with anhydrous MgSO$_4$, and then concentrated under reduced pressure. The obtained product was used without further purification. (1.40 g, 87%, colorless oil).

Step 4. Synthesis of methyl 4-(5-((1-((1-(trifluoromethyl)cyclobutyl)methyl)piperidin-4-yl)methoxy)pyrazin-2-yl)benzoate: To 2-iodo-5-((1-((1-(trifluoromethyl)cyclobutyl)methyl)piperidin-4-yl)methoxy)pyrazine (0.35 g, 0.77 mmol), 4-(methoxycarbonyl)phenylboronic acid (0.15 g, 0.85 mmol), Pd(dbpf)Cl$_2$ (15 mg, 0.02 mmol) and Cs$_2$CO$_3$ (0.74 mg, 2.31 mmol), 1,4-dioxane (10 mL)/water (5 mL) were added. With a microwave radiation, the mixture was heated at 110° C. for 45 minutes, and then cooled to room temperature. To the reaction mixture, water was added, and the mixture was extracted with EtOAc. The organic layer was washed with saturated brine aqueous solution, dried with anhydrous MgSO$_4$, and then concentrated under reduced pressure. The concentrate was purified by column chromatography (SiO$_2$, 12 g cartridge; EtOAc/hexane=5% to 25%), and concentrated to obtain the desired compound (0.21 g, 59%) as white solid.

Step 5. Synthesis of Intermediate 3: Methyl 4-(5-((1-((1-(trifluoromethyl)cyclobutyl)methyl)piperidin-4-yl)methoxy)pyrazin-2-yl)benzoate (0.21 g, 0.45 mmol) and LiOH.H$_2$O (38 mg, 0.91 mmol) were dissolved in THF (10 mL)/water (5 mL) at room temperature. The solution was stirred at 60° C. for 4 h. The reaction mixture was concentrated under reduced pressure. To the concentrate, 1.00 M aqueous HCl solution (10 mL) was added and stirred. The precipitated solid was collected by filtration, and dried to obtain the desired compound (0.20 g, 98%) as white solid.

Synthesis of Intermediate 4: 2-Fluoro-4-(5-((1-((1-(trifluoromethyl)cyclobutyl)methyl)piperidin-4-yl)methoxy)pyrazin-2-yl)benzoic acid

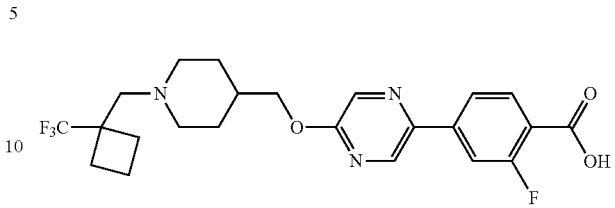

Step 1. Synthesis of ethyl 2-fluoro-4-(5-((1-((1-(trifluoromethyl)cyclobutyl)methyl)piperidin-4-yl)methoxy)pyrazin-2-yl)benzoate: To 2-iodo-5-((1-((1-(trifluoromethyl)cyclobutyl)methyl)piperidin-4-yl)methoxy)pyrazine (Step 3 of Intermediate 3, 0.35 g, 0.77 mmol), 4-(ethoxycarbonyl)-3-fluorophenylboronic acid (0.18 g, 0.85 mmol), Pd(dbpf)Cl$_2$ (15 mg, 0.02 mmol) and Cs$_2$CO$_3$ (0.74 g, 2.31 mmol), 1,4-dioxane (10 mL)/water (5 mL) were added. With a microwave radiation, the mixture was heated at 110° C. for 45 minutes, and then cooled to room temperature. To the reaction mixture, water was added, and the mixture was extracted with EtOAc. The organic layer was washed with saturated brine aqueous solution, dried with anhydrous MgSO$_4$, and then concentrated under reduced pressure. The concentrate was purified by column chromatography (SiO$_2$, 12 g cartridge; EtOAc/hexane=5% to 25%), and concentrated to obtain the desired compound (0.30 g, 79%) as white solid.

Step 2. Synthesis of Intermediate 4: Ethyl 2-fluoro-4-(5-((1-((1-(trifluoromethyl)cyclobutyl)methyl)piperidin-4-yl)methoxy)pyrazin-2-yl)benzoate (0.30 g, 0.61 mmol) and LiOH.H$_2$O (51 mg, 1.21 mmol) were dissolved in THF (10 mL)/water (5 mL) at room temperature. The solution was stirred at 60° C. for 4 h. The reaction mixture was concentrated under reduced pressure. To the concentrate, 1 M aqueous HCl solution (10 mL) was added and stirred. The precipitated solid was collected by filtration, and dried to obtain the desired compound (0.28 g, 99%) as white solid.

Synthesis of Intermediate 5: 3-Fluoro-4-(6-((1-((1-(trifluoromethyl)cyclobutyl)methyl)piperidin-4-yl)methoxy)pyridin-3-yl)benzoic acid

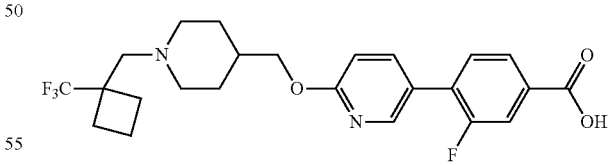

Step 1. tert-butyl 4-((5-bromopyridin-2-yloxy)methyl)piperidin-1-carboxylate: tert-Butyl 4-(hydroxymethyl)piperidin-1-carboxylate (Step 1 of Intermediate 1, 2.00 g, 9.29 mmol) and NaH (60%, 0.55 g, 13.93 mmol) were mixed in DMF (100 mL) at 0° C. The mixture was added with 2,5-dibromopyridine (2.42 g, 10.21 mmol) and stirred at 80° C. for 5 h. To the reaction mixture, water (200 mL) was added. The precipitated solid was collected by filtration, and dried to obtain the desired compound (3.00 g, 87%) as white solid.

Step 2. Synthesis of 5-bromo-2-(piperidin-4-ylmethoxy) pyridine hydrochloride: tert-Butyl 4-((5-bromopyridin-2-yloxy)methyl)piperidin-1-carboxylate (3.00 g, 8.08 mmol) and HCl (4.00 M solution in 1,4-dioxane, 10.10 mL, 40.40 mmol) were mixed in ethyl acetate (200 mL) at room temperature. The mixture was stirred at the same temperature for 12 hours. And then, the precipitated solid was collected by filtration, and dried to obtain the desired compound (2.00 g, 80%) as white solid.

Step 3. Synthesis of (4-((5-bromopyridin-2-yloxy) methyl)piperidin-1-yl)(1-(trifluoromethyl)cyclobutyl) methanone: 5-Bromo-2-(piperidin-4-ylmethoxy)pyridine hydrochloride (2.00 g, 6.50 mmol), 1-(trifluoromethyl)cyclobutanecarboxylic acid (2.18 g, 13.00 mmol), HATU (4.94 g, 13.00 mmol) and DIPEA (5.67 mL, 32.50 mmol) were mixed in DMF (100 mL) at room temperature. The mixture was stirred at the same temperature for 12 h. To the reaction mixture, water was added, and the mixture was extracted with ethyl acetate. The organic layer was washed with saturated NH$_4$Cl aqueous solution, dried with anhydrous MgSO$_4$, and then concentrated under reduced pressure. The concentrate was purified by column chromatography (SiO$_2$, 40 g cartridge; ethyl acetate/hexane=0% to 20%), and concentrated to obtain the desired compound (2.54 g, 92%) as yellow oil.

Step 4. Synthesis of 5-bromo-2-((1-((1-(trifluoromethyl)cyclobutyl)methyl)piperidin-4-yl)methoxy)pyridine: (4-((5-Bromopyridin-2-yloxy)methyl)piperidin-1-yl)(1-(trifluoromethyl)cyclobutyl)methanone (2.54 g, 6.03 mmol) and borane dimethyl sulfide (2.00 M solution in THF, 15.07 mL, 30.14 mmol) were mixed with tetrahydrofuran (150 mL) at 0° C. The mixture was stirred at 60° C. for 12 hours, and then cooled to 0° C. slowly. At the same temperature, MeOH was added thereto slowly thereby to make the reaction completed. To the reaction mixture, water was added, and the mixture was extracted with ethyl acetate. The organic layer was washed with water, dried with anhydrous MgSO$_4$, and then concentrated under reduced pressure. The concentrate was purified by column chromatography (SiO$_2$, 40 g cartridge; ethyl acetate/hexane=0% to 20%), and concentrated to obtain the desired compound (1.07 g, 43%) as colorless oil.

Step 5. Synthesis of ethyl 2-fluoro-4-(6-((1-((1-(trifluoromethyl)cyclobutyl)methyl)piperidin-4-yl)methoxy)pyridin-3-yl)benzoate: To 5-bromo-2-((1-((1-(trifluoromethyl)cyclobutyl)methyl)piperidin-4-yl)methoxy)pyridine (0.50 g, 1.22 mmol), 4-(ethoxycarbonyl)-3-fluorophenylboronic acid (0.26 g, 1.22 mmol), Pd(dbpf)Cl$_2$ (0.04 g, 0.06 mmol) and Cs$_2$CO$_3$ (0.80 g, 2.45 mmol), 1,4-dioxane (8 mL)/water (2 mL) were added. With a microwave radiation, the mixture was heated at 120° C. for 20 minutes, and then cooled to room temperature. To the reaction mixture, water was added, and the mixture was extracted with dichloromethane. The organic layer was washed with saturated NaCl aqueous solution, dried with anhydrous MgSO$_4$, and then concentrated under reduced pressure. The concentrate was purified by column chromatography (SiO$_2$, 12 g cartridge; ethyl acetate/hexane=0% to 20%), and concentrated to obtain the desired compound (0.43 g, 70%) as white solid.

Step 6. Synthesis of Intermediate 5: Ethyl 2-fluoro-4-(6-((1-((1-(trifluoromethyl)cyclobutyl)methyl)piperidin-4-yl)methoxy)pyridin-3-yl)benzoate (0.43 g, 0.87 mmol) and LiOH.H$_2$O (0.18 g, 4.34 mmol) were dissolved in tetrahydrofuran (9 mL)/methanol (3 mL)/water (3 mL) at room temperature. The solution was stirred at the same temperature for 12 hours. From the reaction mixture, the solvent was removed under reduced pressure. To the concentrate, 1N-aqueous HCl solution (10 mL) was added and stirred. The precipitated solid was collected by filtration, washed with water and dried to obtain the desired compound (0.35 g, 86%) as white solid.

Synthesis of Intermediate 6: 2'-Cyano-3-fluoro-4'-((1-(2-fluoro-2-methylpropyl)piperidin-4-yl)methoxy)biphenyl-4-carboxylic acid

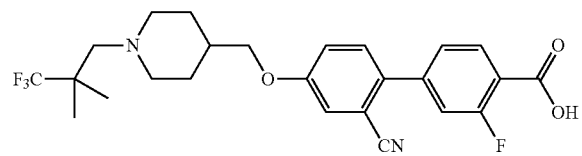

Step 1. Synthesis of tert-butyl 4-((4-bromo-3-cyanophenoxy)methyl)piperidin-1-carboxylate: tert-Butyl 4-((methyl sulfonyloxy)methyl)piperidin-1-carboxylate (Step 2 of Intermediate 1, 2.00 g, 6.81 mmol), 2-bromo-5-hydroxybenzonitrile (1.35 g, 6.87 mmol) and K$_2$CO$_3$ (1.88 g, 13.63 mmol) were dissolved in DMF (50 mL) at 80° C. The solution was stirred at the same temperature for 5 h. To the reaction mixture, water was added, and the mixture was extracted with EtOAc. The organic layer was washed with saturated NH$_4$Cl aqueous solution, dried with anhydrous MgSO$_4$, and then concentrated under reduced pressure. The concentrate was purified by column chromatography (SiO$_2$, 12 g cartridge; EtOAc/hexane=0% to 30%), and concentrated to obtain the desired compound (1.90 g, 70%) as white solid.

Step 2. Synthesis of 2-bromo-5-(piperidin-4-ylmethoxy) benzonitrile hydrochloride: tert-Butyl 4-((4-bromo-3-cyanophenoxy)methyl)piperidin-1-carboxylate (1.90 g, 4.80 mmol) and 4.00 M HCl/1,4-dioxane solution (6.00 mL, 24.03 mmol) were dissolved in CH$_2$Cl$_2$ (15 mL) at room temperature. The solution was stirred at the same temperature for 2 hours. And then, the precipitated solid was collected by filtration, and dried to obtain the desired compound (1.52 g, 95%) as white solid.

Step 3. Synthesis of 2-bromo-5-((1-(2-hydroxy-2-methylpropyl)piperidin-4-yl)methoxy)benzonitrile: To 2-bromo-5-(piperidin-4-ylmethoxy)benzonitrile hydrochloride (1.72 g, 5.18 mmol), 2,2-dimethyl oxirane (4.61 mL, 51.86 mmol) and K$_2$CO$_3$ (3.58 g, 25.93 mmol), EtOH (8 mL)/H$_2$O (2 mL) were added. With a microwave radiation, the mixture was heated at 110° C. for 20 minutes, and then cooled to room temperature. To the reaction mixture, water was added, and the mixture was extracted with EtOAc. The organic layer was washed with saturated brine aqueous solution, dried with anhydrous MgSO$_4$, and then concentrated under reduced pressure. The obtained product was used without further purification (1.70 g, 89%, white solid).

Step 4. Synthesis of 2-bromo-5-((1-(2-fluoro-2-methylpropyl)piperidin-4-yl)methoxy)benzonitrile: 2-Bromo-5-((1-(2-hydroxy-2-methylpropyl)piperidin-4-yl)methoxy) benzonitrile (1.70 g, 4.62 mmol) was dissolved in CH$_2$Cl$_2$ (20 mL). At 0° C., DAST (0.72 mL, 5.55 mmol) was added thereto, followed by stirring at the same temperature for 2 h. To the reaction mixture, saturated NaHCO$_3$ aqueous solution was added, and the mixture was extracted with EtOAc. The organic layer was washed with saturated NaHCO$_3$ aqueous solution, dried with anhydrous MgSO$_4$, and then concentrated under reduced pressure. The concentrate was purified by column chromatography (SiO$_2$, 12 g cartridge; EtOAc/ hexane=0% to 30%), and concentrated to obtain the desired compound (1.10 g, 64%) as white solid.

Step 5. Synthesis of ethyl 2'-cyano-3-fluoro-4'-((1-(2-fluoro-2-methylpropyl)piperidin-4-yl)methoxy)biphenyl-4-carboxylate: To 2-bromo-5-((1-(2-fluoro-2-methylpropyl) piperidin-4-yl)methoxy)benzonitrile (0.30 g, 0.81 mmol), 4-(ethoxycarbonyl)-3-fluorophenylboronic acid (0.17 g, 0.97 mmol), Pd(dppf)Cl$_2$ (0.03 g, 0.04 mmol) and Cs$_2$CO$_3$ (0.52 g, 1.62 mmol), DME (4 mL)/H$_2$O (1 mL) were added. With a microwave radiation, the mixture was heated at 110° C. for 20 minutes, and then cooled to room temperature. The reaction mixture was filtered through Celite pad thereby to remove solid. To the filtrate, water was added, and the mixture was extracted with EtOAc. The organic layer was washed with saturated NH$_4$Cl aqueous solution, dried with anhydrous MgSO$_4$, and then concentrated under reduced pressure. The concentrate was purified by column chromatography (SiO$_2$, 4 g cartridge; EtOAc/hexane=0% to 40%), and concentrated to obtain the desired compound (0.16 g, 43%) as white solid.

Step 6. Synthesis of Intermediate 6: Ethyl 2'-cyano-3-fluoro-4'-((1-(2-fluoro-2-methylpropyl)piperidin-4-yl) methoxy)biphenyl-4-carboxylate (0.16 g, 0.35 mmol) and LiOH.H$_2$O (0.07 g, 1.75 mmol) were dissolved in THF (8 mL)/MeOH (8 mL)/H$_2$O (2 mL) at room temperature. The solution was stirred at the same temperature for 12 h. The reaction mixture was concentrated under reduced pressure. To the concentrate, water (15 mL) was added. The precipitated solid was collected by filtration, and dried to obtain the desired compound (0.15 g, 93%) as white solid.

Synthesis of Intermediate 7: 3-Fluoro-4-(5-((1-((1-(trifluoromethyl)cyclobutyl)methyl)piperidin-4-yl) methoxy)pyrazin-2-yl)benzoic acid

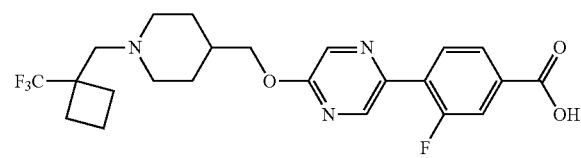 [SMILES: O=C(O)c1ccc(-c2ccc(OCC3CCN(CC4(C(F)(F)F)CCC4)CC3)nc2)c(F)c1]

Step 1. Synthesis of methyl 3-fluoro-4-(5-((1-((1-(trifluoromethyl)cyclobutyl)methyl)piperidin-4-yl)methoxy) pyrazin-2-yl)benzoate: To 2-iodo-5-((1-((1-(trifluoromethyl)cyclobutyl)methyl)piperidin-4-yl)methoxy)pyrazine (Step 3 of Intermediate 3, 0.35 g, 0.77 mmol), 2-fluoro-4-(methoxycarbonyl)phenylboronic acid (0.17 g, 0.85 mmol), Pd(dbpf)Cl$_2$ (15 mg, 0.02 mmol) and Cs$_2$CO$_3$ (0.75 g, 2.31 mmol), 1,4-dioxane (10 mL)/water (5 mL) were added. With a microwave radiation, the mixture was heated at 110° C. for 45 minutes, and then cooled to room temperature. To the reaction mixture, water was added, and the mixture was extracted with EtOAc. The organic layer was washed with saturated brine aqueous solution, dried with anhydrous MgSO$_4$, and then concentrated under reduced pressure. The concentrate was purified by column chromatography (SiO$_2$, 12 g cartridge; EtOAc/hexane=5% to 25%), and concentrated to obtain the desired compound (0.21 g, 57%) as white solid.

Step 2. Synthesis of Intermediate 7: Methyl 3-fluoro-4-(5-((1-((1-(trifluoromethyl)cyclobutyl)methyl)piperidin-4-yl)methoxy)pyrazin-2-yl)benzoate (0.21 g, 0.44 mmol) and LiOH.H$_2$O (37 mg, 0.87 mmol) were dissolved in THF (10 mL)/water (5 mL) at room temperature. The solution was stirred at 60° C. for 4 h. The reaction mixture was concentrated under reduced pressure. To the concentrate, 1.00 M aqueous HCl solution (10 mL) was added and stirred. The precipitated solid was collected by filtration, and dried to obtain the desired compound (0.20 g, 98%) as white solid.

Synthesis of Intermediate 8: 2-Fluoro-4-(5-((1-(2-fluoro-2-methylpropyl)piperidin-4-yl)methoxy)pyrimidin-2-yl)benzoic acid

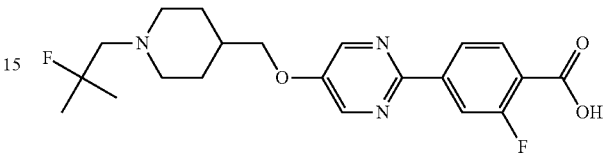

Step 1. Synthesis of tert-butyl 4-((2-chloropyrimidin-5-yloxy)methyl)piperidin-1-carboxylate: tert-Butyl 4-((methylsulfonyloxy)methyl)piperidin-1-carboxylate (Step 2 of Intermediate 1, 2.00 g, 6.82 mmol) was dissolved in DMF (80 mL). K$_2$CO$_3$ (3.33 g, 10.23 mmol) was added thereto, followed by stirring for 5 minutes. 2-Chloropyrimidin-5-ol (890 mg, 6.82 mmol) was added thereto, followed by stirring at 80° C. for 5 h. To the reaction mixture, water was added, and the mixture was extracted with EtOAc. The organic layer was washed with saturated NH$_4$Cl aqueous solution, dried with anhydrous MgSO$_4$, and then concentrated under reduced pressure. The concentrate was purified by silica gel column chromatography (EtOAc/hexane=30%~70%) to obtain white solid (2.10 g, 94%).

Step 2. Synthesis of 2-chloro-5-(piperidin-4-ylmethoxy) pyrimidine hydrochloride: tert-Butyl 4-((2-chloropyrimidin-5-yloxy)methyl)piperidin-1-carboxylate (2.10 g, 6.41 mmol) was dissolved in CH$_2$Cl$_2$ (50 mL). 4 M HCl in 1,4-dioxane (32.03 mL, 128.12 mmol) was added thereto, followed by stirring for 1 hour. The precipitated solid was collected by filtration, thereby to obtain white solid (1.50 g, 88%).

Step 3. Synthesis of 1-(4-((2-chloropyrimidin-5-yloxy) methyl)piperidin-1-yl)-2-methylpropane-2-ol: 2-Chloro-5-(piperidin-4-ylmethoxy)pyrimidine hydrochloride (1.50 g, 5.68 mmol), 2,2-dimethyloxirane (5.06 mL, 56.79 mmol), K$_2$CO$_3$ (392 mg, 2.84 mmol) were dissolved in EtOH (5 mL) and H$_2$O (5 mL). With a microwave radiation, the solution was heated at 110° C. for 15 minutes, and then cooled to room temperature. To the reaction mixture, water was added, and the mixture was extracted with EtOAc. The organic layer was washed with saturated brine aqueous solution, dried with anhydrous MgSO$_4$, and then concentrated under reduced pressure. The obtained white solid (1.70 g, 99%) was used without further purification.

Step 4. Synthesis of 2-chloro-5-((1-(2-fluoro-2-methylpropyl)piperidin-4-yl)methoxy)pyrimidine: 1-(4-((2-Chloropyrimidin-5-yloxy)methyl)piperidin-1-yl)-2-methylpropane-2-ol (1.10 g, 3.66 mmol) were mixed in dichloromethane (20 mL) at 0° C. The mixture was added with DAST (0.57 mL, 4.40 mmol) and stirred at room temperature for 3 h. To the reaction mixture, saturated NaHCO$_3$ aqueous solution was added, and the mixture was extracted with dichloromethane. The organic layer was washed with saturated NaHCO$_3$ aqueous solution, dried with anhydrous MgSO$_4$, and then concentrated under reduced pressure. The obtained product was used without further purification (0.90 g, 81%, white solid).

Step 5. Synthesis of ethyl 2-fluoro-4-(5-((1-(2-fluoro-2-methylpropyl)piperidin-4-yl)methoxy)pyrimidin-2-yl)benzoate: To 2-chloro-5-((1-(2-fluoro-2-methylpropyl)piperidin-4-yl)methoxy)pyrimidine (0.90 g, 2.98 mmol), 4-(ethoxycarbonyl)-3-fluorophenylboronic acid (0.69 g, 3.28 mmol), Pd(dbpf)Cl$_2$ (0.19 g, 0.29 mmol) and Cs$_2$CO$_3$ (1.94 g, 5.96 mmol), dimethoxyethane (8 mL)/water (2 mL) were added. With a microwave radiation, the mixture was heated at 120° C. for 20 minutes, and then cooled to room temperature. The reaction mixture was filtered through Celite pad thereby to remove solid. To the filtrate, saturated NH$_4$Cl aqueous solution was added, and the mixture was extracted with ethyl acetate. The organic layer was washed with saturated NaCl aqueous solution, dried with anhydrous MgSO$_4$, and then concentrated under reduced pressure. The concentrate was purified by column chromatography (SiO$_2$, 40 g cartridge; ethyl acetate/hexane=5% to 30%), and concentrated to obtain the desired compound (0.88 g, 68%) as white solid.

Step 6. Synthesis of Intermediate 8: Ethyl 2-fluoro-4-(5-((1-(2-fluoro-2-methylpropyl)piperidin-4-yl)methoxy)pyrimidin-2-yl)benzoate (0.88 g, 2.03 mmol) and LiOH.H$_2$O (0.42 g, 10.15 mmol) were mixed in THF/MeOH (1:1) (16 mL)/water (2 mL) at room temperature. The mixture was stirred at 80° C. for 5 h. The reaction mixture was concentrated under reduced pressure. To the concentrate, 2M-aqueous HCl solution (10 mL) and water (30 mL) were added. The precipitated solid was collected by filtration, and dried to obtain the desired compound (0.70 g, 85%) as white solid.

Synthesis of Intermediate 9: 3'-Cyano-3-fluoro-4'-((1-(2-fluoro-2-methylpropyl)piperidin-4-yl)methoxy)biphenyl-4-carboxylic acid

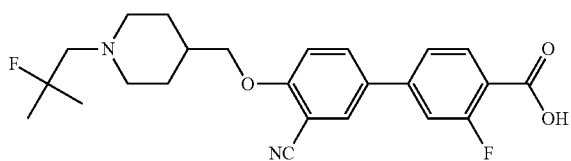 [SMILES: CC(C)(F)CN1CCC(COc2ccc(-c3ccc(C(=O)O)c(F)c3)cc2C#N)CC1]

Step 1. Synthesis of tert-butyl 4-((4-bromo-2-cyanophenoxy)methyl)piperidin-1-carboxylate: tert-Butyl 4-((methylsulfonyloxy)methyl)piperidin-1-carboxylate (Step 2 of Intermediate 1, 0.80 g, 2.73 mmol) was dissolved in ACN (80 mL). At room temperature, 5-bromo-2-hydroxybenzonitrile (0.54 g, 2.73 mmol) was added thereto, followed by stirring for 5 minutes. Cs$_2$CO$_3$ (1.33 g, 4.09 mmol) was added thereto, followed by stirring at 80° C. for 5 h. To the reaction mixture, water was added, and the mixture was extracted with EtOAc. The organic layer was washed with saturated brine aqueous solution, dried with anhydrous MgSO$_4$, and then concentrated under reduced pressure. The concentrate was purified by column chromatography (SiO$_2$, 12 g cartridge; EtOAc/hexane=30%~70%), and concentrated to obtain the desired compound (0.65 g, 60%) as white solid.

Step 2. Synthesis of 5-bromo-2-(piperidin-4-ylmethoxy)benzonitrile hydroxychloride: tert-Butyl 4-((4-bromo-2-cyanophenoxy)methyl)piperidin-1-carboxylate (0.65 mg, 1.66 mmol) was dissolved in CH$_2$Cl$_2$ (10 mL). At room temperature, 4 M HCl/1,4-dioxane solution (414 μL, 1.66 mmol) was added thereto, followed by stirring at the same temperature for 1 hour. And then, the precipitated solid was collected by filtration, and dried to obtain the desired compound (0.54 g, 98%) as white solid.

Step 3. Synthesis of 5-bromo-2-((1-(2-hydroxy-2-methylpropyl)piperidin-4-yl)methoxy)benzonitrile: To 5-bromo-2-(piperidin-4-ylmethoxy)benzonitrile hydroxychloride (0.54 g, 1.63 mmol), 2,2-dimethyl oxirane (1.45 mL, 16.3 mmol) and K$_2$CO$_3$ (0.11 g, 0.81 mmol), EtOH (5 mL)/H$_2$O (5 mL) were added. With a microwave radiation, the mixture was heated at 110° C. for 20 minutes, and then cooled to room temperature. To the reaction mixture, water was added, and the mixture was extracted with EtOAc. The organic layer was washed with saturated brine aqueous solution, dried with anhydrous MgSO$_4$, and then concentrated under reduced pressure. The obtained product, white solid (0.44 g, 73%) was used without further purification.

Step 4. Synthesis of 5-bromo-2-((1-(2-fluoro-2-methylpropyl)piperidin-4-yl)methoxy)benzonitrile: 5-Bromo-2-((1-(2-hydroxy-2-methylpropyl)piperidin-4-yl)methoxy)benzonitrile (0.44 g, 1.20 mmol) was dissolved in CH$_2$Cl$_2$ (10 mL). At 0° C., DAST (158.00 μL, 1.20 mmol) was added thereto, followed by stirring at room temperature for 1 h. To the reaction mixture, water was added, and the mixture was extracted with EtOAc. The organic layer was washed with saturated brine aqueous solution, dried with anhydrous MgSO$_4$, and then concentrated under reduced pressure. The concentrate was purified by column chromatography (SiO$_2$, 12 g cartridge; EtOAc/hexane=30%~70%), and concentrated to obtain the desired compound (0.25 g, 57%) as white solid.

Step 5. Synthesis of ethyl 3'-cyano-3-fluoro-4'-((1-(2-fluoro-2-methylpropyl)piperidin-4-yl)methoxy)biphenyl-4-carboxylate: To 5-bromo-2-((1-(2-fluoro-2-methylpropyl)piperidin-4-yl)methoxy)benzonitrile (0.25 g, 0.69 mmol), 4-(ethoxycarbonyl)-3-fluorophenylboronic acid (0.16 g, 0.76 mmol), Pd(dppf)Cl$_2$ (0.056 g, 0.07 mmol) and Cs$_2$CO$_3$ (0.44 g, 1.38 mmol), water (2 mL)/DME (6 mL) were added. With a microwave radiation, the mixture was heated at 110° C. for 15 minutes, and then cooled to room temperature. To the reaction mixture, water was added, and the mixture was extracted with EtOAc. The organic layer was washed with saturated brine, dried with anhydrous MgSO$_4$, and then concentrated under reduced pressure. The concentrate was purified by silica gel column chromatography (EtOAc/hexane=30%~70%) to obtain white solid (0.20 g, 65%).

Step 6. Synthesis of Intermediate 9: Ethyl 3'-cyano-3-fluoro-4'-((1-(2-fluoro-2-methylpropyl)piperidin-4-yl)methoxy)biphenyl-4-carboxylate (0.20 g, 0.45 mmol) was dissolved in THF (10 mL) and water (5 mL). At room temperature, LiOH.H$_2$O (0.09 g, 2.25 mmol) was added slowly thereto, followed by stirring for 1 hour. After the completion of the reaction, the reaction mixture was concentrated under reduced pressure. The precipitated solid was collected by filtration, and dried to obtain white solid (0.12 g, 62%).

Synthesis of Intermediate 10: 4'-((1-(2-Ethyl-2-fluorobutyl)piperidin-4-yl)methoxy)-2-fluorobiphenyl-4-carboxylic acid

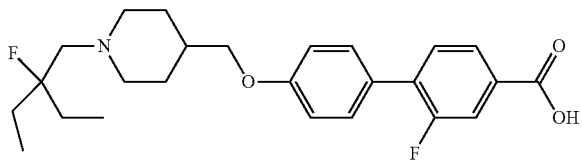 [SMILES: CCC(F)(CC)CN1CCC(COc2ccc(-c3ccc(C(=O)O)cc3F)cc2)CC1]

Step 1. Synthesis of 2,2-diethyloxirane: 3-Methylenepentane (24.63 mL, 201.99 mmol) and mCPBA (55.75 g, 323.19 mmol) were dissolved in DCM (300 mL) at 0° C. The solution was stirred at room temperature for 18 h. To the reaction mixture, $Na_2SO_3$ aqueous solution was added, and the mixture was extracted with ethyl acetate. The organic layer was washed with saturated NaCl aqueous solution, dried with anhydrous $MgSO_4$, and then concentrated under reduced pressure. The obtained product was used without further purification (20.00 g, 97%, colorless oil).

Step 2. Synthesis of 3-((4-((4-bromophenoxy)methyl)piperidin-1-yl)methyl)pentane-3-ol: To 4-((4-bromophenoxy)methyl)piperidine hydrochloride (Step 4 of Intermediate 1, 2.50 g, 8.15 mmol), 2,2-diethyloxirane (Step 1 of Intermediate 10, 4.08 g, 40.76 mmol) and $K_2CO_3$ (2.05 g, 16.30 mmol), ethanol (8 mL)/water (2 mL) were added. With a microwave radiation, the mixture was heated at 110° C. for 15 minutes, and then cooled to room temperature. To the reaction mixture, water was added, and the mixture was extracted with ethyl acetate. The organic layer was washed with saturated NaCl aqueous solution, dried with anhydrous $MgSO_4$, and then concentrated under reduced pressure. The obtained product was used without further purification (2.98 g, 98%, red solid).

Step 3. Synthesis of 4-((4-bromophenoxy)methyl)-1-(2-ethyl-2-fluorobutyl)piperidine: 3-((4-((4-Bromophenoxy)methyl)piperidin-1-yl)methyl)pentane-3-ol (2.98 g, 8.04 mmol) were mixed in dichloromethane (10 mL) at 0° C. The mixture was added with DAST (1.26 mL, 9.65 mmol) and stirred at room temperature for 3 h. To the reaction mixture, saturated $NaHCO_3$ aqueous solution was added, and the mixture was extracted with dichloromethane. The organic layer was washed with saturated $NaHCO_3$ aqueous solution, dried with anhydrous $MgSO_4$, and then concentrated under reduced pressure. The obtained product was used without further purification (2.70 g, 90%, red solid).

Step 4. Synthesis of methyl 4'-((1-(2-ethyl-2-fluorobutyl)piperidin-4-yl)methoxy)-2-fluorobiphenyl-4-carboxylate: To 4-((4-bromophenoxy)methyl)-1-(2-ethyl-2-fluorobutyl)piperidine (0.90 g, 2.41 mmol), 2-fluoro-4-(methoxycarbonyl)phenylboronic acid (0.57 g, 2.90 mmol), Pd(dbpf)Cl$_2$ (0.07 g, 0.12 mmol) and $Cs_2CO_3$ (1.57 g, 4.83 mmol), dimethoxyethane (8 mL)/water (2 mL) were added. With a microwave radiation, the mixture was heated at 120° C. for 20 minutes, and then cooled to room temperature. To the reaction mixture, water was added, and the mixture was extracted with ethyl acetate. The organic layer was washed with saturated NaCl aqueous solution, dried with anhydrous $MgSO_4$, and then concentrated under reduced pressure. The concentrate was purified by column chromatography ($SiO_2$, 40 g cartridge; ethyl acetate/hexane=5% to 70%), and concentrated to obtain the desired compound (0.31 g, 29%) as white solid.

Step 5. Synthesis of Intermediate 10: Methyl 4'-((1-(2-ethyl-2-fluorobutyl)piperidin-4-yl)methoxy)-2-fluorobiphenyl-4-carboxylate (0.31 g, 0.70 mmol) and LiOH.H$_2$O (0.14 g, 3.53 mmol) were mixed in THF/methanol (1:1) (16 mL)/water (2 mL) at room temperature. The mixture was stirred at the same temperature for 5 h. The reaction mixture was concentrated under reduced pressure. To the concentrate, 1M-aqueous HCl solution (15 mL) was added. The precipitated solid was collected by filtration, and dried to obtain the desired compound (0.20 g, 65%) as white solid.

Synthesis of Intermediate 11: 4'-((1-(2-Ethyl-2-fluorobutyl)piperidin-4-yl)methoxy)biphenyl-4-carboxylic acid

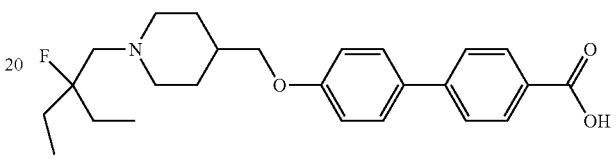

Step 1. Synthesis of methyl 4'-((1-(2-ethyl-2-fluorobutyl)piperidin-4-yl)methoxy)biphenyl-4-carboxylate: To 4-((4-bromophenoxy)methyl)-1-(2-methyl-2-fluorobutyl)piperidine (Step 3 of Intermediate 10, 0.90 g, 2.41 mmol), 4-(methoxycarbonyl)phenylboronic acid (0.522 g, 2.901 mmol), Pd(dbpf)Cl$_2$ (0.07 g, 0.12 mmol) and $Cs_2CO_3$ (1.57 g, 4.83 mmol), dimethoxyethane (8 mL)/water (2 mL) were added. With a microwave radiation, the mixture was heated at 120° C. for 20 minutes, and then cooled to room temperature. To the reaction mixture, water was added, and the mixture was extracted with ethyl acetate. The organic layer was washed with saturated NaCl aqueous solution, dried with anhydrous $MgSO_4$, and then concentrated under reduced pressure. The concentrate was purified by column chromatography ($SiO_2$, 40 g cartridge; ethyl acetate/hexane=5% to 70%), and concentrated to obtain the desired compound (0.21 g, 20%) as white solid.

Step 2. Synthesis of Intermediate 11: Methyl 4'-((1-(2-ethyl-2-fluorobutyl)piperidin-4-yl)methoxy)biphenyl-4-carboxylate (0.21 g, 0.50 mmol) and LiOH H$_2$O (0.10 g, 2.51 mmol) were mixed in THF/methanol (1:1) (16 mL)/water (2 mL) at room temperature. The mixture was stirred at the same temperature for 5 h. The reaction mixture was concentrated under reduced pressure. To the concentrate, 1M-aqueous HCl solution (15 mL) was added. The precipitated solid was collected by filtration, and dried to obtain the desired compound (0.20 g, 96%) as white solid.

Synthesis of Intermediate 12: 4'-((1-(2-Ethyl-2-fluorobutyl)piperidin-4-yl)methoxy)-3-fluorobiphenyl-4-carboxylic acid

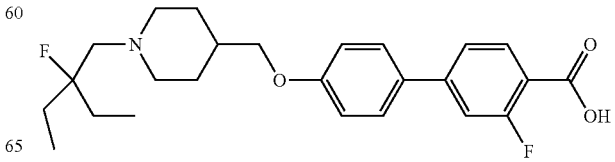

Step 1. Synthesis of methyl 4'-((1-(2-ethyl-2-fluorobutyl)piperidin-4-yl)methoxy)biphenyl-4-carboxylate: To 4-((4-bromophenoxy)methyl)-1-(2-methyl-2-fluorobutyl)piperidine (Step 3 of Intermediate 10, 0.90 g, 2.41 mmol), 4-(ethoxycarbonyl)-3-fluorophenylboronic acid (0.56 g, 2.65 mmol), Pd(dbpf)Cl$_2$ (0.08 g, 0.12 mmol) and Cs$_2$CO$_3$ (1.57 g, 4.83 mmol), dimethoxyethane (8 mL)/water (2 mL) were added. With a microwave radiation, the mixture was heated at 120° C. for 20 minutes, and then cooled to room temperature. To the reaction mixture, water was added, and the mixture was extracted with ethyl acetate. The organic layer was washed with saturated NaCl aqueous solution, dried with anhydrous MgSO$_4$, and then concentrated under reduced pressure. The concentrate was purified by column chromatography (SiO$_2$, 40 g cartridge; ethyl acetate/hexane=5% to 70%), and concentrated to obtain the desired compound (0.35 g, 31%) as white solid.

Step 2. Synthesis of Intermediate 12: Methyl 4'-((1-(2-ethyl-2-fluorobutyl)piperidin-4-yl)methoxy)biphenyl-4-carboxylate (0.35 g, 0.76 mmol) and LiOH.H$_2$O (0.16 g, 3.80 mmol) were mixed in THF/methanol (1:1) (16 mL)/water (2 mL) at room temperature. The mixture was stirred at the same temperature for 5 h. The reaction mixture was concentrated under reduced pressure. To the concentrate, 1M-aqueous HCl solution (15 mL) was added. The precipitated solid was collected by filtration, and dried to obtain the desired compound (0.26 g, 79%) as white solid.

Synthesis of Intermediate 13: 2'-Cyano-4'-((1-(2-ethyl-2-fluorobutyl)piperidin-4-yl)methoxy)-3-fluorobiphenyl-4-carboxylic acid

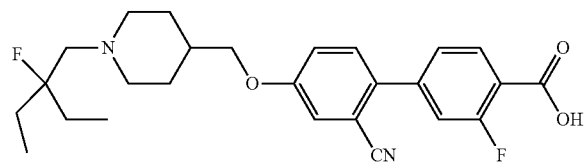

Step 1. Synthesis of 2-bromo-5-((1-(2-ethyl-2-hydroxybutyl)piperidin-4-yl)methoxy)benzonitrile: To 2-bromo-5-(piperidin-4-ylmethoxy)benzonitrile hydrochloride (Step 2 of Intermediate 6, 2.00 g, 6.03 mmol), 2,2-diethyloxirane (3.02 g, 30.15 mmol) and K$_2$CO$_3$ (1.25 g, 9.04 mmol), ethanol (8 mL)/water (2 mL) were added. With a microwave radiation, the mixture was heated at 110° C. for 20 minutes, and then cooled to room temperature. To the reaction mixture, water was added, and the mixture was extracted with ethyl acetate. The organic layer was washed with saturated NaCl aqueous solution, dried with anhydrous MgSO$_4$, and then concentrated under reduced pressure. The obtained product was used without further purification (2.20 g, 92%, yellow solid).

Step 2. Synthesis of 2-bromo-5-((1-(2-ethyl-2-fluorobutyl)piperidin-4-yl)methoxy)benzonitrile: 2-Bromo-5-((1-(2-ethyl-2-hydroxybutyl)piperidin-4-yl)methoxy)benzonitrile (2.20 g, 6.63 mmol) were mixed in dichloromethane (20 mL) at 0° C. The mixture was added with DAST (1.043 mL, 7.960 mmol) and stirred at room temperature for 4 h. To the reaction mixture, saturated NaHCO$_3$ aqueous solution was added, and the mixture was extracted with ethyl acetate. The organic layer was washed with saturated NaHCO$_3$ aqueous solution, dried with anhydrous MgSO$_4$, and then concentrated under reduced pressure. The concentrate was purified by column chromatography (SiO$_2$, 12 g cartridge; ethyl acetate/hexane=0% to 30%), and concentrated to obtain the desired compound (0.79 g, 30%) as colorless oil.

Step 3. Synthesis of ethyl 2'-cyano-4'-((1-(2-ethyl-2-fluorobutyl)piperidin-4-yl)methoxy)-3-fluorobiphenyl-4-carboxylate: To 2-bromo-5-((1-(2-ethyl-2-fluorobutyl)piperidin-4-yl)methoxy)benzonitrile (0.79 g, 1.98 mmol), 4-(ethoxycarbonyl)-3-fluorophenylboronic acid (0.50 g, 2.38 mmol), Pd(dppf)Cl$_2$ (0.07 g, 0.09 mmol) and Cs$_2$CO$_3$ (1.29 g, 3.97 mmol), 1,4-dioxane (8 mL)/water (2 mL) were added. With a microwave radiation, the mixture was heated at 120° C. for 20 minutes, and then cooled to room temperature. To the reaction mixture, water was added, and the mixture was extracted with ethyl acetate. The organic layer was washed with saturated NaCl aqueous solution, dried with anhydrous MgSO$_4$, and then concentrated under reduced pressure. The concentrate was purified by column chromatography (SiO$_2$, 12 g cartridge; ethyl acetate/hexane=0% to 30%), and concentrated to obtain the desired compound (0.73 g, 75%) as white solid.

Step 4. Synthesis of Intermediate 13: Ethyl 2'-cyano-4'-((1-(2-ethyl-2-fluorobutyl)piperidin-4-yl)methoxy)-3-fluorobiphenyl-4-carboxylate (0.75 g, 1.56 mmol) and LiOH.H$_2$O (0.32 g, 7.82 mmol) were mixed in THF/methanol (1:1) (16 mL)/water (2 mL) at room temperature. The mixture was stirred at the same temperature for 5 h. The reaction mixture was concentrated under reduced pressure. To the concentrate, 1M-aqueous HCl solution (10 mL) and water (50 mL) were added. The precipitated solid was collected by filtration, and dried to obtain the desired compound (0.71 g, 99%) as white solid.

Synthesis of Intermediate 14: 4-(5-((1-(2-Ethyl-2-fluorobutyl)piperidin-4-yl)methoxy)pyrimidin-2-yl)-2-fluorobenzoic acid

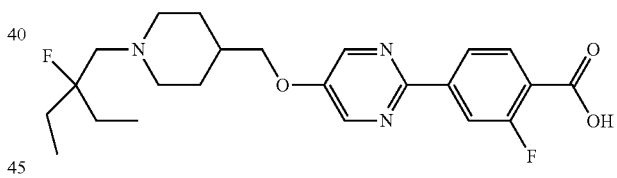

Step 1. Synthesis of 3-((4-((2-chloropyrimidin-5-yloxy)methyl)piperidin-1-yl)methoxy)pentane-3-ol: 2-Chloro-5-(piperidin-4-ylmethoxy)pyrimidine hydrochloride (Step 2 of Intermediate 8, 2.00 g, 7.57 mmol), 2,2-diethyloxirane (3.79 g, 37.85 mmol) and K$_2$CO$_3$ (2.09 g, 15.14 mmol) were mixed with ethanol (12 mL)/water (3 mL). With a microwave radiation, the mixture was heated at 110° C. for 20 minutes, and then cooled to room temperature thereby to make the reaction completed. To the reaction mixture, water was added, and the mixture was extracted with dichloromethane. The organic layer was washed with saturated NaCl aqueous solution, dried with anhydrous MgSO$_4$, filtered, and then concentrated under reduced pressure. The obtained product was used without further purification (2.40 g, 96%, yellow solid).

Step 2. Synthesis of 2-chloro-5-((1-(2-ethyl-2-fluorobutyl)piperidin-4-yl)methoxy)pyrimidine: 3-((4-((2-Chloropyrimidin-5-yloxy)methyl)piperidin-1-yl)methoxy)pentane-3-ol (2.40 g, 7.32 mmol) was dissolved in dichloromethane (20 mL) at 0° C. To the solution, DAST (1.15 mL, 8.78 mmol) was added thereto, followed by stirring at the room temperature for 4 hours. And then, to the reaction mixture, sodium bicarbonate was added at 0° C., followed by stirring for 20 minutes thereby to make the reaction completed. To the reaction mixture, water was added, and the mixture was extracted with ethyl acetate. The organic layer was washed with saturated NaHCO$_3$ aqueous solution, dried with anhydrous MgSO$_4$, filtered, and then concentrated under reduced pressure. The obtained product was used without further purification (1.71 g, 70%, yellow oil).

Step 3. Synthesis of ethyl 4-(5-((1-(2-ethyl-2-fluorobutyl)piperidin-4-yl)methoxy)pyrimidin-2-yl)-2-fluorobenzoate: 2-Chloro-5-((1-(2-ethyl-2-fluorobutyl)piperidin-4-yl)methoxy)pyrimidine (1.71 g, 5.18 mmol), 4-(ethoxycarbonyl)-3-fluorophenylboronic acid (1.64 g, 7.77 mmol), Pd(dppf)Cl$_2$ (0.42 g, 0.51 mmol) and Cs$_2$CO$_3$ (3.37 g, 10.36 mmol) were mixed with 1,4-dioxane (12 mL)/water (3 mL). With a microwave radiation, the mixture was heated at 110° C. for 20 minutes, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=0% to 50%), and concentrated to obtain the desired compound (1.29 g, 57%) as white solid.

Step 4. Synthesis of Intermediate 14: Ethyl 4-(5-((1-(2-ethyl-2-fluorobutyl)piperidin-4-yl)methoxy)pyrimidin-2-yl)-2-fluorobenzoate (1.29 g, 2.97 mmol) and LiOH (0.35 g, 14.87 mmol) were dissolved in tetrahydrofuran (8 mL)/methanol (8 mL)/water (2 mL) at room temperature. The solution was stirred at the same temperature for 5 hours. From the reaction mixture, the solvent was removed under reduced pressure. To the concentrate, 1M-aqueous HCl solution (10 mL) and water (60 mL) was added and stirred. The precipitated solid was collected by filtration, washed with water and dried to obtain the desired compound (1.24 g, 96%) as white solid.

Synthesis of Intermediate 15: 4'-((1-(2-Ethyl-2-fluorobutyl)piperidin-4-yl)methoxy)-3,3'-difluorobiphenyl-4-carboxylic acid

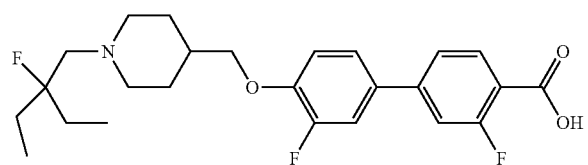 [SMILES: CCC(F)(CC)CN1CCC(COc2ccc(-c3ccc(C(=O)O)c(F)c3)cc2)CC1]

Step 1. Synthesis of tert-butyl 4-((4-bromo-3-fluorophenoxy)methyl)piperidin-1-carboxylate: tert-Butyl 4-((methylsulfonyloxy)methyl)piperidin-1-carboxylate (Step 2 of Intermediate 1, 3.00 g, 10.22 mmol), 4-bromo-3-fluorophenol (2.14 g, 11.24 mmol) and Cs$_2$CO$_3$ (4.33 g, 13.29 mmol) were mixed in acetonitrile (14 mL) at room temperature. The mixture was heated with reflux for 12 hours, and then cooled to room temperature. To the reaction mixture, water was added, and the mixture was extracted with ethyl acetate. The organic layer was washed with saturated NaCl aqueous solution, dried with anhydrous MgSO$_4$, filtered, and then concentrated under reduced pressure to obtain the desired compound, which was used without further purification (3.97 g, 100%, colorless oil).

Step 2. Synthesis of 4-((4-bromo-3-fluorophenoxy)methyl)piperidine hydrochloride: tert-Butyl 4-((4-bromo-3-fluorophenoxy)methyl)piperidin-1-carboxylate (3.95 g, 10.17 mmol) was dissolved in dichloromethane (12 mL) at room temperature. To the solution, HCl (4.00 M solution in 1,4-dioxane, 2.79 mL, 11.19 mmol) was added, followed by stirring at the same temperature for 1 hour. The precipitated solid was collected by filtration, washed with ethyl acetate and dried to obtain the desired compound (3.20 g, 96%) as white solid.

Step 3. Synthesis of 3-((4-((4-bromo-3-fluorophenoxy)methyl)piperidin-1-yl)methyl)pentan-3-ol: 4-((4-Bromo-3-fluorophenoxy)methyl)piperidine hydrochloride (2.00 g, 6.16 mmol), 2,2-diethyloxirane (3.08 g, 30.80 mmol) and K$_2$CO$_3$ (1.70 g, 12.32 mmol) were mixed with ethanol (6 mL)/water (3 mL). With a microwave radiation, the mixture was heated at 120° C. for 20 minutes, and then cooled to room temperature thereby to make the reaction completed. From the reaction mixture, the solvent was removed under reduced pressure. To the obtained concentrate, water was added, and the mixture was extracted with ethyl acetate. The organic layer was washed with saturated NaCl aqueous solution, dried with anhydrous MgSO$_4$, filtered, and then concentrated under reduced pressure. The obtained product was used without further purification (2.20 g, 92%, white solid).

Step 4. Synthesis of 4-((4-bromo-2-fluorophenoxy)methyl)-1-(2-ethyl-2-fluorobutyl)piperidine: 3-((4-((4-Bromo-3-fluorophenoxy)methyl)piperidin-1-yl)methyl)pentan-3-ol (2.20 g, 5.66 mmol) was dissolved in dichloromethane (10 mL) at 0° C. To the solution, DAST (1.18 g, 7.36 mmol) was added, followed by stirring at the room temperature for 3 hours. To the reaction mixture, saturated NaHCO$_3$ aqueous solution was added, and the mixture was extracted with dichloromethane. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=10% to 30%), and concentrated to obtain the desired compound (1.10 g, 49%) as colorless oil.

Step 5. Synthesis of methyl 4'-((1-(2-ethyl-2-fluorobutyl)piperidin-4-yl)methoxy)-3,3'-difluorobiphenyl-4-carboxylate: 4-((4-Bromo-2-fluorophenoxy)methyl)-1-(2-ethyl-2-fluorobutyl)piperidine (0.54 g, 1.38 mmol), 4-(ethoxycarbonyl)-3-fluorophenylboronic acid (0.35 g, 1.66 mmol), Pd(dbpf)Cl$_2$ (0.05 g, 0.06 mmol) and Na$_2$CO$_3$ (0.22 g, 2.07 mmol) were mixed with 1,2-dimethoxyethane (6 mL)/water (2 mL). With a microwave radiation, the mixture was heated at room temperature for 20 minutes, and then cooled to room temperature thereby to make the reaction completed. The reaction mixture was filtered through Celite pad thereby to remove solid. To the filtrate, saturated NaHCO$_3$ aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=15% to 25%), and concentrated to obtain the desired compound (0.39 g, 59%) as white solid.

Step 6. Synthesis of Intermediate 15: Methyl 4'-((1-(2-ethyl-2-fluorobutyl)piperidin-4-yl)methoxy)-3,3'-difluorobiphenyl-4-carboxylate (0.39 g, 0.84 mmol) and LiOH.H$_2$O (0.07 g, 1.68 mmol) were dissolved in tetrahydrofuran (6 mL)/methanol (3 mL)/water (2 mL) at room temperature. The solution was stirred at the same temperature for 8 hours. From the reaction mixture, the solvent was removed under reduced pressure. To the concentrate, a little HCl was added and stirred. The precipitated solid was collected by filtration, washed with ethyl acetate and dried to obtain the desired compound (0.36 g, 96%) as white solid.

Synthesis of Intermediate 16: 4'-((1-(2-Ethyl-2-fluorobutyl)piperidin-4-yl)methoxy)-2'-fluorobiphenyl-4-carboxylic acid

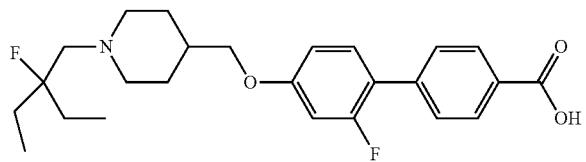 [SMILES: CCC(F)(CC)CN1CCC(COc2ccc(-c3ccc(C(=O)O)cc3)c(F)c2)CC1]

Step 1. Synthesis of tert-butyl 4-((4-bromo-2-fluorophenoxy)methyl)piperidine-1-carboxylate: tert-Butyl 4-((methyl sulfonyloxy)methyl)piperidine-1-carboxylate (Step 2 of Intermediate 1, 3.00 g, 10.22 mmol), 4-bromo-2-fluorophenol (2.14 g, 11.24 mmol) and Cs$_2$CO$_3$ (4.33 g, 13.29 mmol) were mixed in acetonitrile (14 mL) at room temperature. The mixture was heated with reflux for 12 hours, and then cooled to room temperature. To the reaction mixture, water was added, and the mixture was extracted with ethyl acetate. The organic layer was washed with saturated NaCl aqueous solution, dried with anhydrous MgSO$_4$, filtered, and then concentrated under reduced pressure to obtain the desired compound, which was used without further purification (3.95 g, 99%, colorless oil).

Step 2. Synthesis of 4-((4-bromo-2-fluorophenoxy)methyl)piperidine hydrochloride: tert-Butyl 4-((4-bromo-2-fluorophenoxy)methyl)piperidine-1-carboxylate (3.90 g, 10.04 mmol) was dissolved in dichloromethane (12 mL) at room temperature. To the solution, HCl (4.00 M solution in 1,4-dioxane, 2.76 mL, 11.04 mmol) was added, followed by stirring at the same temperature for 1 hour. The precipitated solid was collected by filtration, washed with ethyl acetate and dried to obtain the desired compound (3.20 g, 98%) as white solid.

Step 3. Synthesis of 3-((4-((4-bromo-2-fluorophenoxy)methyl)piperidin-1-yl)methyl)pentane-3-ol: 4-((4-Bromo-2-fluorophenoxy)methyl)piperidine hydrochloride (2.00 g, 6.16 mmol), 2,2-diethyloxirane (3.08 g, 30.80 mmol) and K$_2$CO$_3$ (1.70 g, 12.32 mmol) were mixed with ethanol (6 mL)/water (3 mL). With a microwave radiation, the mixture was heated at 120° C. for 20 minutes, and then cooled to room temperature thereby to make the reaction completed. From the reaction mixture, the solvent was removed under reduced pressure. To the obtained concentrate, water was added, and the mixture was extracted with ethyl acetate. The organic layer was washed with saturated NaCl aqueous solution, dried with anhydrous MgSO$_4$, filtered, and then concentrated under reduced pressure to obtain the desired compound, which was used without further purification (2.15 g, 89%, white solid).

Step 4. Synthesis of 4-((4-bromo-3-fluorophenoxy)methyl)-1-2-ethyl-2-fluorobutyl)piperidine: 3-((4-((4-Bromo-3-fluorophenoxy)methyl)piperidin-1-yl)methyl) pentane-3-ol (2.15 g, 5.53 mmol) was dissolved in dichloromethane (10 mL) at 0° C. To the solution, DAST (1.16 g, 7.19 mmol) was added, followed by stirring at the room temperature for 3 hours. To the reaction mixture, saturated NaHCO$_3$ aqueous solution was added, and the mixture was extracted with dichloromethane. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=0% to 30%), and concentrated to obtain the desired compound (0.95 g, 44%) as colorless oil.

Step 5. Synthesis of methyl 4'-((1-(2-ethyl-2-fluorobutyl)piperidin-4-yl)methoxy)-2'-fluorobiphenyl-4-carboxylate: 4-((4-Bromo-3-fluorophenoxy)methyl)-1-(2-ethyl-2-fluorobutyl)piperidine (0.38 g, 0.97 mmol), 4-(methoxycarbonyl)phenyl boronic acid (0.21 g, 1.16 mmol), Pd(dbpf)Cl$_2$ (0.04 g, 0.04 mmol) and Na$_2$CO$_3$ (0.15 g, 1.46 mmol) were mixed with 1,2-dimethoxyethane (6 mL)/water (2 mL). With a microwave radiation, the mixture was heated at 120° C. for 20 minutes, and then cooled to room temperature thereby to make the reaction completed. The reaction mixture was filtered through Celite pad thereby to remove solid. To the filtrate, saturated NaHCO$_3$ aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=15% to 25%), and concentrated to obtain the desired compound (0.28 g, 64%) as white solid.

Step 6. Synthesis of Intermediate 16: Methyl 4'-((1-(2-ethyl-2-fluorobutyl)piperidin-4-yl)methoxy)-2'-fluorobiphenyl-4-carboxylate (0.28 g, 0.62 mmol) and LiOH.H$_2$O (0.05 g, 1.25 mmol) were dissolved in tetrahydrofuran (6 mL)/methanol (3 mL)/water (2 mL) at room temperature. The solution was stirred at the same temperature for 8 hours. From the reaction mixture, the solvent was removed under reduced pressure. To the concentrate, a little HCl was added and stirred. The precipitated solid was collected by filtration, washed with ethyl acetate and dried to obtain the desired compound (0.26 g, 95%) as white solid.

Synthesis of Intermediate 17: 2-Fluoro-4-(6-((1-(3,3,3-trifluoro-2,2-dimethylpropyl)piperidin-4-yl)methoxy)pyridin-3-yl)benzoic acid

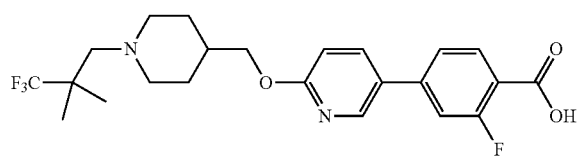 [SMILES: CC(C)(CN1CCC(COc2ccc(-c3ccc(C(=O)O)c(F)c3)cn2)CC1)C(F)(F)F]

Step 1. Synthesis of 1-(4-((5-bromopyridin-2-yloxy)methyl)piperidin-1-yl)-3,3,3-trifluoro-2,2-dimethylpropane-1-one: 5-Bromo-2-(piperidin-4-ylmethoxy)pyridine hydrochloride (Step 2 of Intermediate 5. 1.50 g, 4.87 mmol), HATU (3.70 g, 9.75 mmol) and DIPEA (1.72 mL, 9.75 mmol) were mixed in DMF (20 mL) at room temperature. The mixture was added with 3,3,3-trifluoro-2,2-dimethylpropanoic acid (1.52 g, 9.75 mmol) and stirred at 80° C. for 48 h. To the reaction mixture, water was added, and the mixture was extracted with ethyl acetate. The organic layer was washed with saturated NH$_4$Cl aqueous solution, dried with anhydrous MgSO$_4$, and then concentrated under reduced pressure. The concentrate was purified by column chromatography (SiO$_2$, 12 g cartridge; hexane/ethyl acetate=5% to 20%), and concentrated to obtain the desired compound (0.30 g, 15%) as yellow solid.

Step 2. Synthesis of 5-bromo-2-((1-(3,3,3-trifluoro-2,2-dimethylpropyl)piperidin-4-yl)methoxy)pyridine: 1-(4-((5-Bromopyridin-2-yloxy)methyl)piperidin-1-yl)-3,3,3-trifluoro-2,2-dimethylpropane-1-one (1.02 g, 2.49 mmol) were mixed in tetrahydrofuran (40 mL) at 0° C. The mixture was added with BH$_3$(SMe$_2$) (2.0 M solution in THF, 6.23 mL, 12.46 mmol) and stirred at 50° C. for 5 h. To the reaction mixture, water was added, and the mixture was extracted with ethyl acetate. The organic layer was washed with saturated NaHCO$_3$ aqueous solution, dried with anhydrous MgSO$_4$, and then concentrated under reduced pressure. The concentrate was purified by column chromatography (SiO$_2$, 12 g cartridge; hexane/ethyl acetate=5% to 35%), and concentrated to obtain the desired compound (0.44 g, 44%) as white solid.

Step 3. Synthesis of ethyl 2-fluoro-4-(6-((1-(3,3,3-trifluoro-2,2-dimethylpropyl)piperidin-4-yl)methoxy)pyridin-3-yl)benzoate: To 5-bromo-2-((1-(3,3,3-trifluoro-2,2-dimethylpropyl)piperidin-4-yl)methoxy)pyridine (0.44 g, 1.11 mmol), 4-(ethoxycarbonyl)-3-fluorophenylboronic acid (0.28 g, 1.33 mmol), Pd(dppf)Cl$_2$ (0.09 g, 0.11 mmol) and Cs$_2$CO$_3$ (0.72 g, 2.22 mmol), dimethoxyethane (12 mL)/water (3 mL) were added. With a microwave radiation, the mixture was heated at 110° C. for 20 minutes, and then cooled to room temperature. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO$_4$, and then concentrated under reduced pressure. The concentrate was purified by column chromatography (SiO$_2$, 12 g cartridge; hexane/ethyl acetate=5% to 40%), and concentrated to obtain the desired compound (0.38 g, 70%) as white solid.

Step 4. Synthesis of Intermediate 17: Ethyl 2-fluoro-4-(6-((1-(3,3,3-trifluoro-2,2-dimethylpropyl)piperidin-4-yl)methoxy)pyridin-3-yl)benzoate (0.38 g, 0.78 mmol) were mixed in tetrahydrofuran (6 mL)/MeOH (6 mL)/water (3 mL) at room temperature. The mixture was added with LiOH.H$_2$O (0.16 g, 3.93 mmol) and stirred at the same temperature for 1 h. The reaction mixture was concentrated under reduced pressure. To the concentrate, water (2 mL) and 2M-aqueous HCl solution (1 mL) were added. The precipitated solid was collected by filtration, and dried to obtain the desired compound (0.33 g, 92%) as white solid.

Synthesis of Intermediate 18: 2',3-Difluoro-4'-((1-(3,3,3-trifluoro-2,2-dimethylpropyl)piperidin-4-yl)methoxy)biphenyl-4-carboxylic acid

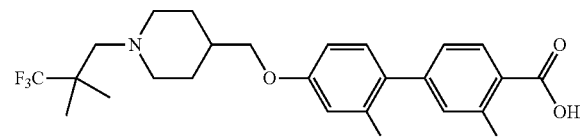

Step 1. 1-(4-((4-bromo-3-fluorophenoxy)methyl)piperidin-1-yl)-3,3,3-trifluoro-2,2-dimethylpropane-1-one: 4-((4-Bromo-3-fluorophenoxy)methyl)piperidine hydrochloride (Step 2 of Intermediate 16, 1.05 g, 3.23 mmol), 3,3,3-trifluoro-2,2-dimethylpropanoic acid (1.01 g, 6.46 mmol), HATU (2.46 g, 6.46 mmol) and DIPEA (1.14 mL, 6.46 mmol) were mixed in DMF (40 mL) at room temperature. The mixture was stirred at 80° C. for 5 h. To the reaction mixture, water was added, and the mixture was extracted with ethyl acetate. The organic layer was washed with saturated NH$_4$Cl aqueous solution, dried with anhydrous MgSO4, and then concentrated under reduced pressure. The concentrate was purified by column chromatography (SiO$_2$, 40 g cartridge; hexane/ethyl acetate=5% to 20%), and concentrated to obtain the desired compound (0.51 g, 37%) as white solid.

Step 2. Synthesis of 4-((4-bromo-3-fluorophenoxy)methyl)-1-(3,3,3-trifluoro-2,2-dimethylpropyl)piperidine: 1-(4-((4-Bromo-3-fluorophenoxy)methyl)piperidin-1-yl)-3,3,3-trifluoro-2,2-dimethylpropane-1-one (1.20 g, 2.81 mmol) were mixed in tetrahydrofuran (20 mL) at 0° C. The mixture was added with BH$_3$(SMe$_2$) (2.0 M solution in THF, 7.03 mL, 14.07 mmol) and stirred at 50° C. for 5 h. To the reaction mixture, water was added, and the mixture was extracted with ethyl acetate. The organic layer was washed with saturated NaCl aqueous solution, dried with anhydrous MgSO$_4$, and then concentrated under reduced pressure. The concentrate was purified by column chromatography (SiO$_2$, 12 g cartridge; hexane/ethyl acetate=0% to 10%), and concentrated to obtain the desired compound (0.81 g, 69%) as colorless oil.

Step 3. Synthesis of ethyl 2',3-difluoro-4'-((1-(3,3,3-trifluoro-2,2-dimethylpropyl)piperidin-4-yl)methoxy)biphenyl-4-carboxylate: 4-((4-Bromo-3-fluorophenoxy)methyl)-1-(3,3,3-trifluoro-2,2-dimethylpropyl)piperidine (0.81 g, 1.96 mmol), 4-(ethoxycarbonyl)-3-fluorophenylboronic acid (0.54 g, 2.55 mmol), Pd(dppf)Cl$_2$ (0.16 g, 0.19 mmol) and Cs$_2$CO$_3$ (0.96 g, 2.94 mmol) were mixed with DMF (10 mL). With a microwave radiation, the mixture was heated at 110° C. for 20 minutes, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=0% to 40%), and concentrated to obtain the desired compound (0.43 g, 43%) as white solid.

Step 4. Synthesis of Intermediate 18: Ethyl 2',3-difluoro-4'-((1-(3,3,3-trifluoro-2,2-dimethylpropyl)piperidin-4-yl)methoxy)biphenyl-4-carboxylate (0.43 g, 0.86 mmol) was dissolved in tetrahydrofuran (6 mL)/methanol (6 mL)/water (3 mL) at room temperature. To the solution, LiOH.H$_2$O (0.18 g, 4.30 mmol) was added, followed by stirring at the same temperature for 1 hour. From the reaction mixture, the solvent was removed under reduced pressure. To the concentrate, water (2 mL) and 1M-aqueous HCl solution (1 mL) were added and stirred. The precipitated solid was collected by filtration, washed with water and dried to obtain the desired compound (0.32 g, 78%) as white solid.

Synthesis of Intermediate 19: 2-Fluoro-4-(5-((1-(3,3,3-trifluoro-2,2-dimethylpropyl)piperidin-4-yl)methoxy)pyridin-2-yl)benzoic acid

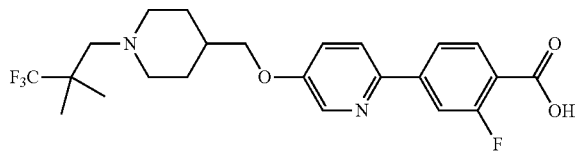

Step 1. ethyl 1-(3,3,3-trifluoro-2,2-dimethylpropanoyl)piperidin-4-carboxylate: 3,3,3-Trifluoro-2,2-dimethylpropanoic acid (1.00 g, 6.40 mmol), ethyl piperidin-4-carboxylate (2.01 g, 12.81 mmol), EDC (2.45 g, 12.81 mmol), HOBt (1.73 g, 12.81 mmol) and DIPEA (2.26 mL, 12.81 mmol) were dissolved in DMF (30 mL) at 80° C. The solution was stirred at the same temperature for 12 hours, and then cooled to room temperature thereby to make the reaction completed. To the reaction mixture, water was added, and the mixture was extracted with ethyl acetate. The organic layer was washed with saturated NH₄Cl aqueous solution, dried with anhydrous MgSO₄, filtered, and then concentrated under reduced pressure. The concentrate was purified by column chromatography (SiO₂, 12 g cartridge; ethyl acetate/hexane=0% to 30%), and concentrated to obtain the desired compound (1.10 g, 58%) as colorless oil.

Step 2. Synthesis of (1-(3,3,3-trifluoro-2,2-dimethylpropyl)piperidin-4-yl)methanol: Ethyl 1-(3,3,3-trifluoro-2,2-dimethylpropanoyl)piperidin-4-carboxylate (1.44 g, 4.87 mmol) was dissolved in tetrahydrofuran (10 mL). At 0° C., LAH (1.0 M solution in THF, 24.38 mL, 24.38 mmol) was added thereto, followed by stirring at the same temperature for 5 minutes. And the reaction mixture was further stirred at 50° C. for 12 hours, and then cooled to room temperature thereby to make the reaction completed. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 12 g cartridge; ethyl acetate/hexane=0% to 30%), and concentrated to obtain the desired compound (0.38 g, 33%) as colorless oil.

Step 3. Synthesis of methyl 2-fluoro-4-(5-hydroxypyridin-2-yl)benzoate: 6-Bromopyridin-3-ol (0.50 g, 2.87 mmol), 3-fluoro-4-(methoxycarbonyl)phenylboronic acid (0.74 g, 3.73 mmol), Pd(dppf)Cl₂ (0.23 g, 0.28 mmol) and Na₂CO₃ (0.45 g, 4.31 mmol) were mixed in tetrahydrofuran (12 mL)/water (6 mL) at room temperature. The mixture was stirred at 70° C. for 18 h. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO₄, and then concentrated under reduced pressure. The concentrate was purified by column chromatography (SiO₂, 12 g cartridge; hexane/ethyl acetate=5% to 70%), and concentrated to obtain the desired compound (0.32 g, 45%) as white solid.

Step 4. Synthesis of methyl 2-fluoro-4-(5-((1-(3,3,3-trifluoro-2,2-dimethylpropyl)piperidin-4-yl)methoxy)pyridin-2-yl)benzoate: Methyl 2-fluoro-4-(5-hydroxypyridin-2-yl)benzoate (0.20 g, 0.80 mmol), (1-(3,3,3-trifluoro-2,2-dimethylpropyl)piperidin-4-yl)methanol (0.38 g, 1.61 mmol), DIAD (0.27 mL, 1.78 mmol) and PPh₃ (0.44 g, 1.69 mmol) were mixed in tetrahydrofuran (10 mL). The mixture was stirred at 0° C. for 5 minutes, and then at room temperature further for 5 hours. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 12 g cartridge; ethyl acetate/hexane=0% to 20%), and concentrated to obtain the desired compound (0.30 g, 79%) as white solid.

Step 5. Synthesis of Intermediate 19: Methyl 2-fluoro-4-(5-((1-(3,3,3-trifluoro-2,2-dimethylpropyl)piperidin-4-yl)methoxy)pyridin-2-yl)benzoate (0.30 g, 0.64 mmol) was dissolved in tetrahydrofuran (3 mL)/methanol (3 mL)/water (1 mL) at room temperature. To the solution, LiOH.H₂O (0.13 g, 3.20 mmol) was added, followed by stirring at the same temperature for 1 hour. From the reaction mixture, the solvent was removed under reduced pressure. To the concentrate, water (2 mL) and 1M-aqueous HCl solution (1 mL) were added and stirred. The precipitated solid was collected by filtration, washed with water and dried to obtain the desired compound (0.25 g, 85%) as white solid.

Synthesis of Intermediate 20: 4-(6-((1-(2,2-Difluorobutyl)piperidin-4-yl)methoxy)pyridin-3-yl)-2-fluorobenzoic acid

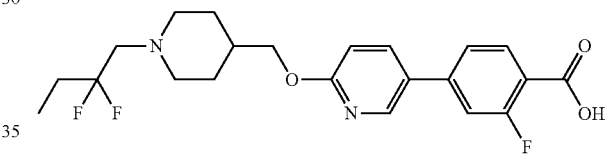

Step 1. Synthesis of 1-(4-((5-bromopyridin-2-yloxy)methyl)piperidin-1-yl)-2,2-difluorobutane-1-one: 5-Bromo-2-(piperidin-4-ylmethoxy)pyridine hydrochloride (Step 4 of Intermediate 5, 1.13 g, 9.10 mmol), HATU (3.46 g, 9.10 mmol) and DIPEA (1.61 mL, 9.10 mmol) were mixed in DMF (20 mL) at 80° C. The mixture was stirred at the same temperature for 14 hours, and then cooled to room temperature thereby to make the reaction completed. To the reaction mixture, water was added, and the mixture was extracted with ethyl acetate. The organic layer was washed with saturated NH₄Cl aqueous solution, dried with anhydrous MgSO₄, filtered, and then concentrated under reduced pressure. The concentrate was purified by column chromatography (SiO₂, 12 g cartridge; ethyl acetate/hexane=0% to 30%), and concentrated to obtain the desired compound (1.00 g, 58%) as colorless oil.

Step 2. Synthesis of 5-bromo-2-((1-(2,2-difluorobutyl)piperidin-4-yl)methoxy)pyridine: 1-(4-((5-Bromopyridin-2-yloxy)methyl)piperidin-1-yl)-2,2-difluorobutane-1-one (0.87 g, 2.32 mmol) was dissolved in tetrahydrofuran (20 mL). The solution was stirred at 0° C. for 5 minutes. BH₃(SMe₂) (5.80 mL, 11.61 mmol) was added thereto. And the reaction mixture was further stirred at 50° C. for 5 hours, and then cooled to room temperature thereby to make the reaction completed. To the reaction mixture, water was added, and the mixture was extracted with ethyl acetate. The organic layer was washed with saturated NaHCO₃ aqueous solution, dried with anhydrous MgSO₄, filtered, and concentrated under reduced pressure. The concentrate was purified by column chromatography (SiO₂, 12 g cartridge;

ethyl acetate/hexane=0% to 20%), and concentrated to obtain the desired compound (0.32 g, 37%) as colorless oil.

Step 3. Synthesis of ethyl 4-(6-((1-(2,2-difluorobutyl)piperidin-4-yl)methoxy)pyridin-3-yl)-2-fluorobenzoate: 5-Bromo-2-((1-(2,2-difluorobutyl)piperidin-4-yl)methoxy)pyridine (0.32 g, 0.88 mmol), 4-(ethoxycarbonyl)-3-fluorophenylboronic acid (0.24 g, 1.14 mmol), Pd(dppf)Cl$_2$ (0.07 g, 0.08 mmol) and Cs$_2$CO$_3$ (0.43 g, 1.32 mmol) were mixed with 1,2-dimethoxyethane (10 mL)/water (2.5 mL). With a microwave radiation, the mixture was heated at 110° C. for 20 minutes, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=0% to 45%), and concentrated to obtain the desired compound (0.21 g, 52%) as white solid.

Step 4. Synthesis of Intermediate 20: Ethyl 4-(6-((1-(2,2-difluorobutyl)piperidin-4-yl)methoxy)pyridin-3-yl)-2-fluorobenzoate (0.21 g, 0.46 mmol) were mixed in tetrahydrofuran (6 mL)/methanol (6 mL)/water (3 mL) at room temperature. The mixture was added with LiOH.H$_2$O (0.09 g, 2.33 mmol) and stirred at the same temperature for 1 hour. From the reaction mixture, the solvent was removed under reduced pressure. To the concentrate, water (2 mL) and 1M-aqueous HCl solution (1 mL) were added and stirred. The precipitated solid was collected by filtration, washed with water and dried to obtain the desired compound (0.17 g, 88%) as white solid.

Synthesis of Intermediate 21: 3-Fluoro-4'-((1-(2,2,3,3,3-pentafluoropropyl)piperidin-4-yl)methoxy)biphenyl-4-carboxylic acid

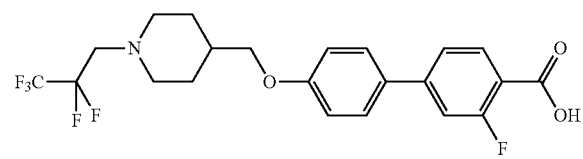

Step 1. Synthesis of 4-((4-bromophenoxy)methyl)-1-(2,2,3,3,3-pentafluoropropyl)piperidine: 2,2,3,3,3-Pentafluoropropyl trifluoromethanesulfonate (Step 4 of Intermediate 1, 0.50 g, 1.77 mmol), 4-((4-bromophenoxy)methyl)piperidine hydrochloride (0.54 g, 1.77 mmol) and triethylamine (0.49 mL, 3.54 mmol) were mixed with 2-propanol (15 mL). With a microwave radiation, the mixture was heated at 140° C. for 1 hour, and then cooled to room temperature thereby to make the reaction completed. From the reaction mixture, the solvent was removed under reduced pressure. The concentrate was purified by column chromatography (SiO$_2$, 40 g cartridge; ethyl acetate/hexane=5% to 10%), and concentrated to obtain the desired compound (0.58 g, 81%) as colorless oil.

Step 2. Synthesis of ethyl 3-fluoro-4'-((1-(2,2,3,3,3-pentafluoropropyl)piperidin-4-yl)methoxy)pyrenyl-4-carboxylate: 4-((4-Bromophenoxy)methyl)-1-(2,2,3,3,3-pentafluoropropyl)piperidine (0.80 g, 1.98 mmol), 4-(ethoxycarbonyl)-3-fluorophenylboronic acid (0.50 g, 2.38 mmol), Pd(dbpf)Cl$_2$ (0.03 g, 0.06 mmol) and cesium carbonate (1.93 g, 5.96 mmol) were mixed with 1,4-dioxane (10 mL)/water (5 mL). With a microwave radiation, the mixture was heated at 110° C. for 30 minutes, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 40 g cartridge; ethyl acetate/hexane=5% to 30%), and concentrated to obtain the desired compound (0.96 g, 98%) as white solid.

Step 3. Synthesis of Intermediate 21: Ethyl 3-fluoro-4'-((1-(2,2,3,3,3-pentafluoropropyl)piperidin-4-yl)methoxy)pyrenyl-4-carboxylate (0.96 g, 1.96 mmol) and LiOH.H$_2$O (0.16 g, 3.92 mmol) were dissolved in tetrahydrofuran (40 mL)/water (20 mL) at room temperature. The solution was stirred at 50° C. for 12 h. The reaction mixture was cooled to room temperature thereby to make the reaction completed. From the reaction mixture, the solvent was removed under reduced pressure. To the concentrate, 1N-aqueous HCl solution (20 mL) was added and stirred. The precipitated solid was collected by filtration, washed with water and dried to obtain the desired compound (0.34 g, 37%) as white solid.

Synthesis of Intermediate 22: 3'-Cyano-4'-((1-(2-ethyl-2-fluorobutyl)piperidin-4-yl)methoxy)-3-fluorobiphenyl-4-carboxylic acid

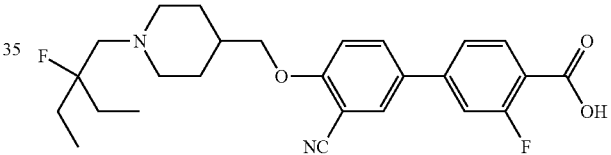

Step 1. Synthesis of 5-bromo-2-((1-(2-ethyl-2-hydroxybutyl)piperidin-4-yl)methoxy)benzonitrile: 5-Bromo-2-(piperidin-4-ylmethoxy)benzonitrile hydrochloride (Step 2 of Intermediate 9, 2.00 g, 6.03 mmol), 2,2-diethyloxirane (Step 1 of Intermediate 10, 3.02 g, 30.15 mmol) and K$_2$CO$_3$ (1.66 g, 12.06 mmol) were mixed with ethanol (12 mL)/water (3 mL). With a microwave radiation, the mixture was heated at 110° C. for 20 minutes, and then cooled to room temperature thereby to make the reaction completed. To the reaction mixture, water was added, and the mixture was extracted with dichloromethane. The organic layer was washed with saturated NaCl aqueous solution, dried with anhydrous MgSO$_4$, filtered, and then concentrated under reduced pressure. The obtained product was used without further purification (2.30 g, 96%, yellow solid).

Step 2. Synthesis of 5-bromo-2-((1-(2-ethyl-2-fluorobutyl)piperidin-4-yl)methoxy)benzonitrile: 5-Bromo-2-((1-(2-ethyl-2-hydroxybutyl)piperidin-4-yl)methoxy)benzonitrile (2.30 g, 5.81 mmol) was dissolved in dichloromethane (20 mL) at 0° C. To the solution, DAST (0.91 mL, 6.98 mmol) was added, followed by stirring at the room temperature for 4 hours. And then, to the reaction mixture, sodium bicarbonate was added at 0° C., followed by stirring for 20 minutes thereby to make the reaction completed. To the reaction mixture, water was added, and the mixture was extracted with dichloromethane. The organic layer was washed with saturated NaHCO$_3$ aqueous solution, dried with anhydrous MgSO$_4$, filtered, and then concentrated under reduced pressure. The obtained product was used without further purification (1.52 g, 65%, yellow solid).

Step 3. Synthesis of ethyl 3'-cyano-4'-((1-(2-ethyl-2-fluorobutyl)piperidin-4-yl)methoxy)-3-fluorobiphenyl-4-carboxylate: 5-Bromo-2-((1-(2-ethyl-2-fluorobutyl)piperidin-4-yl)methoxy)benzonitrile (1.52 g, 3.82 mmol), 4-(ethoxycarbonyl)-3-fluorophenylboronic acid (1.21 g, 5.73 mmol), Pd(dppf)Cl$_2$ (0.31 g, 0.38 mmol) and Cs$_2$CO$_3$ (2.49 g, 7.65 mmol) were mixed with 1,4-dioxane (12 mL)/water (3 mL). With a microwave radiation, the mixture was heated at 110° C. for 20 minutes, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=0% to 30%), and concentrated to obtain the desired compound (1.16 g, 62%) as white solid.

Step 4. Synthesis of Intermediate 22: Ethyl 3'-cyano-4'-((1-(2-ethyl-2-fluorobutyl)piperidin-4-yl)methoxy)-3-fluorobiphenyl-4-carboxylate (1.16 g, 2.39 mmol) and LiOH (0.28 g, 11.96 mmol) were dissolved in tetrahydrofuran (8 mL)/methanol (8 mL)/water (2 mL) at room temperature. The solution was stirred at the same temperature for 5 hours. From the reaction mixture, the solvent was removed under reduced pressure. To the concentrate, 1 M-aqueous HCl solution (10 mL) and water (60 mL) were added and stirred. The precipitated solid was collected by filtration, washed with water and dried to obtain the desired compound (1.03 g, 94%) as white solid.

Synthesis of Intermediate 23: 2-Fluoro-4-(5-((1-(2-fluoro-2-methylpropyl)piperidin-4-yl)methoxy)pyridin-2-yl)benzoic acid

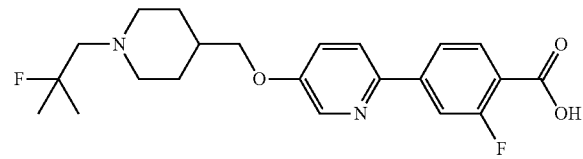

Step 1. Synthesis of tert-butyl 4-(hydroxymethyl)piperidin-1-carboxylate: Piperidin-4-ylmethanol (50.00 g, 434.14 mmol) was mixed in dichloromethane (300 mL) at room temperature. The mixture was added with TEA (72.61 mL, 520.96 mmol) and stirred for 10 minutes. Boc anhydride (104.22 g, 477.55 mmol) was added thereto, followed by stirring at the same temperature for 1 h. To the reaction mixture, water was added, and the mixture was extracted with dichloromethane. The organic layer was washed with saturated NH$_4$Cl aqueous solution, dried with anhydrous MgSO$_4$, and then concentrated under reduced pressure. The obtained product was used without further purification (93.00 g, 99%, white solid).

Step 2. Synthesis of tert-butyl 4-((methylsulfonyloxy)methyl)piperidin-1-carboxylate: tert-Butyl 4-(hydroxymethyl)piperidin-1-carboxylate (93.00 g, 431.97 mmol), MsCl (54.43 g, 475.17 mmol) and TEA (72.25 mL, 518.37 mmol) were mixed in dichloromethane (400 mL) at 0° C. The mixture was stirred at room temperature for 2 h. To the reaction mixture, water was added, and the mixture was extracted with dichloromethane. The organic layer was washed with saturated NH$_4$Cl aqueous solution, dried with anhydrous MgSO$_4$, and then concentrated under reduced pressure. To the concentrate, ethyl acetate (40 mL) and hexane (100 mL) were added. The precipitated solid was collected by filtration, and dried to obtain the desired compound (120.00 g, 94%) as white solid.

Step 3. Synthesis of tert-butyl 4-((6-bromopyridin-3-yloxy)methyl)piperidin-1-carboxylate: tert-Butyl 4-((methylsulfonyloxy)methyl)piperidin-1-carboxylate (12.43 g, 42.36 mmol), 6-bromopyridin-3-ol (8.10 g, 46.60 mmol) and Cs$_2$CO$_3$ (20.70 g, 63.55 mmol) were mixed in acetonitrile (250 mL) at room temperature. The mixture was heated with reflux for 5 hours, and then cooled to room temperature. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=0% to 40%), and concentrated to obtain the desired compound (12.00 g, 76%) as white solid.

Step 4. Synthesis of tert-butyl 4-((6-(4-(ethoxycarbonyl)-3-fluorophenyl)pyridin-3-yloxy)methyl)piperidin-1-carboxylate: tert-Butyl 4-((6-bromopyridin-3-yloxy)methyl)piperidin-1-carboxylate (9.88 g, 26.61 mmol), 4-(ethoxycarbonyl)-3-fluorophenylboronic acid (7.33 g, 34.59 mmol), Pd(dppf)Cl$_2$ (2.17 g, 2.66 mmol) and Cs$_2$CO$_3$ (17.34 g, 53.22 mmol) were mixed in 1,4-dioxane (240 mL)/water (60 mL) at 90° C. The mixture was stirred at the same temperature for 12 hours, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO$_4$, filtered, and then concentrated under reduced pressure. To the concentrate, ethyl acetate (10 mL) and hexane (30 mL) were added and stirred. The precipitated solid was collected by filtration, washed with hexane and dried to obtain the desired compound (9.50 g, 77%) as white solid.

Step 5. Synthesis of ethyl 2-fluoro-4-(5-(piperidin-4-ylmethoxy)pyridin-2-yl)benzoate hydrochloride: tert-Butyl 4-((6-bromopyridin-3-yloxy)methyl)piperidin-1-carboxylate (23.60 g, 51.47 mmol) was dissolved in dichloromethane (500 mL) at room temperature. To the solution, HCl (4.0 M solution in 1,4-dioxane, 51.47 mL, 205.88 mmol) was added, followed by stirring at the same temperature for 1 hour. The precipitated solid was collected by filtration, washed with hexane and dried to obtain the desired compound (20.00 g, 98%) as white solid.

Step 6. Synthesis of ethyl 2-fluoro-4-(5-((1-(2-hydroxy-2-methylpropyl)piperidin-4-yl)methoxy)pyridin-2-yl)benzoate: Ethyl 2-fluoro-4-(5-(piperidin-4-ylmethoxy)pyridin-2-yl)benzoate hydrochloride (20.00 g, 50.65 mmol), 2,2-dimethyl oxirane (45.65 mL, 506.49 mmol) and K$_2$CO$_3$ (3.50 g, 25.32 mmol) were mixed with ethanol (10 mL). With a microwave radiation, the mixture was heated at 110° C. for 15 minutes, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The obtained product was used without further purification (18.00 g, 82%, white solid).

Step 7. Synthesis of ethyl 2-fluoro-4-(5-((1-(2-fluoro-2-methylpropyl)piperidin-4-yl)methoxy)pyridin-2-yl)benzoate: Ethyl 2-fluoro-4-(5-((1-(2-hydroxy-2-methylpropyl)piperidin-4-yl)methoxy)pyridin-2-yl)benzoate (20.10 g, 46.68 mmol) was dissolved in dichloromethane (300 mL). The solution was stirred at 0° C. for 5 minutes. DAST (6.16 mL, 46.68 mmol) was added thereto, followed by stirring at room temperature further for 1 hour. To the reaction mixture, water was added, and the mixture was extracted with dichloromethane. The organic layer was washed with saturated NaHCO$_3$ aqueous solution, dried with anhydrous MgSO$_4$, filtered, and then concentrated under reduced pressure. The obtained product was used without further purification (20.00 g, 99%, brown solid).

Step 8. Synthesis of Intermediate 23: Ethyl 2-fluoro-4-(5-((1-(2-fluoro-2-methylpropyl)piperidin-4-yl)methoxy)pyridin-2-yl)benzoate (20.00 g, 46.24 mmol) and LiOH.H$_2$O (9.70 g, 231.21 mmol) were dissolved in tetrahydrofuran (100 mL)/methanol (100 mL)/water (50 mL) at room temperature. The solution was stirred at the same temperature for 1 hour. From the reaction mixture, the solvent was removed under reduced pressure. The precipitated solid was filtered, washed with water, and dried thereby to obtain the desired compound (18.00 g, 96%) as white solid.

Synthesis of Intermediate 24: 2-Fluoro-4-(5-((1-(2,2,3,3,3-pentafluoropropyl)piperidin-4-yl)methoxy)pyridin-2-yl)benzoic acid

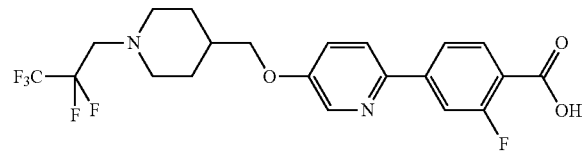 [SMILES: CCC(F)(F)CN1CCC(COc2ccc(-c3ccc(C(=O)O)c(F)c3)cn2)CC1]

Step 1. Synthesis of 2-bromo-5-(piperidin-4-ylmethoxy)pyridine hydrochloride: tert-Butyl 4-((6-bromopyridin-3-yloxy)methyl)piperidin-1-carboxylate (Step 3 of Intermediate 23, 1.10 g, 2.96 mmol) was dissolved in dichloromethane (50 mL). At 0° C., HCl (4.00 M solution in 1,4-dioxane, 2.22 mL, 8.88 mmol) was added thereto, followed by stirring at room temperature for 4 hours. From the reaction mixture, the solvent was removed under reduced pressure. The obtained product was used without further purification (0.85 g, 93%, white solid).

Step 2. Synthesis of 2-bromo-5-((1-(2,2,3,3,3-pentafluoropropyl)piperidin-4-yl)methoxy)pyridine: 2,2,3,3,3-Pentafluoropropyl trifluoromethanesulfonate (0.50 g, 1.77 mmol), 2-bromo-5-(piperidin-4-ylmethoxy)pyridine hydrochloride (0.60 g, 1.95 mmol) and triethylamine (0.35 g, 3.54 mmol) were mixed with 2-propanol (13 mL). With a microwave radiation, the mixture was heated at 140° C. for 1 hour, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=0% to 5%), and concentrated to obtain the desired compound (0.50 g, 70%) as colorless oil.

Step 3. Synthesis of methyl 2-fluoro-4-(5-((1-(2,2,3,3,3-pentafluoropropyl)piperidin-4-yl)methoxy)pyridin-2-yl)benzoate: 2-Bromo-5-((1-(2,2,3,3,3-pentafluoropropyl)piperidin-4-yl)methoxy)pyridine (0.50 g, 1.20 mmol), 3-fluoro-4-(methoxycarbonyl)phenylboronic acid (0.25 g, 1.48 mmol), Pd(dbpf)Cl$_2$ (24 mg, 0.03 mmol) and cesium carbonate (1.20 g, 3.72 mmol) were mixed with 1,4-dioxane (10 mL)/water (4 mL). With a microwave radiation, the mixture was heated at 110° C. for 30 minutes, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 40 g cartridge; ethyl acetate/hexane=5% to 40%), and concentrated to obtain the desired compound (0.30 g, 50%) as white solid.

Step 4. Synthesis of Intermediate 24: Methyl 2-fluoro-4-(5-((1-(2,2,3,3,3-pentafluoropropyl)piperidin-4-yl)methoxy)pyridin-2-yl)benzoate (0.30 g, 0.63 mmol) and LiOH.H$_2$O (53 mg, 1.25 mmol) were dissolved in tetrahydrofuran (30 mL)/water (10 mL) at room temperature. The solution was stirred at 50° C. for 10 hours, and then cooled to room temperature thereby to make the reaction completed. From the reaction mixture, the solvent was removed under reduced pressure. To the concentrate, 1M-aqueous HCl solution (5 mL) was added and stirred. The precipitated solid was collected by filtration, washed with water and dried to obtain the desired compound (0.27 g, 92%) as white solid.

Synthesis of Intermediate 25: (2S,4R)-Methyl 4-hydroxy-2-methylpyrrolidin-2-carboxylate HCl

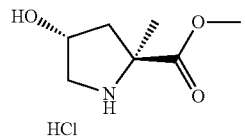

Step 1. Synthesis of (2S,4R)-1-tert-butyl 2-methyl 4-(tert-butyl dimethylsilyloxy)pyrrolidin-1,2-dicarboxylate: (2S,4R)-1-tert-Butyl 2-methyl 4-hydroxypyrrolidin-1,2-dicarboxylate (10.00 g, 40.77 mmol) and tert-butyl dimethyl silyl chloride (7.37 g, 48.93 mmol) were dissolved in DMF (100 mL) at room temperature. To the solution, imidazole (5.55 g, 81.54 mmol) was added, followed by stirring at the same temperature for 16 hours. To the reaction mixture, 0.2 N aqueous HCl solution was added, and the mixture was extracted with ethyl acetate. The organic layer was washed with saturated NaHCO$_3$ aqueous solution, dried with anhydrous MgSO$_4$, filtered, and then concentrated under reduced pressure to obtain the desired compound (14.60 g, 100%) as colorless oil. The obtained product was used without further purification Step 2. Synthesis of (2S,4R)-1-tert-butyl 2-methyl 4-(tert-butyldimethylsilyloxy)-2-methylpyrrolidin-1,2-dicarboxylate; (2R,4R)-1-tert-butyl 2-methyl 4-(tert-butyldimethylsilyloxy)-2-methylpyrrolidin-1,2-dicarboxylate:
Diisopropylamine (9.79 mL, 69.85 mmol) was dissolved in tetrahydrofuran (400 mL). The solution was cooled to 0° C., and n-butyl lithium (1.60 M hexane solution, 43.15 mL, 69.04 mmol) was added thereto slowly, followed by stirring at the same temperature for 10 minutes. The reaction mixture was cooled to −20° C., and 1,3-dimethyl-3,4,5,6-tetrahydro-2(1H)-pyrimidinone (16.70 mL, 138.07 mmol) was added thereto, followed by stirring at the same temperature further for 10 minutes. (2S,4R)-1-tert-Butyl 2-methyl 4-(tert-butyldimethylsilyloxy)pyrrolidin-1,2-dicarboxylate (14.60 g, 40.61 mmol) was dissolved in tetrahydrofuran (100 mL). This solution was added to the reaction mixture. The reaction mixture was heated to 0° C., and stirred for 1 hour. And then, The reaction mixture was cooled to −78° C. Iodomethane (3.79 mL, 60.91 mmol) was added thereto, followed by stirring at the same temperature for 4 hours. To the reaction mixture, saturated ammonium chloride aqueous solution was added, and the mixture was extracted with ethyl acetate. The organic layer was washed with water, dried with anhydrous MgSO$_4$, filtered, and then concentrated under reduced pressure. The concentrate was purified by column chromatography (SiO$_2$, 80 g cartridge; ethyl acetate/hexane=0% to 10%), and concentrated to obtain the desired compound (2S,4R)-1-tert-butyl 2-methyl 4-(tert-butyldimethylsilyloxy)-2-methylpyrrolidin-1,2-dicarboxylate (colorless oil, 6.21 g, 41%) and (2R,4R)-1-tert-butyl 2-methyl 4-(tert-butyldimethylsilyloxy)-2-methylpyrrolidin-1,2-dicarboxylate (colorless oil, 2.02 g, 13%).

$^1$H-NMR (400 MHz, CDCl$_3$) δ 4.40-4.36 (m, 1H), 3.75-3.64 (m, 4H), 3.44-3.33 (m, 1H), 2.32-2.24 (m, 1H), 1.94-1.90 (m, 1H), 1.63-1.61 (m, 3H), 1.44-1.40 (m, 9H), 0.88-0.87 (m, 9H), 0.06-0.05 (m, 6H).

$^1$H-NMR (400 MHz, CDCl$_3$) δ 4.39-4.32 (m, 1H), 3.78-3.64 (m, 4H), 3.33-3.23 (m, 1H), 2.23-2.03 (m, 2H), 1.56-1.55 (m, 3H), 1.44-1.40 (m, 9H), 0.87-0.85 (m, 9H), 0.06-0.04 (m, 6H).

Step 3. Synthesis of (2S,4R)-1-tert-butyl 2-methyl 4-hydroxy-2-methylpyrrolidin-1,2-dicarboxylate: (2S,4R)-1-tert-Butyl 2-methyl 4-(tert-butyldimethylsilyloxy)-2-methylpyrrolidin-1,2-dicarboxylate (6.21 g, 16.62 mmol) was dissolved in tetrahydrofuran (30 mL) at room temperature. To the solution, TBAF (1.00 M tetrahydrofuran solution, 21.61 mL, 21.61 mmol) was added, followed by stirring at the same temperature for 1 hour. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 40 g cartridge; ethyl acetate/hexane=50% to 100%), and concentrated to obtain the desired compound (4.21 g, 98%) as light yellow oil.

Step 4. Synthesis of Intermediate 25: (2S,4R)-1-tert-Butyl 2-methyl 4-hydroxy-2-methylpyrrolidin-1,2-dicarboxylate (4.21 g, 16.24 mmol) was dissolved in 1,4-dioxane (5 mL) at room temperature. To the solution, HCl (4.00 M 1,4-dioxane solution, 16.24 mL, 64.94 mmol) was added, followed by stirring at the same temperature for 1 hour. From the reaction mixture, the solvent was removed under reduced pressure. To the concentrate, diethylether (100 mL) was added and stirred. The precipitated solid was collected by filtration, washed with hexane and dried to obtain the desired compound (3.10 g, 98%) as white solid.

$^1$H-NMR (400 MHz, CD$_3$OD) δ 4.58-4.55 (m, 1H), 3.89 (s, 3H), 3.48-3.44 (m, 1H), 3.40-3.36 (m, 1H), 2.62-2.57 (m, 1H), 2.18-2.13 (m, 1H), 1.82 (s, 3H).

Synthesis of Intermediate 26: (2R,4R)-Methyl 4-hydroxy-2-methylpyrrolidin-2-carboxylate HCl

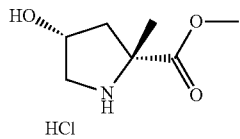

Step 1. Synthesis of (2R,4R)-1-tert-butyl 2-methyl 4-hydroxy-2-methylpyrrolidin-1,2-dicarboxylate: (2R,4R)-1-tert-Butyl 2-methyl 4-(tert-butyldimethylsilyloxy)-2-methylpyrrolidin-1,2-dicarboxylate (Step 2 of Intermediate 25, 2.02 g, 5.40 mmol) was dissolved in tetrahydrofuran (10 mL) at room temperature. To the solution, TBAF (1.00 M solution in THF, 7.03 mL, 7.03 mmol) was added, followed by stirring at the same temperature for 1 hour. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 40 g cartridge; ethyl acetate/hexane=50% to 100%), and concentrated to obtain the desired compound (1.36 g, 97%) as light yellow oil.

Step 2. Synthesis of Intermediate 26: (2R,4R)-1-tert-Butyl 2-methyl 4-hydroxy-2-methylpyrrolidin-1,2-dicarboxylate (1.36 g, 5.24 mmol) was dissolved in 1,4-dioxane (3 mL) at room temperature. To the solution, HCl (4.00 M solution in 1,4-dioxane, 9.17 mL, 36.71 mmol) was added, followed by stirring at the same temperature for 1 hour. From the reaction mixture, the solvent was removed under reduced pressure. To the concentrate, ethyl acetate (10 mL) and diethylether (50 mL) were added and stirred. The precipitated solid was collected by filtration, washed with hexane and dried to obtain the desired compound (0.90 g, 87%) as white solid.

$^1$H-NMR (400 MHz, CD$_3$OD) δ 4.56-4.54 (m, 1H), 3.87 (s, 3H), 3.61-3.57 (m, 1H), 3.40-3.36 (m, 1H), 2.67-2.62 (m, 1H), 2.23-2.18 (m, 1H), 1.73 (s, 3H).

Synthesis of Intermediate 27: 2-Fluoro-4-(5-((1-((1-(trifluoromethyl)cyclobutyl)methyl)piperidin-4-yl)methoxy)pyridin-2-yl)benzoic acid

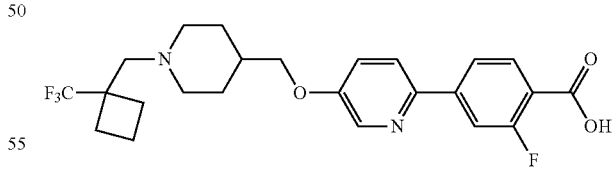

Step 1. Synthesis of methyl 2-fluoro-4-(5-((1-((1-(trifluoromethyl)cyclobutyl)methyl)piperidin-4-yl)methoxy)pyridin-2-yl)benzoate: (1-((1-(Trifluoromethyl)cyclobutyl)methyl)piperidin-4-yl)methanol (Step 2 of Intermediate 3, 0.50 g, 1.99 mmol), methyl 2-fluoro-4-(5-hydroxypyridin-2-yl)benzoate (Step 3 of Intermediate 19, 0.98 g, 3.97 mmol) and PPh$_3$ (1.09 g, 4.17 mmol) were mixed in tetrahydrofuran (30 mL). The mixture was stirred at 0° C. for 10 minutes. DIAD (0.68 mL, 4.37 mmol) was added thereto, followed by stirring at room temperature further for 5 hours. From the reaction mixture, the solvent was removed under reduced pressure. The concentrate was purified by column chromatography (SiO₂, 12 g cartridge; ethyl acetate/hexane=0% to 20%), and concentrated to obtain the desired compound (0.62 g, 64%) as white solid.

Step 2. Synthesis of Intermediate 27: Methyl 2-fluoro-4-(5-((1-((1-(trifluoromethyl)cyclobutyl)methyl)piperidin-4-yl)methoxy)pyridin-2-yl)benzoate (0.62 g, 1.29 mmol) and LiOH (0.15 g, 6.45 mmol) were mixed in tetrahydrofuran (9 mL)/methanol (3 mL)/water (3 mL). The mixture was stirred at room temperature for 20 minutes, and further stirred at 60° C. for 12 hours, and then cooled to room temperature thereby to make the reaction completed. From the reaction mixture, the solvent was removed under reduced pressure. To the concentrate, 1N-aqueous HCl solution was added and stirred. The precipitated solid was collected by filtration, washed with water and dried to obtain the desired compound (0.47 g, 78%) as white solid.

Synthesis of Intermediate 28: 4-(5-((1-(2,2,3,3,3-Pentafluoropropyl)piperidin-4-yl)methoxy)pyrazin-2-yl)benzoic acid

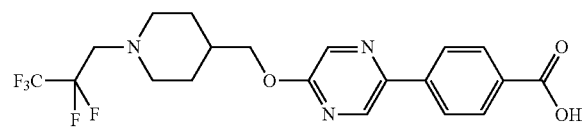

Step 1. Synthesis of tert-butyl 4-((5-bromopyrazin-2-yloxy)methyl)piperidin-1-carboxylate: tert-Butyl 4-(hydroxymethyl)piperidin-1-carboxylate (Step 1 of Intermediate 1, 10.00 g, 46.44 mmol), NaH (60%, 2.78 g, 69.67 mmol) and 2,5-dibromopyrazine (12.15 g, 51.09 mmol) were dissolved in N,N-dimethylformamide (200 mL). The solution was stirred at room temperature for 1 hour, and further stirred at 80° C. for 5 hours, and then cooled to room temperature thereby to make the reaction completed. To the reaction mixture, water (250 mL) was added and stirred. The precipitated solid was collected by filtration, washed with water and dried to obtain the desired compound (11.00 g, 63%) as yellow solid.

Step 2. Synthesis of 2-bromo-5-(piperidin-4-ylmethoxy) pyrazine hydrochloride: tert-Butyl 4-((5-bromopyrazin-2-yloxy)methyl)piperidin-1-carboxylate (11.00 g, 29.54 mmol) and HCl (4.00 M solution in 1,4-dioxane, 22.16 mL, 88.64 mmol) were dissolved in ethyl acetate (10 mL) at room temperature. The solution was stirred at the same temperature for 3 hours. The precipitated solid was collected by filtration, washed with ethyl acetate and dried to obtain 2-bromo-5-(piperidin-4-ylmethoxy)pyrazine hydroxychloride (8.00 g, 87%) as white solid.

Step 3. Synthesis of 2-bromo-5-((1-(2,2,3,3,3-pentafluoropropyl)piperidin-4-yl)methoxy)pyrazine: 2-Bromo-5-(piperidin-4-ylmethoxy)pyrazine hydroxychloride (1.00 g, 3.24 mmol), 2,2,3,3,3-pentafluoropropyl trifluoromethanesulfonate (1.00 g, 3.56 mmol) and TEA (0.54 mL, 3.88 mmol) were mixed with 2-propanol (15 mL). The mixture was stirred at room temperature for 20 minutes. With a microwave radiation, the mixture was heated at 140° C. for 1 hour, and then cooled to room temperature thereby to make the reaction completed. To the reaction mixture, water (20 mL) was added and stirred. The precipitated solid was collected by filtration, washed with water and dried to obtain the desired compound (0.80 g, 61%) as white solid.

Step 4. Synthesis of methyl4-(5-((1-(2,2,3,3,3-pentafluoropropyl)piperidin-4-yl)methoxy)pyrazin-2-yl)benzoate: 2-Bromo-5-((1-(2,2,3,3,3-pentafluoropropyl)piperidin-4-yl)methoxy)pyrazine (0.40 g, 0.99 mmol), 4-(methoxycarbonyl)phenylboronic acid (0.17 g, 0.99 mmol), Pd(dbpf)Cl₂ (0.03 g, 0.04 mmol) and Cs₂CO₃ (0.64 g, 1.97 mmol) were mixed with 1,4-dioxane (12 mL)/water (3 mL). With a microwave radiation, the mixture was heated at 120° C. for 20 minutes, and then cooled to room temperature thereby to make the reaction completed. To the reaction mixture, water was added, and the mixture was extracted with dichloromethane. The organic layer was washed with saturated NaCl aqueous solution, dried with anhydrous MgSO₄, filtered, and then concentrated under reduced pressure. The concentrate was purified by column chromatography (SiO₂, 12 g cartridge; ethyl acetate/hexane=0% to 20%), and concentrated to obtain the desired compound (0.32 g, 70%) as white solid.

Step 5. Synthesis of Intermediate 28: Methyl4-(5-((1-(2,2,3,3,3-pentafluoropropyl)piperidin-4-yl)methoxy)pyrazin-2-yl)benzoate (0.32 g, 0.69 mmol) and LiOH (0.08 g, 3.48 mmol) were mixed with tetrahydrofuran (9 mL)/methanol (3 mL)/water (3 mL). The mixture was stirred at room temperature for 20 minutes, and further stirred at 60° C. for 12 hours, and then cooled to room temperature thereby to make the reaction completed. From the reaction mixture, the solvent was removed under reduced pressure. To the concentrate, water (20 mL) was added and stirred. The precipitated solid was collected by filtration, washed with water and dried to obtain the desired compound (0.30 g, 96%) as white solid.

Synthesis of Intermediate 29: 4-(5-((1-(2-Ethyl-2-fluorobutyl)piperidin-4-yl)methoxy)pyridin-2-yl)-2-fluorobenzoic acid

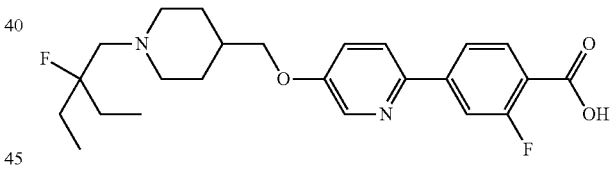

Step 1. Synthesis of 2-bromo-5-(pyridin-4-ylmethoxy) pyridine hydrochloride: tert-Butyl 4-((6-bromopyridin-3-yloxy)methyl)piperidin-1-carboxylate (Step 3 of Intermediate 23, 10.00 g, 26.86 mmol) was dissolved in dichloromethane (200 mL) at room temperature. To the solution, HCl (4.00 M solution in dioxane, 26.86 mL, 107.45 mmol) was added, followed by stirring at the same temperature for 5 hours. The precipitated solid was collected by filtration, washed with dichloromethane and dried to obtain the desired compound (8.10 g, 97%) as white solid.

Step 2. Synthesis of 3-((4-((6-bromopyridin-3-yloxy) methyl)piperidin-1-yl)methyl)pentane-3-ol: 2-Bromo-5-(pyridin-4-ylmethoxy)pyridine hydrochloride (3.00 g, 9.75 mmol), 2,2-diethyloxirane (Step 1 of Intermediate 10. 4.88 g, 48.76 mmol) and K₂CO₃ (2.69 g, 19.50 mmol) were mixed with ethanol (8 mL)/water (2 mL). With a microwave radiation, the mixture was heated at 110° C. for 20 minutes, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The obtained product was used without further purification (3.20 g, 88%, yellow solid).

Step 3. Synthesis of 2-bromo-5-((1-(2-ethyl-2-fluorobutyl)piperidin-4-yl)methoxy)pyridine: 3-((4-((6-Bromopyridin-3-yloxy)methyl)piperidin-1-yl)methyl)pentane-3-ol (3.20 g, 8.61 mmol) was dissolved in dichloromethane (10 mL). The solution was stirred at 0° C. for 10 minutes. DAST (1.46 mL, 11.20 mmol) was added thereto, followed by stirring at room temperature further for 5 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 40 g cartridge; ethyl acetate/hexane=0% to 30%), and concentrated to obtain the desired compound (1.10 g, 34%) as white solid.

Step 4, Synthesis of methyl 4-(5-((1-(2-ethyl-2-fluorobutyl)piperidin-4-yl)methoxy)pyridin-2-yl)-2-fluorobenzoate: 2-Bromo-5-((1-(2-ethyl-2-fluorobutyl)piperidin-4-yl) methoxy)pyridine (1.10 g, 2.94 mmol), 3-fluoro-4-(methoxycarbonyl)phenylboronic acid (0.70 g, 3.53 mmol), Pd(dppf)Cl$_2$ (0.12 g, 0.14 mmol) and Cs$_2$CO$_3$ (1.92 g, 5.89 mmol) were mixed with 1,4-dioxane (8 mL)/water (2 mL). With a microwave radiation, the mixture was heated at 120° C. for 20 minutes, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=0% to 50%), and concentrated to obtain the desired compound (0.95 g, 72%) as white solid.

Step 5. Synthesis of Intermediate 29: Methyl 4-(5-((1-(2-ethyl-2-fluorobutyl)piperidin-4-yl)methoxy)pyridin-2-yl)-2-fluorobenzoate (0.95 g, 2.12 mmol) and LiOH (0.25 g, 10.63 mmol) were dissolved in tetrahydrofuran (16 mL)/methanol (16 mL)/water (4 mL) at room temperature. The solution was stirred at the same temperature for 18 hours. From the reaction mixture, the solvent was removed under reduced pressure. To the concentrate, 1M-aqueous HCl solution (20 mL) and water (80 mL) were added and stirred. The precipitated solid was collected by filtration, washed with water and dried to obtain the desired compound (0.49 g, 54%) as white solid.

Synthesis of Intermediate 30: 3-Fluoro-4-(5-((1-((1-(trifluoromethyl)cyclobutyl)methyl)piperidin-4-yl) methoxy)pyridin-2-yl)benzoic acid

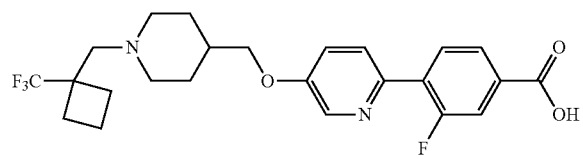

Step 1. Synthesis of methyl 3-fluoro-4-(5-hydroxypyridin-2-yl)benzoate: 6-Bromopyridin-3-ol (5.00 g, 28.73 mmol), 2-fluoro-4-(methoxycarbonyl)phenylboronic acid (6.82 g, 34.48 mmol), Pd(dbpf)Cl$_2$ (0.56 g, 0.86 mmol) and Cs$_2$CO$_3$ (27.91 g, 86.20 mmol) were mixed with 1,4-dioxane (10 mL)/water (5 mL). With a microwave radiation, the mixture was heated at 110° C. for 30 minutes, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 80 g cartridge; ethyl acetate/hexane=5% to 50%), and concentrated to obtain the desired compound (4.20 g, 59%) as white solid.

Step 2. Synthesis of methyl 3-fluoro-4-(5-((1-((1-(trifluoromethyl)cyclobutyl)methyl)piperidin-4-yl)methoxy)pyridin-2-yl)benzoate: (1-((1-(Trifluoromethyl)cyclobutyl)methyl)piperidin-4-yl)methanol (Step 2 of Intermediate 3, 1.00 g, 3.97 mmol), methyl 3-fluoro-4-(5-hydroxypyridin-2-yl)benzoate (1.08 g, 4.37 mmol) and PPh$_3$ (1.35 g, 5.17 mmol) were dissolved in tetrahydrofuran (30 mL) at room temperature. To the solution, DIAD (1.019 mL, 5.173 mmol) was added, followed by stirring at the same temperature for 12 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 40 g cartridge; ethyl acetate/hexane=5% to 20%), and concentrated to obtain the desired compound (0.70 g, 36%) as white solid.

Step 3. Synthesis of Intermediate 30: Methyl 3-fluoro-4-(5-((1-((1-(trifluoromethyl)cyclobutyl)methyl)piperidin-4-yl)methoxy)pyridin-2-yl)benzoate (0.90 g, 1.87 mmol) and LiOH.H$_2$O (0.15 g, 3.74 mmol) were dissolved in tetrahydrofuran (30 mL)/water (5 mL) at room temperature. The solution was stirred at 50° C. for 10 hours, and then cooled to room temperature thereby to make the reaction completed. From the reaction mixture, the solvent was removed under reduced pressure. To the concentrate, 1M-aqueous HCl solution (8 mL) was added and stirred. The precipitated solid was collected by filtration, washed with water and dried to obtain the desired compound (0.80 g, 91%) as white solid.

Synthesis of Intermediate 31: 2-Fluoro-4-(6-((1-((1-(trifluoromethyl)cyclobutyl)methyl)piperidin-4-yl) methoxy)pyridin-3-yl)benzoic acid

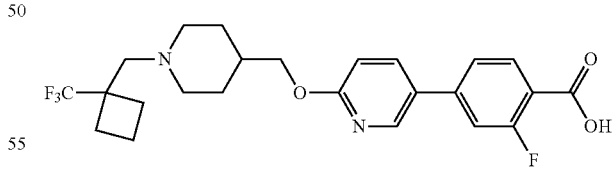

Step 1. Synthesis of methyl 2-fluoro-4-(6-((1-((1-(trifluoromethyl)cyclobutyl)methyl)piperidin-4-yl)methoxy)pyridin-3-yl)benzoate: 5-Bromo-2-((1-((1-(trifluoromethyl)cyclobutyl)methyl)piperidin-4-yl)methoxy)pyridine (Step 4 of Intermediate 5, 0.50 g, 1.22 mmol), 3-fluoro-4-(methoxycarbonyl)phenylboronic acid (0.53 g, 2.70 mmol), Pd(dbpf)Cl$_2$ (0.04 g, 0.07 mmol) and Cs$_2$CO$_3$ (2.38 g, 7.36 mmol) were mixed in 1,4-dioxane (8 mL)/water (4 mL) at room temperature. With a microwave radiation, the mixture was heated at 110° C. for 30 minutes, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=5% to 30%), and concentrated to obtain the desired compound (1.00 g, 84%) as white solid.

Step 2. Synthesis of Intermediate 31: Methyl 2-fluoro-4-(6-((1-((1-(trifluoromethyl)cyclobutyl)methyl)piperidin-4-yl)methoxy)pyridin-3-yl)benzoate (1.00 g, 2.08 mmol) and LiOH.H$_2$O (0.17 g, 4.16 mmol) were dissolved in tetrahydrofuran (50 mL)/water (15 mL) at room temperature. The solution was stirred at 50° C. for 10 hours, and then cooled to room temperature thereby to make the reaction completed. From the reaction mixture, the solvent was removed under reduced pressure. To the concentrate, 1M-aqueous HCl solution (10 mL) was added and stirred. The precipitated solid was collected by filtration, washed with water and dried to obtain the desired compound (0.70 g, 72%) as white solid.

Synthesis of Intermediate 32: 4-(6-((1-((1-(Trifluoromethyl)cyclobutyl)methyl)piperidin-4-yl)methoxy)pyridin-3-yl)benzoic acid

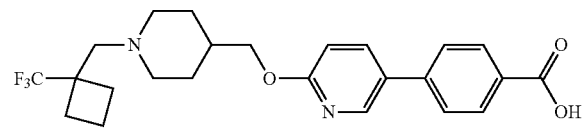

Step 1. Synthesis of methyl 4-(6-((1-((1-(trifluoromethyl)cyclobutyl)methyl)piperidin-4-yl)methoxy)pyridin-3-yl)benzoate: 5-Bromo-2-((1-((1-(trifluoromethyl)cyclobutyl)methyl)piperidin-4-yl)methoxy)pyridine (Step 4 of Intermediate 5, 1.00 g, 2.45 mmol), 4-(methoxycarbonyl)phenylboronic acid (0.48 g, 2.70 mmol), Pd(dbpf)Cl$_2$ (0.04 g, 0.07 mmol) and Cs$_2$CO$_3$ (2.38 g, 7.36 mmol) were mixed in 1,4-dioxane (8 mL)/water (4 mL) at room temperature. With a microwave radiation, the mixture was heated at 110° C. for 30 minutes, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=5% to 30%), and concentrated to obtain the desired compound (1.00 g, 88%) as white solid.

Step 2. Synthesis of Intermediate 32: Methyl 4-(6-((1-((1-(trifluoromethyl)cyclobutyl)methyl)piperidin-4-yl)methoxy)pyridin-3-yl)benzoate (1.00 g, 2.16 mmol) and LiOH.H$_2$O (0.18 g, 4.32 mmol) were dissolved in tetrahydrofuran (50 mL)/water (15 mL) at room temperature. The solution was stirred at 50° C. for 10 hours, and then cooled to room temperature thereby to make the reaction completed. From the reaction mixture, the solvent was removed under reduced pressure. To the concentrate, 1M-aqueous HCl solution (10 mL) was added and stirred. The precipitated solid was collected by filtration, washed with water and dried to obtain the desired compound (0.84 g, 86%) as white solid.

Synthesis of Intermediate 33: 3-Fluoro-4-(5-((1-(2,2,3,3,3-pentafluoropropyl)piperidin-4-yl)methoxy)pyridin-2-yl)benzoic acid

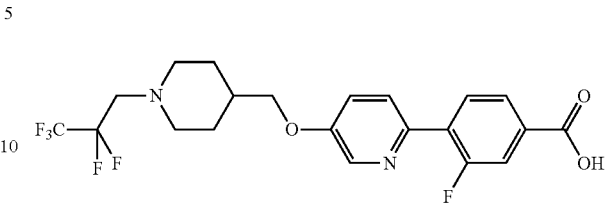

Step 1. Synthesis of tert-butyl 4-(((6-(2-fluoro-4-(methoxycarbonyl)phenyl)pyridin-3-yl)oxy)methyl)piperidin-1-carboxylate: tert-Butyl 4-(((methylsulfonyl)oxy)methyl)piperidin-1-carboxylate (Step 2 of Intermediate 1, 2.00 g, 6.81 mmol), methyl 3-fluoro-4-(5-hydroxypyridin-2-yl)benzoate (Step 1 of Intermediate 30, 1.68 g, 6.81 mmol) and Cs$_2$CO$_3$ (4.44 g, 13.63 mmol) were mixed with acetonitrile (25 mL) at room temperature. The mixture was stirred at 80° C. for 15 hours, and then cooled to room temperature thereby to make the reaction completed. To the reaction mixture, water (40 mL) was added and stirred. The precipitated solid was collected by filtration, washed with water and dried to obtain the desired compound (2.71 g, 89%) as white solid.

Step 2. Synthesis of methyl 3-fluoro-4-(5-(piperidin-4-ylmethoxy)pyridin-2-yl)benzoate hydrochloride: tert-Butyl 4-(((6-(2-fluoro-4-(methoxycarbonyl)phenyl)pyridin-3-yl)oxy)methyl)piperidin-1-carboxylate (2.70 g, 6.07 mmol) and HCl (4.00M solution in 1,4-dioxane, 7.59 mL, 30.30 mmol) were dissolved in DCM (20 mL) at room temperature. The solution was stirred at the same temperature for 18 hours. And then, the precipitated solid was collected by filtration, and dried to obtain the desired compound (2.30 g, 99%) as white solid.

Step 3. Synthesis of methyl 3-fluoro-4-(5-((1-(2,2,3,3,3-pentafluoropropyl)piperidin-4-yl)methoxy)pyridin-2-yl)benzoate: Methyl 3-fluoro-4-(5-(piperidin-4-ylmethoxy)pyridin-2-yl)benzoate hydrochloride (1.00 g, 2.62 mmol), 2,2,3,3,3-pentafluoropropyl trifluoromethanesulfonate (1.48 g, 5.25 mmol) and TEA (0.72 mL, 5.25 mmol) were mixed with 2-propanol (18 mL). With a microwave radiation, the mixture was heated at 140° C. for 1 hour, and then cooled to room temperature thereby to make the reaction completed. From the reaction mixture, the solvent was removed under reduced pressure. The concentrate was purified by column chromatography (SiO$_2$, 40 g cartridge; ethyl acetate/hexane=5% to 10%), and concentrated to obtain the desired compound (0.57 g, 46%) as white solid.

Step 4. Synthesis of Intermediate 33: Methyl 3-fluoro-4-(5-((1-(2,2,3,3,3-pentafluoropropyl)piperidin-4-yl)methoxy)pyridin-2-yl)benzoate (0.57 g, 1.20 mmol) was dissolved in tetrahydrofuran (10 mL)/methanol (5 mL)/water (5 mL) at room temperature. To the solution, LiOH.H$_2$O (0.05 g, 2.41 mmol) was added, followed by stirring at 80° C. for 15 hours. From the reaction mixture, the solvent was removed under reduced pressure. To the concentrate, aqueous HCl solution (20 mL) was added and stirred. The precipitated solid was collected by filtration, washed with water and dried to obtain the desired compound (0.41 g, 73%) as white solid.

Synthesis of Intermediate 34: 4-(5-((1-(2-Ethyl-2-fluorobutyl)piperidin-4-yl)methoxy)pyridin-2-yl)-3-fluorobenzoic acid

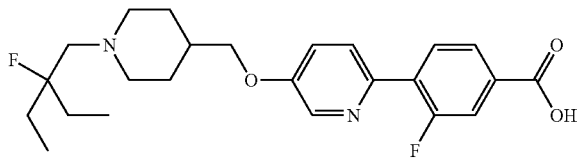 [SMILES: CCC(F)(CC)CN1CCC(COc2ccc(-c3ccc(C(=O)O)cc3F)nc2)CC1]

Step 1. Synthesis of methyl 4-(5-((1-(2-ethyl-2-fluorobutyl)piperidin-4-yl)methoxy)pyridin-2-yl)-3-fluorobenzoate: 2-Bromo-5-((1-(2-ethyl-2-fluorobutyl)piperidin-4-yl)methoxy)pyridine (Step 3 of Intermediate 29, 0.89 g, 2.38 mmol), 2-fluoro-4-(methoxycarbonyl)phenylboronic acid (0.61 g, 3.09 mmol), Pd(dppf)Cl$_2$ (0.09 g, 0.11 mmol) and Cs$_2$CO$_3$ (1.55 g, 4.76 mmol) were mixed with 1,4-dioxane (8 mL)/water (2 mL). With a microwave radiation, the mixture was heated at 120° C. for 20 minutes, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=10% to 50%), and concentrated to obtain the desired compound (0.73 g, 68%) as white solid.

Step 2. Synthesis of Intermediate 34: Methyl 4-(5-((1-(2-ethyl-2-fluorobutyl)piperidin-4-yl)methoxy)pyridin-2-yl)-3-fluorobenzoate (0.73 g, 1.64 mmol) and LiOH (0.19 g, 8.20 mmol) were dissolved in tetrahydrofuran (8 mL)/methanol (8 mL)/water (2 mL) at room temperature. The solution was stirred at the same temperature for 18 hours. From the reaction mixture, the solvent was removed under reduced pressure. To the concentrate, 1M-aqueous HCl solution (20 mL) and water (10 mL) were added and stirred. The precipitated solid was collected by filtration, washed with ethyl acetate and dried to obtain the desired compound (0.58 g, 81%) as white solid.

Synthesis of Intermediate 35: 4-(5-((1-(2-Ethyl-2-fluorobutyl)piperidin-4-yl)methoxy)pyridin-2-yl)benzoic acid

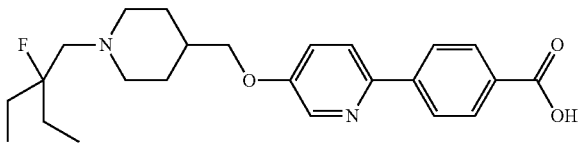 [SMILES: CCC(F)(CC)CN1CCC(COc2ccc(-c3ccc(C(=O)O)cc3)nc2)CC1]

Step 1. Synthesis of methyl 4-(5-((1-(2-ethyl-2-fluorobutyl)piperidin-4-yl)methoxy)pyridin-2-yl)benzoate: 2-Bromo-5-((1-(2-ethyl-2-fluorobutyl)piperidin-4-yl)methoxy)pyridine (1.90 g, 5.09 mmol), 4-(methoxycarbonyl)phenylboronic acid (1.48 g, 7.63 mmol), Pd(dppf)Cl$_2$ (0.20 g, 0.25 mmol) and Cs$_2$CO$_3$ (3.31 g, 10.17 mmol) were mixed with 1,4-dioxane (8 mL)/water (2 mL). With a microwave radiation, the mixture was heated at 120° C. for 20 minutes, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 40 g cartridge; ethyl acetate/hexane=10% to 50%), and concentrated to obtain the desired compound (1.10 g, 50%) as white solid.

Step 2. Synthesis of Intermediate 35: Methyl 4-(5-((1-(2-ethyl-2-fluorobutyl)piperidin-4-yl)methoxy)pyridin-2-yl)benzoate (0.80 g, 1.86 mmol) and LiOH (0.22 g, 9.33 mmol) was dissolved in tetrahydrofuran (12 mL)/methanol (12 mL)/water (3 mL) at room temperature. The solution was stirred at the same temperature for 18 hours. From the reaction mixture, the solvent was removed under reduced pressure. To the concentrate, 1M-aqueous HCl solution (20 mL) and water (60 mL) were added and stirred. The precipitated solid was collected by filtration, washed with water and dried to obtain the desired compound (0.51 g, 66%) as white solid.

Synthesis of Intermediate 36: 4-(6-((1-(2-Ethyl-2-fluorobutyl)piperidin-4-yl)methoxy)pyridin-3-yl)benzoic acid

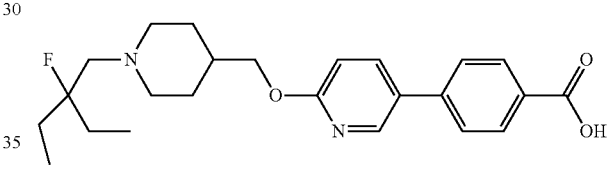

Step 1. Synthesis of 3-((4-(((5-bromopyridin-2-yl)oxy)methyl)piperidin-1-yl)methyl)pentane-3-ol: 5-Bromo-2-(piperidin-4-ylmethoxy)pyridine hydrochloride (Step 2 of Intermediate 5, 3.00 g, 9.75 mmol), 2,2-diethyloxirane (Step 1 of Intermediate 10, 4.88 g, 48.76 mmol) and K$_2$CO$_3$ (2.69 g, 19.50 mmol) were mixed with ethanol (8 mL)/water (2 mL). With a microwave radiation, the mixture was heated at 110° C. for 20 minutes, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The obtained product was used without further purification (3.60 g, 99%, red oil).

Step 2. Synthesis of 5-bromo-2-((1-(2-ethyl-2-fluorobutyl)piperidin-4-yl)methoxy)pyridine: 3-((4-(((5-Bromopyridin-2-yl)oxy)methyl)piperidin-1-yl)methyl)pentane-3-ol (3.60 g, 9.69 mmol) was dissolved in methylene chloride (30 mL). The solution was stirred at 0° C. for 10 minutes. DAST (1.65 mL, 12.60 mmol) was added thereto, followed by stirring at room temperature further for 4 hours. To the reaction mixture, saturated NaHCO$_3$ aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 40 g cartridge; ethyl acetate/hexane=5% to 50%), and concentrated to obtain the desired compound (1.82 g, 50%) as red oil.

Step 3. Synthesis of methyl 4-(6-((1-(2-ethyl-2-fluorobutyl)pyridin-4-yl)methoxy)pyridin-3-yl)benzoate: 5-Bromo-2-((1-(2-ethyl-2-fluorobutyl)piperidin-4-yl)methoxy)pyridine (1.50 g, 4.01 mmol), 4-(methoxycarbonyl)phenylboronic acid (1.16 g, 6.02 mmol), Pd(dppf)Cl₂ (0.16 g, 0.20 mmol) and Cs₂CO₃ (2.61 g, 8.03 mmol) were mixed with 1,4-dioxane (8 mL)/water (2 mL). With a microwave radiation, the mixture was heated at 120° C. for 30 minutes, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 40 g cartridge; ethyl acetate/hexane=0% to 50%), and concentrated to obtain the desired compound (1.40 g, 81%) as white solid.

Step 4. Synthesis of Intermediate 36: Methyl 4-(6-((1-(2-ethyl-2-fluorobutyl)pyridin-4-yl)methoxy)pyridin-3-yl)benzoate (1.40 g, 3.26 mmol) and LiOH (0.39 g, 16.33 mmol) were dissolved in tetrahydrofuran (16 mL)/methanol (16 mL)/water (4 mL) at room temperature. The solution was stirred at the same temperature for 1 hour. From the reaction mixture, the solvent was removed under reduced pressure. To the concentrate, HCl (10 mL) and water (70 mL) were added and stirred. The precipitated solid was collected by filtration, washed with hexane and dried to obtain the desired compound (0.82 g, 60%) as white solid.

Synthesis of Intermediate 37: 4-(6-((1-(2-Ethyl-2-fluorobutyl)piperidin-4-yl)methoxy)pyridin-3-yl)-2-fluorobenzoic acid

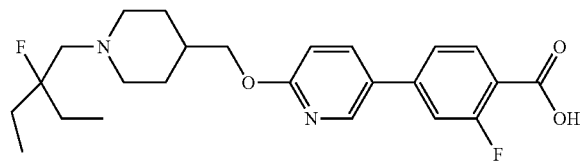

Step 1. Synthesis of ethyl 4-(6-((1-(2-ethyl-2-fluorobutyl)piperidin-4-yl)methoxy)pyridin-3-yl)-2-fluorobenzoate: 5-Bromo-2-((1-(2-ethyl-2-fluorobutyl)piperidin-4-yl)methoxy)pyridine (Step 2 of Intermediate 36, 1.50 g, 4.01 mmol), 4-(ethoxycarbonyl)-3-fluorophenylboronic acid (1.19 g, 6.02 mmol), Pd(dppf)Cl₂ (0.16 g, 0.20 mmol) and Cs₂CO₃ (2.61 g, 8.03 mmol) were mixed with 1,4-dioxane (8 mL)/water (2 mL). With a microwave radiation, the mixture was heated at 120° C. for 30 minutes, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 40 g cartridge; ethyl acetate/hexane=0% to 50%), and concentrated to obtain the desired compound (0.62 g, 33%) as yellow solid.

Step 2. Synthesis of Intermediate 37: Ethyl 4-(6-((1-(2-ethyl-2-fluorobutyl)piperidin-4-yl)methoxy)pyridin-3-yl)-2-fluorobenzoate (0.62 g, 1.34 mmol) and LiOH (0.16 g, 6.73 mmol) were dissolved in tetrahydrofuran (12 mL)/methanol (12 mL)/water (3 mL) at room temperature. The solution was stirred at the same temperature for 1 hour. From the reaction mixture, the solvent was removed under reduced pressure. To the concentrate, 1M-aqueous HCl solution (20 mL) and water (50 mL) were added and stirred. The precipitated solid was collected by filtration, washed with water and dried to obtain the desired compound (0.58 g, 99%) as white solid.

Synthesis of Intermediate 38: 3'-Cyano-4'-((1-(2-fluoro-2-methylpropyl)piperidin-4-yl)methoxy)biphenyl-4-carboxylic acid

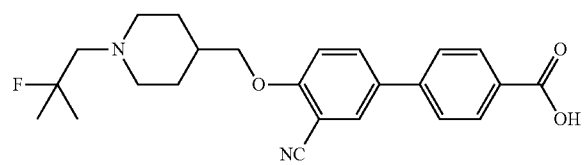 [SMILES: CC(C)(F)CN1CCC(COc2ccc(-c3ccc(C(=O)O)cc3)cc2C#N)CC1]

Step 1. Synthesis of methyl 3'-cyano-4'-((1-(2-fluoro-2-methylpropyl)piperidin-4-yl)methoxy)biphenyl-4-carboxylate: To 5-bromo-2-((1-(2-fluoro-2-methylpropyl)piperidin-4-yl)methoxy)benzonitrile (Step 4 of Intermediate 9, 0.25 g, 0.67 mmol), 4-(methoxycarbonyl)phenylboronic acid (0.14 g, 0.81 mmol), Pd(dppf)Cl₂ (0.02 g, 0.03 mmol) and Cs₂CO₃ (0.44 g, 1.35 mmol), DME (4 mL)/H₂O (1 mL) were added. With a microwave radiation, the mixture was heated at 110° C. for 20 minutes, and then cooled to room temperature. The reaction mixture was filtered through Celite pad thereby to remove solid. To the filtrate, water was added, and the mixture was extracted with EtOAc. The organic layer was washed with saturated NH₄Cl aqueous solution, dried with anhydrous MgSO₄, and then concentrated under reduced pressure. The concentrate was purified by column chromatography (SiO₂, 12 g cartridge; EtOAc/hexane=0% to 30%), and concentrated to obtain the desired compound (0.22 g, 78%) as white solid.

Step 2. Synthesis of Intermediate 38: Methyl 3'-cyano-4'-((1-(2-fluoro-2-methylpropyl)piperidin-4-yl)methoxy)biphenyl-4-carboxylate (0.22 g, 0.53 mmol) and LiOH.H₂O (0.11 g, 2.65 mmol) were dissolved in THF/MeOH (8 mL)/H₂O (2 mL) at room temperature. The solution was stirred at the same temperature for 2 h. The reaction mixture was concentrated under reduced pressure. The precipitated solid was collected by filtration, and dried to obtain the desired compound (0.18 g, 86%) as white solid.

Synthesis of Intermediate 39: 4-(5-((1-(3,3,3-Trifluoro-2,2-dimethylpropyl)piperidin-4-yl)methoxy)pyridin-2-yl)benzoic acid

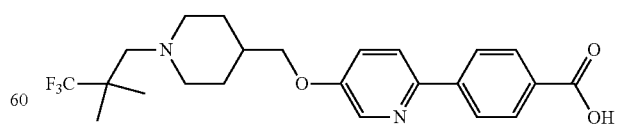

Step 1. Synthesis of methyl 4-(5-((1-(3,3,3-trifluoro-2,2-dimethylpropyl)piperidin-4-yl)methoxy)pyridin-2-yl)benzoate: (1-(3,3,3-Trifluoro-2,2-dimethylpropyl)piperidin-4-yl)methanol (Step 3 of Intermediate 19, 1.40 g, 5.85 mmol), methyl 4-(5-hydroxypyridin-2-yl)benzoate (1.34 g, 5.85 mmol) and triphenylphosphine (1.68 g, 6.43 mmol) were dissolved in THF (16 mL). The solution was stirred at 0° C. for 30 minutes. DIAD (1.14 mL, 5.85 mmol) was added thereto, followed by stirring at room temperature further for 8 hours. To the reaction mixture, saturated ammonium chloride aqueous solution was added, and the mixture was extracted with ethyl acetate. The organic layer was washed with saturated NaCl aqueous solution, dried with anhydrous MgSO$_4$, filtered, and then concentrated under reduced pressure. The obtained product was used without further purification (2.90 g, 110%, white solid).

Step 2. Synthesis of Intermediate 39: Methyl 4-(5-((1-(3,3,3-trifluoro-2,2-dimethylpropyl)piperidin-4-yl)methoxy)pyridin-2-yl)benzoate (2.00 g, 4.44 mmol) and LiOH.H$_2$O (0.21 g, 8.88 mmol) were dissolved in tetrahydrofuran (10 mL)/methanol (6 mL)/water (4 mL) at room temperature. The solution was stirred at 50° C. for 6 hours, and then cooled to room temperature thereby to make the reaction completed. From the reaction mixture, the solvent was removed under reduced pressure. To the concentrate, a small amount of 12N-aqueous HCl solution was added and stirred. The precipitated solid was collected by filtration, washed with methylene chloride and dried to obtain the desired compound (0.20 g, 10%) as white solid.

Synthesis of Intermediate 40: 3-Fluoro-4-(5-((1-(3,3,3-trifluoro-2,2-dimethylpropyl)piperidin-4-yl)methoxy)pyridin-2-yl)benzoic acid

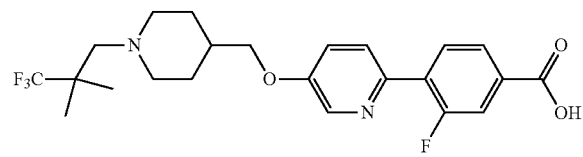 [SMILES: CC(C)(CN1CCC(COc2ccc(-c3ccc(C(=O)O)cc3F)nc2)CC1)C(F)(F)F]

Step 1. Synthesis of methyl 3-fluoro-4-(5-((1-(3,3,3-trifluoro-2,2-dimethylpropyl)piperidin-4-yl)methoxy)pyridin-2-yl)benzoate: (1-(3,3,3-Trifluoro-2,2-dimethylpropyl)piperidin-4-yl)methanol (Step 3 of Intermediate 19, 1.20 g, 5.01 mmol), methyl 3-fluoro-4-(5-hydroxypyridin-2-yl)benzoate (1.24 g, 5.01 mmol) and triphenylphosphine (1.45 g, 5.52 mmol) were dissolved in tetrahydrofuran (20 mL). The solution was stirred at 0° C. for 30 minutes. DIAD (0.98 mL, 5.01 mmol) was added thereto, followed by stirring at room temperature further for 6 hours. To the reaction mixture, saturated ammonium chloride aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=10% to 30%), and concentrated to obtain the desired compound (0.75 g, 31%) as white solid.

Step 2. Synthesis of Intermediate 40: Methyl 3-fluoro-4-(5-((1-(3,3,3-trifluoro-2,2-dimethylpropyl)piperidin-4-yl)methoxy)pyridin-2-yl)benzoate (0.20 g, 0.43 mmol) and LiOH.H$_2$O (0.02 g, 0.85 mmol) were dissolved in tetrahydrofuran (6 mL)/methanol (4 mL)/water (2 mL) at room temperature. The solution was stirred for 6 hours at the same temperature. From the reaction mixture, the solvent was removed under reduced pressure. To the concentrate, a small amount of 12N-aqueous HCl solution was added and stirred. The precipitated solid was collected by filtration, washed with water and dried to obtain the desired compound (0.14 g, 72%) as white solid.

Synthesis of Intermediate 41: 4-(6-((1-(2-Ethyl-2-fluorobutyl)piperidin-4-yl)methoxy)pyridin-3-yl)-3-fluorobenzoic acid

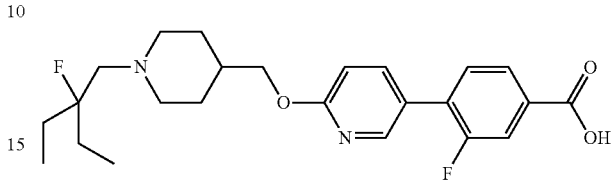

Step 1. Synthesis of methyl 4-(6-((1-(2-ethyl-2-fluorobutyl)piperidin-4-yl)methoxy)pyridin-3-yl)-3-fluorobenzoate: 5-Bromo-2-((1-(2-ethyl-2-fluoro)piperidin-4-yl)methoxy)pyridine (Step 2 of Intermediate 36, 1.50 g, 4.01 mmol), 2-fluoro-4-(methoxycarbonyl)phenylboronic acid (1.19 g, 6.02 mmol), Pd(dppf)Cl$_2$ (0.16 g, 0.20 mmol) and Cs$_2$CO$_3$ (2.61 g, 8.03 mmol) were mixed with 1,4-dioxane (8 mL)/water (2 mL). With a microwave radiation, the mixture was heated at 120° C. for 30 minutes, and then cooled to room temperature thereby to make the reaction completed. The reaction mixture was filtered through Celite pad thereby to remove solid. To the filtrate, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 40 g cartridge; ethyl acetate/hexane=0% to 50%), and concentrated to obtain the desired compound (0.56 g, 31%) as yellow solid.

Step 2. Synthesis of Intermediate 41: Methyl 4-(6-((1-(2-ethyl-2-fluorobutyl)piperidin-4-yl)methoxy)pyridin-3-yl)-3-fluorobenzoate (0.52 g, 1.16 mmol) and LiOH (0.13 g, 5.82 mmol) were dissolved in tetrahydrofuran (12 mL)/methanol (12 mL)/water (3 mL) at room temperature. The solution was stirred at the same temperature for 18 hours. From the reaction mixture, the solvent was removed under reduced pressure. To the concentrate, 1M-aqueous HCl solution (16 mL) and water (40 mL) were added and stirred. The precipitated solid was collected by filtration, washed with water and dried to obtain the desired compound (0.50 g, 99%) as white solid.

2. Synthesis of Compounds

Synthesis of Compound 1148: (S)-1-(2'-Cyano-3-fluoro-4'-((1-(2-fluoro-2-methylpropyl)piperidin-4-yl)methoxy)biphenylcarbonyl)-2-methylpyrrolidin-2-carboxamide

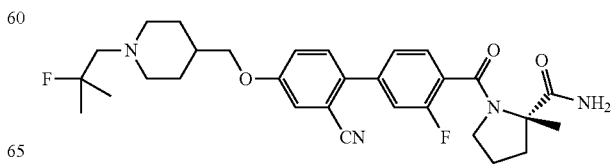

Step 1. (S)-methyl 1-(2'-cyano-3-fluoro-4'-((1-(2-fluoro-2-methylpropyl)piperidin-4-yl)methoxy)biphenylcarbonyl)-2-methylpyrrolidin-2-carboxylate: Intermediate 6 (0.10 g, 0.23 mmol), (S)-methyl 2-methylpyrrolidin-2-carboxylate (0.05 g, 0.35 mmol), EDC (67 mg, 0.35 mmol), HOBt (47 mg, 0.35 mmol) and DIPEA (0.08 mL, 0.46 mmol) were dissolved in DMF (4 mL) at room temperature. The solution was stirred at 80° C. for 12 h. To the reaction mixture, saturated NH₄Cl aqueous solution was added, and the mixture was extracted with ethyl acetate. The organic layer was washed with saturated NaCl aqueous solution, dried with anhydrous MgSO₄, and then concentrated under reduced pressure. The concentrate was purified by column chromatography (SiO₂, 12 g cartridge; ethyl acetate/hexane=5% to 50%), and concentrated to obtain the desired compound (0.11 g, 86%) as white solid.

Step 2. (S)-1-(2'-cyano-3-fluoro-4'-((1-(2-fluoro-2-methylpropyl)piperidin-4-yl)methoxy)biphenylcarbonyl)-2-methylpyrrolidin-2-carboxylic acid: (S)-Methyl 1-(2'-cyano-3-fluoro-4'-((1-(2-fluoro-2-methylpropyl)piperidin-4-yl)methoxy)biphenylcarbonyl)-2-methylpyrrolidin-2-carboxylate (0.11 g, 0.19 mmol) and LiOH.H₂O (17 mg, 0.39 mmol) were dissolved in THF (10 mL)/H₂O (5 mL) at room temperature. The solution was stirred at 60° C. for 12 h. The reaction mixture was concentrated under reduced pressure. The obtained product was used without further purification (0.10 g, 93%, brown solid).

Step 3. Synthesis of Compound 1148: (S)-1-(2'-Cyano-3-fluoro-4'-((1-(2-fluoro-2-methylpropyl)piperidin-4-yl)methoxy)biphenylcarbonyl)-2-methylpyrrolidin-2-carboxylic acid (0.10 g, 0.18 mmol), ammonium chloride (15 mg, 0.27 mmol), EDC (53 mg, 0.27 mmol), HOBt (38 mg, 0.27 mmol) and DIPEA (0.06 mL, 0.37 mmol) were dissolved in DMF (5 mL) at room temperature. The solution was stirred at 80° C. for 14 h. The reaction mixture was concentrated under reduced pressure. The concentrate was purified by column chromatography (Waters, C18, acetonitrile/0.1% TFA in water=5% to 75%), and passed through SPE cartridge (PL-HCO3 MP SPE), followed by concentrating to obtain the desire compound (0.05 g, 50%) as white solid.

¹H NMR (400 MHz, CDCl₃) δ 7.54-7.51 (m, 1H), 7.50-7.42 (m, 2H), 7.39-7.20 (m, 3H), 7.18 (m, 1H), 5.72 (m, 1H), 3.97-3.90 (m, 3H), 3.54-3.52 (m, 2H), 3.27-3.21 (m, 2H), 2.85-2.61 (m, 5H), 2.33-2.27 (m, 2H), 2.16-2.11 (m, 3H), 1.96-1.90 (m, 2H), 1.88 (s, 3H), 1.67-1.61 (m, 6H); MS (ESI) m/z 539.2 (M⁺+H).

Synthesis of Compound 1191: (2S,4R)-1-(2'-Cyano-3-fluoro-4'-((1-(2-fluoro-2-methylpropyl)piperidin-4-yl)methoxy)biphenylcarbonyl)-4-hydroxypyrrolidin-2-carboxamide

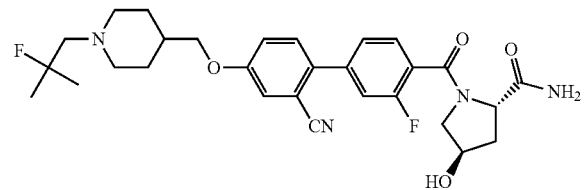 [SMILES: CC(C)(F)CN1CCC(COc2ccc(-c3ccc(C(=O)N4C[C@H](O)C[C@H]4C(N)=O)c(F)c3)c(C#N)c2)CC1]

Step 1. (2S,4R)-methyl 1-(2'-cyano-3-fluoro-4'-((1-(2-fluoro-2-methylpropyl)piperidin-4-yl)methoxy)biphenylcarbonyl)-4-hydroxypyrrolidin-2-carboxylate: Intermediate 6 (0.30 g, 0.70 mmol), (2S,4R)-methyl 4-hydroxypyrrolidin-2-carboxylate (0.12 g, 0.84 mmol), HOBt (0.18 g, 1.40 mmol), EDC (0.26 g, 1.40 mmol) and DIPEA (0.24 mL, 1.40 mmol) were dissolved in DCM (10 mL) at room temperature. The solution was stirred at the same temperature for 18 h. To the reaction mixture, saturated NH₄Cl aqueous solution was added, and the mixture was extracted with ethyl acetate. The organic layer was washed with saturated NaCl aqueous solution, dried with anhydrous MgSO₄, and then concentrated under reduced pressure. The concentrate was purified by column chromatography (SiO₂, 12 g cartridge; methanol/dichloromethane=0% to 30%), and concentrated to obtain the desired compound (0.12 g, 30%) as white solid.

Step 2. (2S,4R)-1-(2'-cyano-3-fluoro-4'-((1-(2-fluoro-2-methylpropyl)piperidin-4-yl)methoxy)biphenylcarbonyl)-4-hydroxypyrrolidin-2-carboxylic acid: (2S,4R)-Methyl 1-(2'-cyano-3-fluoro-4'-((1-(2-fluoro-2-methylpropyl)piperidin-4-yl)methoxy)biphenylcarbonyl)-4-hydroxypyrrolidin-2-carboxylate (0.12 g, 0.21 mmol) and LiOH.H₂O (0.04 g, 1.08 mmol) were dissolved in THF/MeOH (4/4 mL)/H₂O (1 mL) at room temperature. The solution was stirred at the same temperature for 18 h. The reaction mixture was concentrated under reduced pressure. The obtained product was used without further purification (0.10 g, 85%, white solid).

Step 3. Synthesis of Compound 1191: (2S,4R)-1-(2'-Cyano-3-fluoro-4'-((1-(2-fluoro-2-methylpropyl)piperidin-4-yl)methoxy)biphenylcarbonyl)-4-hydroxypyrrolidin-2-carboxylic acid (0.10 g, 0.18 mmol), ammonium chloride (0.05 g, 0.92 mmol), HOBt (0.05 g, 0.36 mmol), EDC (0.07 g, 0.36 mmol) and DIPEA (0.06 mL, 0.36 mmol) were mixed with DMF (20 mL) at 80° C. The mixture was stirred at the same temperature for 18 h. The reaction mixture was concentrated under reduced pressure. The concentrate was purified by column chromatography (Waters, C18, acetonitrile/0.1% TFA in water=5% to 70%), and passed through SPE cartridge (PL-HCO3 MP SPE). The obtained organic layer was concentrated to obtain the desire compound (0.04 g, 40%) as white solid.

¹H NMR (400 MHz, CDCl₃) δ 7.37-7.61 (m, 3H), 7.16-7.30 (m, 3H), 6.99-6.98 (m, 1H), 5.55 (m, 1H), 4.99 (t, 1H, J=7.8 Hz), 4.54 (s, 1H), 3.92-3.93 (m, 3H), 3.66-3.70 (m, 1H), 3.44-3.47 (m, 1H), 3.01-3.28 (m, 2H), 2.65-2.76 (m, 3H), 2.20-2.25 (m, 1H), 2.01-2.08 (m, 4H), 1.78-1.80 (m, 3H), 1.57 (s, 3H), 1.52 (s, 3H); MS (ESI) m/z 541.2 (M⁺+H).

Synthesis of Compound 1192: (2S,4S)-1-(2'-Cyano-3-fluoro-4'-((1-(2-fluoro-2-methylpropyl)piperidin-4-yl)methoxy)biphenylcarbonyl)-4-fluoropyrrolidin-2-carboxamide

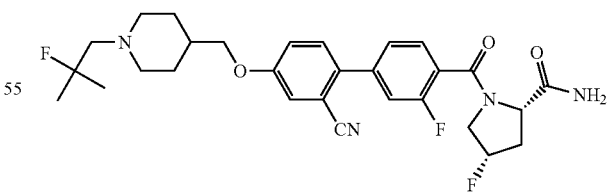

Step 1. (2S,4S)-methyl 1-(2'-cyano-3-fluoro-4'-((1-(2-fluoro-2-methylpropyl)piperidin-4-yl)methoxy)biphenylcarbonyl)-4-fluoropyrrolidin-2-carboxylate: Intermediate 6 (0.30 g, 0.70 mmol), (2S,4S)-methyl 4-fluoropyrrolidin-2-carboxylate (0.12 g, 0.84 mmol), HOBt (0.18 g, 1.40 mmol), EDC (0.26 g, 1.40 mmol) and DIPEA (0.24 mL, 1.40 mmol) were dissolved in DCM (10 mL) at room temperature. The solution was stirred at the same temperature for 18 h. To the reaction mixture, saturated NH₄Cl aqueous solution was added, and the mixture was extracted with ethyl acetate. The organic layer was washed with saturated NaCl aqueous solution, dried with anhydrous MgSO₄, and then concentrated under reduced pressure. The concentrate was purified by column chromatography (SiO₂, 12 g cartridge; methanol/dichloromethane=0% to 30%), and concentrated to obtain the desired compound (0.38 g, 97%) as white solid.

Step 2. (2S,4S)-1-(2'-cyano-3-fluoro-4'-((1-(2-fluoro-2-methylpropyl)piperidin-4-yl)methoxy)biphenylcarbonyl)-4-fluoropyrrolidin-2-carboxylic acid: (2S,4S)-Methyl 1-(2'-cyano-3-fluoro-4'-((1-(2-fluoro-2-methylpropyl)piperidin-4-yl)methoxy)biphenylcarbonyl)-4-fluoropyrrolidin-2-carboxylate (0.325 g, 0.583 mmol) and LiOH.H₂O (0.12 g, 2.91 mmol) were dissolved in THF/MeOH (4/4 mL)/H₂O (1 mL) at room temperature. The solution was stirred at the same temperature for 18 h. The reaction mixture was concentrated under reduced pressure. The obtained product was used without further purification (0.30 g, 94%, white solid).

Step 3. Synthesis of Compound 1192: (2S,4S)-1-(2'-Cyano-3-fluoro-4'-((1-(2-fluoro-2-methylpropyl)piperidin-4-yl)methoxy)biphenylcarbonyl)-4-fluoropyrrolidin-2-carboxylic acid (0.30 g, 0.55 mmol), ammonium chloride (0.14 g, 2.77 mmol), HOBt (0.15 g, 1.10 mmol), EDC (0.21 g, 1.10 mmol) and DIPEA (0.14 g, 1.10 mmol) were mixed with DMF (20 mL) at 80° C. The mixture was stirred at the same temperature for 18 hours, and concentrated under reduced pressure. The concentrate was purified by column chromatography (Waters, C18, acetonitrile/0.1% TFA in water=5% to 70%), and passed through SPE cartridge (PL-HCO3 MP SPE). The obtained organic layer was concentrated to obtain the desire compound (0.03 g, 12%) as yellow solid.

¹H NMR (400 MHz, CDCl₃) δ 7.49-7.59 (m, 1H), 7.38-7.45 (m, 2H), 7.28-7.36 (m, 1H), 7.23-7.17 (m, 2H), 6.63 (s, 1H), 5.78 (s, 1H), 5.20-5.30 (m, 1H), 4.97-5.01 (m, 1H), 3.61-4.07 (m, 6H), 3.32-3.42 (m, 2H), 2.68-2.95 (m, 3H), 2.40-2.44 (m, 1H), 2.00-2.28 (m, 5H), 1.57 (s, 3H), 1.52 (s, 3H); MS (ESI) m/z 543.2 (M⁻+H).

Synthesis of Compound 1198: (2S,4S)-4-Fluoro-1-(4'-((1-((1-(trifluoromethyl)cyclobutyl)methyl)piperidin-4-yl)methoxy)biphenylcarbonyl)pyrrolidin-2-carboxamide

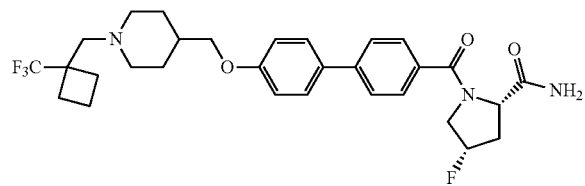 [SMILES: NC(=O)[C@@H]1C[C@H](F)CN1C(=O)c1ccc(-c2ccc(OCC3CCN(CC4(C(F)(F)F)CCC4)CC3)cc2)cc1]

Step 1. (2S,4S)-methyl 4-fluoro-1-(4'-((1-((1-(trifluoromethyl)cyclobutyl)methyl)piperidin-4-yl)methoxy)biphenylcarbonyl)pyrrolidin-2-carboxylate: Intermediate 1 (0.15 g, 0.33 mmol), (2S,4S)-methyl 4-fluoropyrrolidin-2-carboxylate (0.09 g, 0.67 mmol), HATU (0.25 g, 0.67 mmol) and DIPEA (0.29 mL, 1.67 mmol) were mixed in DMF (5 mL) at room temperature. The mixture was stirred at 80° C. for 5 h. From the reaction mixture, the solvent was removed under reduced pressure. To the obtained concentrate, water was added, and the mixture was extracted with dichloromethane. The organic layer was washed with saturated NaCl aqueous solution, dried with anhydrous MgSO₄, and then concentrated under reduced pressure. The concentrate was purified by column chromatography (SiO₂, 12 g cartridge; methanol/dichloromethane=0% to 10%), and concentrated to obtain the desired compound (0.18 g, 93%) as orange color solid.

Step 2. (2S,4S)-4-fluoro-1-(4'-((1-((1-(trifluoromethyl)cyclobutyl)methyl)piperidin-4-yl)methoxy)biphenylcarbonyl)pyrrolidin-2-carboxylic acid: (2S,4S)-Methyl 4-fluoro-1-(4'-((1-((1-(trifluoromethyl)cyclobutyl)methyl)piperidin-4-yl)methoxy)biphenylcarbonyl)pyrrolidin-2-carboxylate (0.18 g, 0.31 mmol) and LiOH (0.06 g, 1.56 mmol) were mixed in tetrahydrofuran (3 mL)/MeOH (1 mL)/H₂O (1 mL) at room temperature. The mixture was stirred at 80° C. for 3 h. The reaction mixture was concentrated under reduced pressure. To the concentrate, water (10 mL) was added. The precipitated solid was collected by filtration, and dried to obtain the desired compound (0.15 g, 85%) as white solid.

Step 3. Synthesis of Compound 1198: (2S,4S)-4-Fluoro-1-(4'-((1-((1-(trifluoromethyl)cyclobutyl)methyl)piperidin-4-yl)methoxy)biphenylcarbonyl)pyrrolidin-2-carboxylic acid (0.15 g, 0.26 mmol), HATU (0.20 g, 0.53 mmol) and DIPEA (0.23 mL, 1.33 mmol) were mixed in DMF (5 mL) at room temperature. The mixture was added with NH₄Cl (0.07 g, 1.33 mmol) and stirred at 60° C. for 12 h. The reaction mixture was concentrated under reduced pressure. The concentrate was purified by column chromatography (Waters, C18, acetonitrile/0.1% TFA in water=5% to 75%), and passed through SPE cartridge (PL-HCO3 MP SPE), followed by concentrating to obtain the desire compound (0.05 g, 37%) as pale yellow solid.

¹H NMR (400 MHz, CDCl₃) δ 7.55-7.46 (m, 6H), 6.91 (d, 2H, J=8.3 Hz), 5.25-4.87 (m, 2H), 3.99-3.90 (m, 1H), 3.80-3.75 (m, 2H), 3.67-3.57 (m, 4H), 2.97-2.94 (m, 2H), 2.63-2.37 (m, 3H), 2.27-2.17 (m, 5H), 2.09-1.78 (m, 6H); MS (ESI) m/z 562 (M⁺+H).

Synthesis of Compound 1199: (2S,4R)-4-Hydroxy-1-(4'-((1-((1-(trifluoromethyl)cyclobutyl)methyl)piperidin-4-yl)methoxy)biphenylcarbonyl)pyrrolidin-2-carboxamide

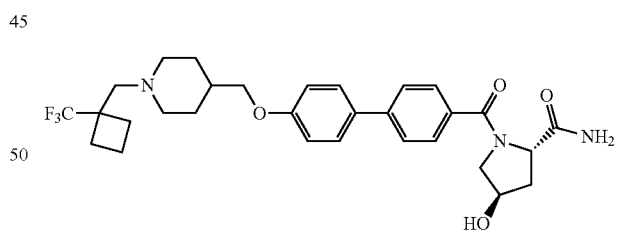

Step 1. (2S,4R)-methyl 4-hydroxy-1-(4'-((1-((1-(trifluoromethyl)cyclobutyl)methyl)piperidin-4-yl)methoxy)biphenylcarbonyl)pyrrolidin-2-carboxylate: Intermediate 1 (0.15 g, 0.33 mmol), (2S,4R)-methyl 4-hydroxypyrrolidin-2-carboxylate (0.09 g, 0.67 mmol), HATU (0.25 g, 0.67 mmol) and DIPEA (0.29 mL, 1.67 mmol) were mixed in DMF (5 mL) at room temperature. The mixture was stirred at 80° C. for 5 h. From the reaction mixture, the solvent was removed under reduced pressure. To the obtained concentrate, water was added, and the mixture was extracted with dichloromethane. The organic layer was washed with saturated NaCl aqueous solution, dried with anhydrous MgSO₄, and then concentrated under reduced pressure. The concentrate was purified by column chromatography (SiO$_2$, 12 g cartridge; methanol/dichloromethane=0% to 10%), and concentrated to obtain the desired compound (0.17 g, 88%) as pale yellow solid.

Step 2. (2S,4R)-4-hydroxy-1-(4'-((1-((1-(trifluoromethyl) cyclobutyl)methyl)piperidin-4-yl)methoxy)biphenylcarbonyl)pyrrolidin-2-carboxylic acid: (2S,4R)-Methyl 4-hydroxy-1-(4'-((1-((1-(trifluoromethyl)cyclobutyl)methyl) piperidin-4-yl)methoxy)biphenylcarbonyl)pyrrolidin-2-carboxylate (0.17 g, 0.29 mmol) and LiOH (0.06 g, 1.47 mmol) were mixed in THF (3 mL)/methanol (1 mL)/H$_2$O (1 mL) at room temperature. The mixture was stirred at 80° C. for 5 h. The reaction mixture was concentrated under reduced pressure. The obtained product was used without further purification (0.15 g, 90%, yellow oil).

Step 3. Synthesis of Compound 1199: (2S,4R)-4-Hydroxy-1-(4'-((1-((1-(trifluoromethyl)cyclobutyl)methyl)piperidin-4-yl)methoxy)biphenylcarbonyl)pyrrolidin-2-carboxylic acid (0.15 g, 0.26 mmol), HATU (0.20 g, 0.53 mmol) and DIPEA (0.23 mL, 1.33 mmol) were mixed in DMF (5 mL) at room temperature. The mixture was added with NH$_4$Cl (0.07 g, 1.33 mmol) and stirred at 60° C. for 12 h. From the reaction mixture, the solvent was removed under reduced pressure. To the obtained concentrate, water was added, and the mixture was extracted with dichloromethane. The organic layer was washed with water, dried with anhydrous MgSO$_4$, and then concentrated under reduced pressure. The concentrate was purified by column chromatography (Waters, C18, acetonitrile/0.1% TFA in water=5% to 70%), and passed through SPE cartridge (PL-HCO3 MP SPE), followed by concentrating to obtain the desire compound (0.03 g, 25%) as pale yellow solid.

$^1$H NMR (400 MHz, CDCl$_3$) δ 7.60-7.54 (m, 4H), 7.49 (d, 2H, J=8.0 Hz), 6.95 (d, 2H, J=8.8 Hz), 4.81-4.80 (m, 1H), 4.40 (brs, 1H), 3.83-3.76 (m, 3H), 3.56-3.53 (m, 1H), 2.91-2.88 (m, 2H), 2.54 (s, 2H), 2.31-2.17 (m, 6H), 2.08-1.78 (m, 6H), 1.44-1.41 (m, 2H); MS (ESI) m/z 560 (M$^+$+H).

Synthesis of Compound 1200: (2S,4R)-1-(2-Fluoro-4-(5-((1-((1-(trifluoromethyl)cyclobutyl)methyl) piperidin-4-yl)methoxy)pyrazin-2-yl)benzoyl)-4-hydroxypyrrolidin-2-carboxamide

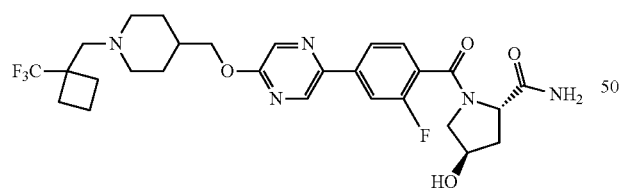

Step 1. (2S,4R)-methyl 1-(2-fluoro-4-(5-((1-((1-(trifluoromethyl)cyclobutyl)methyl)piperidin-4-yl)methoxy) pyrazin-2-yl)benzoyl)-4-hydroxypyrrolidin-2-carboxylate: Intermediate 4 (0.12 g, 0.25 mmol), HATU (0.19 g, 0.51 mmol) and DIPEA (0.22 mL, 1.28 mmol) were mixed in DMF (3 mL) at room temperature. The mixture was added with (2S,4R)-methyl4-hydroxypyrrolidin-2-carboxylate (0.06 g, 0.51 mmol) and stirred at 60° C. for 12 h. From the reaction mixture, the solvent was removed under reduced pressure. To the obtained concentrate, water was added, and the mixture was extracted with dichloromethane. The organic layer was washed with water, dried with anhydrous MgSO$_4$, and then concentrated under reduced pressure. The concentrate was purified by column chromatography (SiO$_2$, 12 g cartridge; methanol/dichloromethane=0% to 10%), and concentrated to obtain the desired compound (0.15 g, 98%) as pale yellow solid.

Step 2. (2S,4R)-1-(2-fluoro-4-(5-((1-((1-(trifluoromethyl) cyclobutyl)methyl)piperidin-4-yl)methoxy)pyrazin-2-yl) benzoyl)-4-hydroxypyrrolidin-2-carboxylic acid: (2S,4R)-Methyl 1-(2-fluoro-4-(5-((1-((1-(trifluoromethyl) cyclobutyl)methyl)piperidin-4-yl)methoxy)pyrazin-2-yl) benzoyl)-4-hydroxypyrrolidin-2-carboxylate (0.12 g, 0.20 mmol) and LiOH.H$_2$O (0.04 g, 1.00 mmol) were mixed in THF (12 mL)/methanol (4 mL)/H$_2$O (4 mL) at room temperature. The mixture was stirred at 80° C. for 5 h. The reaction mixture was concentrated under reduced pressure. To the concentrate, 1 N aqueous HCl solution was added. The precipitated solid was collected by filtration, and dried to obtain the desired compound (0.05 g, 49%) as white solid.

Step 3. Synthesis of Compound 1200: (2S,4R)-1-(2-Fluoro-4-(5-((1-((1-(trifluoromethyl)cyclobutyl)methyl)piperidin-4-yl)methoxy)pyrazin-2-yl)benzoyl)-4-hydroxypyrrolidin-2-carboxylic acid (0.07 g, 0.12 mmol), HATU (0.09 g, 0.24 mmol) and DIPEA (0.10 mL, 0.60 mmol) were dissolved in DMF (5 mL). The solution was stirred at room temperature for 30 minutes. Ammonium chloride (0.03 g, 0.60 mmol) was added thereto. And the reaction mixture was further stirred at 60° C. for 12 hours, and then cooled to room temperature thereby to make the reaction completed. From the reaction mixture, the solvent was removed under reduced pressure. To the obtained concentrate, dichloromethane (10 mL) and water (10 mL) were added, followed by filtering through plastic filter. The obtained organic layer was concentrated, and the obtained concentrate was purified by chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.03 g, 50%) as white solid.

$^1$H NMR (400 MHz, CDCl$_3$) δ 8.48 (s, 1H), 8.25 (s, 1H), 7.74-7.66 (m, 2H), 7.57 (t, 1H, J=6.0 Hz), 4.84 (t, 1H, J=10.0 Hz), 4.43 (brs, 1H), 4.23 (d, 2H, J=6.0 Hz), 3.70-3.67 (m, 1H), 3.43-3.37 (m, 2H), 36.22 (brs, 2H), 2.91 (brs, 2H), 2.67-2.35 (m, 5H), 2.31-1.88 (m, 9H); MS (ESI) m/z 580 (M$^+$+H).

Synthesis of Compound 1204: (2S,4R)-1-(4'-((1-(2-Ethyl-2-fluorobutyl)piperidin-4-yl)methoxy)biphenylcarbonyl)-4-hydroxypyrrolidin-2-carboxamide

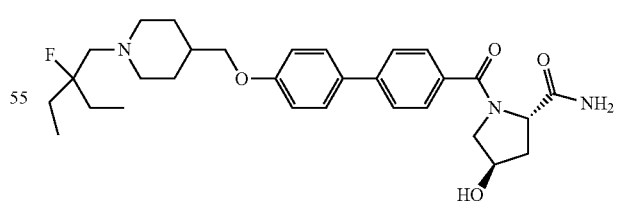

Step 1. (2S,4R)-methyl 1-(4'-((1-(2-ethyl-2-fluorobutyl) piperidin-4-yl)methoxy)biphenylcarbonyl)-4-hydroxypyrrolidin-2-carboxylate: Intermediate 11 (0.10 g, 0.24 mmol), (2S,4R)-methyl4-hydroxypyrrolidin-2-carboxylate hydrochloride (0.06 g, 0.36 mmol), HATU (0.18 g, 0.48 mmol) and DIPEA (0.08 mL, 0.48 mmol) were mixed in DMF (10 mL) at room temperature. The mixture was stirred at 50° C.

for 5 h. To the reaction mixture, water was added. The mixture was extracted with ethyl acetate, filtered through plastic filter attached with Na$_2$SO$_4$ cartridge to remove the solid residue and the aqueous layer, and then concentrated under reduced pressure. The concentrate was purified by column chromatography (SiO$_2$, 4 g cartridge; methanol/dichloromethane=0% to 15%), and concentrated to obtain the desired compound (0.09 g, 72%) as yellow solid.

Step 2. (2S,4R)-1-(4'-((1-(2-ethyl-2-fluorobutyl)piperidin-4-yl)methoxy)biphenylcarbonyl)-4-hydroxypyrrolidin-2-carboxylic acid: (2S,4R)-Methyl 1-(4'-((1-(2-ethyl-2-fluorobutyl)piperidin-4-yl)methoxy)biphenylcarbonyl)-4-hydroxypyrrolidin-2-carboxylate (0.09 g, 0.17 mmol) and LiOH.H$_2$O (0.03 g, 0.87 mmol) were mixed with THF/methanol (1:1) (8 mL)/water (1 mL) at 50° C. The mixture was stirred at the same temperature for 18 h. The reaction mixture was concentrated under reduced pressure. The obtained product was used without further purification (0.09 g, 97%, yellow solid).

Step 3. Synthesis of Compound 1204: (2S,4R)-1-(4'-((1-(2-Ethyl-2-fluorobutyl)piperidin-4-yl)methoxy)biphenylcarbonyl)-4-hydroxypyrrolidin-2-carboxylic acid (0.09 g, 0.171 mmol), ammonium chloride (0.02 g, 0.51 mmol), HATU (0.19 g, 0.51 mmol) and DIPEA (0.06 mL, 0.34 mmol) were mixed in DMF (10 mL) at room temperature. The mixture was stirred at 50° C. for 18 h. The reaction mixture was concentrated under reduced pressure. The concentrate was purified by column chromatography (Waters, C18, acetonitrile/0.1% TFA in water=5% to 70%), and concentrated. The obtained concentrate was dissolved in solvent, and passed through SPE cartridge (PL-HCO3 MP SPE), followed by concentrating to obtain the desire compound (0.01 g, 10%) as white solid.

$^1$H NMR (400 MHz, CDCl$_3$) δ 7.59-7.53 (m, 4H), 7.49 (d, 2H, J=8.6 Hz), 6.94 (d, 1H, J=8.6 Hz), 5.82 (s, 1H), 4.88-4.92 (m, 1H), 4.43 (s, 1H), 3.82 (d, 2H, J=5.9 Hz), 3.57-3.77 (m, 2H), 2.98-3.26 (m, 2H), 2.15-2.61 (m, 6H), 1.50-1.91 (m, 11H), 0.88 (t, 6H, J=7.5 Hz); MS (ESI) m/z 526.3 (M$^+$+H).

Synthesis of Compound 1205: (2S,4R)-1-(4'-((1-(2-Ethyl-2-fluorobutyl)piperidin-4-yl)methoxy)-2-fluorobiphenylcarbonyl)-4-hydroxypyrrolidin-2-carboxamide

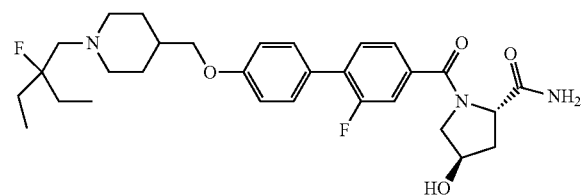 [SMILES: CCC(F)(CC)CN1CCC(COc2ccc(-c3ccc(C(=O)N4C[C@H](O)C[C@H]4C(N)=O)cc3F)cc2)CC1]

Step 1. (2S,4R)-methyl 1-(4'-((1-(2-ethyl-2-fluorobutyl)piperidin-4-yl)methoxy)-2-fluorobiphenylcarbonyl)-4-hydropyrrolidin-2-carboxylate: Intermediate 10 (0.10 g, 0.23 mmol), (2S,4R)-methyl 4-hydroxypyrrolidin-2-carboxylate hydrochloride (0.06 g, 0.34 mmol), HATU (0.17 g, 0.46 mmol) and DIPEA (0.08 mL, 0.46 mmol) were mixed in DMF (10 mL) at room temperature. The mixture was stirred at 50° C. for 5 h. To the reaction mixture, water was added. The mixture was extracted with dichloromethane, filtered through plastic filter attached with Na$_2$SO$_4$ cartridge to remove the solid residue and the aqueous layer, and then concentrated under reduced pressure. The concentrate was purified by column chromatography (SiO$_2$, 4 g cartridge; methanol/dichloromethane=0% to 15%), and concentrated to obtain the desired compound (0.10 g, 81%) as yellow oil.

Step 2. (2S,4R)-1-(4'-((1-(2-ethyl-2-fluorobutyl)piperidin-4-yl)methoxy)-2-fluorobiphenylcarbonyl)-4-hydroxypyrrolidin-2-carboxylic acid: (2S,4R)-Methyl 1-(4'-((1-(2-ethyl-2-fluorobutyl)piperidin-4-yl)methoxy)-2-fluorobiphenylcarbonyl)-4-hydroxypyrrolidin-2-carboxylate (0.10 g, 0.18 mmol) and LiOH.H$_2$O (0.03 g, 0.94 mmol) were mixed in THF/methanol (1:1) (8 mL)/water (1 mL) at 50° C. The mixture was stirred at the same temperature for 18 h. The reaction mixture was concentrated under reduced pressure. The obtained product was used without further purification (0.10 g, 97%, yellow solid).

Step 3. Synthesis of Compound 1205: (2S,4R)-1-(4'-((1-(2-Ethyl-2-fluorobutyl)piperidin-4-yl)methoxy)-2-fluorobiphenylcarbonyl)-4-hydropyrrolidin-2-carboxylic acid (0.10 g, 0.18 mmol), ammonium chloride (0.02 g, 0.55 mmol), HATU (0.20 g, 0.55 mmol) and DIPEA (0.06 mL, 0.36 mmol) were mixed in DMF (10 mL) at room temperature. The mixture was stirred at 50° C. for 18 h. The reaction mixture was purified by column chromatography (Waters, C18, acetonitrile/0.1% TFA in water=5% to 70%), and concentrated. The obtained concentrate was dissolved in solvent, and passed through SPE cartridge (PL-HCO3 MP SPE), followed by concentrating to obtain the desire compound (0.01 g, 14%) as white solid.

$^1$H NMR (400 MHz, CDCl$_3$) δ 7.30-7.54 (m, 5H), 6.89 (d, 2H, J=8.7 Hz), 6.23 (s, 1H), 4.91 (s, 1H), 4.42 (m, 1H), 3.60-3.76 (m, 3H), 3.53-3.55 (m, 1H), 2.92-3.15 (m, 2H), 2.01-2.63 (m, 7H), 1.46-1.76 (m, 8H), 1.32-1.43 (m, 2H), 0.88 (t, 6H, J=7.5 Hz); MS (ESI) m/z 544.3 (M$^+$+H).

Synthesis of Compound 1206: (S)-1-(2-Fluoro-4-(5-((1-(2-fluoro-2-methylpropyl)piperidin-4-yl)methoxy)pyrimidin-2-yl)benzoyl)-2-methylpyrrolidin-2-carboxamide

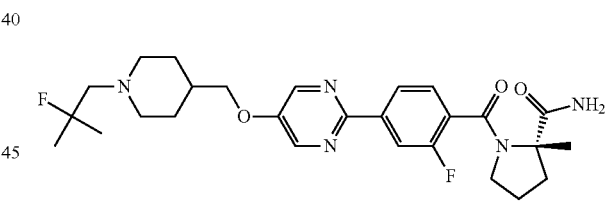

Step 1. (S)-methyl 1-(2-fluoro-4-(5-((1-(2-fluoro-2-methylpropyl)piperidin-4-yl)methoxy)pyrimidin-2-yl)benzoyl)-2-methylpyrrolidin-2-carboxylate: Intermediate 8 (0.20 g, 0.49 mmol), (S)-methyl 2-methylpyrrolidin-2-carboxylate (0.10 g, 0.74 mmol), HATU (0.37 g, 0.98 mmol) and DIPEA (0.17 mL, 0.98 mmol) were mixed in DMF (15 mL) at 50° C. The mixture was stirred at the same temperature for 18 h. From the reaction mixture, the solvent was removed under reduced pressure. To the obtained concentrate, saturated NH$_4$Cl aqueous solution was added. The mixture was extracted with dichloromethane, filtered through plastic filter to remove the solid residue and the aqueous layer, and then concentrated under reduced pressure. The concentrate was purified by column chromatography (SiO$_2$, 4 g cartridge; methanol/dichloromethane=0% to 15%), and concentrated to obtain the desired compound (0.13 g, 52%) as yellow solid.

Step 2. (S)-1-(2-fluoro-4-(5-((1-(2-fluoro-2-methylpropyl)piperidin-4-yl)methoxy)pyrimidin-2-yl)benzoyl)-2- methylpyrrolidin-2-carboxylic acid: (S)-Methyl 1-(2-fluoro-4-(5-((1-(2-fluoro-2-methylpropyl)piperidin-4-yl)methoxy)pyrimidin-2-yl)benzoyl)-2-methylpyrrolidin-2-carboxylate (0.16 g, 0.32 mmol) and LiOH.H$_2$O (0.06 g, 1.62 mmol) were mixed in THF/MeOH (1:1) (16 mL)/water (4 mL) at 50° C. The mixture was stirred at the same temperature for 18 h. The reaction mixture was concentrated under reduced pressure. The precipitated solid was collected by filtration, and dried to obtain the desired compound (0.16 g, 99%) as yellow solid.

Step 3. Synthesis of Compound 1206: (S)-1-(2-Fluoro-4-(5-((1-(2-fluoro-2-methylpropyl)piperidin-4-yl)methoxy)pyrimidin-2-yl)benzoyl)-2-methylpyrrolidin-2-carboxylic acid (0.16 g, 0.32 mmol), ammonium chloride (0.05 g, 0.97 mmol), HATU (0.36 g, 0.97 mmol) and DIPEA (0.11 mL, 0.64 mmol) were mixed in DMF (20 mL) at room temperature. The mixture was stirred at 50° C. for 18 h. To the reaction mixture, water was added, and the mixture was extracted with ethyl acetate. The organic layer was washed with saturated NaCl aqueous solution, dried with anhydrous MgSO$_4$, and then concentrated under reduced pressure. The concentrate was purified by column chromatography (SiO$_2$, 4 g cartridge; methanol/dichloromethane=0% to 15%), and concentrated to obtain the desired compound (0.05 g, 30%) as white solid.

$^1$H NMR (400 MHz, CDCl$_3$) δ 8.44 (s, 2H), 8.19 (dd, 1H, J=8.0, 1.5 Hz), 8.09 (dd, 1H, J=11.1, 1.2 Hz), 7.46 (t, 1H, 7.5 Hz), 7.06 (s, 1H), 5.61 (s, 1H), 3.94 (d, 2H, J=6.0 Hz), 3.44-3.48 (m, 2H), 2.94-3.00 (m, 2H), 2.58-2.63 (m, 1H), 2.46-2.40 (m, 2H), 2.16-2.19 (m, 2H), 1.76-2.15 (m, 9H). 1.42-1.48 (m, 2H), 1.38 (s, 3H), 1.32 (s, 3H); MS (ESI) m/z 516.2 (M$^+$+H).

Synthesis of Compound 1207: (S)-1-(2-Fluoro-4-(5-((1-(2-fluoro-2-methylpropyl)pyridin-4-yl)methoxy)pyridin-2-yl)benzoyl)-2-methylpyrrolidin-2-carboxamide

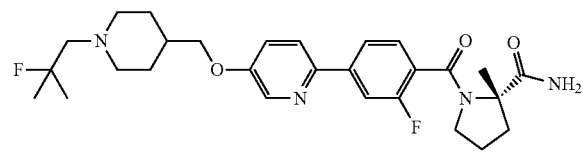 [SMILES: CC(C)(F)CN1CCC(COc2ccc(-c3ccc(C(=O)N4CCC[C@@]4(C)C(N)=O)c(F)c3)nc2)CC1]

Step 1. (S)-methyl 1-(2-fluoro-4-(5-((1-(2-fluoro-2-methylpropyl)piperidin-4-yl)methoxy)pyridin-2-yl)benzoyl)-2-methylpyrrolidin-2-carboxylate: Intermediate 23 (1.00 g, 2.47 mmol), (S)-methyl 2-methylpyrrolidin-2-carboxylate (0.70 g, 4.94 mmol), EDC (0.94 g, 4.94 mmol), HOBt (0.66 g, 4.94 mmol) and DIPEA (0.87 mL, 4.94 mmol) were dissolved in dichloromethane (50 mL) at room temperature. The solution was stirred at the same temperature for 12 hours. To the reaction mixture, water was added, and the mixture was extracted with ethyl acetate. The organic layer was washed with saturated NH$_4$Cl aqueous solution, dried with anhydrous MgSO$_4$, filtered, and then concentrated under reduced pressure. The concentrate was purified by column chromatography (SiO$_2$, 12 g cartridge; methanol/dichloromethane=0% to 10%), and concentrated to obtain the desired compound (0.88 g, 67%) as white solid.

Step 2. (S)-1-(2-Fluoro-4-(5-((1-(2-fluoro-2-methylpropyl)piperidin-4-yl)methoxy)pyridin-2-yl)benzoyl)-2-methylpyrrolidin-2-carboxylic acid: (S)-Methyl 1-(2-fluoro-4-(5-((1-(2-fluoro-2-methylpropyl)piperidin-4-yl)methoxy)pyridin-2-yl)benzoyl)-2-methylpyrrolidin-2-carboxylate (0.60 g, 1.13 mmol) was dissolved in tetrahydrofuran (6 mL)/methanol (6 mL)/water (3 mL) at room temperature. To the solution, LiOH.H$_2$O (0.23 g, 5.66 mmol) was added, followed by stirring at the same temperature for 1 hour. From the reaction mixture, the solvent was removed under reduced pressure. To the concentrate, water (2 mL) and 1N-aqueous HCl solution (1 mL) were added and stirred. The precipitated solid was collected by filtration, washed with water and dried to obtain the desired compound (0.31 g, 53%) as white solid.

Step 3. Synthesis of Compound 1207: (S)-1-(2-Fluoro-4-(5-((1-(2-fluoro-2-methylpropyl)piperidin-4-yl)methoxy)pyridin-2-yl)benzoyl)-2-methylpyrrolidin-2-carboxylic acid (0.31 g, 0.60 mmol), NH$_4$Cl (0.32 g, 6.01 mmol), HATU (0.45 g, 1.203 mmol) and DIPEA (0.21 mL, 1.20 mmol) were dissolved in DMF (10 mL) at 80° C. The solution was stirred at the same temperature for 14 hours, and then cooled to room temperature thereby to make the reaction completed. To the reaction mixture, water was added, and the mixture was extracted with ethyl acetate. The organic layer was washed with saturated NH$_4$Cl aqueous solution, dried with anhydrous MgSO$_4$, filtered, and then concentrated under reduced pressure. The concentrate was purified by column chromatography (SiO$_2$, 12 g cartridge; methanol/dichloromethane=0% to 10%), and concentrated to obtain the desired compound (0.15 g, 48%) as brown solid.

$^1$H NMR (400 MHz, CD$_3$OD) δ 8.33 (brs, 1H), 7.89-7.79 (m, 3H), 7.59-7.55 (m, 1H), 7.52-7.48 (m, 1H), 4.04-4.02 (m, 2H), 3.80-3.77 (m, 2H), 3.62-3.56 (m, 2H), 3.50-3.45 (m, 2H), 3.24-3.17 (m, 2H), 2.36-2.30 (m, 1H), 2.20-2.00 (m, 6H), 1.91-1.79 (m, 2H), 1.78 (s, 3H), 1.62 (s, 3H), 1.59 (s, 3H); MS (ESI) m/z 515.2 (M$^+$+H).

Synthesis of Compound 1208: (2S,4R)-1-(2-Fluoro-4-(6-((1-(3,3,3-trifluoro-2,2-dimethylpropyl)piperidin-4-yl)methoxy)pyridin-3-yl)benzoyl)-4-hydroxypyrrolidin-2-carboxamide

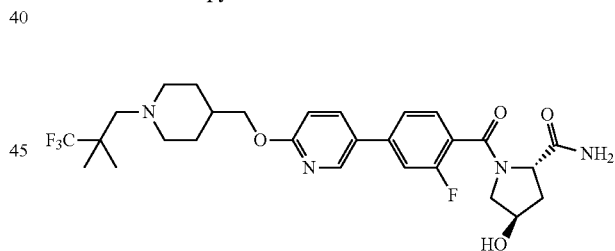

Step 1. (2S,4R)-methyl 1-(2-fluoro-4-(6-((1-(3,3,3-trifluoro-2,2-dimethylpropyl)piperidin-4-yl)methoxy)pyridin-3-yl)benzoyl)-4-hydroxypyrrolidin-2-carboxylate: Intermediate 17 (0.20 g, 0.44 mmol), (2S,4R)-methyl 4-hydroxypyrrolidin-2-carboxylate hydrochloride (0.16 g, 0.88 mmol), EDC (0.16 g, 0.88 mmol), HOBt (0.11 g, 0.88 mmol) and DIPEA (0.15 mL, 0.88 mmol) were mixed in dichloromethane (3 mL) at room temperature. The mixture was stirred at the same temperature for 12 h. To the reaction mixture, water was added, and the mixture was extracted with ethyl acetate. The organic layer was washed with saturated NaCl aqueous solution, dried with anhydrous MgSO$_4$, and then concentrated under reduced pressure. The concentrate was purified by column chromatography (SiO$_2$, 12 g cartridge; dichloromethane/methanol=0% to 10%), and concentrated to obtain the desired compound (0.13 g, 50%) as white solid.

Step 2. (2S,4R)-1-(2-fluoro-4-(6-((1-(3,3,3-trifluoro-2,2-dimethylpropyl)piperidin-4-yl)methoxy)pyridin-3-yl)benzoyl)-4-hydroxypyrrolidin-2-carboxylic acid: (2S,4R)-Methyl 1-(2-fluoro-4-(6-((1-(3,3,3-trifluoro-2,2-dimethylpropyl)piperidin-4-yl)methoxy)pyridin-3-yl)benzoyl)-4-hydroxypyrrolidin-2-carboxylate (0.13 g, 0.22 mmol) were mixed in tetrahydrofuran (6 mL)/MeOH (6 mL)/water (3 mL) at room temperature. The mixture was added with LiOH.H₂O (0.04 g, 1.11 mmol) and stirred at the same temperature for 1 h. The reaction mixture was concentrated under reduced pressure. To the concentrate, water (2 mL) and 2 M-aqueous HCl solution (1 mL) were added. The precipitated solid was collected by filtration, and dried to obtain the desired compound (0.12 g, 98%) as white solid.

Step 3. Synthesis of Compound 1208: (2S,4R)-1-(2-Fluoro-4-(6-((1-(3,3,3-trifluoro-2,2-dimethylpropyl)piperidin-4-yl)methoxy)pyridin-3-yl)benzoyl)-4-hydroxypyrrolidin-2-carboxylic acid (0.12 g, 0.22 mmol), NH₄Cl (0.11 g, 2.20 mmol), HATU (0.16 g, 0.44 mmol) and DIPEA (0.07 mL, 0.44 mmol) were mixed in DMF (5 mL) at room temperature. The mixture was stirred at 80° C. for 24 h. To the reaction mixture, water was added, and the mixture was extracted with ethyl acetate. The organic layer was washed with saturated NH₄Cl aqueous solution, dried with anhydrous MgSO₄, and then concentrated under reduced pressure. The concentrate was purified by column chromatography (SiO₂, 12 g cartridge; dichloromethane/methanol=0% to 10%), and concentrated to obtain the desired compound (0.08 g, 64%) as white solid.

¹H NMR (400 MHz, CDCl₃) δ 8.57-8.57 (m, 1H), 8.12-8.11 (m, 1H), 7.67 (d, 1H, J=11.6 Hz), 7.63-7.60 (m, 1H), 7.56-7.54 (m, 1H), 7.46 (s, 0.7H,), 7.21 (s, 0.2H), 7.02 (s, 0.7H), 6.94-6.91 (m, 1H), 6.80 (s, 0.2H), 5.18 (m, 0.3H), 5.04 (d, 0.7H, J=3.2 Hz), 4.51-4.43 (m, 1H), 4.36-4.28 (m, 1H), 4.17 (d, 2H, J=6.2 Hz), 3.59-3.57 (m, 1H), 3.19-3.16 (m, 1H), 2.80 (d, 2H, J=11.0 Hz), 2.38 (s, 2H), 2.36-2.22 (m, 2H), 2.28-2.16 (m, 1H), 1.97-1.90 (m, 1H), 1.71 (d, 3H, J=11.2 Hz), 1.38-1.33 (m, 2H), 1.08 (s, 6H); MS (ESI) m/z 567.2 (M⁺+H).

Synthesis of Compound 1209: (2S,4S)-4-Fluoro-1-(4-(5-((1-((1-(trifluoromethyl)cyclobutyl)methyl)piperidin-4-yl)methoxy)pyrazin-2-yl)benzoyl)pyrrolidin-2-carboxamide

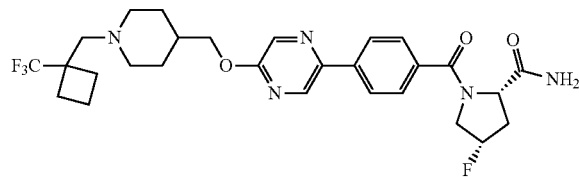 [SMILES: NC(=O)[C@@H]1C[C@H](F)CN1C(=O)c1ccc(-c2cnc(OCC3CCN(CC4(C(F)(F)F)CCC4)CC3)cn2)cc1]

Step 1. (2S,4S)-Methyl 4-fluoro-1-(4-(5-((1-((1-(trifluoromethyl)cyclobutyl)methyl)piperidin-4-yl)methoxy)pyrazin-2-yl)benzoyl)pyrrolidin-2-carboxylate: Intermediate 3 (0.10 g, 0.22 mmol), HATU (0.16 g, 0.44 mmol) and DIPEA (0.19 mL, 1.11 mmol) were mixed in DMF (3 mL) at room temperature. The mixture was added with (2S,4S)-methyl 4-fluoropyrrolidin-2-carboxylate (0.06 g, 0.44 mmol) and stirred at 60° C. for 12 h. The reaction mixture was concentrated under reduced pressure. The concentrate was purified by column chromatography (SiO₂, 12 g cartridge; methanol/dichloromethane=0% to 10%), and concentrated to obtain the desired compound (0.07 g, 54%) as pale yellow solid.

Step 2. (2S,4S)-4-fluoro-1-(4-(5-((1-((1-(trifluoromethyl)cyclobutyl)methyl)piperidin-4-yl)methoxy)pyrazin-2-yl)benzoyl)pyrrolidin-2-carboxylic acid: (2S,4S)-Methyl 4-fluoro-1-(4-(5-((1-((1-(trifluoromethyl)cyclobutyl)methyl)piperidin-4-yl)methoxy)pyrazin-2-yl)benzoyl)pyrrolidin-2-carboxylate (0.07 g, 0.12 mmol) and LiOH (0.01 g, 0.60 mmol) were mixed in THF (3 mL)/H₂O (1 mL)/methanol (1 mL) at room temperature. The mixture was stirred at the same temperature for 12 h. The reaction mixture was concentrated under reduced pressure. To the concentrate, water (10 mL) was added and stirred, followed by adding of 1 N HCl. The precipitated solid was collected by filtration, and dried to obtain the desired compound (0.06 g, 87%) as white solid.

Step 3. Synthesis of Compound 1209: (2S,4S)-4-Fluoro-1-(4-(5-((1-((1-(trifluoromethyl)cyclobutyl)methyl)piperidin-4-yl)methoxy)pyrazin-2-yl)benzoyl)pyrrolidin-2-carboxylic acid (0.06 g, 0.10 mmol), HATU (0.08 g, 0.21 mmol) and DIPEA (0.09 mL, 0.53 mmol) were mixed in DMF (5 mL) at room temperature. The mixture was added with NH₄Cl (0.02 g, 0.53 mmol), stirred at 60° C. for 12 hours, and then concentrated under reduced pressure. The concentrate was purified by column chromatography (Waters, C18, acetonitrile/0.1% TFA in water=5% to 70%), and concentrated. The obtained concentrate was dissolved in solvent, and passed through SPE cartridge (PL-HCO3 MP SPE), followed by concentrating to obtain the desire compound (0.03 g, 58%) as white solid.

¹H NMR (400 MHz, CDCl₃) δ 8.53 (s, 1H), 8.30 (s, 1H), 8.00-7.99 (m, 2H), 7.65 (d, 2H, J=8.3 Hz), 5.32-5.19 (m, 1H), 5.03-5.01 (m, 1H), 4.24 (d, 2H, J=6.3 Hz), 4.01-3.93 (m, 1H), 3.44-2.93 (m, 1H), 2.59-2.22 (m, 7H), 2.13-1.80 (m, 7H), 1.51-1.26 (m, 5H); MS (ESI) m/z 565 (M⁺+H).

Synthesis of Compound 1210: (2S,4S)-1-(4'-((1-(2-Ethyl-2-fluorobutyl)piperidin-4-yl)methoxy)-2-fluorobiphenylcarbonyl)-4-fluoropyrrolidin-2-carboxamide

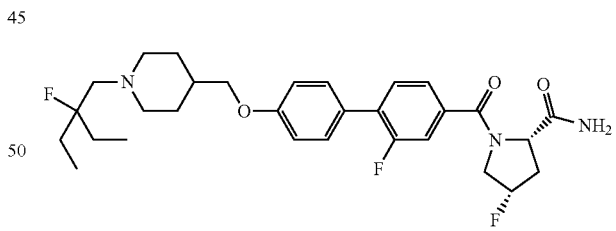

Step 1. (2S,4S)-methyl 1-(4'-((1-(2-ethyl-2-fluorobutyl)piperidin-4-yl)methoxy)-2-fluorobiphenylcarbonyl)-4-fluoropyrrolidin-2-carboxylate: Intermediate 10 (0.10 g, 0.23 mmol), (2S,4S)-methyl 4-fluoropyrrolidin-2-carboxylate (0.05 g, 0.34 mmol), HATU (0.17 g, 0.46 mmol) and DIPEA (0.08 mL, 0.46 mmol) were mixed in DMF (10 mL) at room temperature. The mixture was stirred at 50° C. for 5 h. To the reaction mixture, water was added. The mixture was extracted with dichloromethane, filtered through plastic filter attached with Na₂SO₄ cartridge to remove the solid residue and the aqueous layer, and then concentrated under reduced pressure. The concentrate was purified by column chromatography (SiO₂, 4 g cartridge; methanol/dichloromethane=0% to 15%), and concentrated to obtain the desired compound (0.10 g, 83%) as yellow oil.

Step 2. (2S,4S)-1-(4'-((1-(2-ethyl-2-fluorobutyl)piperidin-4-yl)methoxy)-2-fluorobiphenylcarbonyl)-4-fluoropyrrolidin-2-carboxylic acid: (2S,4S)-Methyl 1-(4'-((1-(2-ethyl-2-fluorobutyl)piperidin-4-yl)methoxy)-2-fluorobiphenylcarbonyl)-4-fluoropyrrolidin-2-carboxylate (0.10 g, 0.19 mmol) and LiOH.H$_2$O (0.04 g, 0.96 mmol) were mixed in THF/methanol (1:1) (8 mL)/water (1 mL) at 50° C. The mixture was stirred at the same temperature for 18 h. The reaction mixture was concentrated under reduced pressure. To the concentrate, 1M-aqueous HCl solution (20 mL) was added. The precipitated solid was collected by filtration, and dried to obtain the desired compound (0.08 g, 80%) as yellow solid.

Step 3. Synthesis of Compound 1210: (2S,4S)-1-(4'-((1-(2-Ethyl-2-fluorobutyl)piperidin-4-yl)methoxy)-2-fluorobiphenylcarbonyl)-4-fluoropyrrolidin-2-carboxylic acid (0.08 g, 0.15 mmol), ammonium chloride (0.02 g, 0.46 mmol), HATU (0.17 g, 0.46 mmol) and DIPEA (0.05 mL, 0.31 mmol) were mixed in DMF (10 mL) at room temperature. The mixture was stirred at 50° C. for 18 h. The reaction mixture was concentrated under reduced pressure. The concentrate was purified by column chromatography (Waters, C18, acetonitrile/0.1% TFA in water=5% to 70%), and concentrated. The obtained concentrate was dissolved in solvent, And passed through SPE cartridge (PL-HCO3 MP SPE), followed by concentrating to obtain the desire compound (0.01 g, 11%) as white solid.

$^1$H NMR (400 MHz, CDCl$_3$) δ 7.31-7.63 (m, 5H), 6.97 (d, 2H, J=8.8 Hz), 5.62-6.71 (m, 1H), 5.00-5.02 (m, 1H), 5.00-5.02 (m, 1H), 3.93-4.02 (m, 1H), 3.86 (d, 2H, J=5.8 Hz), 3.59-3.81 (m, 1H), 3.27-2.16 (m, 7H), 1.51-1.88 (m, 11H), 0.91 (t, 6H, J=7.5 Hz); MS (ESI) m/z 546.2 (M$^+$+H).

Synthesis of Compound 1211: (2S,4S)-1-(4'-((1-(2-Ethyl-2-fluorobutyl)piperidin-4-yl)methoxy)-3-fluorobiphenylcarbonyl)-4-fluoropyrrolidin-2-carboxamide

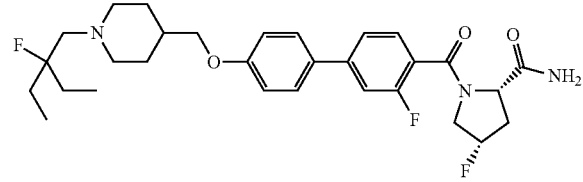 [SMILES: CCC(F)(CC)CN1CCC(COc2ccc(-c3ccc(C(=O)N4C[C@@H](F)C[C@H]4C(N)=O)c(F)c3)cc2)CC1]

Step 1. (2S,4S)-methyl 1-(4'-((1-(2-ethyl-2-fluorobutyl)piperidin-4-yl)methoxy)-3-fluorobiphenylcarbonyl)-4-fluoropyrrolidin-2-carboxylate: Intermediate 12 (0.10 g, 0.23 mmol), (2S,4S)-methyl 4-fluoropyrrolidin-2-carboxylate (0.05 g, 0.34 mmol), HATU (0.17 g, 0.46 mmol) and DIPEA (0.08 mL, 0.46 mmol) were mixed in DMF (10 mL) at room temperature. The mixture was stirred at 50° C. for 5 hours, To the reaction mixture, water was added. The mixture was extracted with dichloromethane, filtered through plastic filter attached with Na$_2$SO$_4$ cartridge to remove the solid residue and the aqueous layer, and then concentrated under reduced pressure. The concentrate was purified by column chromatography (SiO$_2$, 4 g cartridge; methanol/dichloromethane=0% to 15%), and concentrated to obtain the desired compound (0.10 g, 83%) as yellow oil.

Step 2. (2S,4S)-methyl 1-(4'-((1-(2-ethyl-2-fluorobutyl)piperidin-4-yl)methoxy)-3-fluorobiphenylcarbonyl)-4-fluoropyrrolidin-2-carboxylic acid: (2S,4S)-Methyl 1-(4'-((1-(2-ethyl-2-fluorobutyl)piperidin-4-yl)methoxy)-3-fluorobiphenylcarbonyl)-4-fluoropyrrolidin-2-carboxylate (0.12 g, 0.21 mmol) and LiOH.H$_2$O (0.05 g, 1.07 mmol) were mixed in THF/methanol (1:1) (8 mL)/water (1 mL) at 50° C. The mixture was stirred at the same temperature for 18 h. The reaction mixture was concentrated under reduced pressure. To the concentrate, 1M-aqueous HCl solution (20 mL) was added. The precipitated solid was collected by filtration, and dried to obtain the desired compound (0.09 g, 76%) as yellow solid.

Step 3. Synthesis of Compound 1211: (2S,4S)-Methyl 1-(4'-((1-(2-ethyl-2-fluorobutyl)piperidin-4-yl)methoxy)-3-fluorobiphenylcarbonyl)-4-fluoropyrrolidin-2-carboxylic acid (0.09 g, 0.16 mmol), ammonium chloride (0.02 g, 0.49 mmol), HATU (0.18 g, 0.49 mmol) and DIPEA (0.05 mL, 0.32 mmol) were mixed in DMF (10 mL) at room temperature. The mixture was stirred at 50° C. for 18 h. The reaction mixture was concentrated under reduced pressure. The concentrate was purified by column chromatography (Waters, C18, acetonitrile/0.1% TFA in water=5% to 70%), and concentrated. The obtained concentrate was dissolved in solvent, and passed through SPE cartridge (PL-HCO3 MP SPE), followed by concentrating to obtain the desire compound (14 mg, 15%) as white solid.

$^1$H NMR (400 MHz, CDCl$_3$) δ 7.27-7.51 (m, 5H), 6.97 (d, 2H, J=8.8 Hz), 6.65 (s, 1H), 5.60 (s, 1H), 5.18-5.31 (m, 1H), 4.99 (d, 2H, J=9.8 Hz), 3.81-3.90 (m, 2H), 3.59-3.72 (m, 1H), 2.88-3.10 (m, 2H), 2.54-2.70 (m, 2H), 2.15-2.42 (m, 6H), 1.54-1.96 (m, 10H), 0.90 (t, 6H, J=7.5 Hz); MS (ESI) m/z 546.3 (M$^+$+H).

Synthesis of Compound 1220: (2S,3S)-1-(2-Fluoro-4'-((1-((1-(trifluoromethyl)cyclobutyl)methyl)piperidin-4-yl)methoxy)biphenylcarbonyl)-3-hydroxypyrrolidin-2-carboxamide

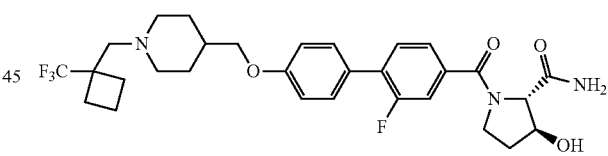

Intermediate 2 (0.15 g, 0.32 mmol), HATU (0.24 g, 0.64 mmol) and DIPEA (0.28 mL, 1.61 mmol) were mixed in DMF (10 mL). The mixture was stirred at room temperature for 20 minutes. (2S,3S)-3-hydroxypyrrolidin-2-carboxamide (0.08 g, 0.64 mmol) was added thereto. And the reaction mixture was further stirred at 60° C. for 12 hours, and then cooled to room temperature thereby to make the reaction completed. From the reaction mixture, the solvent was removed under reduced pressure. To the obtained concentrate, water was added, and the mixture was extracted with dichloromethane. The organic layer was washed with saturated NaCl aqueous solution, dried with anhydrous MgSO$_4$, filtered, and then concentrated under reduced pressure. The concentrate was purified by column chromatography (Waters, C18; acetonitrile/0.1%-trifluoroacetic acid aqueous solution=5% to 65%), and passed through SPE cartridge (PL-HCO3 MP SPE) to obtain the desire compound (0.07 g, 38%) as pale yellow solid.

¹H NMR (400 MHz, CDCl₃+CD3OD) δ 7.44-7.28 (m, 5H), 6.91-6.87 (m, 2H), 3.84-3.82 (m, 2H), 3.76-3.65 (m, 2H), 3.15-3.11 (m, 3H), 2.81-2.62 (brs, 2H), 2.37-2.29 (m, 2H), 2.25-2.15 (m, 3H), 2.11-1.69 (m, 11H); MS (ESI) m/z 578 (M⁻+H).

Synthesis of Compound 1229: (2S,3S)-1-(2'-Cyano-4'-((1-(2-ethyl-2-fluorobutyl)piperidin-4-yl)methoxy)-3-fluorobiphenylcarbonyl)-3-hydroxypyrrolidin-2-carboxamide

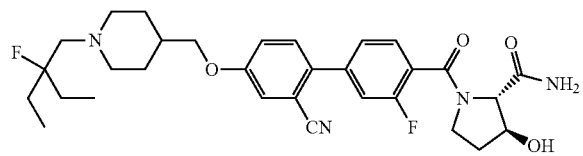 [SMILES: CCC(F)(CC)CN1CCC(COc2ccc(-c3ccc(C(=O)N4CC[C@H](O)[C@H]4C(N)=O)c(F)c3)c(C#N)c2)CC1]

Intermediate 13 (0.07 g, 0.15 mmol), (2S,3S)-3-hydropyrrolidin-2-carboxamide (0.03 g, 0.23 mmol), HATU (0.17 g, 0.46 mmol) and DIPEA (0.04 g, 0.30 mmol) were mixed in DMF (4 mL) at room temperature. The mixture was stirred at 50° C. for 18 h. To the reaction mixture, water was added, and the mixture was extracted with ethyl acetate. The organic layer was washed with saturated NaCl aqueous solution, dried with anhydrous MgSO₄, and then concentrated under reduced pressure. The concentrate was purified by column chromatography (Waters, C18, acetonitrile/0.1% TFA in water=5% to 70%), and concentrated to obtain the desired compound (0.05 g, 55%) as yellow oil.

¹H NMR (400 MHz, CDCl₃) δ 7.55 (t, 1H, J=7.5 Hz), 7.33-7.43 (m, 2H), 7.24-7.26 (m, 1H), 7.20-7.21 (m, 1H), 7.12-7.17 (m, 1H), 6.31 (s, 1H), 4.62-4.64 (m, 2H), 3.84 (d, 2H, J=6.1 Hz), 3.63-3.67 (m, 2H), 3.10-3.13 (m, 2H), 2.67-2.69 (m, 3H), 2.13-2.23 (m, 4H), 2.01-2.08 (m, 1H), 1.91-1.94 (m, 3H), 1.79-1.82 (m, 4H), 1.71-1.75 (m, 2H), 0.89 (t, 6H, J=7.5 Hz); MS (ESI) m/z 569.2 (M⁺+H).

Synthesis of Compound 1235: (2S,3S)-1-(3-Fluoro-4-(6-((1-((1-(trifluoromethyl)cyclobutyl)methyl)piperidin-4-yl)methoxy)pyridin-3-yl)benzoyl)-3-hydroxypyrrolidin-2-carboxamide

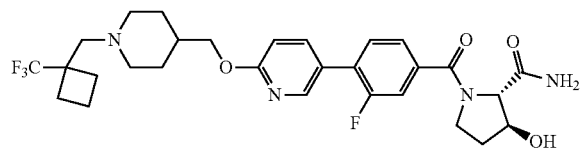 [SMILES: NC(=O)[C@@H]1[C@@H](O)CCN1C(=O)c1ccc(-c2ccc(OCC3CCN(CC4(C(F)(F)F)CCC4)CC3)nc2)c(F)c1]

Intermediate 5 (0.07 g, 0.15 mmol), EDC (0.05 g, 0.30 mmol), HOBt (0.04 g, 0.30 mmol) and DIPEA (0.13 mL, 0.75 mmol) were mixed in DMF (2 mL). The mixture was stirred at room temperature for 30 minutes. (2S,3S)-3-Hydroxypyrrolidin-2-carboxamide (0.03 g, 0.30 mmol) was added thereto. And the reaction mixture was further stirred at 60° C. for 12 hours, and then cooled to room temperature thereby to make the reaction completed. From the reaction mixture, the solvent was removed under reduced pressure. To the obtained concentrate, water was added. The mixture was extracted with dichloromethane, filtered through plastic filter attached with anhydrous Na₂SO₄ cartridge to remove the solid residue and the aqueous layer, and then concentrated under reduced pressure. The concentrate was purified by column chromatography (Waters, C18; acetonitrile/0.1%-trifluoroacetic acid aqueous solution=0% to 65%), and passed through SPE cartridge (PL-HCO3 MP SPE), followed by concentrating to obtain the desire compound (0.04 g, 56%) as white solid.

¹H NMR (400 MHz, CD₃OD) δ 8.38-8.36 (m, 1H), 7.95-7.93 (m, 1H), 7.62-7.51 (m, 3H), 6.95-6.93 (m, 1H), 4.48-4.23 (m, 3H), 3.76-3.73 (m, 2H), 3.65-3.61 (m, 3H), 3.23-3.21 (m, 2H), 2.51-2.47 (m, 2H), 2.32-2.12 (m, 13H); MS (ESI) m/z 579 (M⁺+H).

Synthesis of Compound 1238: (S)-1-(4-(6-((1-(2,2-Difluorobutyl)piperidin-4-yl)methoxy)pyridin-3-yl)-2-fluorobenzoyl)pyrrolidin-2-carboxamide

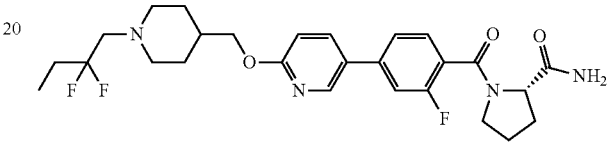

Intermediate 20 (0.04 g, 0.09 mmol), (S)-pyrrolidin-2-carboxamide (0.02 g, 0.18 mmol), EDC (0.03 g, 0.18 mmol), HOBt (0.02 g, 0.18 mmol) and DIPEA (0.03 mL, 0.18 mmol) were dissolved in dichloromethane (1 mL) at room temperature. The solution was stirred at the same temperature for 12 hours. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 4 g cartridge; methanol/dichloromethane=0% to 10%), and concentrated to obtain the desired compound (0.03 g, 73%) as white solid.

¹H NMR (400 MHz, CDCl₃) δ 8.38-8.37 (m, 1H), 7.80-7.77 (m, 1H), 7.54-7.50 (m, 1H), 7.41-7.39 (m, 1H), 7.31-7.28 (m, 1H), 6.93 (brs, 1H), 6.85 (d, 1H, J=8.6 Hz), 5.59 (brs, 1H), 4.84-4.81 (m, 1H), 4.21 (d, 2H, J=6.1 Hz), 3.58-3.52 (m, 1H), 3.47-3.41 (m, 1H), 3.06-3.03 (m, 2H), 2.79-2.72 (m, 2H), 2.50-2.46 (m, 1H), 2.32 (brs, 2H), 2.16-1.83 (m, 8H), 1.51-1.26 (m, 2H), 1.05-1.01 (m, 3H); MS (ESI) m/z 567.2 (M⁺+H).

Synthesis of Compound 1239: (S)-1-(3-Fluoro-4'-((1-(2,2,3,3,3-pentafluoropropyl)piperidin-4-yl)methoxy)biphenylcarbonyl)pyrrolidin-2-carboxamide

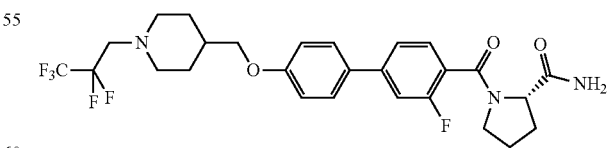

Intermediate 21 (0.05 g, 0.10 mmol), (S)-pyrrolidin-2-carboxamide (25 mg, 0.21 mmol), HATU (0.08 g, 0.21 mmol) and DIPEA (0.03 mL, 0.21 mmol) were dissolved in DMF (4 mL) at room temperature. The solution was stirred at 80° C. for 12 hours, and then cooled to room temperature thereby to make the reaction completed. To the reaction mixture, saturated ammonium chloride aqueous solution was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 4 g cartridge; ethyl acetate/hexane=5% to 50%), and concentrated to obtain the desired compound (24 mg, 39%) as white solid.

¹H NMR (400 MHz, CDCl₃) δ 7.54-7.41 (m, 4H), 7.32-7.29 (m, 1H), 7.00-6.95 (m, 3H), 5.52 (m, 1H), 4.84 (m, 1H), 3.88 (m, 2H), 3.55 (m, 1H), 3.45 (m, 1H), 3.11 (m, 4H), 2.50-2.46 (m, 3H), 2.13-2.06 (m, 2H), 1.93-1.89 (m, 4H), 1.80-1.52 (m, 2H); MS (ESI) m/z 558.2 (M⁺+H).

Synthesis of Compound 1240: (2S,4R)-1-(2',3-Difluoro-4'-((1-(3,3,3-trifluoro-2,2-dimethylpropyl)piperidin-4-yl)methoxy)biphenylcarbonyl)-4-hydroxypyrrolidin-2-carboxamide

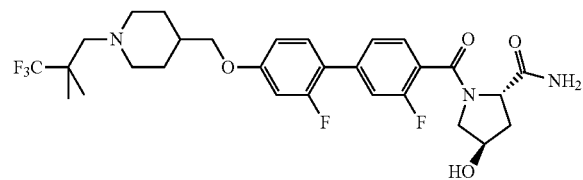 [SMILES: CC(C)(CN1CCC(COc2ccc(-c3ccc(C(=O)N4C[C@H](O)C[C@H]4C(N)=O)c(F)c3)c(F)c2)CC1)C(F)(F)F]

Step 1. (2S,4R)-methyl 1-(2',3-difluoro-4'-((1-(3,3,3-trifluoro-2,2-dimethylpropyl)piperidin-4-yl)methoxy)biphenyl carbonyl)-4-hydroxypyrrolidin-2-carboxylate: Intermediate 18 (0.20 g, 0.42 mmol), (2S,4R)-methyl 4-hydroxypyrrolidin-2-carboxylate hydrochloride (0.15 g, 0.84 mmol), EDC (0.16 g, 0.84 mmol), HOBt (0.11 g, 0.84 mmol) and DIPEA (0.15 mL, 0.84 mmol) were dissolved in dichloromethane (5 mL) at room temperature. The solution was stirred at the same temperature for 12 hours. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 12 g cartridge; methanol/dichloromethane=0% to 10%), and concentrated to obtain the desired compound (0.14 g, 55%) as white solid.

Step 2. (2S,4R)-Methyl 1-(2',3-difluoro-4'-((1-(3,3,3-trifluoro-2,2-dimethylpropyl)piperidin-4-yl)methoxy)biphenyl carbonyl)-4-hydroxypyrrolidin-2-carboxylate (0.14 g, 0.23 mmol) was dissolved in tetrahydrofuran (6 mL)/methanol (6 mL)/water (3 mL) at room temperature. To the solution, LiOH.H₂O (0.05 g, 1.18 mmol) was added, followed by stirring at the same temperature for 1 hour. From the reaction mixture, the solvent was removed under reduced pressure. The obtained product was used without further purification (0.11 g, 79%, white solid).

Step 3. Synthesis of Compound 1240: (2S,4R)-1-(2',3-Difluoro-4'-((1-(3,3,3-trifluoro-2,2-dimethylpropyl)piperidin-4-yl)methoxy)biphenylcarbonyl)-4-hydroxypyrrolidin-2-carboxylic acid (0.11 g, 0.18 mmol), NH₄Cl (0.02 g, 0.37 mmol), HATU (0.14 g, 0.37 mmol) and DIPEA (0.06 mL, 0.37 mmol) were dissolved in DMF (10 mL) at 80° C. The solution was stirred at the same temperature for 14 hours, and then cooled to room temperature thereby to make the reaction completed. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 12 g cartridge; methanol/dichloromethane=0% to 10%), and concentrated to obtain the desired compound (0.02 g, 18%) as white solid.

¹H NMR (400 MHz, CDCl₃) δ 7.55-7.41 (m, 1H), 7.38-7.28 (m, 3H), 7.13 (brs, 1H), 6.79-6.70 (m, 2H), 5.72-5.69 (m, 1H), 5.00-4.97 (m, 1H), 4.52 (s, 1H), 3.83 (d, 2H, J=5.5 Hz), 3.80-3.69 (m, 1H), 3.48-3.45 (m, 1H), 2.90-2.84 (m, 1H), 2.67-2.59 (m, 1H), 2.42 (s, 1H), 2.38-2.26 (m, 3H), 1.80-1.62 (m, 5H), 1.43-1.40 (m, 2H), 1.30 (s, 1H), 1.13 (s, 6H); MS (ESI) m/z 584.2 (M⁺+H).

Synthesis of Compound 1241: (2S,4R)-1-(4-(6-((1-(2,2-Difluorobutyl)piperidin-4-yl)methoxy)pyridin-3-yl)-2-fluorobenzoyl)-4-hydroxypyrrolidin-2-carboxamide

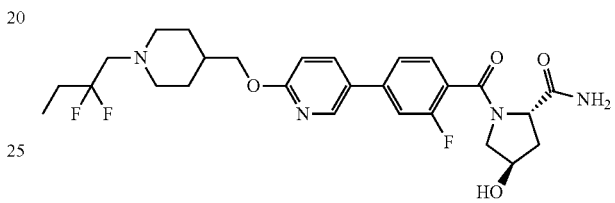

Step 1. (2S,4R)-methyl 1-(4-(6-((1-(2,2-difluorobutyl)piperidin-4-yl)methoxy)pyridin-3-yl)-2-fluorobenzoyl)-4-hydroxypyrrolidin-2-carboxylate: Intermediate 20 (0.13 g, 0.32 mmol), (2S,4R)-methyl 4-hydroxypyrrolidin-2-carboxylate hydrochloride (0.11 g, 0.63 mmol), EDC (0.12 g, 0.63 mmol), HOBt (0.08 g, 0.63 mmol) and DIPEA (0.11 mL, 0.63 mmol) were dissolved in dichloromethane (3 mL) at room temperature. The solution was stirred at the same temperature for 12 hours. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 12 g cartridge; methanol/dichloromethane=0% to 10%), and concentrated to obtain the desired compound (0.11 g, 66%) as white solid.

Step 2. (2S,4R)-1-(4-(6-((1-(2,2-difluorobutyl)piperidin-4-yl)methoxy)pyridin-3-yl)-2-fluorobenzoyl)-4-hydroxy-pyrrolidin-2-carboxylic acid: (2S,4R)-Methyl 1-(4-(6-((1-(2,2-difluorobutyl)piperidin-4-yl)methoxy)pyridin-3-yl)-2-fluorobenzoyl)-4-hydroxypyrrolidin-2-carboxylate (0.11 g, 0.20 mmol) was dissolved in tetrahydrofuran (6 mL)/methanol (6 mL)/water (3 mL) at room temperature. To the solution, LiOH.H₂O (0.04 g, 1.00 mmol) was added, followed by stirring at the same temperature for 1 hour. From the reaction mixture, the solvent was removed under reduced pressure. The obtained product was used without further purification (0.08 g, 74%, white solid).

Step 3. Synthesis of Compound 1241: (2S,4R)-1-(4-(6-((1-(2,2-Difluorobutyl)piperidin-4-yl)methoxy)pyridin-3-yl)-2-fluorobenzoyl)-4-hydroxypyrrolidin-2-carboxylic acid (0.08 g, 0.14 mmol), NH₄Cl (0.01 g, 0.29 mmol), HATU (0.11 g, 0.29 mmol) and DIPEA (0.05 mL, 0.29 mmol) were dissolved in DMF (10 mL) at 80° C. The solution was stirred at the same temperature for 14 hours, and then cooled to room temperature thereby to make the reaction completed. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 12 g cartridge; methanol/dichloromethane=0% to 10%), and concentrated to obtain the desired compound (0.02 g, 26%) as white solid.

¹H NMR (400 MHz, CDCl₃) δ 8.46-8.42 (m, 1H), 8.03-8.00 (m, 1H), 7.62-7.48 (m, 3H), 6.93-6.89 (m, 1H), 4.76-4.72 (m, 0.8H), 4.45-4.44 (m, 1.2H), 4.21-4.18 (m, 2H), 3.79-3.75 (m, 1H), 3.39-3.36 (m, 1H), 3.04-3.01 (m, 2H), 2.76-2.68 (m, 2H), 2.37-2.35 (m, 1H), 2.29-2.14 (m, 3H), 2.02-1.91 (m, 2H), 1.83-1.80 (m, 3H), 1.47-1.44 (m, 2H), 1.04-1.00 (m, 3H); MS (ESI) 535.1 m/z (M⁺+H).

Synthesis of Compound 1244: (2S,3S)-1-(4'-((1-(2-Ethyl-2-fluorobutyl)piperidin-4-yl)methoxy)-3,3'-difluorobiphenylcarbonyl)-3-hydroxypyrrolidin-2-carboxamide

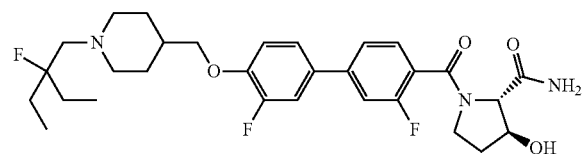 [SMILES: CCC(F)(CC)CN1CCC(COc2ccc(-c3ccc(C(=O)N4CC[C@H](O)[C@H]4C(N)=O)c(F)c3)cc2F)CC1]

Intermediate 15 (0.17 g, 0.37 mmol), EDC (0.14 g, 0.75 mmol), HOBt (0.10 g, 0.75 mmol) and DIPEA (0.14 g, 1.13 mmol) were dissolved in dichloromethane (2 mL) at room temperature. To the solution, (2S,3S)-3-hydroxypyrrolidine-2-carboxamide (0.07 g, 0.56 mmol) was added, followed by stirring at the same temperature for 16 hours. To the reaction mixture, saturated ammonium chloride aqueous solution was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 12 g cartridge; methanol/dichloromethane=2% to 10%), and concentrated to obtain the desired compound (0.08 g, 37%) as white solid.

¹H NMR (400 MHz, CD₃OD) δ 7.53 (m, 1H), 7.46 (m, 4H), 7.17 (m, 1H), 4.49-4.23 (m, 2H), 3.97 (m, 2H), 3.90 (m, 1H), 3.09 (m, 2H), 2.58 (m, 2H), 2.23 (m, 3H), 1.77 (m, 4H), 1.69 (m, 4H), 1.53 (m, 2H), 1.38 (m, 2H), 0.92 (t, 6H, J=7.5 Hz); MS (ESI) 562.3 m/z (M⁺+H).

Synthesis of Compound 1245: (2S,3S)-1-(4'-((1-(2-Ethyl-2-fluorobutyl)piperidin-4-yl)methoxy)-2'-fluorobiphenylcarbonyl)-3-hydroxypyrrolidin-2-carboxamide

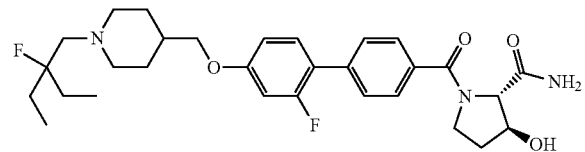 [SMILES: CCC(F)(CC)CN1CCC(COc2ccc(-c3ccc(C(=O)N4CC[C@H](O)[C@H]4C(N)=O)cc3)c(F)c2)CC1]

Intermediate 16 (0.13 g, 0.30 mmol), EDC (0.11 g, 0.60 mmol), HOBt (0.08 g, 0.60 mmol) and DIPEA (0.11 g, 0.90 mmol) were dissolved in dichloromethane (2 mL) at room temperature. To the solution, (2S,3S)-3-hydroxylpyrrolidine-2-carboxamide (0.05 g, 0.45 mmol) was added, followed by stirring at the same temperature for 16 hours. To the reaction mixture, saturated ammonium chloride aqueous solution was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 12 g cartridge; methanol/dichloromethane=2% to 10%), and concentrated to obtain the desired compound (0.07 g, 42%) as white solid.

¹H NMR (400 MHz, CD₃OD) δ 7.64 (m, 4H), 7.41 (m, 2H), 6.82 (m, 1H), 4.60-4.21 (m, 2H), 3.86 (m, 3H), 3.73 (m, 2H), 3.05 (m, 2H), 2.54-2.48 (m, 2H), 2.17 (m, 3H), 1.77-1.64 (m, 8H), 1.43 (m, 2H), 1.35 (m, 2H), 0.89 (t, 6H, J=7.5 Hz); MS (ESI) 544.2 m/z (M⁺+H).

Synthesis of Compound 1249: (2S,3S)-1-(2-Fluoro-4-(5-((1-((1-(trifluoromethyl)cyclobutyl)methyl)piperidin-4-yl)methoxy)pyrazin-2-yl)benzoyl)-3-hydroxypyrrolidin-2-carboxamide

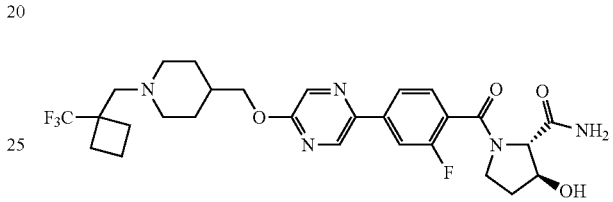

Intermediate 4 (0.06 g, 0.12 mmol), EDC (0.04 g, 0.25 mmol), HOBt (0.03 g, 0.25 mmol) and DIPEA (0.11 mL, 0.64 mmol) were mixed in DMF (5 mL). The mixture was stirred at room temperature for 30 minutes. (2S,3S)-3-Hydroxypyrrolidin-2-carboxamide (0.03 g, 0.25 mmol) was added thereto. And the reaction mixture was further stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.04 g, 56%) as white solid.

¹H NMR (400 MHz, CDCl₃) δ 8.48 (m, 1H), 8.24 (m, 1H), 7.74-7.70 (m, 2H), 7.55-7.51 (m, 1H), 4.53-4.51 (m, 2H), 4.26-4.24 (m, 3H), 3.62-3.48 (m, 6H), 2.81-2.78 (m, 5H), 2.40-1.82 (m, 9H); MS (ESI) m/z 580 (M⁺+H).

Synthesis of Compound 1253: (2S,3S)-1-(3-Fluoro-4-(5-((1-((1-(trifluoromethyl)cyclobutyl)methyl)piperidin-4-yl)methoxy)pyrazin-2-yl)benzoyl)-3-hydroxypyrrolidin-2-carboxamide

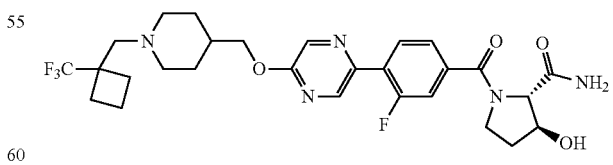

Intermediate 7 (0.05 g, 0.10 mmol), EDC (0.04 g, 0.21 mmol), HOBt (0.02 g, 0.21 mmol) and DIPEA (0.09 mL, 0.53 mmol) were mixed in DMF (5 mL). The solution was stirred at room temperature for 30 minutes. (2S,3S)-3-Hydroxypyrrolidin-2-carboxamide (0.02 g, 0.21 mmol) was added thereto. And the reaction mixture was further stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.03 g, 48%) as white solid.

$^1$H NMR (400 MHz, CD$_3$OD) δ 8.64 (m, 1H), 8.36-8.35 (m, 1H), 8.07-8.05 (m, 1H), 7.58-7.53 (m, 2H), 4.67-4.45 (m, 3H), 4.32 (d, 2H, J=6.0 Hz), 3.76-3.73 (m, 1H), 3.21 (m, 2H), 3.04-3.01 (m, 2H), 2.75-2.45 (m, 2H), 2.34-2.32 (m, 2H), 2.24-2.17 (m, 3H), 2.06-1.94 (m, 6H), 1.63-1.60 (m, 2H); MS (ESI) m/z 580.3 (M$^+$+H).

Synthesis of Compound 1255: (2S,4R)-1-(2-Fluoro-4'-((1-((1-trifluoromethyl)cyclobutyl)methyl)piperidin-4-yl)methoxy)biphenylcarbonyl)-4-hydroxypyrrolidin-2-carboxamide

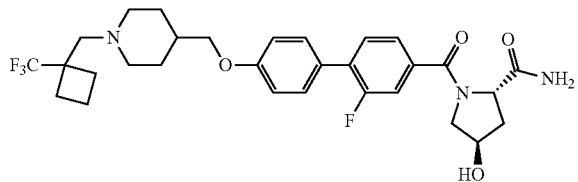

Step 1. (2S,4R)-Methyl 1-(2-fluoro-4'-((1-((1-(trifluoromethyl)cyclobutyl)methyl)piperidin-4-yl)methoxy)biphenyl carbonyl)-4-hydroxypyrrolidin-2-carboxylate: Intermediate 2 (0.07 g, 0.15 mmol), EDC (0.05 g, 0.30 mmol), HOBt (0.04 g, 0.30 mmol) and DIPEA (0.13 mL, 0.75 mmol) were mixed in DMF (5 mL). The mixture was stirred at room temperature for 30 minutes. (2S,4R)-Methyl 4-hydroxypyrrolidin-2-carboxylate hydrochloride (0.05 g, 0.30 mmol) was added thereto. And the reaction mixture was further stirred at 60° C. for 12 hours, and then cooled to room temperature thereby to make the reaction completed. From the reaction mixture, the solvent was removed under reduced pressure. The concentrate was purified by column chromatography (SiO$_2$, 12 g cartridge; methanol/dichloromethane=0% to 10%), and concentrated to obtain the desired compound (0.06 g, 67%) as white solid.

Step 2. (2S,4R)-1-(2-fluoro-4'-((1-((1-(trifluoromethyl)cyclobutyl)methyl)piperidin-4-yl)methoxy)biphenylcarbonyl)-4-hydroxypyrrolidin-2-carboxylic acid: (2S,4R)-Methyl 1-(2-fluoro-4'-((1-((1-(trifluoromethyl)cyclobutyl)methyl)piperidin-4-yl)methoxy)biphenyl carbonyl)-4-hydroxypyrrolidin-2-carboxylate (0.06 g, 0.10 mmol) were mixed in THF (3 mL)/H$_2$O (1 mL)/methanol (1 mL). The mixture was stirred at room temperature for 30 minutes. LiOH (0.01 g, 0.50 mmol) was added thereto. And the reaction mixture was further stirred at 60° C. for 12 hours, and then cooled to room temperature thereby to make the reaction completed. From the reaction mixture, the solvent was removed under reduced pressure. The obtained product was used without further purification (0.03 g, 54%, white solid).

Step 3. Synthesis of Compound 1255: (2S,4R)-1-(2-Fluoro-4'-((1-((1-(trifluoromethyl)cyclobutyl)methyl)piperidin-4-yl)methoxy)biphenyl carbonyl)-4-hydroxypyrrolidin-2-carboxylic acid (0.03 g, 0.05 mmol), EDC (0.02 g, 0.11 mmol), HOBt (0.01 g, 0.11 mmol) and DIPEA (0.04 mL, 0.27 mmol) were mixed in DMF (5 mL). The mixture was stirred at room temperature for 30 hours, and NH$_4$Cl (0.01 g, 0.27 mmol) was added thereto. And the reaction mixture was further stirred at 60° C. for 12 hours, and then cooled to room temperature thereby to make the reaction completed. From the reaction mixture, the solvent was removed under reduced pressure. To the obtained concentrate, water was added, and the mixture was extracted with dichloromethane. The organic layer was washed with saturated NaCl aqueous solution, dried with anhydrous MgSO$_4$, filtered, and then concentrated under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.01 g, 37%) as white solid.

$^1$H NMR (400 MHz, CD$_3$OD) δ 7.60-7.48 (m, 5H), 7.36-7.28 (m, 2H), 5.07-4.91 (m, 3H), 4.77-4.44 (m, 1H), 3.93-3.83 (m, 3H), 3.78-3.66 (m, 1H), 3.20-3.13 (m, 2H), 2.41-2.13 (m, 8H), 1.99-1.97 (m, 2H), 1.91-1.68 (m, 5H); MS (ESI) m/z 578.1 (M$^+$+H).

Synthesis of Compound 1256: (2S,4R)-1-(3-Fluoro-4'-((1-(2,2,3,3,3-pentafluoropropyl)piperidin-4-yl)methoxy)biphenylcarbonyl)-4-hydroxypyrrolidin-2-carboxamide

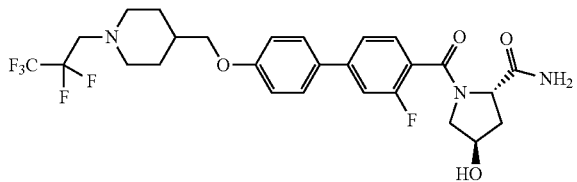

Step 1. (2S,4R)-methyl 1-(3-fluoro-4'-((1-(2,2,3,3,3-pentafluoropropyl)piperidin-4-yl)methoxy)biphenylcarbonyl)-4-hydroxypyrrolidin-2-carboxylate: Intermediate 21 (0.10 g, 0.21 mmol), (2S,4R)-methyl 4-hydroxypyrrolidin-2-carboxylate hydrochloride (79 mg, 0.43 mmol), HATU (0.16 g, 0.43 mmol) and DIPEA (0.07 mL, 0.43 mmol) were dissolved in DMF (4 mL) at room temperature. The solution was stirred at 60° C. for 12 hours, and then cooled to room temperature thereby to make the reaction completed. To the reaction mixture, saturated ammonium chloride aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; ethyl acetate/hexane=5% to 30%), and concentrated to obtain the desired compound (0.12 g, 94%) as colorless oil.

Step 2. (2S,4R)-1-(3-fluoro-4'-((1-(2,2,3,3,3-pentafluoropropyl)piperidin-4-yl)methoxy)biphenylcarbonyl)-4-hydroxypyrrolidin-2-carboxylic acid: (2S,4R)-Methyl 1-(3-fluoro-4'-((1-(2,2,3,3,3-pentafluoropropyl)piperidin-4-yl)methoxy)biphenylcarbonyl)-4-hydroxypyrrolidin-2-carboxylate (0.12 g, 0.20 mmol) and LiOH.H$_2$O (17 mg, 0.40 mmol) were dissolved in tetrahydrofuran (25 mL)/water (10 mL) at room temperature. The solution was stirred at 50° C. for 12 h. The reaction mixture was cooled to room temperature thereby to make the reaction completed. From the reaction mixture, the solvent was removed under reduced pressure. The obtained product was used without further purification (0.11 g, 93%, white solid).

Step 3. Synthesis of Compound 1256: (2S,4R)-1-(3-Fluoro-4'-((1-(2,2,3,3,3-pentafluoropropyl)piperidin-4-yl)methoxy)biphenylcarbonyl)-4-hydroxypyrrolidin-2-carboxylic acid (0.11 g, 0.19 mmol), ammonium chloride (0.02 g, 0.38 mmol), EDC (0.05 g, 0.28 mmol), HOBt (39 mg, 0.28 mmol) and DIPEA (0.04 g, 0.38 mmol) were dissolved in DMF (8 mL) at room temperature. The solution was stirred at 60° C. for 14 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and concentrated to obtain the desired compound (0.03 g, 27%) as white solid.

$^1$H NMR (400 MHz, CDCl$_3$+CD$_3$OD) δ 7.48-7.44 (m, 3H), 7.36-7.33 (m, 1H), 7.29-7.22 (m, 1H), 6.92-6.89 (m, 2H), 4.73 (m, 1H), 4.37 (m, 1H), 3.82 (m, 2H), 3.67 (m, 2H), 3.33-3.29 (m, 6H), 2.77 (m, 2H), 2.26 (m, 2H), 1.89-1.86 (m, 3H); MS (ESI) m/z 574.1 (M$^+$+H).

Synthesis of Compound 1257: (2S,4R)-1-(4-(5-((1-(2-Ethyl-2-fluorobutyl)piperidin-4-yl)methoxy)pyrimidin-2-yl)-2-fluorobenzoyl)-4-hydroxypyrrolidin-2-carboxamide

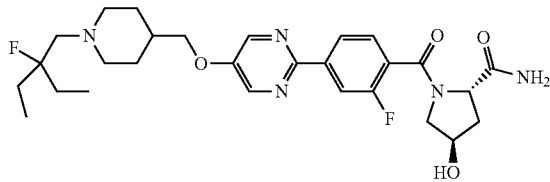 [SMILES: CCC(F)(CC)CN1CCC(COc2cnc(-c3ccc(C(=O)N4C[C@H](O)C[C@H]4C(N)=O)c(F)c3)nc2)CC1]

Step 1. (2S,4R)-methyl 1-(4-(5-((1-(2-ethyl-2-fluorobutyl)piperidin-4-yl)methoxy)pyrimidin-2-yl)-2-fluorobenzoyl)-4-hydroxypyrrolidin-2-carboxylate: Intermediate 14 (0.30 g, 0.69 mmol), (2S,4R)-methyl 4-hydroxypyrrolidin-2-carboxylate hydrochloride (0.18 g, 1.03 mmol), HOBt (0.18 g, 1.38 mmol), EDC (0.26 g, 1.38 mmol) and DIPEA (0.24 mL, 1.38 mmol) were dissolved in dichloromethane (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; methanol/dichloromethane=0% to 15%), and concentrated to obtain the desired compound (0.26 g, 67%) as white solid.

Step 2. (2S,4R)-1-(4-(5-((1-(2-ethyl2-fluorobutyl)piperidin-4-yl)methoxy)pyrimidin-2-yl)-2-fluorobenzoyl)-4-hydroxypyrrolidin-2-carboxylic acid: (2S,4R)-Methyl 1-(4-(5-((1-(2-ethyl-2-fluorobutyl)piperidin-4-yl)methoxy)pyrimidin-2-yl)-2-fluorobenzoyl)-4-hydroxypyrrolidin-2-carboxylate (0.26 g, 0.46 mmol) and LiOH (0.05 g, 2.31 mmol) were dissolved in tetrahydrofuran (8 mL)/methanol (8 mL)/water (2 mL) at room temperature. The solution was stirred at the same temperature for 18 hours. From the reaction mixture, the solvent was removed under reduced pressure. The obtained product was used without further purification (0.24 g, 94%, yellow oil).

Step 3. Synthesis of Compound 1257: (2S,4R)-1-(4-(5-((1-(2-Ethyl2-fluorobutyl)piperidin-4-yl)methoxy)pyrimidin-2-yl)-2-fluorobenzoyl)-4-hydroxypyrrolidin-2-carboxylic acid (0.30 g, 0.54 mmol), ammonium chloride (0.08 g, 1.64 mmol), HOBt (0.14 g, 1.09 mmol), EDC (0.21 g, 1.09 mmol) and DIPEA (0.18 mL, 1.09 mmol) were dissolved in dichloromethane (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; methanol/dichloromethane=0% to 10%), and concentrated to obtain the desired compound (0.10 g, 33%) as yellow solid.

$^1$H NMR (400 MHz, CDCl$_3$) δ 8.57-8.59 (m, 2H), 8.14-8.28 (m, 2H), 7.41-7.65 (m, 1H), 4.72-4.76 (m, 1H), 4.43-4.44 (m, 1H), 4.04-4.07 (m, 2H), 3.76-3.79 (m, 1H), 3.33-3.38 (m, 4H), 3.03-3.06 (m, 2H), 2.46-2.52 (m, 2H), 2.34-2.36 (m, 1H), 2.13-2.19 (m, 3H), 1.81-1.84 (m, 3H), 1.66-1.75 (m, 4H), 1.47-1.51 (m, 2H), 0.92 (t, 6H, J=7.5 Hz); MS (ESI) m/z 546.2 (M$^+$+H).

Synthesis of Compound 1258: (2S,4R)-1-(2-Fluoro-4'-((1-((1-(trifluoromethyl)cyclobutyl)methyl)piperidin-4-yl)methoxy)biphenylcarbonyl)-4-hydroxy-2-methylpyrrolidin-2-carboxamide

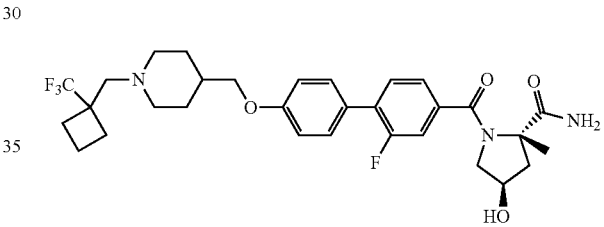

Step 1. (2S,4R)-methyl 1-(2-fluoro-4'-((1-((1-(trifluoromethyl)cyclobutyl)methyl)piperidin-4-yl)methoxy)biphenylcarbonyl)-4-hydroxy-2-methylpyrrolidin-2-carboxylate: Intermediate 2 (0.20 g, 0.43 mmol), Intermediate 25 (0.10 g, 0.51 mmol), EDC (0.16 g, 0.85 mmol), HOBt (0.11 g, 0.85 mmol) and DIPEA (0.16 g, 1.28 mmol) were dissolved in dichloromethane (6 mL) at room temperature. The solution was stirred at the same temperature for 8 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/dichloromethane=0% to 5%), and concentrated to obtain the desired compound (0.19 g, 72%) as white solid.

Step 2. (2S,4R)-1-(2-fluoro-4'-((1-((1-(trifluoromethyl)cyclobutyl)methyl)piperidin-4-yl)methoxy)biphenylcarbonyl)-4-hydroxy-2-methylpyrrolidin-2-carboxylic acid: (2S,4R)-Methyl 1-(2-fluoro-4'-((1-((1-(trifluoromethyl)cyclobutyl)methyl)piperidin-4-yl)methoxy)biphenylcarbonyl)-4-hydroxy-2-methylpyrrolidin-2-carboxylate (0.19 g, 0.31 mmol) and LiOH.H$_2$O (0.02 g, 0.62 mmol) were dissolved in tetrahydrofuran (10 mL)/methanol (5 mL)/water (3 mL) at room temperature. The solution was stirred at 50° C. for 8 hours, and then cooled to room temperature thereby to make the reaction completed. From the reaction mixture, the solvent was removed under reduced pressure. To the concentrate, a small amount of 12N-aqueous HCl solution was added and stirred. The precipitated solid was collected by filtration, washed with ethyl acetate and dried to obtain the desired compound (0.15 g, 80%) as white solid.

Step 3. Synthesis of Compound 1258: (2S,4R)-1-(2-Fluoro-4'-((1-((1-(trifluoromethyl)cyclobutyl)methyl)piperidin-4-yl)methoxy)biphenylcarbonyl)-4-hydroxy-2-methylpyrrolidin-2-carboxylic acid (0.15 g, 0.25 mmol), NH₄Cl (0.04 g, 0.75 mmol), EDC (0.09 g, 0.50 mmol), HOBt (0.06 g, 0.50 mmol) and DIPEA (0.09 g, 0.75 mmol) were dissolved in DMF (2 mL) at room temperature. The solution was stirred at 70° C. for 2 hours, and then cooled to room temperature thereby to make the reaction completed. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 4 g cartridge; methanol/dichloromethane=0% to 10%), and concentrated to obtain the desired compound (0.09 g, 63%) as white solid.

$^1$H NMR (400 MHz, CD₃OD) δ 7.53 (m, 3H), 7.42 (m, 2H), 7.03 (d, 2H, J=8.8 Hz), 4.61 (s, 1H), 4.45 (m, 1H), 3.90-3.85 (m, 3H), 3.57 (m, 1H), 2.95-2.92 (m, 2H), 2.58 (s, 2H), 2.46 (dd, 1H, J=12.8, 5.0 Hz), 2.24 (m, 4H), 2.15-1.89 (s, 3H), 1.82 (m, 3H), 1.46 (m, 3H); MS (ESI) m/z 592.2 (M⁺+H).

Synthesis of Compound 1259: (S)-1-(3'-Cyano-3-fluoro-4'-((1-(2-fluoro-2-methylpropyl)piperidin-4-yl)methoxy)biphenylcarbonyl)-2-methylpyrrolidin-2-carboxamide

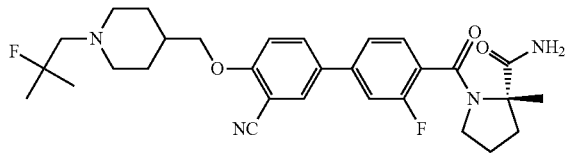 [SMILES: CC(C)(F)CN1CCC(COc2ccc(-c3ccc(C(=O)N4CCC[C@@]4(C)C(N)=O)c(F)c3)cc2C#N)CC1]

Step 1. (S)-methyl 1-(3'-cyano-3-fluoro-4'-((1-(2-fluoro-2-methylpropyl)piperidin-4-yl)methoxy)biphenylcarbonyl)-2-methylpyrrolidin-2-carboxylate: Intermediate 9 (0.25 g, 0.58 mmol), (S)-methyl 2-methylpyrrolidin-2-carboxylate hydrochloride (0.21 g, 1.16 mmol), HOBt (0.15 g, 1.16 mmol), EDC (0.22 g, 1.16 mmol) and DIPEA (0.15 g, 1.16 mmol) were dissolved in dichloromethane (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 4 g cartridge; methanol/dichloromethane=0% to 15%), and concentrated to obtain the desired compound (0.22 g, 68%) as white solid.

Step 2. (S)-1-(3'-cyano-3-fluoro-4'-((1-(2-fluoro-2-methylpropyl)piperidin-4-yl)methoxy)biphenylcarbonyl)-2-methylpyrrolidin-2-carboxylic acid: (S)-Methyl 1-(3'-cyano-3-fluoro-4'-((1-(2-fluoro-2-methylpropyl)piperidin-4-yl)methoxy)biphenylcarbonyl)-2-methylpyrrolidin-2-carboxylate (0.25 g, 0.45 mmol) and LiOH (0.05 g, 2.25 mmol) were dissolved in tetrahydrofuran (8 mL)/methanol (8 mL)/water (2 mL) at room temperature. The solution was stirred at the same temperature for 18 hours. From the reaction mixture, the solvent was removed under reduced pressure. The obtained product was used without further purification (0.18 g, 73%, yellow oil).

Step 3. Synthesis of Compound 1259: (S)-1-(3'-Cyano-3-fluoro-4'-((1-(2-fluoro-2-methylpropyl)piperidin-4-yl)methoxy)biphenylcarbonyl)-2-methylpyrrolidin-2-carboxylic acid (0.18 g, 0.33 mmol), ammonium chloride (0.05 g, 1.00 mmol), HOBt (0.09 g, 0.66 mmol), EDC (0.12 g, 0.66 mmol) and DIPEA (0.08 g, 0.66 mmol) were dissolved in DMF (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (32 mg, 17%) as white solid.

$^1$H NMR (400 MHz, CDCl₃) δ 7.65-7.70 (m, 2H), 7.46 (t, 1H, J=7.4 Hz), 7.30-7.33 (m, 1H), 7.20-7.25 (m, 1H), 6.99-7.01 (m, 1H), 6.95 (s, 1H), 5.91 (s, 1H), 3.96 (d, 2H, J=6.0 Hz), 3.43-3.48 (m, 2H), 3.32-3.34 (m, 2H), 2.78-2.85 (m, 2H), 2.51-2.60 (m, 3H), 1.85-1.97 (m, 6H), 1.77-1.79 (m, 5H), 1.48 (s, 3H), 1.43 (s, 3H); MS (ESI) m/z 539.2 (M⁺+H).

Synthesis of Compound 1261: (2S,4R)-1-(3'-Cyano-3-fluoro-4'-((1-(2-fluoro-2-methylpropyl)piperidin-4-yl)methoxy)biphenylcarbonyl)-4-hydroxypyrrolidin-2-carboxamide

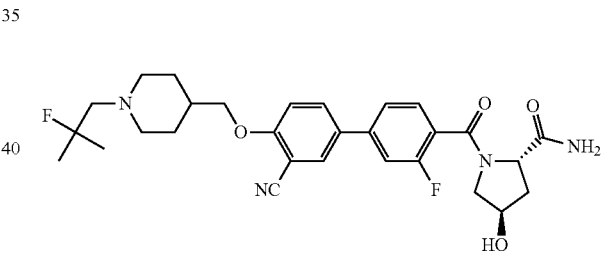

Step 1. (2S,4R)-methyl 1-(3'-cyano-3-fluoro-4'-((1-(2-fluoro-2-methylpropyl)piperidin-4-yl)methoxy)biphenylcarbonyl)-4-hydroxypyrrolidin-2-carboxylate: Intermediate 9 (0.25 g, 0.58 mmol), (2S,4R)-methyl 4-hydroxypyrrolidin-2-carboxylate hydrochloride (0.21 g, 1.16 mmol), HOBt (0.15 g, 1.16 mmol), EDC (0.22 g, 1.16 mmol) and DIPEA (0.15 g, 1.16 mmol) were dissolved in dichloromethane (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 4 g cartridge; methanol/dichloromethane=0% to 15%), and concentrated to obtain the desired compound (0.21 g, 64%) as white solid.

Step 2. (2S,4R)-1-(3'-cyano-3-fluoro-4'-((1-(2-fluoro-2-methylpropyl)piperidin-4-yl)methoxy)biphenylcarbonyl)-4-hydroxypyrrolidin-2-carboxylic acid: (2S,4R)-Methyl 1-(3'-cyano-3-fluoro-4'-((1-(2-fluoro-2-methylpropyl)piperidin-4-yl)methoxy)biphenylcarbonyl)-4-hydroxypyrrolidin-2- carboxylate (0.21 g, 0.37 mmol) and LiOH (0.05 g, 1.89 mmol) were dissolved in tetrahydrofuran (16 mL)/methanol (16 mL)/water (4 mL) at room temperature. The solution was stirred at the same temperature for 18 hours. From the reaction mixture, the solvent was removed under reduced pressure. The obtained product was used without further purification (0.15 g, 75%, yellow oil).

Step 3. Synthesis of Compound 1261: (2S,4R)-1-(3'-Cyano-3-fluoro-4'-((1-(2-fluoro-2-methylpropyl)piperidin-4-yl)methoxy)biphenylcarbonyl)-4-hydroxypyrrolidin-2-carboxylic acid (0.15 g, 0.28 mmol), ammonium chloride (0.05 g, 0.85 mmol), HOBt (0.07 g, 0.56 mmol), EDC (0.10 g, 0.56 mmol) and DIPEA (0.07 g, 0.56 mmol) were dissolved in DMF (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (Waters, C18; acetonitrile/0.1%-trifluoroacetic acid aqueous solution=0% to 30%), and passed through SPE cartridge (PL-HCO3 MP SPE), followed by concentrating to obtain the desire compound (0.01 g, 6%) as white solid.

$^1$H NMR (400 MHz, CDCl$_3$) δ 7.66-7.70 (m, 2H), 7.48 (t, 1H, J=7.4 Hz), 7.28-7.35 (m, 1H), 7.18-7.20 (m, 1H), 6.98-7.01 (m, 1H), 4.67-4.71 (m, 1H), 4.39 (s, 1H), 3.94 (s, 1H), 3.93-3.95 (m, 2H), 3.59-3.94 (m, 5H), 3.27-3.48 (m, 4H), 2.79-2.93 (m, 2H), 2.20-2.26 (m, 2H), 1.91-2.10 (m, 6H), 1.40-1.47 (m, 6H); MS (ESI) m/z 541.2 (M$^+$+H).

Synthesis of Compound 1262: 1-(2-Fluoro-4-(5-((1-((1-(trifluoromethyl)cyclobutyl)methyl)piperidin-4-yl)methoxy)pyrazin-2-yl)benzoyl)-4-hydroxypiperidin-2-carboxamide

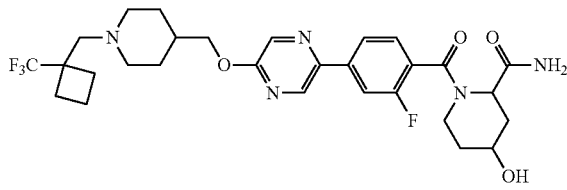 [SMILES: NC(=O)C1CC(O)CCN1C(=O)c1ccc(-c2cnc(OCC3CCN(CC4(C(F)(F)F)CCC4)CC3)cn2)cc1F]

Step 1. methyl 1-(2-fluoro-4-(5-((1-((1-(trifluoromethyl)cyclobutyl)methyl)piperidin-4-yl)methoxy)pyrazin-2-yl)benzoyl)-4-hydroxypiperidin-2-carboxylate: Intermediate 4 (0.12 g, 0.25 mmol), methyl 4-hydroxypiperidin-2-carboxylate HCl (0.10 g, 0.51 mmol), EDC (0.09 g, 0.51 mmol), HOBt (0.06 g, 0.51 mmol) and DIPEA (0.09 mL, 0.51 mmol) were dissolved in DMF (4 mL) at room temperature. The solution was stirred at 60° C. for 10 hours, and then cooled to room temperature thereby to make the reaction completed. To the reaction mixture, saturated ammonium chloride aqueous solution was added, and the mixture was extracted with dichloromethane. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; ethyl acetate/hexane=5% to 70%), and concentrated to obtain the desired compound (0.07 g, 44%) as colorless oil.

Step 2. 1-(2-fluoro-4-(5-((1-((1-(trifluoromethyl)cyclobutypmethyl)piperidin-4-yl)methoxy)pyrazin-2-yl)benzoyl)-4-hydroxypiperidin-2-carboxylic acid: Methyl 1-(2-fluoro-4-(5-((1-((1-(trifluoromethyl)cyclobutyl)methyl)piperidin-4-yl)methoxy)pyrazin-2-yl)benzoyl)-4-hydroxypiperidin-2-carboxylate (0.07 g, 0.11 mmol) and LiOH.H$_2$O (0.01 g, 0.23 mmol) were dissolved in tetrahydrofuran (30 mL)/water (10 mL) at room temperature. The solution was stirred at 50° C. for 10 hours, and then cooled to room temperature thereby to make the reaction completed. From the reaction mixture, the solvent was removed under reduced pressure. The obtained product was used without further purification (68 mg, 99%, yellow solid).

Step 3. Synthesis of Compound 1262: 1-(2-Fluoro-4-(5-((1-((1-(trifluoromethyl)cyclobutyl)methyl)piperidin-4-yl)methoxy)pyrazin-2-yl)benzoyl)-4-hydroxypiperidin-2-carboxylic acid (68 mg, 0.11 mmol), ammonium chloride (0.01 g, 0.22 mmol), EDC (0.04 g, 0.22 mmol), HOBt (0.03 g, 0.22 mmol) and DIPEA (0.04 mL, 0.22 mmol) were dissolved in DMF (10 mL) at room temperature. The solution was stirred at 60° C. for 10 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.02 g, 29%) as white solid.

$^1$H NMR (400 MHz, CD$_3$OD) δ 8.73-8.71 (m, 1H), 8.32-8.31 (m, 1H), 7.96-7.89 (m, 2H), 7.65-7.42 (m, 1H), 5.22 (m, 1H), 4.31 (m, 2H), 4.12 (m, 2H), 3.80 (m, 1H), 3.41 (m, 1H), 3.15 (m, 2H), 2.92 (m, 2H), 2.60-2.40 (m, 3H), 2.31 (m, 2H), 2.18 (m, 2H), 2.10-1.50 (m, 9H); MS (ESI) m/z 594.1 (M$^+$+H).

Synthesis of Compound 1263: (S)-1-(2-Fluoro-4-(5-((1-((1-(trifluoromethyl)cyclobutyl)methyl)piperidin-4-yl)methoxy)pyrazin-2-yl)benzoyl)-2-methyl-pyrrolidin-2-carboxamide

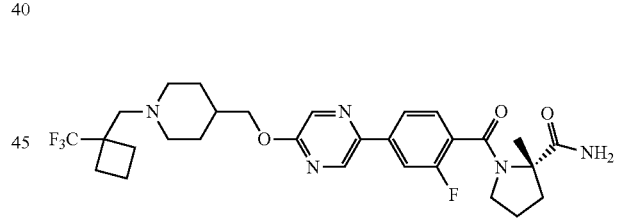

Step 1. (S)-methyl 1-(2-fluoro-4-(5-((1-((1-(trifluoromethyl)cyclobutyl)methyl)piperidin-4-yl)methoxy)pyrazin-2-yl)benzoyl)-2-methylpyrrolidin-2-carboxylate: Intermediate 4 (0.12 g, 0.25 mmol), (S)-methyl 2-methylpyrrolidin-2-carboxylate HCl (0.09 g, 0.51 mmol), EDC (0.09 g, 0.51 mmol), HOBt (0.06 g, 0.51 mmol) and DIPEA (0.09 mL, 0.51 mmol) were dissolved in DMF (4 mL) at room temperature. The solution was stirred at 60° C. for 10 hours, and then cooled to room temperature thereby to make the reaction completed. To the reaction mixture, saturated ammonium chloride aqueous solution was added, and the mixture was extracted with dichloromethane. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; ethyl acetate/hexane=5% to 50%), and concentrated to obtain the desired compound (0.13 g, 85%) as colorless oil.

Step 2. (S)-1-(2-fluoro-4-(5-((1-((1-(trifluoromethyl)cyclobutyl)methyl)piperidin-4-yl)methoxy)pyrazin-2-yl)benzoyl)-2-methylpyrrolidin-2-carboxylic acid: (S)-Methyl 1-(2-fluoro-4-(5-((1-((1-(trifluoromethyl)cyclobutyl)methyl)piperidin-4-yl)methoxy)pyrazin-2-yl)benzoyl)-2-methylpyrrolidin-2-carboxylate (0.13 g, 0.21 mmol) and LiOH.H₂O (18 mg, 0.43 mmol) were dissolved in tetrahydrofuran (30 mL)/water (10 mL) at room temperature. The solution was stirred at 50° C. for 10 hours, and then cooled to room temperature thereby to make the reaction completed. From the reaction mixture, the solvent was removed under reduced pressure. The obtained product was used without further purification (0.12 g, 94%, yellow solid).

Step 3. Synthesis of Compound 1263: (S)-1-(2-Fluoro-4-(5-((1-((1-(trifluoromethyl)cyclobutyl)methyl)piperidin-4-yl)methoxy)pyrazin-2-yl)benzoyl)-2-methylpyrrolidin-2-carboxylic acid (0.12 g, 0.20 mmol), ammonium chloride (0.02 g, 0.41 mmol), EDC (0.08 g, 0.41 mmol), HOBt (0.05 g, 0.41 mmol) and DIPEA (0.07 mL, 0.41 mmol) were dissolved in DMF (10 mL) at room temperature. The solution was stirred at 60° C. for 10 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.03 g, 25%) as white solid.

¹H NMR (400 MHz, CD₃OD) δ 8.71 (m, 1H), 8.31 (m, 1H), 7.93-7.86 (m, 2H), 7.61-7.57 (m, 1H), 4.30 (m, 2H), 3.57 (m, 2H), 3.12 (m, 2H), 2.90-2.84 (m, 2H), 2.49 (m, 2H), 2.34 (m, 3H), 2.29 (m, 2H), 2.28-1.83 (m, 8H), 1.76 (s, 3H), 1.60-1.50 (m, 2H); MS (ESI) m/z 578.2 (M⁺+H).

Synthesis of Compound 1264: (S)-1-(2-Fluoro-4-(5-((1-(2,2,3,3,3-pentafluoropropyl)piperidin-4-yl)methoxy)pyridin-2-yl)benzoyl)pyrrolidin-2-carboxamide

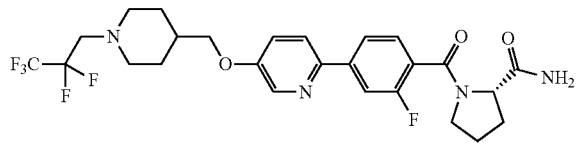 [SMILES: NC(=O)[C@@H]1CCCN1C(=O)c1ccc(-c2ccc(OCC3CCN(CC(F)(F)C(F)(F)F)CC3)cn2)cc1F]

Intermediate 24 (0.05 g, 0.10 mmol), (S)-pyrrolidin-2-carboxamide (25 mg, 0.21 mmol), EDC (0.04 g, 0.21 mmol), HOBt (0.02 g, 0.21 mmol) and DIPEA (0.03 mL, 0.21 mmol) were dissolved in DMF (4 mL) at room temperature. The solution was stirred at 60° C. for 10 hours, and then cooled to room temperature thereby to make the reaction completed. To the reaction mixture, saturated ammonium chloride aqueous solution was added, and the mixture was extracted with dichloromethane. The organic layer was washed with saturated NaCl aqueous solution, dried with anhydrous MgSO₄, filtered, and then concentrated under reduced pressure. The concentrate was purified by column chromatography (SiO₂, 4 g cartridge; ethyl acetate/hexane=5% to 70%), and concentrated to obtain the desired compound (35 mg, 58%) as white solid.

¹H NMR (400 MHz, CDCl₃) δ 8.40 (m, 1H), 7.80-7.78 (m, 2H), 7.70 (m, 1H), 7.54-7.50 (m, 1H), 7.33-7.30 (m, 1H), 6.94 (br, 1H), 5.54 (br, 1H), 4.84-4.81 (m, 1H), 3.93 (m, 2H), 3.56-3.40 (m, 2H), 3.11 (m, 4H), 2.59-2.45 (m, 3H), 2.21-2.04 (m, 3H), 1.92-1.90 (m, 3H), 1.62 (m, 2H); MS (ESI) m/z 559.1 (M⁺+H).

Synthesis of Compound 1265: (2S,4R)-1-(2-Fluoro-4-(5-((1-(2,2,3,3,3-pentafluoropropyl)piperidin-4-yl)methoxy)pyridin-2-yl)benzoyl)-4-hydroxypyrrolidin-2-carboxamide

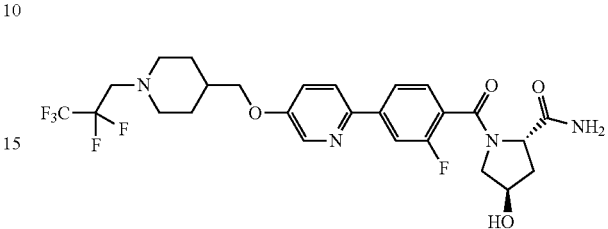

Step 1. (2S,4R)-methyl 1-(2-fluoro-4-(5-((1-(2,2,3,3,3-pentafluoropropyl)piperidin-4-yl)methoxy)pyridin-2-yl)benzoyl)-4-hydroxypyrrolidin-2-carboxylate: Intermediate 24 (0.10 g, 0.21 mmol), (2S,4R)-methyl 4-hydroxypyrrolidin-2-carboxylate HCl (79 mg, 0.43 mmol), EDC (0.08 g, 0.43 mmol), HOBt (0.05 g, 0.43 mmol) and DIPEA (0.07 mL, 0.43 mmol) were dissolved in DMF (4 mL) at room temperature. The solution was stirred at 60° C. for 10 hours, and then cooled to room temperature thereby to make the reaction completed. To the reaction mixture, saturated ammonium chloride aqueous solution was added, and the mixture was extracted with dichloromethane. The organic layer was washed with saturated NaCl aqueous solution, dried with anhydrous MgSO₄, filtered, and then concentrated under reduced pressure. The concentrate was purified by column chromatography (SiO₂, 4 g cartridge; ethyl acetate/hexane=5% to 50%), and concentrated to obtain the desired compound (0.11 g, 86%) as colorless oil.

Step 2. (2S,4R)-1-(2-fluoro-4-(5-((1-(2,2,3,3,3-pentafluoropropyl)piperidin-4-yl)methoxy)pyridin-2-yl)benzoyl)-4-hydroxypyrrolidin-2-carboxylic acid: (2S,4R)-Methyl 1-(2-fluoro-4-(5-((1-(2,2,3,3,3-pentafluoropropyl)piperidin-4-yl)methoxy)pyridin-2-yl)benzoyl)-4-hydroxypyrrolidin-2-carboxylate (0.11 g, 0.18 mmol) and LiOH.H₂O (16 mg, 0.37 mmol) were dissolved in tetrahydrofuran (30 mL)/water (10 mL) at room temperature. The solution was stirred at 50° C. for 10 hours, and then cooled to room temperature thereby to make the reaction completed. From the reaction mixture, the solvent was removed under reduced pressure. The obtained product was used without further purification (0.10 g, 93%, white solid).

Step 3. Synthesis of Compound 1265: (2S,4R)-1-(2-Fluoro-4-(5-((1-(2,2,3,3,3-pentafluoropropyl)piperidin-4-yl)methoxy)pyridin-2-yl)benzoyl)-4-hydroxypyrrolidin-2-carboxylic acid (0.10 g, 0.17 mmol), ammonium chloride (19 mg, 0.34 mmol), EDC (0.06 g, 0.34 mmol), HOBt (0.04 g, 0.34 mmol) and DIPEA (0.06 mL, 0.34 mmol) were dissolved in DMF (10 mL) at room temperature. The solution was stirred at 60° C. for 10 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.02 g, 20%) as white solid.

¹H NMR (400 MHz, CD₃OD) δ 8.35 (m, 1H), 7.91-7.79 (m, 3H), 7.65-7.61 (m, 1H), 7.51-7.48 (m, 1H), 4.74 (m, 1H), 4.44 (m, 1H), 4.00 (m, 2H), 3.76 (m, 1H), 3.43-3.27 (m, 3H), 3.21 (m, 2H), 2.66 (m, 2H), 2.38 (m, 1H), 2.18 (m, 1H), 1.95 (m, 3H), 1.57 (m, 2H); MS (ESI) m/z 575.2 (M⁺+H).

Synthesis of Compound 1266: (S)-1-(2-Fluoro-4-(5-((1-(2,2,3,3,3-pentafluoropropyl)piperidin-4-yl)methoxy)pyridin-2-yl)benzoyl)-2-methylpyrrolidin-2-carboxamide

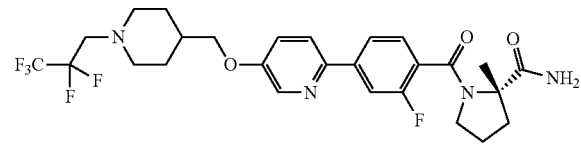 [SMILES: C[C@@]1(C(N)=O)CCCN1C(=O)c1ccc(-c2ccc(OCC3CCN(CC(F)(F)C(F)(F)F)CC3)cn2)cc1F]

Step 1. (S)-methyl 1-(2-fluoro-4-(5-((1-(2,2,3,3,3-pentafluoropropyl)piperidin-4-yl)methoxy)pyridin-2-yl)benzoyl)-2-methylpyrrolidin-2-carboxylate: Intermediate 24 (0.10 g, 0.21 mmol), (S)-methyl 2-methylpyrrolidin-2-carboxylate HCl (0.07 g, 0.43 mmol), EDC (0.08 g, 0.43 mmol), HOBt (0.05 g, 0.43 mmol) and DIPEA (0.07 mL, 0.43 mmol) were dissolved in DMF (4 mL) at room temperature. The solution was stirred at 60° C. for 12 hours, and then cooled to room temperature thereby to make the reaction completed. To the reaction mixture, saturated ammonium chloride aqueous solution was added, and the mixture was extracted with dichloromethane. The organic layer was washed with saturated NaCl aqueous solution, dried with anhydrous MgSO₄, filtered, and then concentrated under reduced pressure. The concentrate was purified by column chromatography (SiO₂, 4 g cartridge; ethyl acetate/hexane=5% to 40%), and concentrated to obtain the desired compound (0.11 g, 86%) as colorless oil.

Step 2. (S)-1-(2-fluoro-4-(5-((1-(2,2,3,3,3-pentafluoropropyl)piperidin-4-yl)methoxy)pyridin-2-yl)benzoyl)-2-methylpyrrolidin-2-carboxylic acid: (S)-Methyl 1-(2-fluoro-4-(5-((1-(2,2,3,3,3-pentafluoropropyl)piperidin-4-yl)methoxy)pyridin-2-yl)benzoyl)-2-methylpyrrolidin-2-carboxylate (0.11 g, 0.18 mmol) and LiOH·H₂O (16 mg, 0.37 mmol) were dissolved in tetrahydrofuran (30 mL)/water (10 mL) at room temperature. The solution was stirred at 50° C. for 10 hours, and then cooled to room temperature thereby to make the reaction completed. From the reaction mixture, the solvent was removed under reduced pressure. The obtained product was used without further purification (0.10 g, 93%, white solid).

Step 3. Synthesis of Compound 1266: (S)-1-(2-Fluoro-4-(5-((1-(2,2,3,3,3-pentafluoropropyl)piperidin-4-yl)methoxy)pyridin-2-yl)benzoyl)-2-methylpyrrolidin-2-carboxylic acid (0.10 g, 0.17 mmol), ammonium chloride (19 mg, 0.34 mmol), EDC (0.06 g, 0.34 mmol), HOBt (0.04 g, 0.34 mmol) and DIPEA (0.06 mL, 0.34 mmol) were dissolved in DMF (10 mL) at room temperature. The solution was stirred at 60° C. for 10 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.02 g, 20%) as white solid.

¹H NMR (400 MHz, CD₃OD) δ 8.35 (m, 1H), 7.90-7.80 (m, 3H), 7.52-7.48 (m, 2H), 3.98 (m, 2H), 3.57 (m, 2H), 3.17-3.02 (m, 4H), 2.43 (m, 2H), 2.31 (m, 1H), 2.10-2.01 (m, 3H), 1.87 (m, 3H), 1.72 (s, 3H), 1.51-1.47 (m, 2H); MS (ESI) m/z 574.2 (M⁺+H).

Synthesis of Compound 1267: (S)-1-(2-Fluoro-4-(5-((1-(3,3,3-trifluoro-2,2-dimethylpropyl)piperidin-4-yl)methoxy)pyridin-2-yl)benzoyl)pyrrolidin-2-carboxamide

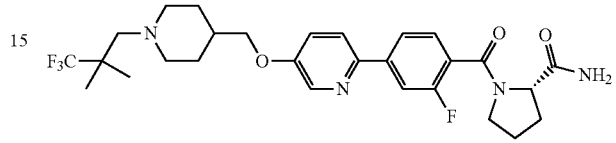

Intermediate 19 (0.05 g, 0.12 mmol), (S)-pyrrolidin-2-carboxamide (0.02 g, 0.24 mmol), EDC (0.04 g, 0.24 mmol), HOBt (0.03 g, 0.24 mmol) and DIPEA (0.04 mL, 0.24 mmol) were dissolved in dichloromethane (1 mL) at room temperature. The solution was stirred at the same temperature for 12 hours. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 12 g cartridge; methanol/dichloromethane=0% to 10%), and concentrated to obtain the desired compound (0.04 g, 63%) as white solid.

¹H NMR (400 MHz, CDCl₃) δ 8.39 (d, 1H, J=2.8 Hz), 7.79-7.76 (m, 2H), 7.70-7.68 (m, 1H), 7.53-7.49 (m, 1H), 7.30-7.27 (m, 1H), 6.94 (brs, 1H), 5.53 (brs, 1H), 4.84-4.82 (m, 1H), 3.91 (d, 2H, J=6.0 Hz), 3.56-3.50 (m, 1H), 3.45-3.39 (m, 1H), 2.87-2.85 (m, 2H), 2.50-2.46 (m, 1H), 2.42 (s, 2H), 2.38-2.33 (m, 2H), 2.15-2.04 (m, 2H), 1.94-1.90 (m, 1H), 1.89-1.81 (m, 3H), 1.48-1.42 (m, 2H), 1.16 (s, 6H); MS (ESI) m/z 551.1 (M⁺+H).

Synthesis of Compound 1268: (2S,4R)-1-(2-Fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxamide

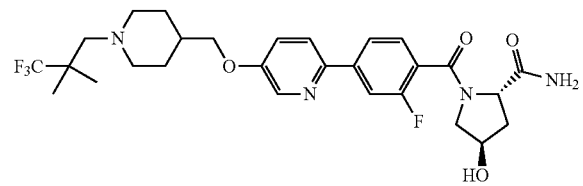 [SMILES: CC(C)(CN1CCC(COc2ccc(-c3ccc(C(=O)N4C[C@H](O)C[C@H]4C(N)=O)c(F)c3)nc2)CC1)C(F)(F)F]

Step 1. (2S,4R)-methyl 1-(2-fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxylate: Intermediate 19 (0.16 g, 0.37 mmol), (2S,4R)-methyl 4-hydroxypyrrolidin-2-carboxylate hydrochloride (0.13 g, 0.73 mmol), EDC (0.14 g, 0.73 mmol), HOBt (0.10 g, 0.73 mmol) and DIPEA (0.13 mL, 0.73 mmol) were dissolved in dichloromethane (10 mL) at room temperature. The solution was stirred at the same temperature for 12 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/dichloromethane=0% to 10%), and concentrated to obtain the desired compound (0.17 g, 80%) as white solid.

Step 2. (2S,4R)-1-(2-fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxylic acid: (2S,4R)-Methyl 1-(2-fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxylate (0.17 g, 0.29 mmol) was dissolved in tetrahydrofuran (3 mL)/methanol (3 mL)/water (1 mL) at room temperature. To the solution, LiOH.H$_2$O (0.06 g, 1.48 mmol) was added, followed by stirring at the same temperature for 1 hour. From the reaction mixture, the solvent was removed under reduced pressure. The obtained product was used without further purification (0.12 g, 71%, white solid).

Step 3. Synthesis of Compound 1268: (2S,4R)-1-(2-Fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxylic acid (0.12 g, 0.21 mmol), NH$_4$Cl (0.11 g, 2.16 mmol), EDC (0.08 g, 0.43 mmol), HOBt (0.05 g, 0.43 mmol) and DIPEA (0.07 mL, 0.43 mmol) were mixed in DMF (5 mL). The mixture was stirred at room temperature for 5 minutes, and further stirred at 80° C. for 14 hours, and then cooled to room temperature thereby to make the reaction completed. To the reaction mixture, water was added, and the mixture was extracted with ethyl acetate. The organic layer was washed with saturated NH$_4$Cl aqueous solution, dried with anhydrous MgSO$_4$, filtered, and then concentrated under reduced pressure. The concentrate was purified by column chromatography (SiO$_2$, 12 g cartridge; methanol/dichloromethane=0% to 10%), and concentrated to obtain the desired compound (0.09 g, 74%) as white solid.

$^1$H NMR (400 MHz, CDCl$_3$) δ 8.35-8.33 (m, 1H), 7.90-7.79 (m, 3H), 7.64-7.60 (m, 1H), 7.49-7.46 (m, 1H), 4.75 (t, 1H J=8.4 Hz), 4.45-4.43 (m, 1H), 3.98-3.95 (m, 2H), 3.79-3.76 (m, 1H), 3.40-3.36 (m, 1H), 2.91-2.88 (m, 2H), 2.44 (s, 2H), 2.39-2.34 (m, 3H), 2.34-2.14 (m, 1H), 1.83-1.80 (m, 3H), 1.49-1.14 (m, 2H), 1.16 (s, 6H); MS (ESI) m/z 567.1 (M$^+$+H).

Synthesis of Compound 1269: (S)-1-(2-Fluoro-4-(5-((1-(3,3,3-trifluoro-2,2-dimethylpropyl)piperidin-4-yl)methoxy)pyridin-2-yl)benzoyl)-2-methylpyrrolidin-2-carboxamide

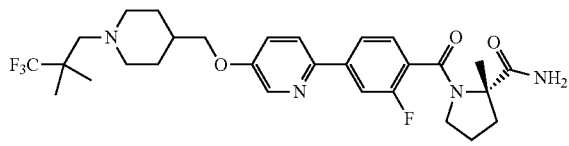 [SMILES: CC(C)(CN1CCC(COc2ccc(-c3ccc(C(=O)N4CCC[C@@]4(C)C(N)=O)c(F)c3)nc2)CC1)C(F)(F)F]

Step 1. (S)-methyl 1-(2-fluoro-4-(5-((1-(3,3,3-trifluoro-2,2-dimethylpropyl)piperidin-4-yl)methoxy)pyridin-2-yl)benzoyl)2-methylpyrrolidin-2-carboxylate: Intermediate 19 (0.20 g, 0.44 mmol), (S)-methyl 2-methylpyrrolidin-2-carboxylate hydrochloride (0.15 g, 0.88 mmol), EDC (0.16 g, 0.88 mmol), HOBt (0.11 g, 0.88 mmol) and DIPEA (0.15 mL, 0.88 mmol) were dissolved in dichloromethane (5 mL) at room temperature. The solution was stirred at the same temperature for 12 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/dichloromethane=0% to 10%), and concentrated to obtain the desired compound (0.21 g, 82%) as white solid.

Step 2. (S)-1-(2-fluoro-4-(5-((1-(3,3,3-trifluoro-2,2-dimethylpropyl)piperidin-4-yl)methoxy)pyridin-2-yl)benzoyl)-2-methylpyrrolidin-2-carboxylic acid: (S)-Methyl 1-(2-fluoro-4-(5-((1-(3,3,3-trifluoro-2,2-dimethylpropyl)piperidin-4-yl)methoxy)pyridin-2-yl)benzoyl)2-methylpyrrolidin-2-carboxylate (0.21 g, 0.36 mmol) and LiOH.H$_2$O (0.07 g, 1.81 mmol) were dissolved in tetrahydrofuran (6 mL)/methanol (6 mL)/water (3 mL) at room temperature. The solution was stirred at the same temperature for 1 hour. From the reaction mixture, the solvent was removed under reduced pressure. The obtained product was used without further purification (0.12 g, 58%, white solid).

Step 3. Synthesis of Compound 1269: (S)-1-(2-Fluoro-4-(5-((1-(3,3,3-trifluoro-2,2-dimethylpropyl)piperidin-4-yl)methoxy)pyridin-2-yl)benzoyl)-2-methylpyrrolidin-2-carboxylic acid (0.12 g, 0.21 mmol), NH$_4$Cl (0.11 g, 2.12 mmol), EDC (0.08 g, 0.42 mmol), HOBt (0.05 g, 0.42 mmol) and DIPEA (0.07 mL, 0.42 mmol) were dissolved in DMF (10 mL). The solution was stirred at room temperature for 5 minutes, and further stirred at 80° C. for 14 hours, and then cooled to room temperature thereby to make the reaction completed. To the reaction mixture, water was added, and the mixture was extracted with ethyl acetate. The organic layer was washed with saturated NH$_4$Cl aqueous solution, dried with anhydrous MgSO$_4$, filtered, and then concentrated under reduced pressure. The concentrate was purified by column chromatography (SiO$_2$, 12 g cartridge; methanol/dichloromethane=0% to 10%), and concentrated to obtain the desired compound (0.07 g, 61%) as white solid.

$^1$H NMR (400 MHz, CDCl$_3$) δ 8.39-8.38 (m, 1H), 7.78-7.75 (m, 2H), 7.69-7.67 (m, 1H), 7.47 (t, 1H, J=7.6 Hz), 7.30-7.27 (m, 1H), 7.16 (brs, 1H), 5.41 (brs, 1H), 3.91 (d, 2H, J=6.0 Hz), 3.53-3.48 (m, 2H), 2.87-2.85 (m, 2H), 2.72-2.64 (m, 1H), 2.42 (s, 2H), 2.39-2.33 (m, 2H), 1.96-1.79 (m, 6H), 1.66 (s, 3H), 1.48-1.41 (m, 2H), 1.16 (s, 6H); MS (ESI) m/z 565.2 (M$^+$+H).

Synthesis of Compound 1271: (2S,4R)-1-(2-Fluoro-4-(5-((1-(2-fluoro-2-methylpropyl)piperidin-4-yl)methoxy)pyridin-2-yl)benzoyl)-4-hydroxy-2-methylpyrrolidin-2-carboxamide

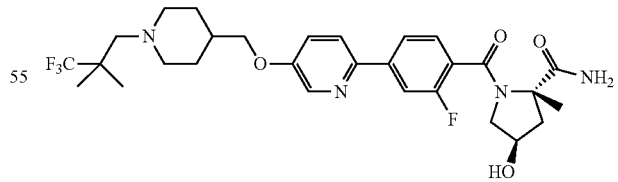

Step 1. (2S,4R)-methyl 1-(2-fluoro-4-(5-((1-(2-fluoro-2-methylpropyl)piperidin-4-yl)methoxy)pyridin-2-yl)benzoyl)-4-hydroxy-2-methylpyrrolidin-2-carboxylate: Intermediate 32 (0.45 g, 1.11 mmol), EDC (0.42 g, 2.22 mmol), HOBt (0.30 g, 2.22 mmol) and DIPEA (0.43 g, 3.33 mmol) were dissolved in dichloromethane (10 mL) at room temperature. To the solution, Intermediate 25 (0.26 g, 1.33 mmol) was added, followed by stirring at the same temperature. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/dichloromethane=0% to 5%), and concentrated to obtain the desired compound (0.41 g, 67%) as white solid.

Step 2. (2S,4R)-1-(2-fluoro-4-(5-((1-(2-fluoro-2-methylpropyl)piperidin-4-yl)methoxy)pyridin-2-yl)benzoyl)-4-hydroxy-2-methylpyrrolidin-2-carboxylic acid: (2S,4R)-Methyl 1-(2-fluoro-4-(5-((1-(2-fluoro-2-methylpropyl)piperidin-4-yl)methoxy)pyridin-2-yl)benzoyl)-4-hydroxy-2-methylpyrrolidin-2-carboxylate (0.40 g, 0.73 mmol) and LiOH.H$_2$O (0.03 g, 1.46 mmol) were dissolved in tetrahydrofuran (10 mL)/methanol (6 mL)/water (4 mL) at room temperature. The solution was stirred at the same temperature for 1 hour. From the reaction mixture, the solvent was removed under reduced pressure. To the concentrate, a small amount of 12N-aqueous HCl solution was added and stirred. The precipitated solid was collected by filtration, washed with ethyl acetate and dried to obtain the desired compound (0.38 g, 97%) as white solid.

Step 3. Synthesis of Compound 1271: (2S,4R)-1-(2-Fluoro-4-(5-((1-(2-fluoro-2-methylpropyl)piperidin-4-yl)methoxy)pyridin-2-yl)benzoyl)-4-hydroxy-2-methylpyrrolidin-2-carboxylic acid (0.36 g, 0.67 mmol), EDC (0.26 g, 1.35 mmol), HOBt (0.18 g, 1.35 mmol) and DIPEA (0.26 g, 2.03 mmol) were dissolved in DMF (4 mL) at room temperature. To the solution, NH$_4$Cl (0.11 g, 2.03 mmol) was added, followed by stirring at 80° C. for 6 hours. And then, the reaction mixture was cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (SO3H on Si), followed by concentrating to obtain the desire compound (0.04 g, 12%) as light brown solid.

$^1$H NMR (400 MHz, CD$_3$OD) δ 8.33 (d, 1H, J=2.8 Hz), 7.88-7.78 (m, 3H), 7.53 (t, 1H, J=7.5 Hz), 7.47 (dd, 1H, J=8.8, 2.9 Hz), 4.42 (m, 1H), 3.97 (d, 2H, J=5.9 Hz), 3.75 (dd, 1H, J=11.0, 5.2 Hz), 3.42 (dd, 1H, J=10.9, 3.5 Hz), 3.05-3.03 (m, 2H), 2.51-2.44 (m, 3H), 2.21-2.15 (m, 2H), 2.05 (dd, 1H, J=13.0, 4.1 Hz), 1.88 (s, 3H), 1.81 (m, 3H), 1.53-1.44 (m, 2H), 1.37 (s, 3H), 1.32 (s, 3H); MS (ESI) m/z 531.2 (M$^-$+H).

Synthesis of Compound 1272: (2S,4R)-1-(3'-Cyano-4'-((1-(2-ethyl-2-fluorobutyl)piperidin-4-yl)methoxy)-3-fluorobiphenylcarbonyl)-4-hydroxypyrrolidin-2-carboxamide

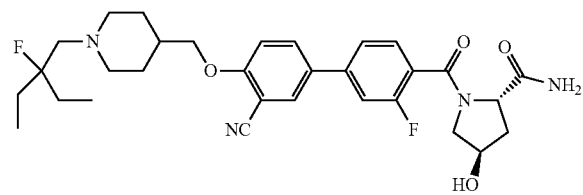 [SMILES: CCC(F)(CC)CN1CCC(COc2ccc(-c3ccc(C(=O)N4C[C@H](O)C[C@H]4C(N)=O)c(F)c3)cc2C#N)CC1]

Intermediate 22 (0.12 g, 0.26 mmol), (2S,4R)-4-hydroxypyrrolidin-2-carboxamide hydrochloride (0.08 g, 0.52 mmol), HOBt (0.07 g, 0.52 mmol), EDC (0.10 g, 0.52 mmol) and DIPEA (0.09 mL, 0.52 mmol) were dissolved in dichloromethane (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; methanol/dichloromethane=0% to 15%), and concentrated to obtain the desired compound (0.07 g, 46%) as white solid.

$^1$H NMR (400 MHz, CD$_3$OD) δ 7.91-7.98 (m, 2H), 7.60-7.64 (m, 1H), 7.45-7.57 (m, 2H), 7.25-7.29 (m, 1H), 4.72-4.76 (m, 1H), 4.43-4.54 (m, 1H), 4.03-4.05 (m, 2H), 3.75-3.79 (m, 1H), 3.35-3.38 (m, 1H), 3.07-3.09 (m, 2H), 2.52-2.58 (m, 2H), 2.34-2.38 (m, 1H), 2.14-2.23 (m, 3H), 1.86-1.89 (m, 3H), 1.67-1.77 (m, 4H), 1.49-1.55 (m, 2H), 0.92 (t, 6H, J=7.5 Hz); MS (ESI) m/z 569.3 (M$^+$+H).

Synthesis of Compound 1276: (2S,4R)-1-(3'-Cyano-3-fluoro-4'-((1-(2-fluoro-2-methylpropyl)piperidin-4-yl)methoxy)biphenylcarbonyl)-4-hydroxy-2-methylpyrrolidin-2-carboxamide

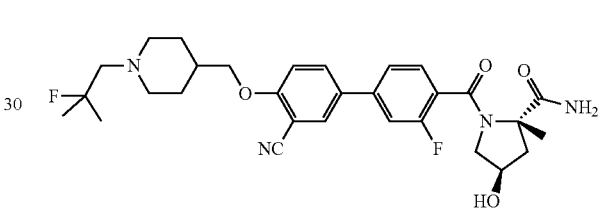

Step 1. (2S,4R)-methyl 1-(3'-cyano-3-fluoro-4'-((1-(2-fluoro-2-methylpropyl)piperidin-4-yl)methoxy)biphenylcarbonyl)-4-hydroxy-2-methylpyrrolidin-2-carboxylate:
Intermediate 9 (0.40 g, 0.93 mmol), EDC (0.35 g, 1.86 mmol), HOBt (0.25 g, 1.86 mmol) and DIPEA (0.36 g, 2.80 mmol) were dissolved in dichloromethane (8 mL) at room temperature. To the solution, Intermediate 25 (0.21 g, 1.12 mmol) was added, followed by stirring at the same temperature. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/dichloromethane=0% to 5%), and concentrated to obtain the desired compound (0.32 g, 60%) as white solid.

Step 2. (2S,4R)-1-(3'-cyano-3-fluoro-4'-((1-(2-fluoro-2-methylpropyl)piperidin-4-yl)methoxy)biphenylcarbonyl)-4-hydroxy-2-methylpyrrolidin-2-carboxylic acid: (2S,4R)-Methyl 1-(3'-cyano-3-fluoro-4'-((1-(2-fluoro-2-methylpropyl)piperidin-4-yl)methoxy)biphenylcarbonyl)-4-hydroxy-2-methylpyrrolidin-2-carboxylate (0.30 g, 0.52 mmol) and LiOH.H$_2$O (0.02 g, 1.05 mmol) were dissolved in tetrahydrofuran (8 mL)/methanol (4 mL)/water (2 mL) at room temperature. The solution was stirred at 50° C. for 6 hours, and then cooled to room temperature thereby to make the reaction completed. From the reaction mixture, the solvent was removed under reduced pressure. To the concentrate, a small amount of 12 N-aqueous HCl solution was added and stirred. The precipitated solid was collected by filtration, washed with ethyl acetate and dried to obtain the desired compound (0.25 g, 85%) as white solid.

Step 3. Synthesis of Compound 1276: (2S,4R)-1-(3'-Cyano-3-fluoro-4'-((1-(2-fluoro-2-methylpropyl)piperidin-4-yl)methoxy)biphenylcarbonyl)-4-hydroxy-2-methylpyrrolidin-2-carboxylic acid (0.20 g, 0.36 mmol), EDC (0.13 g, 0.72 mmol), HOBt (0.09 g, 0.72 mmol) and DIPEA (0.14 g, 1.08 mmol) were dissolved in N,N-dimethylformamide (3 mL) at room temperature. To the solution, NH₄Cl (0.05 g, 1.08 mmol) was added, followed by stirring at 80° C. for 16 hours. And then, the reaction mixture was cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and concentrated by passing through SPE cartridge (PL-HCO3 MP SPE). The obtained concentrate was purified by chromatography (SiO₂, 4 g cartridge; methanol/dichloromethane=3% to 10%), and concentrated to obtain the desired compound (0.02 g, 12%) as white solid.

¹H NMR (400 MHz, CD₃OD) δ 8.00 (d, 1H, J=2.4 Hz), 7.97 (dd, 1H, J=10.2, 7.8 Hz), 7.59-7.50 (m, 3H), 7.30 (d, 1H, J=8.9 Hz), 4.55 (m, 1H), 3.93 (m, 1H), 3.50 (m, 1H), 3.09-3.06 (m, 2H), 2.55-2.50 (m, 3H), 2.21 (m, 2H), 2.14 (m, 1H), 1.93 (s, 3H), 1.90-1.86 (m, 3H), 1.53 (m, 2H), 1.40 (s, 3H), 1.34 (s, 3H)

Synthesis of Compound 1277: (2R,4R)-1-(3'-Cyano-3-fluoro-4'-((1-(2-fluoro-2-methylpropyl)piperidin-4-yl)methoxy)biphenylcarbonyl)-4-hydroxy-2-methylpyrrolidin-2-carboxamide

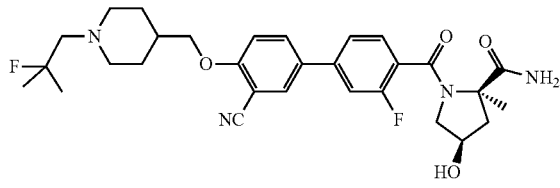 [SMILES: CC(C)(F)CN1CCC(COc2ccc(-c3ccc(C(=O)N4C[C@H](O)C[C@]4(C)C(N)=O)c(F)c3)cc2C#N)CC1]

Step 1. (2R,4R)-methyl 1-(3'-cyano-3-fluoro-4'-((1-(2-fluoro-2-methylpropyl)piperidin-4-yl)methoxy)biphenylcarbonyl)-4-hydroxy-2-methylpyrrolidin-2-carboxylate: Intermediate 9 (0.40 g, 0.93 mmol), EDC (0.35 g, 1.86 mmol), HOBt (0.25 g, 1.86 mmol) and DIPEA (0.36 g, 2.80 mmol) were dissolved in dichloromethane (6 mL) at room temperature. To the solution, Intermediate 26 (0.21 g, 1.12 mmol) was added, followed by stirring at the same temperature for 30 minutes. To the reaction mixture, water was added, and the mixture was extracted with dichloromethane. The organic layer was washed with saturated NaCl aqueous solution, dried with anhydrous MgSO₄, filtered, and then concentrated under reduced pressure. The concentrate was purified by column chromatography (SiO₂, 12 g cartridge; methanol/dichloromethane=0% to 5%), and concentrated to obtain the desired compound (0.19 g, 35%) as white solid.

Step 2. (2R,4R)-1-(3'-cyano-3-fluoro-4'-((1-(2-fluoro-2-methylpropyl)piperidin-4-yl)methoxy)biphenylcarbonyl)-4-hydroxy-2-methylpyrrolidin-2-carboxylic acid: (2R,4R)-Methyl 1-(3'-cyano-3-fluoro-4'-((1-(2-fluoro-2-methylpropyl)piperidin-4-yl)methoxy)biphenylcarbonyl)-4-hydroxy-2-methylpyrrolidin-2-carboxylate (0.18 g, 0.31 mmol) and LiOH.H₂O (0.02 g, 0.63 mmol) were dissolved in tetrahydrofuran (8 mL)/methanol (4 mL)/water (2 mL) at room temperature. The solution was stirred at 50° C. for 8 hours, and then cooled to room temperature thereby to make the reaction completed. From the reaction mixture, the solvent was removed under reduced pressure. To the concentrate, a small amount of 12 N-aqueous HCl solution was added and stirred. The precipitated solid was collected by filtration, washed with ethyl acetate and dried to obtain the desired compound (0.17 g, 96%) as white solid.

Step 3. Synthesis of Compound 1277: (2R,4R)-1-(3'-Cyano-3-fluoro-4'-((1-(2-fluoro-2-methylpropyl)piperidin-4-yl)methoxy)biphenylcarbonyl)-4-hydroxy-2-methylpyrrolidin-2-carboxylic acid (0.15 g, 0.27 mmol), EDC (0.10 g, 0.54 mmol), HOBt (0.07 g, 0.54 mmol) and DIPEA (0.10 g, 0.81 mmol) were dissolved in N,N-dimethylformamide (3 mL) at room temperature. To the solution, NH₄Cl (0.04 g, 0.81 mmol) was added, followed by stirring at the same temperature for 24 hours. From the reaction mixture, the solvent was removed under reduced pressure. The concentrate was purified by column chromatography (Waters, C18; acetonitrile/0.1%-trifluoroacetic acid aqueous solution=5% to 70%), and concentrated by passing through SPE cartridge (PL-HCO3 MP SPE). The obtained concentrate was purified by chromatography (SiO₂, 4 g cartridge; methanol/dichloromethane=3% to 10%), and concentrated to obtain the desired compound (0.03 g, 23%) as white solid.

¹H NMR (400 MHz, CD₃OD) δ 7.99 (d, 1H, J=2.3 Hz), 7.95 (dd, 1H, J=8.8, 2.4 Hz), 7.59-7.51 (m, 3H), 7.29 (d, 1H, J=8.9 Hz), 4.36 (m, 1H), 4.05 (d, 2H, J=6.1 Hz), 3.76-3.72 (m, 1H), 3.45 (m, 1H), 3.07-3.04 (m, 2H), 2.53-2.47 (m, 2H), 2.37 (m, 1H), 2.26 (m, 3H), 1.85 (m, 3H), 1.71 (s, 3H), 1.55-1.50 (m, 2H), 1.39 (s, 3H), 1.34 (s, 3H); MS (ESI) m/z 555.2 (M⁺+H).

Synthesis of Compound 1278: (2S,4R)-1-(2'-Cyano-3-fluoro-4'-((1-(2-fluoro-2-methylpropyl)piperidin-4-yl)methoxy)biphenylcarbonyl)-4-hydroxy-2-methylpyrrolidin-2-carboxamide

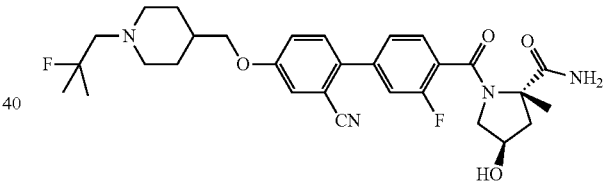

Step 1. (2S,4R)-methyl 1-(2'-cyano-3-fluoro-4'-((1-(2-fluoro-2-methylpropyl)piperidin-4-yl)methoxy)biphenylcarbonyl)-4-hydroxy-2-methylpyrrolidin-2-carboxylate: Intermediate 6 (0.35 g, 0.81 mmol), EDC (0.31 g, 1.63 mmol), HOBt (0.22 g, 1.63 mmol) and DIPEA (0.31 g, 2.45 mmol) were dissolved in dichloromethane (6 mL) at room temperature. To the solution, Intermediate 25 (0.19 g, 0.98 mmol) was added, followed by stirring at the same temperature for 1 h. To the reaction mixture, water was added, and the mixture was extracted with dichloromethane. The organic layer was washed with saturated NaCl aqueous solution, dried with anhydrous MgSO₄, filtered, and then concentrated under reduced pressure. The concentrate was purified by column chromatography (SiO₂, 12 g cartridge; methanol/dichloromethane=0% to 5%), and concentrated to obtain the desired compound (0.16 g, 34%) as yellow oil.

Step 2. (2S,4R)-1-(2'-cyano-3-fluoro-4'-((1-(2-fluoro-2-methylpropyl)piperidin-4-yl)methoxy)biphenylcarbonyl)-4-hydroxy-2-methylpyrrolidin-2-carboxylic acid: (2S,4R)-Methyl 1-(2'-cyano-3-fluoro-4'-((1-(2-fluoro-2-methylpropyl)piperidin-4-yl)methoxy)biphenylcarbonyl)-4-hydroxy-2-methylpyrrolidin-2-carboxylate (0.16 g, 0.28 mmol) and LiOH.H₂O (0.03 g, 0.56 mmol) were dissolved in tetrahydrofuran (8 mL)/methanol (4 mL)/water (2 mL) at room temperature. The solution was stirred at 50° C. for 8 hours, and then cooled to room temperature thereby to make the reaction completed. From the reaction mixture, the solvent was removed under reduced pressure. To the concentrate, a small amount of 12 N-aqueous HCl solution was added and stirred. The precipitated solid was collected by filtration, washed with ethyl acetate and dried to obtain the desired compound (0.15 g, 96%) as white solid.

Step 3. Synthesis of Compound 1278: (2S,4R)-1-(2'-Cyano-3-fluoro-4'-((1-(2-fluoro-2-methylpropyl)piperidin-4-yl)methoxy)biphenylcarbonyl)-4-hydroxy-2-methylpyrrolidin-2-carboxylic acid (0.14 g, 0.25 mmol), EDC (0.09 g, 0.50 mmol), HOBt (0.06 g, 0.50 mmol) and DIPEA (0.09 g, 0.75 mmol) were dissolved in N,N-dimethylformamide (3 mL) at room temperature. To the solution, NH₄Cl (0.04 g, 0.75 mmol) was added, followed by stirring at the same temperature for 24 hours. From the reaction mixture, the solvent was removed under reduced pressure. The concentrate was purified by column chromatography (Waters, C18; acetonitrile/0.1%-trifluoroacetic acid aqueous solution=5% to 70%), and concentrated by passing through SPE cartridge (PL-HCO3 MP SPE). The obtained concentrate was purified by chromatography (SiO₂, 4 g cartridge; methanol/dichloromethane=3% to 10%), and concentrated to obtain the desired compound (0.03 g, 21%) as white solid.

1H NMR (400 MHz, CD₃OD) δ 7.61-7.53 (m, 2H), 7.48-7.39 (m, 3H), 7.33 (dd, 1H, J=8.7, 2.6 Hz), 4.45 (m, 1H), 3.94 (d, 2H, J=5.8 Hz), 3.77 (m, 1H), 3.47-3.43 (m, 1H), 3.06-3.03 (m, 2H), 2.55-2.46 (m, 3H), 2.21-2.15 (m, 2H), 2.08 (m, 1H), 1.90 (s, 3H), 1.82 (m, 3H), 1.52-1.46 (m, 2H), 1.39 (s, 3H), 1.34 (s, 3H); MS (ESI) m/z 555.2 (M⁺+H).

Synthesis of Compound 1279: (2S,4R)-1-(4-(5-((1-(2-Ethyl-2-fluorobutyl)piperidin-4-yl)methoxy)pyridin-2-yl)-2-fluorobenzoyl)-4-hydroxypyrrolidin-2-carboxamide

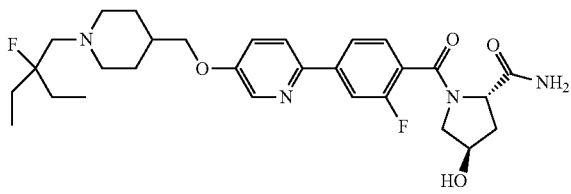 [SMILES: CCC(F)(CC)CN1CCC(COc2ccc(-c3ccc(C(=O)N4C[C@H](O)C[C@H]4C(N)=O)c(F)c3)nc2)CC1]

Intermediate 29 (0.07 g, 0.16 mmol), (2S,4R)-4-hydroxypyrrolidin-2-carboxamide hydrochloride (0.05 g, 0.32 mmol), EDC (0.04 g, 0.32 mmol), HOBt (0.06 g, 0.32 mmol) and DIPEA (0.05 mL, 0.32 mmol) were dissolved in dichloromethane (5 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO₄, filtered, and then concentrated under reduced pressure. The concentrate was purified by column chromatography (SiO₂, 4 g cartridge; methanol/dichloromethane=0% to 15%), and concentrated to obtain the desired compound (0.04 g, 54%) as white solid.

¹H NMR (400 MHz, CD₃OD) δ 8.33-8.35 (m, 1H), 7.79-7.90 (m, 3H), 7.60-7.64 (m, 1H), 7.46-7.50 (m, 1H), 4.72-4.76 (m, 1H), 4.43-4.44 (m, 1H), 3.95-3.98 (m, 2H), 3.75-3.84 (m, 1H), 3.36 (s, 1H), 3.02-3.05 (m, 2H), 2.45- 2.51 (m, 2H), 2.34-2.39 (m, 1H), 2.12-2.20 (m, 3H), 1.66-2.83 (m, 7H), 1.46-1.52 (m, 2H), 0.92 (t, 6H, J=7.5 Hz); MS (ESI) m/z 545.2 (M⁺+H).

Synthesis of Compound 1280: (2S,4R)-1-(2-Fluoro-4-(5-((1-((1-(trifluoromethyl)cyclobutyl)methyl)piperidin-4-yl)methoxy)pyridin-2-yl)benzoyl)-4-hydroxypyrrolidin-2-carboxamide

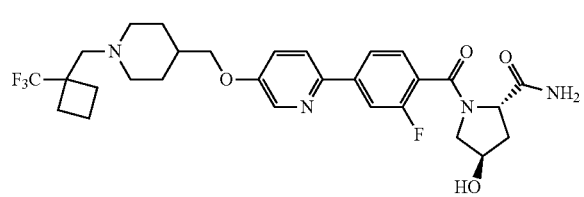

Intermediate 27 (0.06 g, 0.12 mmol), EDC (0.04 g, 0.25 mmol), HOBt (0.03 g, 0.25 mmol) and DIPEA (0.11 mL, 0.64 mmol) were mixed in N,N-dimethylformamide (10 mL). The mixture was stirred at room temperature for 30 minutes. (2S,4R)-4-Hydroxypyrrolidin-2-carboxamide hydrochloride (0.04 g, 0.25 mmol) was added thereto. And the reaction mixture was further stirred at 60° C. for 12 hours, and then cooled to room temperature thereby to make the reaction completed. From the reaction mixture, the solvent was removed under reduced pressure. To the obtained concentrate, water was added, and the mixture was extracted with dichloromethane. The organic layer was washed with saturated NaCl aqueous solution, dried with anhydrous MgSO₄, filtered, and then concentrated under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.03 g, 47%) as white solid.

¹H NMR (400 MHz, CD₃OD) δ 8.30 (m, 1H), 7.87-7.75 (m, 3H), 7.60-7.58 (m, 1H), 7.47-7.44 (m, 1H), 4.72-4.70 (m, 2H), 4.40 (brs, 1H), 4.00 (d, 2H, J=8.0 Hz), 3.72-3.79 (m, 2H), 3.41-3.32 (m, 3H), 2.40-2.27 (m, 6H), 2.12-2.02 (m, 7H), 1.79-1.62 (m, 2H); MS (ESI) m/z 579.2 (M⁺+H).

Synthesis of Compound 1281: (2S,4R)-4-Hydroxy-1-(4-(5-((1-(2,2,3,3,3-pentafluoropropyl)piperidin-4-yl)methoxy)pyrazin-2-yl)benzoyl)pyrrolidin-2-carboxamide

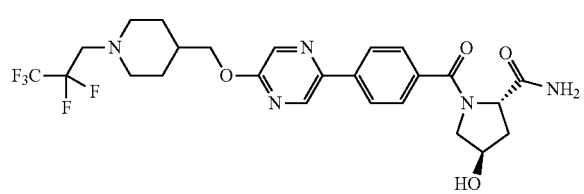

Intermediate 28 (0.09 g, 0.20 mmol), EDC (0.07 g, 0.40 mmol), HOBt (0.05 g, 0.40 mmol) and DIPEA (0.17 mL, 1.01 mmol) were mixed in N,N-dimethylformamide (10 mL). The mixture was stirred at room temperature for 20 minutes. (2S,4R)-4-Hydroxypyrrolidin-2-carboxamide hydrochloride (0.06 g, 0.40 mmol) was added thereto. And the reaction mixture was further stirred at 60° C. for 12 hours, and then cooled to room temperature thereby to make the reaction completed. To the reaction mixture, water (10 mL) was added, followed by stirring. The precipitated solid was filtered, washed with water, and dried. The obtained material was purified by chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.09 g, 79%) as white solid.

$^1$H NMR (400 MHz, CD$_3$OD) δ 8.70 (s, 1H), 8.31 (s, 1H), 8.09-8.07 (m, 2H), 7.78-7.76 (m, 2H), 4.45 (brs, 1H), 4.29 (d, 2H, J=6.2 Hz), 3.95-3.91 (m, 1H), 3.51 (d, 1H, J=12.0 Hz), 3.23-3.07 (m, 5H), 2.49 (t, 2H, J=12.0 Hz), 2.41-2.38 (m, 1H), 2.20-2.12 (m, 1H), 1.88-1.85 (m, 3H), 1.52-1.49 (m, 2H); MS (ESI) m/z 558.2 (M$^+$+H).

Synthesis of Compound 1286: (2S,4R)-1-(3-Fluoro-4-(5-((1-((1-(trifluoromethyl)cyclobutyl)methyl)piperidin-4-yl)methoxy)pyridin-2-yl)benzoyl)-4-hydroxypyrrolidin-2-carboxamide

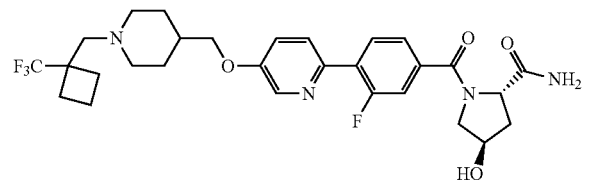

Intermediate 30 (0.08 g, 0.17 mmol), (2S,4R)-4-hydroxypyrrolidin-2-carboxamide hydrochloride (0.03 g, 0.20 mmol), HATU (0.13 g, 0.34 mmol) and DIPEA (0.06 mL, 0.34 mmol) were dissolved in N,N-dimethylformamide (3 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.04 g, 40%) as white solid.

$^1$H NMR (400 MHz, CD$_3$OD) δ 8.37 (m, 1H), 7.97-7.93 (m, 1H), 7.82-7.80 (m, 1H), 7.59-7.50 (m, 3H), 4.89-4.73 (m, 1H), 4.65 (m, 1H), 4.44 (m, 1H), 3.99-3.89 (m, 2H), 3.87-3.73 (m, 1H), 3.52 (m, 1H), 2.96-2.93 (m, 2H), 2.59 (s, 2H), 2.39 (m, 1H), 2.38-1.83 (m, 12H), 1.59-1.41 (m, 2H); MS (ESI) m/z 579.2 (M$^+$+H).

Synthesis of Compound 1287: (2S,4R)-1-(4-(5-((1-(2-Ethyl-2-fluorobutyl)piperidin-4-yl)methoxy)pyridin-2-yl)-3-fluorobenzoyl)-4-hydroxypyrrolidin-2-carboxamide

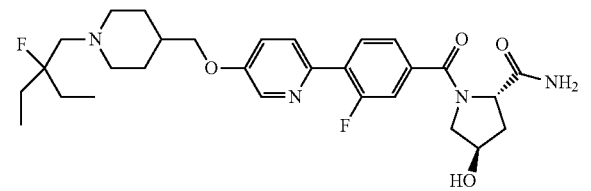 [SMILES: CCC(F)(CC)CN1CCC(COc2ccc(-c3ccc(C(=O)N4C[C@H](O)C[C@H]4C(N)=O)cc3F)nc2)CC1]

Intermediate 34 (0.07 g, 0.16 mmol), (2S,4R)-4-hydroxypyrrolidin-2-carboxamide hydrochloride (0.05 g, 0.32 mmol), HOBt (0.04 g, 0.32 mmol), EDC (0.06 g, 0.32 mmol) and DIPEA (0.05 mL, 0.32 mmol) were dissolved in methylene chloride (10 mL) at room temperature. The solution was stirred at 50° C. for 18 hours, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.04 g, 47%) as white solid.

$^1$H NMR (400 MHz, CD$_3$OD) δ 8.34-8.33 (m, 1H), 7.90-7.86 (m, 1H), 7.78-7.76 (m, 1H), 7.53-7.46 (m, 3H), 4.70-4.66 (m, 1H), 4.38 (s, 1H), 4.02-4.01 (m, 2H), 3.86-3.82 (m, 1H), 3.74-3.71 (m, 2H), 3.45-3.39 (m, 3H), 3.18-3.08 (m, 2H), 2.39-2.21 (m, 1H), 2.10-2.06 (m, 4H), 1.86-1.72 (m, 6H), 0.96 (t, 6H, J=7.5 Hz); MS (ESI) m/z 545.2 (M++H).

Synthesis of Compound 1288: (2S,4R)-1-(3'-Cyano-4'-((1-(2-fluoro-2-methylpropyl)piperidin-4-yl)methoxy)biphenylcarbonyl)-4-hydroxypyrrolidin-2-carboxamide

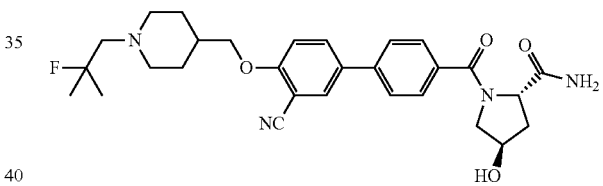

Intermediate 38 (0.07 g, 0.17 mmol), EDC (0.06 g, 0.34 mmol), HOBt (0.04 g, 0.34 mmol) and DIPEA (0.06 g, 0.51 mmol) were dissolved in methylene chloride (2 mL) at room temperature. To the solution, (2S,4R)-4-hydroxypyrrolidin-2-carboxamide hydrochloride (0.03 g, 0.20 mmol) was added, followed by stirring at the same temperature. To the reaction mixture, water was added. The mixture was extracted with ethyl acetate, filtered through plastic filter attached with anhydrous Na$_2$SO$_4$ cartridge to remove the solid residue and the aqueous layer, and then concentrated under reduced pressure. The concentrate was purified by column chromatography (Waters, C18; acetonitrile/trifluoroacetic acid=5% to 70%), and passed through SPE cartridge (PL-HCO3 MP SPE), followed by concentrating to obtain the desire compound (0.05 g, 65%) as white solid.

$^1$H NMR (400 MHz, CD$_3$OD) δ 7.85 (m, 2H), 7.71 (d, 2H, J=8.4 Hz), 7.61 (m, 2H), 7.18 (d, 1H, J=6.4 Hz), 4.24 (s, 2H), 4.01 (d, 2H, J=6.3 Hz), 3.87 (m, 1H), 3.52 (d, 1H, J=11.2 Hz), 3.05-3.02 (m, 2H), 2.52 (s, 1H), 2.46 (s, 1H), 2.33 (m, 1H), 2.22-2.13 (m, 3H), 1.91-1.85 (m, 3H), 1.45 (m, 2H), 1.39 (s, 3H), 1.34 (s, 3H); MS (ESI) m/z 523.2 (M$^+$+H).

Synthesis of Compound 1290: (2S,4R)-1-(2-Fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxamide

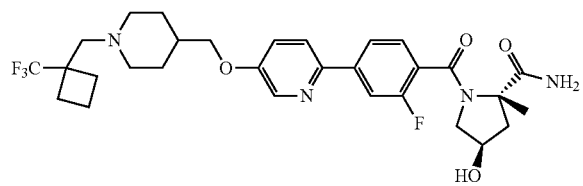 [SMILES: C[C@@]1(C(N)=O)C[C@@H](O)CN1C(=O)c1ccc(-c2ccc(OCC3CCN(CC4(C(F)(F)F)CCC4)CC3)cn2)cc1F]

Step 1. (2S,4R)-methyl 1-(2-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxylate: Intermediate 27 (0.30 g, 0.64 mmol), EDC (0.24 g, 1.28 mmol), HOBt (0.17 g, 1.28 mmol) and DIPEA (0.56 mL, 3.21 mmol) were mixed in N,N-dimethylformamide (10 mL). The mixture was stirred at room temperature for 30 minutes. (2S,4R)-methyl 4-hydroxy-2-methylpyrrolidin-2-carboxylate (0.12 g, 0.77 mmol) was added thereto. And the reaction mixture was further stirred at 60° C. for 12 hours, and then cooled to room temperature thereby to make the reaction completed. From the reaction mixture, the solvent was removed under reduced pressure. The concentrate was purified by column chromatography (SiO$_2$, 12 g cartridge; methanol/methylene chloride=0% to 5%), and concentrated to obtain the desired compound (0.18 g, 46%) as white solid.

Step 2. (2S,4R)-1-(2-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxylic acid: (2S,4R)-Methyl 1-(2-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxylate (0.18 g, 0.29 mmol) and LiOH (0.03 g, 1.48 mmol) were mixed in tetrahydrofuran (9 mL)/methanol (3 mL)/water (3 mL) at room temperature. The mixture was stirred at the same temperature for 12 hours. From the reaction mixture, the solvent was removed under reduced pressure. To the concentrate, water (25 mL) was added and stirred. The precipitated solid was collected by filtration, washed with water and dried to obtain the desired compound (0.15 g, 85%) as yellow solid.

Step 3. Synthesis of Compound 1290: (2S,4R)-1-(2-Fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxylic acid (0.15 g, 0.25 mmol), EDC (0.09 g, 0.50 mmol), HOBt (0.06 g, 0.50 mmol) and DIPEA (0.22 mL, 1.26 mmol) were mixed in N,N-dimethylformamide (10 mL). The mixture was stirred at room temperature for 1 hour, and NH$_4$Cl (0.02 g, 0.50 mmol) was added thereto. And the reaction mixture was further stirred at 60° C. for 12 hours, and then cooled to room temperature thereby to make the reaction completed. From the reaction mixture, the solvent was removed under reduced pressure. To the obtained concentrate, water was added, and the mixture was extracted with dichloromethane. The organic layer was washed with saturated NaCl aqueous solution, dried with anhydrous MgSO$_4$, filtered, and then concentrated under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.03 g, 47%) as white solid.

$^1$H NMR (400 MHz, CDCl$_3$) δ 8.32 (s, 1H), 7.71-7.63 (m, 2H), 7.47-7.43 (m, 1H), 7.28-7.25 (m, 2H), 7.01 (brs, 1H), 5.93 (brs, 1H), 4.41-4.38 (m, 1H), 3.90-3.89 (m, 2H), 3.68-3.64 (m, 1H), 3.59-3.58 (m, 1H), 2.67-2.48 (m, 3H), 2.27-2.16 (m, 3H), 2.02-1.95 (m, 4H), 1.90-1.17 (m, 12H); MS (ESI) m/z 593.2 (M$^+$+H).

Synthesis of Compound 1291: (2S,4R)-1-(4-(5-((1-(2-Ethyl-2-fluorobutyl)piperidin-4-yl)methoxy)pyridin-2-yl)-2-fluorobenzoyl)-4-hydroxy-2-methylpyrrolidin-2-carboxamide

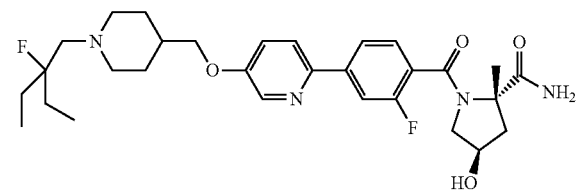 [SMILES: CCC(F)(CC)CN1CCC(COc2ccc(-c3ccc(C(=O)N4C[C@H](O)C[C@@]4(C)C(N)=O)c(F)c3)nc2)CC1]

Step 1. (2S,4R)-methyl 1-(4-(5-((1-(2-ethyl-2-fluorobutyl)piperidin-4-yl)methoxy)pyridin-2-yl)-2-fluorobenzoyl)-4-hydroxy-2-methylpyrrolidin-2-carboxylate: Intermediate 29 (0.25 g, 0.57 mmol), (2S,4R)-methyl 4-hydroxy-2-methylpyrrolidin-2-carboxylate hydrochloride (0.22 g, 1.15 mmol), HOBt (0.15 g, 1.15 mmol), EDC (0.22 g, 1.15 mmol) and DIPEA (0.14 g, 1.15 mmol) were dissolved in methylene chloride (15 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/methylene chloride=0% to 15%), and concentrated to obtain the desired compound (0.22 g, 66%) as white solid.

Step 2. 4-(5-((1-(2-ethyl-2-fluorobutyl)piperidin-4-yl)methoxy)pyridin-2-yl)-2-fluorobenzoic acid: (2S,4R)-Methyl 1-(4-(5-((1-(2-ethyl-2-fluorobutyl)piperidin-4-yl)methoxy)pyridin-2-yl)-2-fluorobenzoyl)-4-hydroxy-2-methylpyrrolidin-2-carboxylate (0.22 g, 0.38 mmol) and LiOH (0.04 g, 1.91 mmol) were dissolved in tetrahydrofuran (12 mL)/methanol (12 mL)/water (3 mL) at room temperature. The solution was stirred at 50° C. for 18 hours, and then cooled to room temperature thereby to make the reaction completed. From the reaction mixture, the solvent was removed under reduced pressure. The obtained product was used without further purification (0.20 g, 93%, white solid).

Step 3. Synthesis of Compound 1291: 4-(5-((1-(2-Ethyl-2-fluorobutyl)piperidin-4-yl)methoxy)pyridin-2-yl)-2-fluorobenzoic acid (0.27 g, 0.48 mmol), ammonium chloride (0.07 g, 1.44 mmol), HOBt (0.13 g, 0.96 mmol), EDC (0.18 g, 0.96 mmol) and DIPEA (0.17 mL, 0.96 mmol) were dissolved in N,N-dimethylformamide (15 mL) at 80° C. The solution was stirred at the same temperature for 18 hours, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.03 g, 12%) as white solid.

$^1$H NMR (400 MHz, CD$_3$OD) δ 8.35 (d, 1H, J=2.8 Hz), 7.90-7.80 (m, 3H), 7.57-7.48 (m, 2H), 4.46-4.43 (m, 1H), 4.00-3.98 (m, 2H), 3.78-3.74 (m, 1H), 3.46-3.42 (m, 1H), 3.14-3.11 (m, 2H), 2.64-2.58 (m, 2H), 2.51-2.46 (m, 1H), 2.38-2.20 (m, 1H), 2.09-2.04 (m, 1H), 1.90-1.85 (m, 6H), 1.78-1.68 (m, 5H), 1.54-1.51 (m, 2H), 0.93 (t, 6H, J=7.5 Hz); MS (ESI) m/z 559.2 (M++H).

Synthesis of Compound 1292: (2S,4R)-1-(4-(5-((1-(2-Ethyl-2-fluorobutyl)piperidin-4-yl)methoxy)pyridin-2-yl)-3-fluorobenzoyl)-4-hydroxy-2-methylpyrrolidin-2-carboxamide

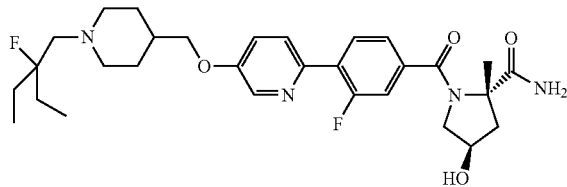 [SMILES: CCC(F)(CC)CN1CCC(COc2ccc(-c3ccc(C(=O)N4C[C@H](O)C[C@@]4(C)C(N)=O)cc3F)nc2)CC1]

Step 1. (2S,4R)-methyl 1-(4-(5-((1-(2-ethyl-2-fluorobutyl)piperidin-4-yl)methoxy)pyridin-2-yl)-3-fluorobenzoyl)-4-hydroxy-2-methylpyrrolidin-2-carboxylate: Intermediate 34 (0.25 g, 0.57 mmol), (2S,4R)-methyl 4-hydroxy-2-methylpyrrolidin-2-carboxylate hydrochloride (0.22 g, 1.15 mmol), HOBt (0.15 g, 1.15 mmol), EDC (0.22 g, 1.15 mmol) and DIPEA (0.20 mL, 1.15 mmol) were dissolved in methylene chloride (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/methylene chloride=0% to 15%), and concentrated to obtain the desired compound (0.30 g, 90%) as white solid.

Step 2. (2S,4R)-1-(4-(5-((1-(2-ethyl-2-fluorobutyl)piperidin-4-yl)methoxy)pyridin-2-yl)-3-fluorobenzoyl)-4-hydroxy-2-methylpyrrolidin-2-carboxylic acid: (2S,4R)-Methyl 1-(4-(5-((1-(2-ethyl-2-fluorobutyl)piperidin-4-yl)methoxy)pyridin-2-yl)-3-fluorobenzoyl)-4-hydroxy-2-methylpyrrolidin-2-carboxylate (0.30 g, 0.52 mmol) and LiOH (0.06 g, 2.61 mmol) were dissolved in tetrahydrofuran (8 mL)/methanol (8 mL)/water (2 mL) at 50° C. The solution was stirred at the same temperature for 18 hours, and then cooled to room temperature thereby to make the reaction completed. From the reaction mixture, the solvent was removed under reduced pressure. The obtained product was used without further purification (0.28 g, 95%, white solid).

Step 3. Synthesis of Compound 1292: (2S,4R)-1-(4-(5-((1-(2-Ethyl-2-fluorobutyl)piperidin-4-yl)methoxy)pyridin-2-yl)-3-fluorobenzoyl)-4-hydroxy-2-methylpyrrolidin-2-carboxylic acid (0.29 g, 0.51 mmol), ammonium chloride (0.08 g, 1.55 mmol), HOBt (0.14 g, 1.03 mmol), EDC (0.19 g, 1.03 mmol) and DIPEA (0.18 mL, 1.03 mmol) were dissolved in N,N-dimethylformamide (20 mL) at room temperature. The solution was stirred at 80° C. for 18 hours, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (Waters, C18; ethyl acetate/hexane=0% to 30%), and passed through SPE cartridge (PL-HCO3 MP SPE), followed by concentrating to obtain the desire compound (0.13 g, 44%) as white solid.

$^1$H NMR (400 MHz, CD$_3$OD) δ 8.38 (d, 1H, J=3.0 Hz), 7.94 (t, 1H, J=7.9 Hz), 7.82-7.79 (m, 1H), 7.52-7.42 (m, 3H), 4.48-4.43 (m, 1H), 4.02-4.01 (m, 2H), 3.88-3.84 (m, 1H), 3.57-3.53 (m, 1H), 3.33-3.21 (m, 2H), 2.89-2.77 (m, 2H), 2.55-2.42 (m, 3H), 2.10-2.06 (m, 1H), 1.97-1.90 (m, 6H), 1.82-1.72 (m, 4H), 1.64-1.61 (m, 2H), 0.95 (t, 6H, J=7.5 Hz); MS (ESI) m/z 560.2 (M$^+$+H).

Synthesis of Compound 1294: (2S,4R)-1-(2-Fluoro-4-(5-((1-(3,3,3-trifluoro-2,2-dimethylpropyl)piperidin-4-yl)methoxy)pyridin-2-yl)benzoyl)-4-hydroxy-2-methylpyrrolidin-2-carboxamide

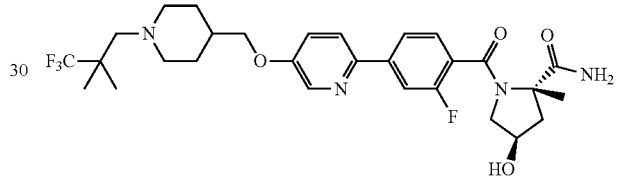

Step 1. (2S,4R)-methyl 1-(2-fluoro-4-(5-((1-(3,3,3-trifluoro-2,2-dimethylpropyl)piperidin-4-yl)methoxy)pyridin-2-yl)benzoyl)-4-hydroxy-2-methylpyrrolidin-2-carboxylate: Intermediate 19 (0.30 g, 0.66 mmol), EDC (0.25 g, 1.32 mmol), HOBt (0.17 g, 1.32 mmol) and DIPEA (0.35 mL, 1.98 mmol) were dissolved in methylene chloride (6 mL) at room temperature. To the solution, Intermediate 25 (0.15 g, 0.79 mmol) was added, followed by stirring at the same temperature for 14 hours. To the reaction mixture, saturated ammonium chloride aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/methylene chloride=0% to 10%), and concentrated to obtain the desired compound (0.25 g, 63%) as yellow oil.

Step 2. (2S,4R)-1-(2-fluoro-4-(5-((1-(3,3,3-trifluoro-2,2-dimethylpropyl)piperidin-4-yl)methoxy)pyridin-2-yl)benzoyl)-4-hydroxy-2-methylpyrrolidin-2-carboxylic acid: (2S,4R)-Methyl 1-(2-fluoro-4-(5-((1-(3,3,3-trifluoro-2,2-dimethylpropyl)piperidin-4-yl)methoxy)pyridin-2-yl)benzoyl)-4-hydroxy-2-methylpyrrolidin-2-carboxylate (0.25 g, 0.42 mmol) and LiOH.H$_2$O (0.02 g, 0.84 mmol) were dissolved in tetrahydrofuran (8 mL)/methanol (4 mL)/water (3 mL) at 50° C. The solution was stirred at the same temperature for 8 hours, and then cooled to room temperature thereby to make the reaction completed. From the reaction mixture, the solvent was removed under reduced pressure. To the concentrate, a small amount of 12N-aqueous HCl solution was added and stirred. The precipitated solid was collected by filtration, washed with ethyl acetate and dried to obtain the desired compound (0.21 g, 86%) as white solid.

Step 3. Synthesis of Compound 1294: (2S,4R)-1-(2-Fluoro-4-(5-((1-(3,3,3-trifluoro-2,2-dimethylpropyl)piperidin-4-yl)methoxy)pyridin-2-yl)benzoyl)-4-hydroxy-2-methylpyrrolidin-2-carboxylic acid (0.15 g, 0.26 mmol), EDC (0.10 g, 0.51 mmol), HOBt (0.07 g, 0.51 mmol) and DIPEA (0.10 g, 0.77 mmol) were dissolved in N,N-dimethylformamide (2 mL) at room temperature. To the solution, $NH_4Cl$ (0.04 g, 0.77 mmol) was added, followed by stirring at 50° C. for 8 hours. And then, the reaction mixture was cooled to room temperature thereby to make the reaction completed. From the reaction mixture, the solvent was removed under reduced pressure. To the obtained concentrate, water was added, and the mixture was extracted with ethyl acetate. The organic layer was washed with saturated NaCl aqueous solution, dried with anhydrous $MgSO_4$, filtered, and then concentrated under reduced pressure. The concentrate was purified by column chromatography ($SiO_2$, 4 g cartridge; methanol/methylene chloride=0% to 10%), and concentrated. The obtained concentrate was purified again by chromatography (Waters, C18; acetonitrile/trifluoroacetic acid=5% to 70%), and passed through SPE cartridge (PL-HCO3 MP SPE), followed by concentrating to obtain the desire compound (0.02 g, 13%) as white solid.

$^1$H NMR (400 MHz, $CD_3OD$) δ 8.36 (d, 1H, 2.8 Hz), 7.84 (m, 3H), 7.58 (t, 1H, 7.5 Hz), 7.51 (dd, 1H, 8.8, 3.0 Hz), 4.00 (d, 2H, 5.8 Hz), 3.59 (t, 2H, 6.6 Hz), 3.09 (m, 2H), 2.58 (s, 1H), 2.52 (s, 1H), 2.35 (m, 1H), 2.25 (t, 2H, J=11.4 Hz), 2.09-2.00 (m, 3H), 1.87-1.85 (m, 3H), 1.77 (s, 3H), 1.51 (m, 2H), 1.36 (s, 3H), 1.31 (s, 3H); MS (ESI) m/z 581.2 ($M^++H$).

Synthesis of Compound 1295: (2S,4R)-1-(2-Fluoro-4-(6-((1-(3,3,3-trifluoro-2,2-dimethylpropyl)piperidin-4-yl)methoxy)pyridin-3-yl)benzoyl)-4-hydroxy-2-methylpyrrolidin-2-carboxamide

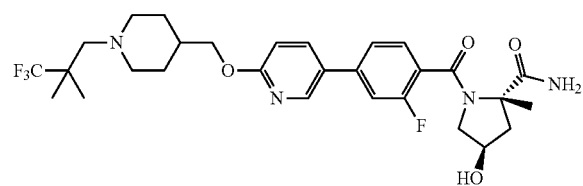 [SMILES: CC(C)(CN1CCC(COc2ccc(-c3ccc(C(=O)N4C[C@H](O)C[C@@]4(C)C(N)=O)c(F)c3)cn2)CC1)C(F)(F)F]

Step 1. (2S,4R)-methyl 1-(2-fluoro-4-(6-((1-(3,3,3-trifluoro-2,2-dimethylpropyl)piperidin-4-yl)methoxy)pyridin-3-yl)benzoyl)-4-hydroxy-2-methylpyrrolidin-2-carboxylate: Intermediate 17 (0.30 g, 0.66 mmol), EDC (0.25 g, 1.32 mmol), HOBt (0.18 g, 1.32 mmol) and DIPEA (0.25 g, 1.98 mmol) were dissolved in methylene chloride (6 mL) at room temperature. To the solution, Intermediate 25 (0.15 g, 0.79 mmol) was added, followed by stirring at the same temperature for 1 hour. To the reaction mixture, water was added, and the mixture was extracted with methylene chloride. The organic layer was washed with saturated NaCl aqueous solution, dried with anhydrous $MgSO_4$, filtered, and then concentrated under reduced pressure. The concentrate was purified by column chromatography ($SiO_2$, 12 g cartridge; methanol/methylene chloride=0% to 10%), and concentrated to obtain the desired compound (0.25 g, 63%) as white solid.

Step 2. (2S,4R)-1-(2-fluoro-4-(6-((1-(3,3,3-trifluoro-2,2-dimethylpropyl)piperidin-4-yl)methoxy)pyridin-3-yl)benzoyl)-4-hydroxy-2-methylpyrrolidin-2-carboxylic acid: (2S,4R)-Methyl 1-(2-fluoro-4-(6-((1-(3,3,3-trifluoro-2,2-dimethylpropyl)piperidin-4-yl)methoxy)pyridin-3-yl)benzoyl)-4-hydroxy-2-methylpyrrolidin-2-carboxylate (0.25 g, 0.42 mmol) and $LiOH \cdot H_2O$ (0.02 g, 0.84 mmol) were dissolved in tetrahydrofuran (8 mL)/methanol (4 mL)/water (3 mL) at room temperature. The solution was stirred at 50° C. for 5 hours, and then cooled to room temperature thereby to make the reaction completed. From the reaction mixture, the solvent was removed under reduced pressure. To the concentrate, a small amount of 12 N-aqueous HCl solution was added and stirred. The precipitated solid was collected by filtration, washed with ethyl acetate and dried to obtain the desired compound (0.19 g, 77%) as yellow solid.

Step 3. Synthesis of Compound 1295: (2S,4R)-1-(2-Fluoro-4-(6-((1-(3,3,3-trifluoro-2,2-dimethylpropyl)piperidin-4-yl)methoxy)pyridin-3-yl)benzoyl)-4-hydroxy-2-methylpyrrolidin-2-carboxylic acid (0.15 g, 0.26 mmol), EDC (0.10 g, 0.51 mmol), HOBt (0.07 g, 0.51 mmol) and DIPEA (0.10 g, 0.77 mmol) were dissolved in N,N-dimethylformamide (3 mL) at room temperature. To the solution, $NH_4Cl$ (0.04 g, 0.77 mmol) was added, followed by stirring at 50° C. for 8 hours. And then, the reaction mixture was cooled to room temperature thereby to make the reaction completed. From the reaction mixture, the solvent was removed under reduced pressure. The concentrate was purified by column chromatography (Waters, C18; acetonitrile/trifluoroacetic acid=5% to 70%), and passed through SPE cartridge (PL-HCO3 MP SPE), followed by concentrating to obtain the desire compound (0.11 g, 73%) as white solid.

$^1$H NMR (400 MHz, $CD_3OD$) δ 8.44 (d, 1H, J=2.5 Hz), 8.03 (dd, 1H, J=8.7, 2.6 Hz), 7.56 (d, 2H, J=3.9 Hz), 7.51 (d, 1H, J=11.1 Hz), 6.93 (d, 1H, J=8.7 Hz), 4.47 (m, 1H), 4.18 (d, 2H, J=6.0 Hz), 3.77 (dd, 1H, J=11.0, 5.2 Hz), 3.45 (dd, 1H, J=10.9, 3.7 Hz), 2.89-2.87 (m, 2H), 2.49 (dd, 1H, J=13.4, 5.6 Hz), 2.43 (s, 1H), 2.35 (t, 2H, J=10.9 Hz), 2.08 (dd, 1H, J=13.2, 4.1 Hz), 1.89 (s, 3H), 1.77 (m, 3H), 1.43 (m, 2H), 1.13 (s, 6H); MS (ESI) m/z 581.1 ($M^++H$).

Synthesis of Compound 1297: (S)-1-(2-Fluoro-4-(5-((1-((1-(trifluoromethyl)cyclobutyl)methyl)piperidin-4-yl)methoxy)pyridin-2-yl)benzoyl)-2-methylpyrrolidin-2-carboxamide

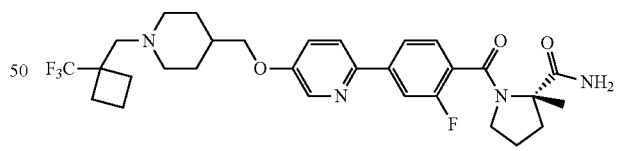

Step 1. (S)-methyl 1-(2-fluoro-4-(5-((1-((1-(trifluoromethyl)cyclobutyl)methyl)piperidin-4-yl)methoxy)pyridin-2-yl)benzoyl)-2-methylpyrrolidin-2-carboxylate: Intermediate 27 (0.15 g, 0.32 mmol), EDC (0.12 g, 0.64 mmol), HOBt (0.08 g, 0.64 mmol) and DIPEA (0.28 mL, 1.60 mmol) were dissolved in N,N-dimethylformamide (10 mL). The solution was stirred at room temperature for 25 minutes. (S)-methyl 2-methylpyrrolidin-2-carboxylate (0.07 g, 0.64 mmol) was added thereto. And the reaction mixture was further stirred at 60° C. for 12 hours, and then cooled to room temperature thereby to make the reaction completed. From the reaction mixture, the solvent was removed under reduced pressure. To the obtained concentrate, water was added, and the mixture was extracted with methylene chloride. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/methylene chloride=0% to 5%), and concentrated to obtain the desired compound (0.12 g, 63%) as yellow solid.

Step 2. (S)-1-(2-fluoro-4-(5-((1-((1-(trifluoromethyl)cyclobutyl)methyl)piperidin-4-yl)methoxy)pyridin-2-yl)benzoyl)-2-methylpyrrolidin-2-carboxylic acid: (S)-Methyl 1-(2-fluoro-4-(5-((1-((1-(trifluoromethyl)cyclobutyl)methyl)piperidin-4-yl)methoxy)pyridin-2-yl)benzoyl)-2-methylpyrrolidin-2-carboxylate (0.12 g, 0.20 mmol) and LiOH (0.02 g, 1.01 mmol) were mixed in tetrahydrofuran (9 mL)/methanol (3 mL)/water (3 mL). The mixture was stirred at room temperature for 20 minutes, and further stirred at 60° C. for 5 hours, and then cooled to room temperature thereby to make the reaction completed. From the reaction mixture, the solvent was removed under reduced pressure. The obtained product was used without further purification (0.10 g, 85%, white solid).

Step 3. Synthesis of Compound 1297: (S)-1-(2-Fluoro-4-(5-((1-((1-(trifluoromethyl)cyclobutyl)methyl)piperidin-4-yl)methoxy)pyridin-2-yl)benzoyl)-2-methylpyrrolidin-2-carboxylic acid (0.10 g, 0.17 mmol), EDC (0.06 g, 0.34 mmol), HOBt (0.04 g, 0.34 mmol) and DIPEA (0.15 mL, 0.86 mmol) were mixed in N,N-dimethylformamide (10 mL). The mixture was stirred at room temperature for 30 minutes. NH$_4$Cl (0.01 g, 0.34 mmol) was added thereto. And the reaction mixture was further stirred at 60° C. for 12 hours, and then cooled to room temperature thereby to make the reaction completed. From the reaction mixture, the solvent was removed under reduced pressure. To the obtained concentrate, water was added, and the mixture was extracted with methylene chloride. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/methylene chloride=0% to 5%), and concentrated to obtain the desired compound (0.05 g, 52%) as pale yellow solid.

$^1$H NMR (400 MHz, CDCl$_3$) δ 8.41-8.37 (m, 1H), 7.77-7.74 (m, 2H), 7.70-7.66 (m, 1H), 7.46 (t, 1H, J=8.0 Hz), 7.31-7.13 (m, 1H), 7.12 (brs, 1H), 5.43 (brs, 1H), 3.92 (d, 2H, J=8.0 Hz), 3.53-3.48 (m, 2H), 3.03-2.89 (m, 2H), 2.67-2.65 (m, 3H), 2.32-2.18 (m, 6H), 2.08-0.98 (m, 13H); MS (ESI) m/z 577.1 (M$^+$+H).

Synthesis of Compound 1299: (S)-1-(4-(5-((1-(2-Ethyl-2-fluorobutyl)piperidin-4-yl)methoxy)pyridin-2-yl)-2-fluorobenzoyl)-2-methylpyrrolidin-2-carboxamide

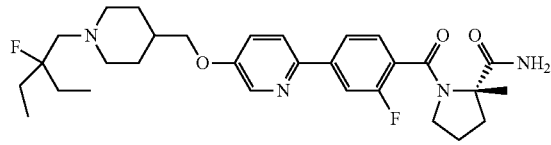

Step 1. (S)-methyl 1-(4-(5-((1-(2-ethyl-2-fluorobutyl)piperidin-4-yl)methoxy)pyridin-2-yl)-2-fluorobenzoyl)-2-methylpyrrolidin-2-carboxylate: Intermediate 29 (0.15 g, 0.34 mmol), (S)-methyl 2-methylpyrrolidin-2-carboxylate hydrochloride (0.12 g, 0.69 mmol), EDC (0.09 g, 0.69 mmol), HOBt (0.13 g, 0.69 mmol) and DIPEA (0.12 mL, 0.69 mmol) were dissolved in methylene chloride (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; ethyl acetate/hexane=0% to 30%), and concentrated to obtain the desired compound (0.19 g, 98%) as white solid.

Step 2. (S)-1-(4-(5-((1-(2-ethyl-2-fluorobutyl)piperidin-4-yl)methoxy)pyridin-2-yl)-2-fluorobenzoyl)-2-methylpyrrolidin-2-carboxylic acid: (S)-Methyl 1-(4-(5-((1-(2-ethyl-2-fluorobutyl)piperidin-4-yl)methoxy)pyridin-2-yl)-2-fluorobenzoyl)-2-methylpyrrolidin-2-carboxylate (0.19 g, 0.34 mmol) and LiOH (0.04 g, 1.70 mmol) were dissolved in tetrahydrofuran (4 mL)/methanol (4 mL)/water (1 mL) at room temperature. The solution was stirred at the same temperature for 18 hours. From the reaction mixture, the solvent was removed under reduced pressure. To the concentrate, 1M-aqueous HCl solution (10 mL) and water (20 mL) were added and stirred. The precipitated solid was collected by filtration, washed with water and dried to obtain the desired compound (0.16 g, 87%) as white solid.

Step 3. Synthesis of Compound 1299: (S)-1-(4-(5-((1-(2-Ethyl-2-fluorobutyl)piperidin-4-yl)methoxy)pyridin-2-yl)-2-fluorobenzoyl)-2-methylpyrrolidin-2-carboxylic acid (0.16 g, 0.29 mmol), NH$_4$Cl (0.04 g, 0.89 mmol), EDC (0.08 g, 0.59 mmol), HOBt (0.11 g, 0.59 mmol) and DIPEA (0.10 mL, 0.596 mmol) were dissolved in N,N-dimethylformamide (10 mL) at room temperature. The solution was stirred at 50° C. for 18 hours, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; methanol/methylene chloride=0% to 15%), and concentrated to obtain the desired compound (0.05 g, 32%) as white solid.

$^1$H NMR (400 MHz, CDCl$_3$) δ 8.37 (d, 1H, J=2.8 Hz), 7.73-7.76 (m, 2H), 7.65-7.67 (m, 1H), 7.43-7.47 (m, 1H), 7.25-7.28 (m, 1H), 7.14 (s, 1H), 5.47 (s, 1H), 3.88-3.89 (m, 2H), 3.46-3.49 (m, 2H), 2.64-2.70 (m, 1H), 2.41-2.47 (m, 2H), 2.10-2.17 (m, 2H), 1.82-1.89 (m, 8H), 1.54-1.78 (m, 5H), 1.41-1.46 (m, 2H), 0.89 (t, 6H, J=7.5 Hz); MS (ESI) m/z 543.2 (M$^+$+H).

Synthesis of Compound 1300: (S)-1-(2-Fluoro-4-(5-((1-((1-(trifluoromethyl)cyclobutyl)methyl)piperidin-4-yl)methoxy)pyridin-2-yl)benzoyl)pyrrolidin-2-carboxamide

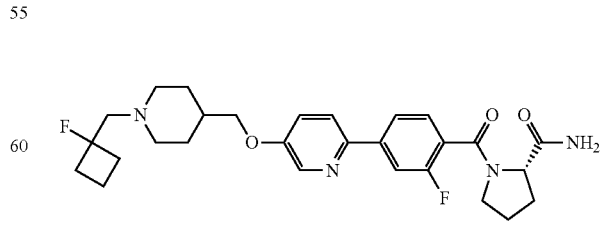

Intermediate 27 (0.07 g, 0.15 mmol), EDC (0.05 g, 0.30 mmol), HOBt (0.04 g, 0.30 mmol) and DIPEA (0.13 mL, 0.75 mmol) were mixed in N,N-dimethylformamide (10 mL). The mixture was stirred at room temperature for 30 minutes. (S)-Pyrrolidin-2-carboxamide (0.03 g, 0.30 mmol) was added thereto. And the reaction mixture was further stirred at 60° C. for 12 hours, and then cooled to room temperature thereby to make the reaction completed. From the reaction mixture, the solvent was removed under reduced pressure. To the obtained concentrate, water was added, and the mixture was extracted with methylene chloride. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/methylene chloride=0% to 5%), and concentrated to obtain the desired compound (0.02 g, 32%) as white solid.

$^1$H NMR (400 MHz, CDCl$_3$) δ 8.38 (m, 1H), 7.78-7.75 (m, 2H), 7.67 (d, 1H, J=12.0 Hz), 7.52-7.48 (m, 1H), 7.29-7.26 (m, 1H), 6.95 (brs, 1H), 5.71 (brs, 1H), 4.83-4.80 (m, 1H), 3.92-3.89 (m, 2H), 3.54-3.50 (m, 1H), 3.44-3.40 (m, 1H), 2.92-2.90 (m, 2H), 2.55 (s. 2H), 2.46-2.42 (m, 5H), 2.28-1.88 (m, 12H); MS (ESI) m/z 563.2 (M$^+$+H).

Synthesis of Compound 1301: (S)-2-Methyl-1-(4-(5-((1-(2,2,3,3,3-pentafluoropropyl)piperidin-4-yl)methoxy)pyrazin-2-yl)benzoyl)pyrrolidin-2-carboxamide

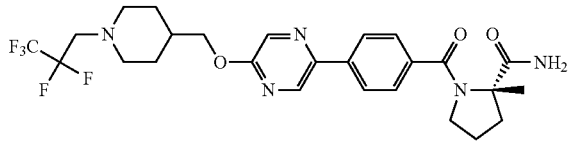 [SMILES: C[C@@]1(C(N)=O)CCCN1C(=O)c1ccc(-c2cnc(OCC3CCN(CC(F)(F)C(F)(F)F)CC3)cn2)cc1]

Step 1. (S)-methyl 2-methyl-1-(4-(5-((1-(2,2,3,3,3-pentafluoropropyl)piperidin-4-yl)methoxy)pyrazin-2-yl)benzoyl)pyrrolidin-2-carboxylate: Intermediate 28 (0.09 g, 0.20 mmol), EDC (0.07 g, 0.40 mmol), HOBt (0.05 g, 0.40 mmol) and DIPEA (0.17 mL, 1.01 mmol) were dissolved in N,N-dimethylformamide (10 mL). The solution was stirred at room temperature for 30 minutes. (S)-Methyl 2-methyl-pyrrolidin-2-carboxylate (0.05 g, 0.40 mmol) was added thereto. And the reaction mixture was further stirred at 60° C. for 24 hours, and then cooled to room temperature thereby to make the reaction completed. To the reaction mixture, water (20 mL) was added, followed by stirring. The precipitated solid was filtered, washed with water, and dried. The obtained material was purified by chromatography (SiO$_2$, 4 g cartridge; ethyl acetate/hexane=5% to 70%), and concentrated to obtain the desired compound (0.03 g, 27%) as white solid.

Step 2. (S)-2-methyl-1-(4-(5-((1-(2,2,3,3,3-pentafluoropropyl)piperidin-4-yl)methoxy)pyrazin-2-yl)benzoyl)pyrrolidin-2-carboxylic acid: (S)-Methyl 2-methyl-1-(4-(5-((1-(2,2,3,3,3-pentafluoropropyl)piperidin-4-yl)methoxy)pyrazin-2-yl)benzoyl)pyrrolidin-2-carboxylate (0.03 g, 0.05 mmol) and LiOH (0.01 g, 0.28 mmol) were dissolved in tetrahydrofuran (12 mL)/methanol (4 mL)/water (4 mL). The solution was stirred at room temperature for 1 hour, and further stirred at 60° C. for 2 hours, and then cooled to room temperature thereby to make the reaction completed. From the reaction mixture, the solvent was removed under reduced pressure. The obtained product was used without further purification (0.03 g, 96.%, white solid).

Step 3. Synthesis of Compound 1301: (S)-2-Methyl-1-(4-(5-((1-(2,2,3,3,3-pentafluoropropyl)piperidin-4-yl)methoxy)pyrazin-2-yl)benzoyl)pyrrolidin-2-carboxylic acid (0.03 g, 0.05 mmol), EDC (0.02 g, 0.10 mmol), HOBt (0.01 g, 0.10 mmol) and DIPEA (0.04 mL, 0.27 mmol) were mixed in N,N-dimethylformamide (10 mL). The mixture was stirred at room temperature for 20 minutes. NH$_4$Cl (0.01 g, 0.10 mmol) was added thereto. And the reaction mixture was further stirred at 50° C. for 12 hours, and then cooled to room temperature thereby to make the reaction completed. From the reaction mixture, the solvent was removed under reduced pressure. To the obtained concentrate, water was added, and the mixture was extracted with methylene chloride. The organic layer was washed with saturated NaCl aqueous solution, dried with anhydrous MgSO$_4$, filtered, and then concentrated under reduced pressure. The concentrate was purified by column chromatography (SiO$_2$, 12 g cartridge; methanol/methylene chloride=0% to 10%), and concentrated to obtain the desired compound (0.02 g, 76%) as white solid.

$^1$H NMR (400 MHz, CDCl$_3$) δ 8.51 (s, 1H), 8.29 (s, 1H), 7.96-7.94 (d, 2H, J=8.0 Hz), 7.59-7.57 (m, 2H), 7.16 (brs, 1H), 5.52 (brs, 1H), 4.23 (d, 2H, J=4.0 Hz) 3.57 (m, 2H), 3.13-3.11 (m, 1H), 3.04-2.96 (m, 1H), 2.39-2.36 (m, 1H), 2.05 (m, 2H), 1.90-1.84 (m, 9H), 1.49-1.46 (m, 1H), 1.27-1.23 (m, 3H); MS (ESI) m/z 556.2 (M$^+$+H).

Synthesis of Compound 1305: (2S,4R)-1-(4-(5-((1-(2-Ethyl-2-fluorobutyl)piperidin-4-yl)methoxy)pyridin-2-yl)benzoyl)-4-hydroxypyrrolidin-2-carboxamide

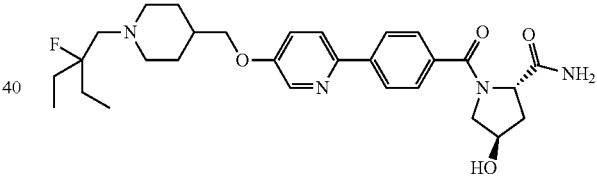

Intermediate 35 (0.08 g, 0.19 mmol), (2S,4R)-4-hydroxy pyrrolidin-2-carboxamide hydrochloride (0.06 g, 0.38 mmol), HOBt (0.05 g, 0.38 mmol), EDC (0.07 g, 0.38 mmol) and DIPEA (0.06 mL, 0.38 mmol) were dissolved in methylene chloride (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.03 g, 37%) as white solid.

$^1$H NMR (400 MHz, CD$_3$OD) δ 8.28 (d, 1H, J=2.8 Hz), 7.97-7.91 (m, 2H), 7.82-7.78 (m, 1H), 7.71-7.50 (m, 2H), 7.44-7.41 (m, 1H), 4.72-4.70 (m, 1H), 4.60 (s, 1H), 3.98-3.96 (m, 2H), 3.88-3.84 (m, 1H), 3.78-3.43 (m, 4H), 3.35-3.25 (m, 1H), 3.12-3.03 (m, 2H), 2.35-2.30 (m, 1H), 2.10-2.01 (m, 4H), 1.87-1.74 (m, 6H), 0.95 (t, 6H, J=7.5 Hz); MS (ESI) m/z 527.3 (M$^+$+H).

Synthesis of Compound 1306: (2S,4R)-1-(4-(6-((1-(2-Ethyl-2-fluorobutyl)piperidin-4-yl)methoxy)pyridin-3-yl)benzoyl)-4-hydroxypyrrolidin-2-carboxamide

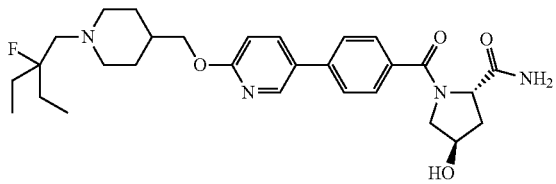 [SMILES: CCC(F)(CC)CN1CCC(COc2ccc(-c3ccc(C(=O)N4C[C@H](O)C[C@H]4C(N)=O)cc3)cn2)CC1]

Intermediate 36 (0.08 g, 0.19 mmol), (2S,4R)-4-hydroxypyrrolidin-2-carboxamide hydrochloride (0.06 g, 0.38 mmol), HOBt (0.05 g, 0.38 mmol), EDC (0.07 g, 0.38 mmol) and DIPEA (0.06 mL, 0.38 mmol) were dissolved in methylene chloride (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.02 g, 25%) as white solid.

$^1$H NMR (400 MHz, CD$_3$OD) δ 8.37-8.33 (m, 1H), 7.97-7.94 (m, 1H), 7.70-7.49 (m, 4H), 6.86-6.83 (m, 1H), 4.71-4.67 (m, 1H), 4.37 (s, 1H), 4.12 (d, 2H, J=6.0 Hz), 3.87-3.77 (m, 1H), 3.45 (d, 1H, J=11.4 Hz), 2.98 (d, 2H, J=11.8 Hz), 2.44 (m, 2H), 2.34-2.28 (m, 1H), 2.12-1.99 (m, 3H), 1.75-1.60 (m, 7H), 1.44-1.35 (m, 2H), 0.85 (t, 6H, J=7.5 Hz); MS (ESI) m/z 527.3 (M$^+$+H).

Synthesis of Compound 1307: (2S,4R)-1-(4-(6-((1-(2-Ethyl-2-fluorobutyl)piperidin-4-yl)methoxy)pyridin-3-yl)-3-fluorobenzoyl)-4-hydroxypyrrolidin-2-carboxamide

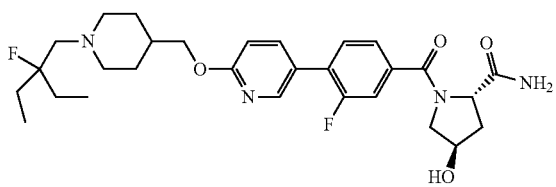 [SMILES: CCC(F)(CC)CN1CCC(COc2ccc(-c3ccc(C(=O)N4C[C@H](O)C[C@H]4C(N)=O)cc3F)cn2)CC1]

Intermediate 41 (0.08 g, 0.18 mmol), (2S,4R)-4-hydroxypyrrolidin-2-carboxamide hydrochloride (0.06 g, 0.37 mmol), HOBt (0.05 g, 0.37 mmol), EDC (0.07 g, 0.37 mmol) and DIPEA (0.06 mL, 0.37 mmol) were dissolved in methylene chloride (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.01 g, 16%) as white solid.

$^1$H NMR (400 MHz, CD$_3$OD) δ 8.29 (s, 1H), 7.94-7.86 (m, 1H), 7.58-7.46 (m, 3H), 6.87-6.84 (m, 1H), 4.70-4.66 (m, 1H), 4.37 (s, 1H), 4.13 (d, 2H, J=6.0 Hz), 3.86-3.82 (m, 1H), 3.45-3.42 (m, 1H), 2.98 (d, 2H, J=11.5 Hz), 2.46-2.40 (m, 2H), 2.34-2.29 (m, 1H), 2.11-2.02 (m, 3H), 1.76-1.60 (m, 7H), 1.44-1.38 (m, 2H), 0.85 (t, 6H, J=7.5 Hz); MS (ESI) m/z 545.2 (M$^-$+H).

Synthesis of Compound 1308: (2S,4R)-1-(4-(6-((1-(2-Ethyl-2-fluorobutyl)piperidin-4-yl)methoxy)pyridin-3-yl)-2-fluorobenzoyl)-4-hydroxypyrrolidin-2-carboxamide

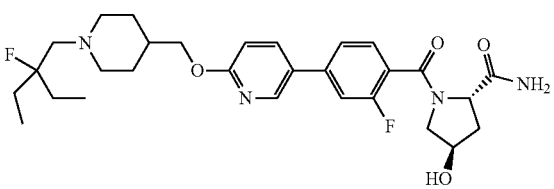 [SMILES: CCC(F)(CC)CN1CCC(COc2ccc(-c3ccc(C(=O)N4C[C@H](O)C[C@H]4C(N)=O)c(F)c3)cn2)CC1]

Intermediate 37 (0.08 g, 0.18 mmol), (2S,4R)-4-hydroxypyrrolidin-2-carboxamide hydrochloride (0.06 g, 0.37 mmol), HOBt (0.05 g, 0.37 mmol), EDC (0.07 g, 0.37 mmol) and DIPEA (0.06 mL, 0.37 mmol) were dissolved in methylene chloride (10 mL) at room temperature. The solution was stirred at the same temperature for 18 hours. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (Waters, C18; acetonitrile/0.1%-trifluoroacetic acid aqueous solution=5% to 70%), and passed through SPE cartridge (PL-HCO3 MP SPE), followed by concentrating to obtain the desire compound (0.01 g, 14%) as white solid.

$^1$H NMR (400 MHz, CDCl$_3$) δ 8.40-8.39 (m, 1H), 7.97-7.94 (m, 1H), 7.58-7.41 (m, 3H), 6.86-6.84 (m, 1H), 4.68 (t, 1H, J=8.4 Hz), 4.37 (s, 1H), 4.13-4.11 (m, 2H), 3.73-3.69 (m, 1H), 3.31 (d, 1H, J=11.6 Hz), 2.98-2.95 (m, 2H), 2.45-2.39 (m, 2H), 2.35-2.28 (m, 1H), 2.11-2.05 (m, 3H), 1.75-1.60 (m, 7H), 1.40-1.37 (m, 2H), 0.85 (t, 6H, J=7.5 Hz); MS (ESI) m/z 545.3 (M++H).

Synthesis of Compound 1309: (2S,4R)-1-(4-(5-((1-(2-Ethyl-2-fluorobutyl)piperidin-4-yl)methoxy)pyridin-2-yl)benzoyl)-4-hydroxy-2-methylpyrrolidin-2-carboxamide

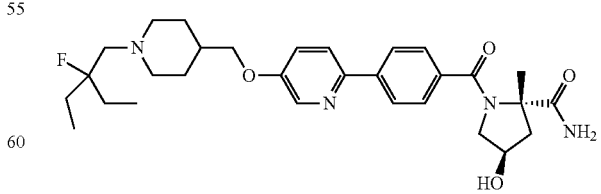

Step 1. (2S,4R)-methyl 1-(4-(5-((1-(2-ethyl-2-fluorobutyl)piperidin-4-yl)methoxy)pyridin-2-yl)benzoyl)-4-hydroxy-2-methylpyrrolidin-2-carboxylate: Intermediate 35 (0.25 g, 0.60 mmol), (2S,4R)-methyl 4-hydroxy-2-methylpyrrolidin-2-carboxylate hydrochloride (0.23 g, 1.20 mmol), HOBt (0.16 g, 1.20 mmol), EDC (0.23 g, 1.20 mmol) and DIPEA (0.21 mL, 1.20 mmol) were dissolved in methylene chloride (15 mL) at room temperature. The solution was stirred at the same temperature for 18 hours. To the reaction mixture, water was added, and the mixture was extracted with methylene chloride. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; methanol/methylene chloride=0% to 15%), and concentrated to obtain the desired compound (0.25 g, 75%) as white solid.

Step 2. (2S,4R)-1-(4-(5-((1-(2-ethyl-2-fluorobutyl)piperidin-4-yl)methoxy)pyridin-2-yl)benzoyl)-4-hydroxy-2-methylpyrrolidin-2-carboxylic acid: (2S,4R)-Methyl 1-(4-(5-((1-(2-ethyl-2-fluorobutyl)piperidin-4-yl)methoxy)pyridin-2-yl)benzoyl)-4-hydroxy-2-methylpyrrolidin-2-carboxylate (0.25 g, 0.45 mmol) and LiOH (0.05 g, 2.27 mmol) were dissolved in tetrahydrofuran (8 mL)/methanol (8 mL)/water (2 mL) at room temperature.

The solution was stirred at 50° C. for 18 hours, and then cooled to room temperature thereby to make the reaction completed. From the reaction mixture, the solvent was removed under reduced pressure. The obtained product was used without further purification (0.24 g, 99%, white solid).

Step 3. Synthesis of Compound 1309: (2S,4R)-1-(4-(5-((1-(2-Ethyl-2-fluorobutyl)piperidin-4-yl)methoxy)pyridin-2-yl)benzoyl)-4-hydroxy-2-methylpyrrolidin-2-carboxylic acid (0.24 g, 0.45 mmol), ammonium chloride (0.07 g, 1.35 mmol), HOBt (0.12 g, 0.90 mmol), EDC (0.17 g, 0.90 mmol) and DIPEA (0.16 mL, 0.90 mmol) were dissolved in N,N-dimethylformamide (12 mL) at room temperature. The solution was stirred at 80° C. for 18 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=0% to 30%), and passed through SPE cartridge (PL-HCO3 MP SPE), followed by concentrating to obtain the desire compound (0.09 g, 38%) as white solid.

$^1$H NMR (400 MHz, CDCl$_3$) δ 8.36-8.35 (m, 1H), 7.93 (d, 2H, J=8.2 Hz), 7.66 (d, 1H, J=8.7 Hz), 7.55-7.51 (m, 2H), 7.27-7.24 (m, 1H), 5.48 (s, 1H), 4.46-4.43 (m, 1H), 3.90-3.87 (m, 2H), 3.69-3.53 (m, 2H), 3.00-2.72 (m, 3H), 2.70-2.14 (m, 4H), 2.04-1.89 (m, 3H), 1.82-1.44 (m, 10H), 1.28-1.25 (m, 2H), 0.89 (t, 6H, J=7.5 Hz); MS (ESI) m/z 541.3 (M++H).

Synthesis of Compound 1311: (2S,4R)-1-(3-Fluoro-4-(5-((1-(2,2,3,3,3-pentafluoropropyl)piperidin-4-yl)methoxy)pyridin-2-yl)benzoyl)-4-hydroxypyrrolidin-2-carboxamide

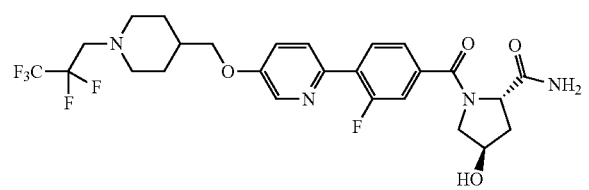 [SMILES: NC(=O)[C@@H]1C[C@@H](O)CN1C(=O)c1ccc(-c2ccc(OCC3CCN(CC(F)(F)C(F)(F)F)CC3)cn2)c(F)c1]

Intermediate 33 (0.08 g, 0.17 mmol), (2S,4R)-4-hydroxypyrrolidin-2-carboxamide hydrochloride (0.03 g, 0.20 mmol), HATU (0.13 g, 0.34 mmol) and DIPEA (0.06 mL, 0.34 mmol) were mixed in DMF (2 mL) at room temperature. The mixture was stirred at 60° C. for 12 hours, and then cooled to room temperature thereby to make the reaction completed. From the reaction mixture, the solvent was removed under reduced pressure. The concentrate was purified by column chromatography (Waters, C18; 0.1%-trifluoroacetic acid aqueous solution/acetonitrile=5% to 65%), and passed through SPE cartridge (PL-HCO3 MP SPE), followed by concentrating to obtain the desire compound (0.04 g, 41%) as brown solid.

$^1$H NMR (400 MHz, CD$_3$OD) δ 8.39 (d, 1H, J=2.8 Hz), 7.96 (t, 1H, J=7.9 Hz), 7.82 (d, 1H, J=8.7 Hz), 7.60-7.50 (m, 3H), 4.76 (t, 1H, J=8.7 Hz), 4.45 (s, 1H), 4.01 (d, 2H, J=5.8 Hz), 3.92 (dd, 1H, J=11.4, 3.4 Hz), 3.52 (d, 1H, J=11.4 Hz), 3.16-3.04 (m, 4H), 2.47-2.37 (m, 3H), 2.17-2.10 (m, 1H), 1.88 (d, 3H, J=10.2 Hz), 1.51 (q, 2H, J=11.5 Hz); MS (ESI) m/z 575.2 (M++H).

Synthesis of Compound 1312: (S)-1-(3-Fluoro-4-(5-((1-(2,2,3,3,3-pentafluoropropyl)piperidin-4-yl)methoxy)pyridin-2-yl)benzoyl)pyrrolidin-2-carboxamide

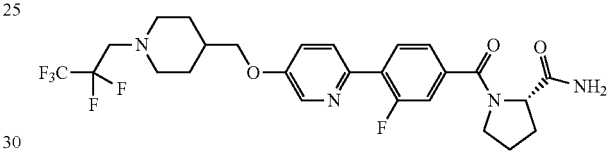

Intermediate 33 (0.05 g, 0.10 mmol), (S)-pyrrolidin-2-carboxamide (0.01 g, 0.16 mmol), EDC (0.03 g, 0.16 mmol), HOBt (0.02 g, 0.16 mmol) and DIPEA (0.03 mL, 0.21 mmol) were dissolved in DMF (2 mL) at room temperature. The solution was stirred at 60° C. for 15 hours, and then cooled to room temperature thereby to make the reaction completed. From the reaction mixture, the solvent was removed under reduced pressure. The concentrate was purified by column chromatography (Waters, C18; 0.1%-trifluoroacetic acid aqueous solution/acetonitrile=5% to 65%), and passed through SPE cartridge (PL-HCO3 MP SPE), followed by concentrating to obtain the desire compound (0.04 g, 78%) as white solid.

$^1$H NMR (400 MHz, CDCl$_3$) δ 8.42 (d, 1H, J=2.8 Hz), 8.05 (t, 1H, J=7.9 Hz), 7.80 (d, 1H, J=8.8 Hz), 7.44 (dd, 1H, J=8.0, 1.3 Hz), 7.35 (td, 2H, J=9.9, 1.7 Hz), 6.94 (s, 1H), 5.58 (s, 1H), 4.77 (t, 1H, J=6.3 Hz), 3.93 (d, 2H, J=5.9 Hz), 3.66-3.60 (m, 1H), 3.56-3.50 (m, 1H), 3.14 (bs, 4H), 2.56 (bs, 2H), 2.46-2.38 (m, 1H), 2.17-2.04 (m, 2H), 1.91-1.83 (m, 4H), 1.61 (bd, 2H, J=8.3 Hz); MS (ESI) m/z 559.2 (M++H).

Synthesis of Compound 1313: (S)-1-(3-Fluoro-4-(5-((1-(2,2,3,3,3-pentafluoropropyl)piperidin-4-yl)methoxy)pyridin-2-yl)benzoyl)-2-methylpyrrolidin-2-carboxamide

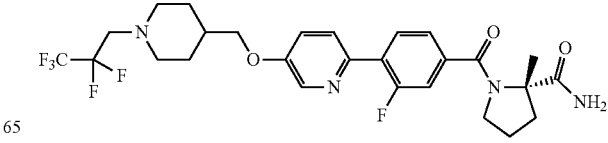

Step 1. (S)-methyl 1-(3-fluoro-4-(5-((1-(2,2,3,3,3-pentafluoropropyl)piperidin-4-yl)methoxy)pyridin-2-yl)benzoyl)-2-methylpyrrolidin-2-carboxylate: Intermediate 33 (0.10 g, 0.21 mmol), (S)-methyl 2-methylpyrrolidin-2-carboxylate hydrochloride (0.05 g, 0.28 mmol), EDC (0.08 g, 0.43 mmol), HOBt (0.05 g, 0.43 mmol) and DIPEA (0.07 mL, 0.43 mmol) were mixed in DMF (2 mL) at room temperature. The mixture was stirred at 60° C. for 15 hours, and then cooled to room temperature thereby to make the reaction completed. From the reaction mixture, the solvent was removed under reduced pressure. The concentrate was purified by column chromatography (SiO$_2$, 4 g cartridge; 0.1%-hexane aqueous solution/ethyl acetate=20% to 45%), and concentrated to obtain the desired compound (0.11 g, 91%) as yellow oil.

Step 2. (S)-1-(3-fluoro-4-(5-((1-(2,2,3,3,3-pentafluoropropyl)piperidin-4-yl)methoxy)pyridin-2-yl)benzoyl)-2-methylpyrrolidin-2-carboxylic acid: (S)-Methyl 1-(3-fluoro-4-(5-((1-(2,2,3,3,3-pentafluoropropyl)piperidin-4-yl)methoxy)pyridin-2-yl)benzoyl)-2-methylpyrrolidin-2-carboxylate (0.15 g, 0.25 mmol) and LiOH (0.01 g, 0.51 mmol) were dissolved in tetrahydrofuran (10 mL)/water (3 mL)/methanol (3 mL) at room temperature. The solution was stirred at 50° C. for 15 hours, and then cooled to room temperature thereby to make the reaction completed. From the reaction mixture, the solvent was removed under reduced pressure. The obtained product was used without further purification (0.14 g, 98%, white solid).

Step 3. Synthesis of Compound 1313: (S)-1-(3-Fluoro-4-(5-((1-(2,2,3,3,3-pentafluoropropyl)piperidin-4-yl)methoxy)pyridin-2-yl)benzoyl)-2-methylpyrrolidin-2-carboxylic acid (0.14 g, 0.25 mmol), ammonium chloride (0.02 g, 0.50 mmol), EDC (0.09 g, 0.50 mmol), HOBt (0.06 g, 0.56 mmol) and DIPEA (0.09 mL, 0.50 mmol) were dissolved in DMF (4 mL) at room temperature. The solution was stirred at 60° C. for 15 hours, and then cooled to room temperature thereby to make the reaction completed. From the reaction mixture, the solvent was removed under reduced pressure. The concentrate was purified by column chromatography (Waters, C18; 0.1%-trifluoroacetic acid aqueous solution/acetonitrile=5% to 65%), and passed through SPE cartridge (PL-HCO3 MP SPE), followed by concentrating to obtain the desire compound (0.08 g, 60%) as yellow oil.

$^1$H NMR (400 MHz, CD$_3$OD) δ 8.38 (d, 1H, J=2.8 Hz), 7.94 (t, 1H, J=7.9 Hz), 7.81 (dd, 1H, J=8.7, 1.6 Hz), 7.53-7.46 (m, 3H), 4.00 (d, 2H, J=5.9 Hz), 3.72-3.68 (m, 1H), 3.38 (s, 2H), 3.16-3.03 (m, 4H), 2.44 (t, 2H, J=11.0 Hz), 2.34-2.24 (m, 1H), 2.11-1.98 (m, 3H), 1.89-1.87 (m, 3H), 1.77 (s, 3H), 1.50 (ddd, 2H, J=24.6, 12.6, 3.0 Hz); MS (ESI) m/z 573.3 (M++H).

Synthesis of Compound 1314: (S)-1-(3-Fluoro-4-(5-((1-((1-(trifluoromethyl)cyclobutyl)methyl)piperidin-4-yl)methoxy)pyridin-2-yl)benzoyl)pyrrolidin-2-carboxamide

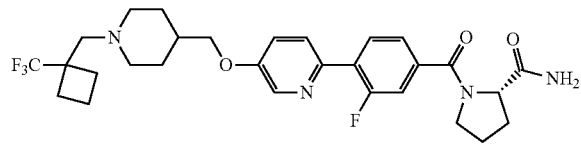 [SMILES: NC(=O)[C@@H]1CCCN1C(=O)c1ccc(-c2ccc(OCC3CCN(CC4(C(F)(F)F)CCC4)CC3)cn2)c(F)c1]

Intermediate 30 (0.05 g, 0.10 mmol), (S)-pyrrolidin-2-carboxamide (0.01 g, 0.13 mmol), EDC (0.04 g, 0.21 mmol), HOBt (0.02 g, 0.21 mmol) and DIPEA (0.03 mL, 0.21 mmol) were dissolved in N,N-dimethylformamide (4 mL) at room temperature. The solution was stirred at 60° C. for 12 hours, and then cooled to room temperature thereby to make the reaction completed. To the reaction mixture, saturated ammonium chloride aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; ethyl acetate/hexane=0% to 30%), and concentrated to obtain the desired compound (0.03 g, 49%) as white solid.

$^1$H NMR (400 MHz, CDCl$_3$+CD$_3$OD) δ 8.38 (m, 1H), 7.94 (m, 1H), 7.72 (m, 1H), 7.42-7.34 (m, 2H), 7.28-7.25 (m, 1H), 4.65 (m, 1H), 4.31 (m, 0.5H), 3.89 (m, 2H), 3.72 (m, 0.5H), 3.68-3.42 (m, 2H), 2.91-2.81 (m, 2H), 2.80-2.65 (m, 3H), 2.52 (s, 2H), 2.28-1.77 (m, 11H), 1.44 (m, 2H); MS (ESI) m/z 563.3 (M$^+$+H).

Synthesis of Compound 1315: (S)-1-(3-Fluoro-4-(5-((1-((1-(trifluoromethyl)cyclobutyl)methyl)piperidin-4-yl)methoxy)pyridin-2-yl)benzoyl)-2-methyl-pyrrolidin-2-carboxamide

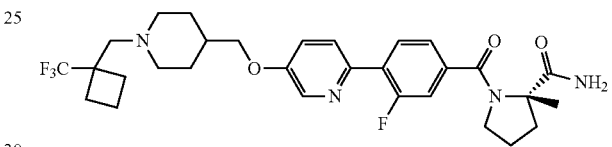

Step 1. (S)-methyl 1-(3-fluoro-4-(5-((1-((1-(trifluoromethyl)cyclobutyl)methyl)piperidin-4-yl)methoxy)pyridin-2-yl)benzoyl)-2-methylpyrrolidin-2-carboxylate: Intermediate 30 (0.10 g, 0.21 mmol), (S)-methyl 2-methylpyrrolidin-2-carboxylate hydrochloride (0.05 g, 0.27 mmol), EDC (0.08 g, 0.42 mmol), HOBt (0.05 g, 0.42 mmol) and DIPEA (0.07 mL, 0.42 mmol) were dissolved in N,N-dimethylformamide (4 mL) at room temperature. The solution was stirred at 60° C. for 12 hours, and then cooled to room temperature thereby to make the reaction completed. To the reaction mixture, saturated ammonium chloride aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; ethyl acetate/hexane=25% to 90%), and concentrated to obtain the desired compound (0.08 g, 63%) as white solid.

Step 2. (S)-1-(3-fluoro-4-(5-((1-((1-(trifluoromethyl)cyclobutyl)methyl)piperidin-4-yl)methoxy)pyridin-2-yl)benzoyl)-2-methylpyrrolidin-2-carboxylic acid: (S)-Methyl 1-(3-fluoro-4-(5-((1-((1-(trifluoromethyl)cyclobutyl)methyl)piperidin-4-yl)methoxy)pyridin-2-yl)benzoyl)-2-methylpyrrolidin-2-carboxylate (0.11 g, 0.18 mmol) and LiOH.H$_2$O (0.01 g, 0.37 mmol) were dissolved in tetrahydrofuran (15 mL)/water (5 mL) at room temperature. The solution was stirred at 50° C. for 10 hours, and then cooled to room temperature thereby to make the reaction completed. From the reaction mixture, the solvent was removed under reduced pressure. The obtained product was used without further purification (0.10 g, 93%, white solid).

Step 3. Synthesis of Compound 1315: (S)-1-(3-Fluoro-4-(5-((1-((1-(trifluoromethyl)cyclobutyl)methyl)piperidin-4-yl)methoxy)pyridin-2-yl)benzoyl)-2-methylpyrrolidin-2-carboxylic acid (0.10 g, 0.17 mmol), ammonium chloride (0.02 g, 0.51 mmol), EDC (0.06 g, 0.34 mmol), HOBt (0.04 g, 0.34 mmol) and DIPEA (0.06 mL, 0.34 mmol) were dissolved in N,N-dimethylformamide (5 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.04 g, 40%) as white solid.

$^1$H NMR (400 MHz, CDCl$_3$+CD$_3$OD) δ 8.33 (m, 1H), 7.95 (m, 1H), 7.71 (m, 1H), 7.38-7.32 (m, 2H), 7.29-7.21 (m, 1H), 3.89 (m, 2H), 3.60 (m, 2H), 3.42-3.91 (m, 3H), 2.91-2.20 (m, 10H), 2.19-1.88 (m, 7H), 1.75 (m, 4H); MS (ESI) m/z 577.3 (M$^+$+H).

Synthesis of Compound 1316: (2S,4R)-1-(3-Fluoro-4-(6-((1-((1-(trifluoromethyl)cyclobutyl)methyl)piperidin-4-yl)methoxy)pyridin-3-yl)benzoyl)-4-hydroxypyrrolidin-2-carboxamide

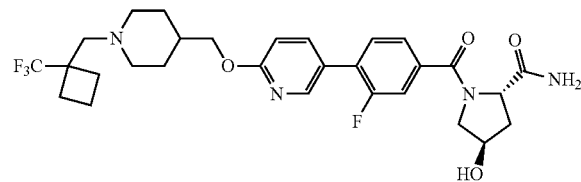 [SMILES: NC(=O)[C@@H]1C[C@@H](O)CN1C(=O)c1ccc(-c2ccc(OCC3CCN(CC4(C(F)(F)F)CCC4)CC3)nc2)c(F)c1]

Intermediate 5 (0.08 g, 0.17 mmol), (2S,4R)-4-hydroxypyrrolidin-2-carboxamide hydrochloride (0.03 g, 0.20 mmol), HATU (0.13 g, 0.34 mmol) and DIPEA (0.06 mL, 0.34 mmol) were dissolved in N,N-dimethylformamide (2 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.03 g, 30%) as white solid.

$^1$H NMR (400 MHz, CDCl$_3$+CD$_3$OD) δ 8.28 (m, 1H), 7.79 (m, 1H), 7.45-7.41 (m, 3H), 6.81 (m, 1H), 4.82 (m, 1H), 4.45 (m, 1H), 4.22 (m, 2H), 3.80 (m, 1H), 3.56 (m, 1H), 3.43 (m, 2H), 3.22 (m, 2H), 2.77 (m, 2H), 2.60-2.20 (m, 5H), 2.19-1.99 (m, 6H), 1.83 (m, 2H); MS (ESI) m/z 579.3 (M$^+$+H).

Synthesis of Compound 1317: (2S,4R)-1-(2-Fluoro-4-(6-((1-((1-(trifluoromethyl)cyclobutyl)methyl)piperidin-4-yl)methoxy)pyridin-3-yl)benzoyl)-4-hydroxypyrrolidin-2-carboxamide

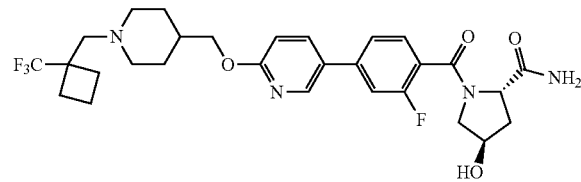 [SMILES: NC(=O)[C@@H]1C[C@@H](O)CN1C(=O)c1ccc(-c2ccc(OCC3CCN(CC4(C(F)(F)F)CCC4)CC3)nc2)cc1F]

Intermediate 31 (0.08 g, 0.17 mmol), (2S,4R)-4-hydroxypyrrolidin-2-carboxamide hydrochloride (0.03 g, 0.20 mmol), HATU (0.13 g, 0.34 mmol) and DIPEA (0.06 mL, 0.34 mmol) were dissolved in N,N-dimethylformamide (2 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.04 g, 40%) as white solid.

$^1$H NMR (400 MHz, CDCl$_3$+CD$_3$OD) δ 8.26 (m, 1H), 7.75 (m, 1H), 7.54 (m, 1H), 7.28 (m, 1H), 7.22 (m, 1H), 6.78 (m, 1H), 4.78 (m, 1H), 4.40 (m, 1H), 4.17 (m, 2H), 3.66 (m, 1H), 3.43-3.62 (m, 7H), 2.39-2.21 (m, 6H), 2.18-1.91 (m, 5H), 1.81 (m, 2H); MS (ESI) m/z 579.3 (M$^+$+H).

Synthesis of Compound 1318: (S)-1-(3-Fluoro-4-(6-((1-((1-(trifluoromethyl)cyclobutyl)methyl)piperidin-4-yl)methoxy)pyridin-3-yl)benzoyl)-2-methyl-pyrrolidin-2-carboxamide

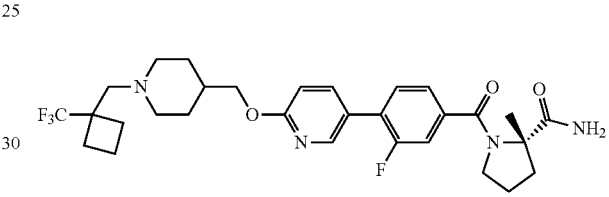

Step 1. (S)-methyl 1-(3-fluoro-4-(6-((1-((1-(trifluoromethyl)cyclobutyl)methyl)piperidin-4-yl)methoxy)pyridin-3-yl)benzoyl)-2-methylpyrrolidin-2-carboxylate: Intermediate 5 (0.12 g, 0.25 mmol), (S)-methyl 2-methylpyrrolidin-2-carboxylate hydrochloride (0.06 g, 0.33 mmol), EDC (0.09 g, 0.51 mmol), HOBt (0.07 g, 0.51 mmol) and DIPEA (0.09 mL, 0.51 mmol) were dissolved in N,N-dimethylformamide (4 mL) at room temperature. The solution was stirred at 60° C. for 12 hours, and then cooled to room temperature thereby to make the reaction completed. To the reaction mixture, saturated ammonium chloride aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; ethyl acetate/hexane=10% to 90%), and concentrated to obtain the desired compound (0.10 g, 65%) as colorless oil.

Step 2. (S)-1-(3-fluoro-4-(6-((1-((1-(trifluoromethyl)cyclobutyl)methyl)piperidin-4-yl)methoxy)pyridin-3-yl)benzoyl)-2-methylpyrrolidin-2-carboxylic acid: (S)-Methyl 1-(3-fluoro-4-(6-((1-((1-(trifluoromethyl)cyclobutyl)methyl)piperidin-4-yl)methoxy)pyridin-3-yl)benzoyl)-2-methylpyrrolidin-2-carboxylate (0.07 g, 0.12 mmol) and LiOH (6 mg, 0.25 mmol) were dissolved in tetrahydrofuran (8 mL)/water (4 mL) at room temperature. The solution was stirred at 50° C. for 10 hours, and then cooled to room temperature thereby to make the reaction completed. From the reaction mixture, the solvent was removed under reduced pressure. The obtained product was used without further purification (0.07 g, 95%, white solid).

Step 3. Synthesis of Compound 1318: (S)-1-(3-Fluoro-4-(6-((1-((1-(trifluoromethyl)cyclobutyl)methyl)piperidin-4-yl)methoxy)pyridin-3-yl)benzoyl)-2-methylpyrrolidin-2- carboxylic acid (0.07 g, 0.12 mmol), ammonium chloride (0.01 g, 0.24 mmol), EDC (0.04 g, 0.24 mmol), HOBt (0.03 g, 0.24 mmol) and DIPEA (0.04 mL, 0.24 mmol) were dissolved in N,N-dimethylformamide (4 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.03 g, 42%) as white solid.

$^1$H NMR (400 MHz, CDCl$_3$+CD$_3$OD) δ 8.32 (m, 1H), 7.80 (m, 1H), 7.46 (m, 1H), 7.37-7.27 (m, 2H), 6.83 (m, 1H), 4.27 (m, 2H), 3.65-3.60 (m, 2H), 3.45-3.29 (m, 2H), 3.16-3.08 (m, 2H), 2.64 (m, 2H), 2.53-2.38 (m, 4H), 2.09-1.70 (m, 10H), 1.68-1.31 (m, 4H); MS (ESI) m/z 577.3 (M$^+$+H).

Synthesis of Compound 1319: (S)-1-(2-Fluoro-4-(6-((1-((1-(trifluoromethyl)cyclobutyl)methyl)piperidin-4-yl)methoxy)pyridin-3-yl)benzoyl)-2-methyl-pyrrolidin-2-carboxamide

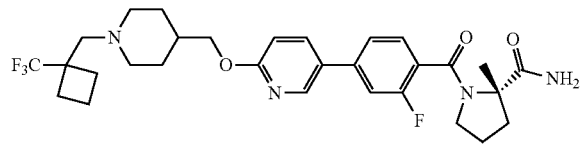 [SMILES: C[C@@]1(C(N)=O)CCCN1C(=O)c1ccc(-c2ccc(OCC3CCN(CC4(C(F)(F)F)CCC4)CC3)nc2)cc1F]

Step 1. (S)-methyl 1-(2-fluoro-4-(6-((1-((1-(trifluoromethyl)cyclobutyl)methyl)piperidin-4-yl)methoxy)pyridin-3-yl)benzoyl)-2-methylpyrrolidin-2-carboxylate: Intermediate 31 (0.12 g, 0.25 mmol), (S)-methyl 2-methylpyrrolidin-2-carboxylate hydrochloride (0.06 g, 0.33 mmol), EDC (0.09 g, 0.51 mmol), HOBt (0.07 g, 0.51 mmol) and DIPEA (0.09 mL, 0.51 mmol) were dissolved in N,N-dimethylformamide (4 mL) at room temperature. The solution was stirred at 60° C. for 12 hours, and then cooled to room temperature thereby to make the reaction completed. To the reaction mixture, saturated ammonium chloride aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; ethyl acetate/hexane=10% to 90%), and concentrated to obtain the desired compound (0.10 g, 65%) as colorless oil.

Step 2. (S)-1-(2-fluoro-4-(6-((1-((1-(trifluoromethyl)cyclobutyl)methyl)piperidin-4-yl)methoxy)pyridin-3-yl)benzoyl)-2-methylpyrrolidin-2-carboxylic acid: (S)-Methyl 1-(2-fluoro-4-(6-((1-((1-(trifluoromethyl)cyclobutyl)methyl)piperidin-4-yl)methoxy)pyridin-3-yl)benzoyl)-2-methylpyrrolidin-2-carboxylate (0.10 g, 0.16 mmol) and LiOH (8 mg, 0.33 mmol) were dissolved in tetrahydrofuran (8 mL)/water (4 mL) at room temperature. The solution was stirred at 50° C. for 10 hours, and then cooled to room temperature thereby to make the reaction completed. From the reaction mixture, the solvent was removed under reduced pressure. The obtained product was used without further purification (0.09 g, 97%, white solid).

Step 3. Synthesis of Compound 1319: (S)-1-(2-Fluoro-4-(6-((1-((1-(trifluoromethyl)cyclobutyl)methyl)piperidin-4-yl)methoxy)pyridin-3-yl)benzoyl)-2-methylpyrrolidin-2-carboxylic acid (0.09 g, 0.16 mmol), ammonium chloride (0.01 g, 0.32 mmol), EDC (0.06 g, 0.32 mmol), HOBt (0.04 g, 0.32 mmol) and DIPEA (0.05 mL, 0.32 mmol) were dissolved in N,N-dimethylformamide (4 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.03 g, 36%) as white solid.

$^1$H NMR (400 MHz, CDCl$_3$+CD$_3$OD) δ 8.32 (m, 1H), 7.76 (m, 1H), 7.46 (m, 1H), 7.37 (m, 1H), 7.24 (m, 1H), 6.81 (m, 1H), 4.21 (m, 2H), 3.50 (m, 2H), 3.18 (m, 2H), 2.90 (m, 2H), 2.52 (m, 2H), 2.38-2.16 (m, 5H), 2.14-1.82 (m, 8H), 1.89 (m, 3H), 1.67 (m, 2H); MS (ESI) m/z 577.3 (M$^+$+H).

Synthesis of Compound 1320: (S)-2-Methyl-1-(4-(6-((1-((1-(trifluoromethyl)cyclobutyl)methyl)piperidin-4-yl)methoxy)pyridin-3-yl)benzoyl)pyrrolidin-2-carboxamide

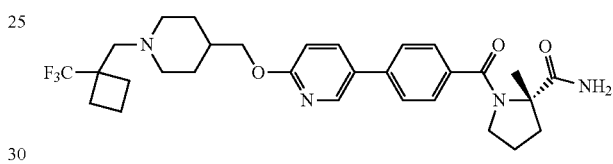

Step 1. (S)-methyl 2-methyl-1-(4-(6-((1-((1-(trifluoromethyl)cyclobutyl)methyl)piperidin-4-yl)methoxy)pyridin-3-yl)benzoyl)pyrrolidin-2-carboxylate: Intermediate 32 (0.12 g, 0.26 mmol), (S)-methyl 2-methylpyrrolidin-2-carboxylate hydrochloride (0.06 g, 0.34 mmol), EDC (0.10 g, 0.53 mmol), HOBt (0.07 g, 0.53 mmol) and DIPEA (0.09 mL, 0.53 mmol) were dissolved in N,N-dimethylformamide (4 mL) at room temperature. The solution was stirred at 60° C. for 12 hours, and then cooled to room temperature thereby to make the reaction completed. To the reaction mixture, saturated ammonium chloride aqueous solution was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; ethyl acetate/hexane=10% to 90%), and concentrated to obtain the desired compound (0.10 g, 65%) as colorless oil.

Step 2. (S)-2-methyl-1-(4-(6-((1-((1-(trifluoromethyl)cyclobutyl)methyl)piperidin-4-yl)methoxy)pyridin-3-yl)benzoyl)pyrrolidin-2-carboxylic acid: (S)-Methyl 2-methyl-1-(4-(6-((1-((1-(trifluoromethyl)cyclobutyl)methyl)piperidin-4-yl)methoxy)pyridin-3-yl)benzoyl)pyrrolidin-2-carboxylate (0.11 g, 0.19 mmol) and LiOH (9 mg, 0.38 mmol) were dissolved in tetrahydrofuran (8 mL)/water (4 mL) at room temperature. The solution was stirred at 50° C. for 10 hours, and then cooled to room temperature thereby to make the reaction completed. From the reaction mixture, the solvent was removed under reduced pressure. The obtained product was used without further purification (0.10 g, 93%, white solid).

Step 3. Synthesis of Compound 1320: (S)-2-Methyl-1-(4-(6-((1-((1-(trifluoromethyl)cyclobutyl)methyl)piperidin-4-yl)methoxy)pyridin-3-yl)benzoyl)pyrrolidin-2-carboxylic acid (0.10 g, 0.17 mmol), ammonium chloride (0.01 g, 0.35 mmol), EDC (0.06 g, 0.35 mmol), HOBt (0.04 g, 0.35 mmol) and DIPEA (0.06 mL, 0.35 mmol) were dissolved in N,N-dimethylformamide (4 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.03 g, 30%) as white solid.

$^1$H NMR (400 MHz, CDCl$_3$+CD$_3$OD) δ 8.27 (m, 1H), 7.75 (m, 1H), 7.54-7.49 (m, 4H), 6.76 (m, 1H), 4.15 (m, 2H), 3.81-3.20 (m, 6H), 2.93 (m, 2H), 2.41-2.25 (m, 5H), 2.11-1.82 (m, 10H), 1.71 (s, 3H); MS (ESI) m/z 559.3 (M$^+$+H).

Synthesis of Compound 1321: (2R,4R)-1-(4'-((1-(2-Ethyl-2-fluorobutyl)piperidin-4-yl)methoxy)-2-fluorobiphenylcarbonyl)-4-hydroxypyrrolidin-2-carboxamide

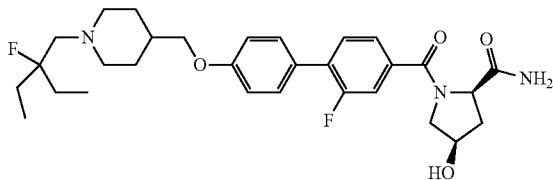 [SMILES: CCC(F)(CC)CN1CCC(COc2ccc(-c3ccc(C(=O)N4C[C@H](O)C[C@@H]4C(N)=O)cc3F)cc2)CC1]

Intermediate 10 (0.20 g, 0.36 mmol), EDC (0.14 g, 0.73 mmol), HOBt (0.10 g, 0.73 mmol) and DIPEA (0.14 g, 1.10 mmol) were dissolved in N,N-dimethylformamide (5 mL) at room temperature. To the solution, NH$_4$Cl (0.06 g, 1.10 mmol) was added, followed by stirring at 50° C. for 16 hours. And then, the reaction mixture was cooled to room temperature thereby to make the reaction completed. From the reaction mixture, the solvent was removed under reduced pressure. The concentrate was purified by column chromatography (Waters, C18; acetonitrile/trifluoroacetic acid=5% to 70%), and passed through SPE cartridge (PL-HCO3 MP SPE), followed by concentrating to obtain the desire compound (0.14 g, 70%) as white solid.

$^1$H NMR (400 MHz, CD$_3$OD) δ 7.50 (m, 5H), 7.01 (d, 2H, J=8.7 Hz), 3.88 (d, 2H, J=5.8 Hz), 3.70 (m, 1H), 3.03-3.00 (m, 2H), 2.51 (s, 1H), 2.45 (s, 1H), 2.29 (d, 2H, J=4.6 Hz), 2.13 (m, 2H), 1.82 (m, 3H), 1.71-1.65 (m, 4H), 1.33 (m, 2H), 1.22 (m, 2H), 0.90 (t, 6H, J=7.5 Hz); MS (ESI) m/z 544.3 (M$^+$+H).

Synthesis of Compound 1322: (2S,4R)-4-Hydroxy-1-(4-(5-((1-(3,3,3-trifluoro-2,2-dimethylpropyl)piperidin-4-yl)methoxy)pyridin-2-yl)benzoyl)pyrrolidin-2-carboxamide

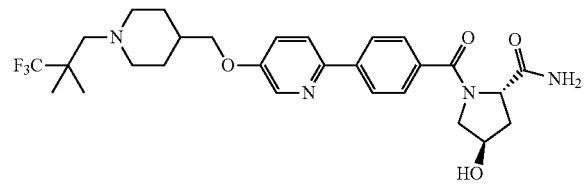 [SMILES: CC(C)(CN1CCC(COc2ccc(-c3ccc(C(=O)N4C[C@H](O)C[C@H]4C(N)=O)cc3)nc2)CC1)C(F)(F)F]

Intermediate 39 (0.07 g, 0.16 mmol), EDC (0.06 g, 0.32 mmol), HOBt (0.04 g, 0.32 mmol) and DIPEA (0.06 g, 0.48 mmol) were dissolved in N,N-dimethylformamide (5 mL) at room temperature. To the solution, (2S,4R)-4-hydroxypyrrolidin-2-carboxamide hydrochloride (0.03 g, 0.19 mmol) was added, followed by stirring at the same temperature. From the reaction mixture, the solvent was removed under reduced pressure. The concentrate was purified by column chromatography (Waters, C$_{18}$; acetonitrile/trifluoroacetic acid=5% to 70%), and passed through SPE cartridge (PL-HCO3 MP SPE), followed by concentrating to obtain the desire compound (0.04 g, 51%) as white solid.

$^1$H NMR (400 MHz, CD$_3$OD) δ 8.32 (d, 1H, J=2.8 Hz), 7.99 (d, 2H, J=6.7 Hz), 7.85 (d, 1H, J=8.8 Hz), 7.75 (d, 2H, J=6.5 Hz), 7.48 (dd, 1H, J=8.8, 2.9 Hz), 4.76 (m, 2H), 4.44 (m, 1H), 3.97-3.91 (m, 3H), 3.53 (m, 1H), 2.90-2.88 (m, 2H), 2.44 (s, 2H), 2.37 (m, 2H), 2.14 (m, 1H), 1.83-1.80 (m, 2H), 1.48 (m, 2H), 1.36 (s, 6H); MS (ESI) m/z 549.3 (M$^+$+H).

Synthesis of Compound 1323: (2S,4R)-1-(3-Fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxamide

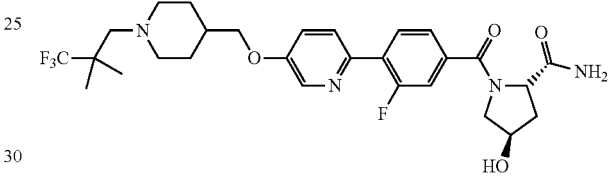

Intermediate 40 (0.07 g, 0.15 mmol), EDC (0.06 g, 0.31 mmol), HOBT (0.04 g, 0.31 mmol) and DIPEA (0.06 g, 0.46 mmol) were dissolved in methylene chloride (2 mL)/N,N-dimethylformamide (1 mL) at room temperature. To the solution, (2S,4R)-4-hydroxypyrrolidin-2-carboxamide hydrochloride (0.03 g, 0.18 mmol) was added, followed by stirring at the same temperature for 8 hours. From the reaction mixture, the solvent was removed under reduced pressure. The concentrate was purified by column chromatography (Waters, C$_{18}$; acetonitrile/trifluoroacetic acid=5% to 70%), and passed through SPE cartridge (SO3H on Si), followed by concentrating to obtain the desire compound (0.03 g, 40%) as white solid.

$^1$H NMR (400 MHz, CD$_3$OD) δ 8.35 (d, 1H, J=2.8 Hz), 7.87 (t, 1H, J=6.8 Hz), 7.64 (m, 2H), 7.53 (m, 2H), 7.38 (m, 1H), 4.75 (m, 2H), 4.45 (m, 1H), 3.96 (d, 2H, J=5.8 Hz), 3.91 (dd, 1H, J=11.5, 3.5 Hz), 3.52 (d, 1H, J=11.4 Hz), 2.92 (d, 2H, J=11.4 Hz), 2.47 (s, 2H), 2.43 (m, 2H), 2.16 (m, 1H), 1.83 (m, 2H), 1.80 (m, 2H), 1.13 (s, 6H); MS (ESI) m/z 567.3 (M$^+$+H).

Synthesis of Compound 1325: (2S,4R)-1-(3-Fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxamide

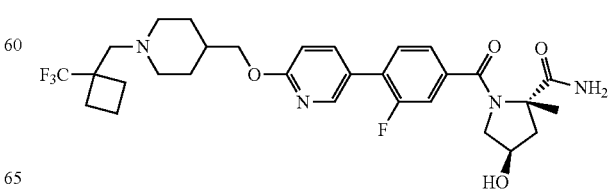

Step 1. (2S,4R)-methyl 1-(3-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxylate: Intermediate 5 (0.20 g, 0.42 mmol), Intermediate 25 (0.08 g, 0.42 mmol), EDC (0.16 g, 0.85 mmol), HOBt (0.11 g, 0.85 mmol) and DIPEA (0.15 mL, 0.85 mmol) were dissolved in N,N-dimethylformamide (3 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (SiO₂, 4 g cartridge; ethyl acetate/hexane=10% to 90%), and concentrated to obtain the desired compound (0.15 g, 57%) as colorless oil.

Step 2. (2S,4R)-1-(3-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxylic acid: (2S,4R)-Methyl 1-(3-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxylate (0.15 g, 0.24 mmol) and LiOH (12 mg, 0.49 mmol) were dissolved in tetrahydrofuran (8 mL)/water (3 mL) at room temperature. The solution was stirred at 50° C. for 10 hours, and then cooled to room temperature thereby to make the reaction completed. From the reaction mixture, the solvent was removed under reduced pressure. The obtained product was used without further purification (0.10 g, 68%, white solid).

Step 3. Synthesis of Compound 1325: (2S,4R)-1-(3-Fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxylic acid (0.06 g, 0.10 mmol), ammonium chloride (0.01 g, 0.30 mmol), EDC (0.03 g, 0.20 mmol), HOBt (0.02 g, 0.20 mmol) and DIPEA (0.03 mL, 0.20 mmol) were dissolved in N,N-dimethylformamide (3 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.03 g, 50%) as white solid.

¹H NMR (400 MHz, CD₃OD) δ 8.35 (m, 1H), 7.93 (m, 1H), 7.62 (m, 1H), 7.43 (m, 2H), 6.93 (m, 1H), 4.43 (m, 1H), 4.20 (m, 2H), 3.88-3.82 (m, 1H), 3.60-3.53 (m, 1H), 2.93 (m, 2H), 2.58 (m, 2H), 2.51-2.41 (m, 1H), 2.31-2.21 (m, 4H), 2.20-2.13 (m, 2H), 2.15-1.92 (m, 3H), 1.91 (s, 3H), 1.90-1.78 (m, 3H), 1.47 (m, 2H); MS (ESI) m/z 593.3 (M⁺+H).

Synthesis of Compound 1326: (2S,4R)-1-(2-Fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxamide

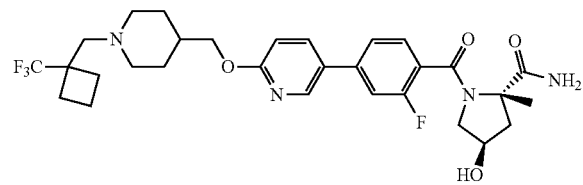 [SMILES: C[C@@]1(C(N)=O)C[C@@H](O)CN1C(=O)c1ccc(-c2ccc(OCC3CCN(CC4(C(F)(F)F)CCC4)CC3)nc2)cc1F]

Step 1. (2S,4R)-methyl 1-(2-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxylate: Intermediate 31 (0.20 g, 0.42 mmol), Intermediate 25 (0.08 g, 0.42 mmol), EDC (0.16 g, 0.85 mmol), HOBt (0.11 g, 0.85 mmol) and DIPEA (0.15 mL, 0.85 mmol) were dissolved in N,N-dimethylformamide (3 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (SiO₂, 4 g cartridge; ethyl acetate/hexane=10% to 90%), and concentrated to obtain the desired compound (0.17 g, 65%) as colorless oil.

Step 2. (2S,4R)-1-(2-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxylic acid: (2S,4R)-Methyl 1-(2-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxylate (0.17 g, 0.28 mmol) and LiOH (13 mg, 0.56 mmol) were dissolved in tetrahydrofuran (8 mL)/water (3 mL) at room temperature. The solution was stirred at 50° C. for 10 hours, and then cooled to room temperature thereby to make the reaction completed. From the reaction mixture, the solvent was removed under reduced pressure. The obtained product was used without further purification (0.10 g, 60%, white solid).

Step 3. Synthesis of Compound 1326: (2S,4R)-1-(2-Fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxylic acid (0.06 g, 0.10 mmol), ammonium chloride (0.01 g, 0.30 mmol), EDC (0.03 g, 0.20 mmol), HOBt (0.02 g, 0.20 mmol) and DIPEA (0.03 mL, 0.20 mmol) were dissolved in N,N-dimethylformamide (3 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.03 g, 50%) as white solid.

¹H NMR (400 MHz, CDCl₃+CD₃OD) δ 8.29 (m, 1H), 7.74 (m, 1H), 7.42 (m, 1H), 7.34 (m, 1H), 7.24 (m, 1H), 6.78 (m, 1H), 4.37 (m, 1H), 4.13 (m, 2H), 3.63 (m, 1H), 3.39 (m, 1H), 2.85 (m, 2H), 2.60 (m, 1H), 2.49 (m, 2H), 2.22-2.12 (m, 4H), 2.05-1.83 (m, 8H), 1.78 (m, 3H), 1.41 (m, 2H); MS (ESI) m/z 593.3 (M⁺+H).

Synthesis of Compound 1327: (2S,4R)-4-Hydroxy-2-methyl-1-(4-(6-((1-((1-(trifluoromethyl)cyclobutyl)methyl)piperidin-4-yl)methoxy)pyridin-3-yl)benzoyl)pyrrolidin-2-carboxamide

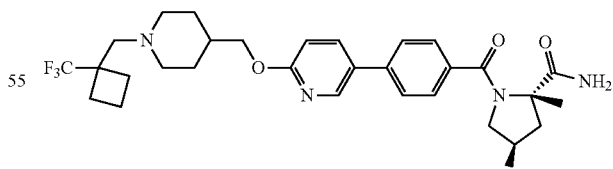

Step 1. (2S,4R)-methyl 4-hydroxy-2-methyl-1-(4-(6-((1-((1-(trifluoromethyl)cyclobutyl)methyl)piperidin-4-yl)methoxy)pyridin-3-yl)benzoyl)pyrrolidin-2-carboxylate: Intermediate 32 (0.20 g, 0.44 mmol), Intermediate 25 (0.08 g, 0.44 mmol), EDC (0.17 g, 0.89 mmol), HOBt (0.12 g, 0.89 mmol) and DIPEA (0.15 mL, 0.89 mmol) were dissolved in N,N-dimethylformamide (3 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (SiO$_2$, 4 g cartridge; ethyl acetate/hexane=10% to 90%), and concentrated to obtain the desired compound (0.15 g, 57%) as colorless oil.

Step 2. (2S,4R)-4-hydroxy-2-methyl-1-(4-(6-((1-((1-(trifluoromethyl)cyclobutyl)methyl)piperidin-4-yl)methoxy)pyridin-3-yl)benzoyl)pyrrolidin-2-carboxylic acid: (2S,4R)-Methyl 4-hydroxy-2-methyl-1-(4-(6-((1-((1-(trifluoromethyl)cyclobutyl)methyl)piperidin-4-yl)methoxy)pyridin-3-yl)benzoyl)pyrrolidin-2-carboxylate (0.15 g, 0.25 mmol) and LiOH (12 mg, 0.50 mmol) were dissolved in tetrahydrofuran (8 mL)/water (3 mL) at room temperature. The solution was stirred at 50° C. for 10 hours, and then cooled to room temperature thereby to make the reaction completed. From the reaction mixture, the solvent was removed under reduced pressure. The obtained product was used without further purification (0.10 g, 68%, white solid).

Step 3. Synthesis of Compound 1327: (2S,4R)-4-Hydroxy-2-methyl-1-(4-(6-((1-((1-(trifluoromethyl)cyclobutyl)methyl)piperidin-4-yl)methoxy)pyridin-3-yl)benzoyl)pyrrolidin-2-carboxylic acid (0.05 g, 0.09 mmol), ammonium chloride (0.01 g, 0.28 mmol), EDC (0.03 g, 0.19 mmol), HOBt (0.02 g, 0.19 mmol) and DIPEA (0.03 mL, 0.19 mmol) were dissolved in N,N-dimethylformamide (3 mL) at room temperature. The solution was stirred at 60° C. for 12 hours, and then cooled to room temperature thereby to make the reaction completed. From the reaction mixture, the solvent was removed under reduced pressure. The concentrate was purified by column chromatography (Waters, C18; acetonitrile/0.1%-trifluoroacetic acid aqueous solution=5% to 70%), and passed through SPE cartridge (PL-HCO3 MP Resin), followed by concentrating to obtain the desire compound (0.03 g, 63%) as white solid.

$^1$H NMR (400 MHz, CDCl$_3$+CD$_3$OD) δ 8.30 (m, 1H), 7.77 (m, 1H), 7.51 (m, 4H), 6.78 (m, 1H), 4.38 (m, 1H), 4.12 (m, 2H), 3.71 (m, 1H), 3.50 (m, 1H), 2.85 (m, 2H), 2.58 (m, 1H), 2.49 (m, 2H), 2.22-2.13 (m, 4H), 2.03-1.87 (m, 5H), 1.84 (m, 3H), 1.74 (m, 3H), 1.42 (m, 2H); MS (ESI) m/z 575.3 (M$^+$+H).

Synthesis of Compound 1328: (2S,4R)-1-(4-(6-((1-(2-Ethyl-2-fluorobutyl)piperidin-4-yl)methoxy)pyridin-3-yl)benzoyl)-4-hydroxy-2-methylpyrrolidin-2-carboxamide

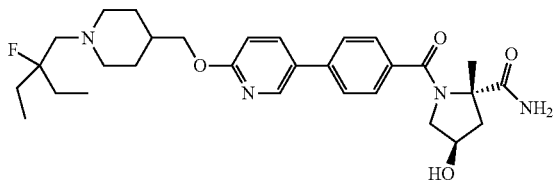 [SMILES: CCC(F)(CC)CN1CCC(COc2ccc(-c3ccc(C(=O)N4C[C@H](O)C[C@@]4(C)C(N)=O)cc3)cn2)CC1]

Step 1. (2S,4R)-methyl 1-(4-(6-((1-(2-ethyl-2-fluorobutyl)piperidin-4-yl)methoxy)pyridin-3-yl)benzoyl)-4-hydroxy-2-methylpyrrolidin-2-carboxylate: Intermediate 36 (0.20 g, 0.48 mmol), (2S,4R)-methyl 4-hydroxy-2-methylpyrrolidin-2-carboxylate hydrochloride (0.10 g, 0.53 mmol), HOBt (0.13 g, 0.96 mmol), EDC (0.18 g, 0.96 mmol) and DIPEA (0.17 mL, 0.96 mmol) were dissolved in methylene chloride (10 mL) at room temperature. The solution was stirred at 40° C. for 18 hours, and then cooled to room temperature thereby to make the reaction completed. To the reaction mixture, water was added, and the mixture was extracted with methylene chloride. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; methanol/methylene chloride=0% to 15%), and concentrated to obtain the desired compound (0.14 g, 53%) as yellow oil.

Step 2. (2S,4R)-1-(4-(6-((1-(2-ethyl-2-fluorobutyl)piperidin-4-yl)methoxy)pyridin-3-yl)benzoyl)-4-hydroxy-2-methylpyrrolidin-2-carboxylic acid: (2S,4R)-Methyl 1-(4-(6-((1-(2-ethyl-2-fluorobutyl)piperidin-4-yl)methoxy)pyridin-3-yl)benzoyl)-4-hydroxy-2-methylpyrrolidin-2-carboxylate (0.14 g, 0.25 mmol) and LiOH (0.03 g, 1.28 mmol) were dissolved in tetrahydrofuran (8 mL)/methanol (8 mL)/water (2 mL) at room temperature. The solution was stirred at 50° C. for 18 hours, and then cooled to room temperature thereby to make the reaction completed. From the reaction mixture, the solvent was removed under reduced pressure. The obtained product was used without further purification (0.13 g, 99%, yellow solid).

Step 3. Synthesis of Compound 1328: (2S,4R)-1-(4-(6-((1-(2-Ethyl-2-fluorobutyl)piperidin-4-yl)methoxy)pyridin-3-yl)benzoyl)-4-hydroxy-2-methylpyrrolidin-2-carboxylic acid (0.13 g, 0.25 mmol), ammonium chloride (0.04 g, 0.76 mmol), HOBt (0.06 g, 0.51 mmol), EDC (0.09 g, 0.51 mmol) and DIPEA (0.09 mL, 0.51 mmol) were dissolved in N,N-dimethylformamide (10 mL) at room temperature. The solution was stirred at 50° C. for 18 hours, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (Waters, C18; acetonitrile/trifluoroacetic acid=5% to 70%), and passed through SPE cartridge (PL-HCO3 MP SPE), followed by concentrating to obtain the desire compound (0.02 g, 18%) as white solid.

$^1$H NMR (400 MHz, CDCl$_3$) δ 8.35 (s, 1H), 7.79-7.77 (m, 1H), 7.57-7.53 (m, 4H), 6.81 (d, 1H, J=8.8 Hz), 5.45 (s, 1H), 4.52-4.19 (m, 1H), 4.25-4.15 (m, 2H), 3.84-3.58 (m, 2H), 3.15-2.85 (m, 4H), 2.44-2.06 (m, 4H), 1.96-1.64 (m, 12H), 1.53-1.42 (m, 2H), 0.91-0.73 (m, 6H); MS (ESI) m/z 541.4 (M$^+$+H).

Synthesis of Compound 1329: (2S,4R)-1-(3-Fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxamide

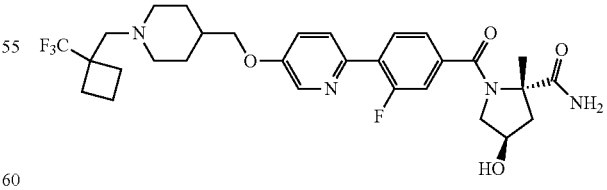

Step 1. (2S,4R)-methyl 1-(3-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxylate: Intermediate 30 (0.20 g, 0.42 mmol), (2S,4R)-methyl 4-hydroxy-2-methylpyrrolidin-2-carboxylate hydrochloride (0.09 g, 0.47 mmol), HOBt (0.11 g, 0.85 mmol), EDC (0.16 g, 0.85 mmol) and DIPEA (0.15 mL, 0.85 mmol) were dissolved in methylene chloride (10 mL) at room temperature. The solution was stirred at 40° C. for 18 hours, and then cooled to room temperature thereby to make the reaction completed. To the reaction mixture, water was added, and the mixture was extracted with methylene chloride. The organic layer was washed with saturated NaCl aqueous solution, dried with anhydrous MgSO$_4$, filtered, and then concentrated under reduced pressure. The concentrate was purified by column chromatography (SiO$_2$, 4 g cartridge; ethyl acetate/hexane=0% to 15%), and concentrated to obtain the desired compound (0.18 g, 71%) as colorless oil.

Step 2. (2S,4R)-1-(3-fluoro-4-(5-((1-((1-(trifluoromethyl) cyclobutyl)methyl)piperidin-4-yl)methoxy)pyridin-2-yl) benzoyl)-4-hydroxy-2-methylpyrrolidin-2-carboxylic acid: (2S,4R)-Methyl 1-(3-fluoro-4-(6-((1-((1-(trifluoromethyl) cyclobutyl)methyl)piperidin-4-yl)methoxy)pyridin-3-yl) benzoyl)-4-hydroxy-2-methylpyrrolidin-2-carboxylate (0.19 g, 0.31 mmol) and LiOH (0.03 g, 1.58 mmol) were dissolved in tetrahydrofuran (8 mL)/methanol (8 mL)/water (2 mL) at room temperature. The solution was stirred at 50° C. for 18 hours, and then cooled to room temperature thereby to make the reaction completed. From the reaction mixture, the solvent was removed under reduced pressure. The obtained product was used without further purification (0.18 g, 99%, white solid).

Step 3. Synthesis of Compound 1329: (2S,4R)-1-(3-Fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxylic acid (0.18 g, 0.31 mmol), ammonium chloride (0.05 g, 0.94 mmol), HOBt (0.08 g, 0.63 mmol), EDC (0.12 g, 0.63 mmol) and DIPEA (0.11 mL, 0.63 mmol) were dissolved in N,N-dimethylformamide (10 mL) at room temperature. The solution was stirred at 50° C. for 18 hours, and then cooled to room temperature thereby to make the reaction completed. To the reaction mixture, water was added, and the mixture was extracted with ethyl acetate. The organic layer was washed with saturated NaCl aqueous solution, dried with anhydrous MgSO$_4$, filtered, and then concentrated under reduced pressure. The concentrate was purified by column chromatography (Waters, C18; acetonitrile/trifluoroacetic acid=5% to 70%), and passed through SPE cartridge (PL-HCO3 MP SPE), followed by concentrating to obtain the desire compound (0.09 g, 48%) as white solid.

$^1$H NMR (400 MHz, CDCl$_3$) δ 8.32 (d, 1H, J=2.9 Hz), 7.86 (t, 1H, J=7.9 Hz), 7.70-7.68 (m, 1H), 7.35-7.24 (m, 3H), 4.41-4.35 (m, 1H), 3.89 (d, 2H, J=6.0 Hz), 3.73-3.69 (m, 2H), 3.50-3.46 (m, 1H), 3.37-3.34 (m, 4H), 3.34-3.02 (m, 2H), 2.79-2.76 (m, 2H), 2.58-2.54 (m, 2H), 2.45-2.12 (m, 4H), 2.06-1.85 (m, 8H), 1.70-1.58 (m, 2H); MS (ESI) m/z 593.3 (M$^+$+H).

The structural formulae of the above compounds are as following Tables 1 to 10.

TABLE 1

| Compound | Structure |
|---|---|
| 1148 | 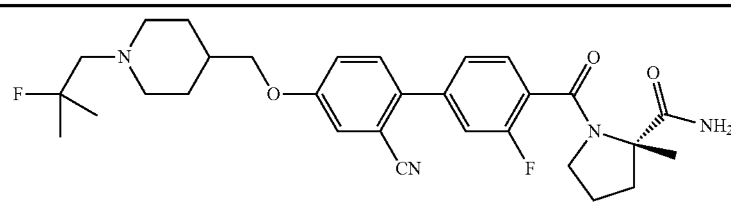 |
| 1191 | 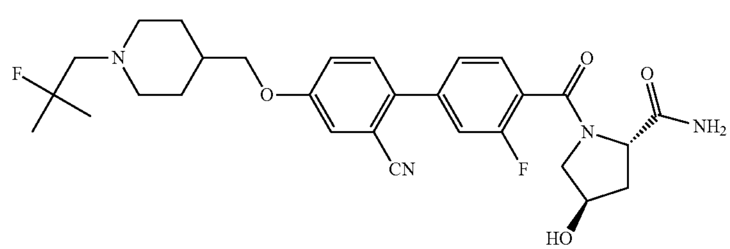 [SMILES: CC(C)(F)CN1CCC(COc2ccc(-c3ccc(C(=O)N4C[C@H](O)C[C@H]4C(N)=O)c(F)c3)c(C#N)c2)CC1] |
| 1192 | 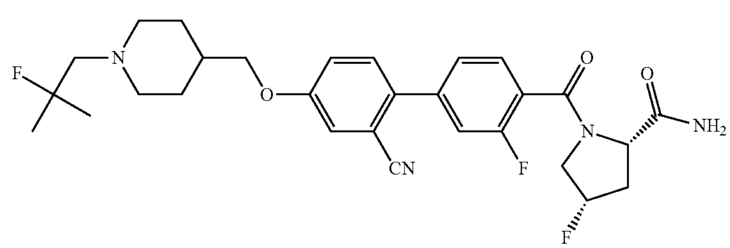 [SMILES: CC(C)(F)CN1CCC(COc2ccc(-c3ccc(C(=O)N4C[C@@H](F)C[C@H]4C(N)=O)c(F)c3)c(C#N)c2)CC1] |

TABLE 1-continued

| Compound | Structure |
|---|---|
| 1198 | 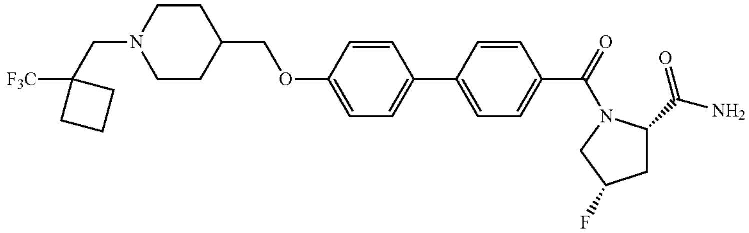 [SMILES: NC(=O)[C@@H]1C[C@H](F)CN1C(=O)c1ccc(-c2ccc(OCC3CCN(CC4(C(F)(F)F)CCC4)CC3)cc2)cc1] |
| 1199 | 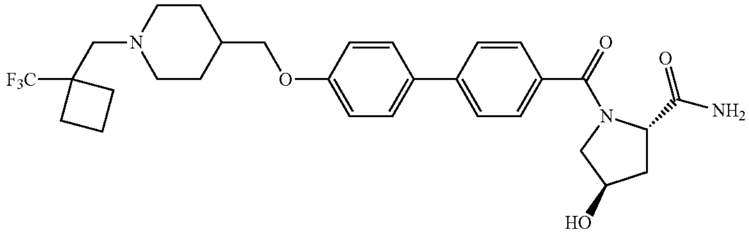 [SMILES: NC(=O)[C@@H]1C[C@@H](O)CN1C(=O)c1ccc(-c2ccc(OCC3CCN(CC4(C(F)(F)F)CCC4)CC3)cc2)cc1] |
| 1200 | 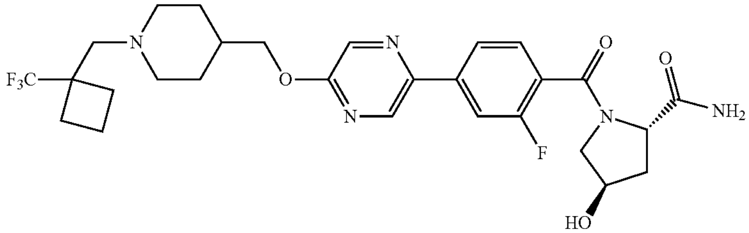 [SMILES: NC(=O)[C@@H]1C[C@@H](O)CN1C(=O)c1ccc(-c2cnc(OCC3CCN(CC4(C(F)(F)F)CCC4)CC3)cn2)cc1F] |
| 1204 | 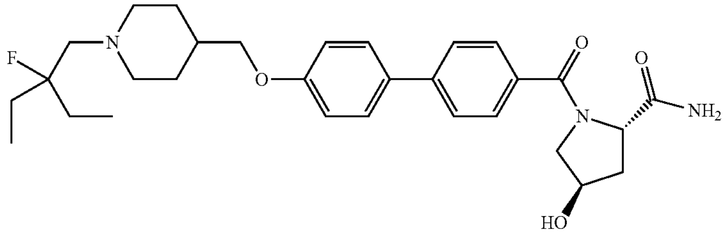 [SMILES: CCC(F)(CC)CN1CCC(COc2ccc(-c3ccc(C(=O)N4C[C@H](O)C[C@H]4C(N)=O)cc3)cc2)CC1] |
| 1205 | 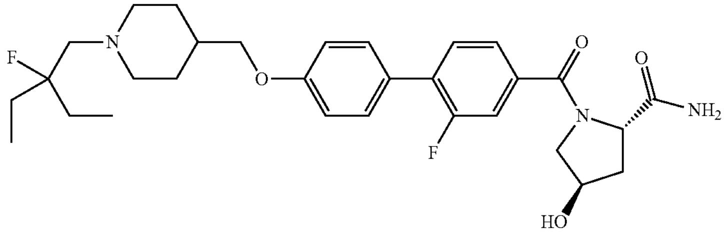 [SMILES: CCC(F)(CC)CN1CCC(COc2ccc(-c3ccc(C(=O)N4C[C@H](O)C[C@H]4C(N)=O)cc3F)cc2)CC1] |

TABLE 2

| Compound | Structure |
|---|---|
| 1206 | 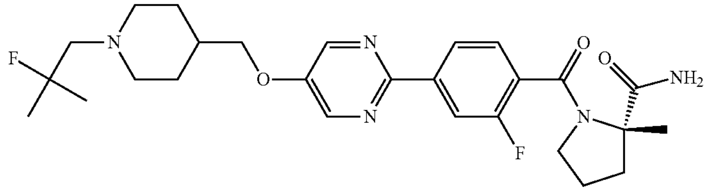 [SMILES: CC(C)(F)CN1CCC(COc2cnc(-c3ccc(C(=O)N4CCC[C@@]4(C)C(N)=O)c(F)c3)nc2)CC1] |

TABLE 2-continued

| Compound | Structure |
|---|---|
| 1207 | 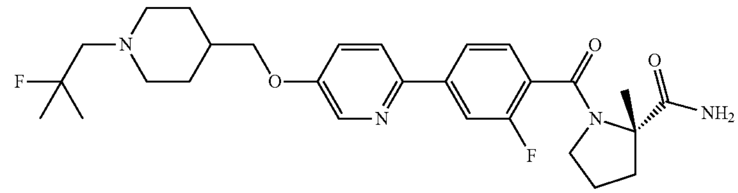 [SMILES: CC(C)(F)CN1CCC(COc2ccc(-c3ccc(C(=O)N4CCC[C@@]4(C)C(N)=O)c(F)c3)nc2)CC1] |
| 1208 | 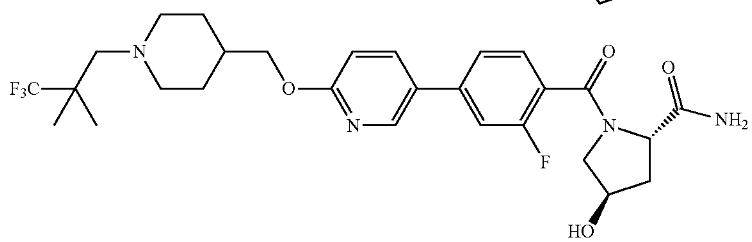 |
| 1209 | 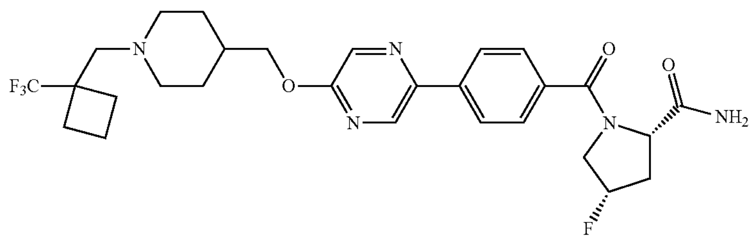 |
| 1210 | 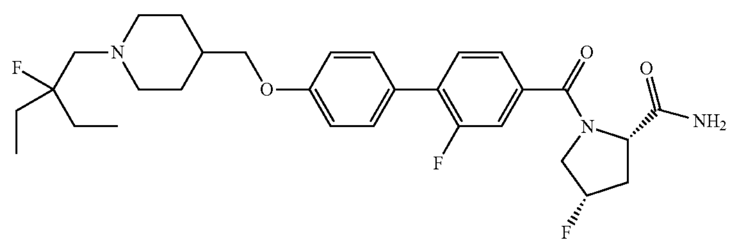 [SMILES: CCC(F)(CC)CN1CCC(COc2ccc(-c3ccc(C(=O)N4C[C@@H](F)C[C@H]4C(N)=O)cc3F)cc2)CC1] |
| 1211 | 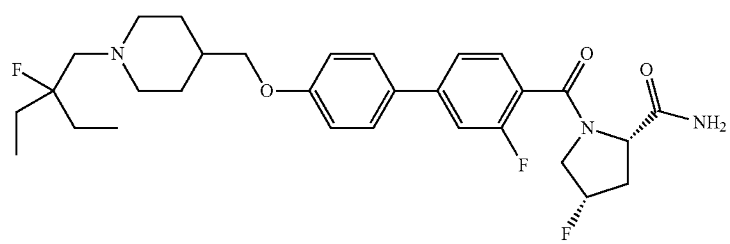 [SMILES: CCC(F)(CC)CN1CCC(COc2ccc(-c3ccc(C(=O)N4C[C@@H](F)C[C@H]4C(N)=O)c(F)c3)cc2)CC1] |
| 1220 | 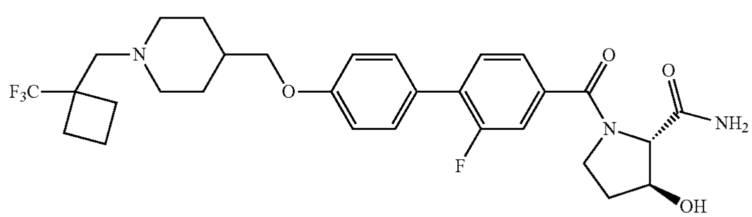 [SMILES: NC(=O)[C@@H]1[C@@H](O)CCN1C(=O)c1ccc(-c2ccc(OCC3CCN(CC4(C(F)(F)F)CCC4)CC3)cc2)c(F)c1] |
| 1229 | 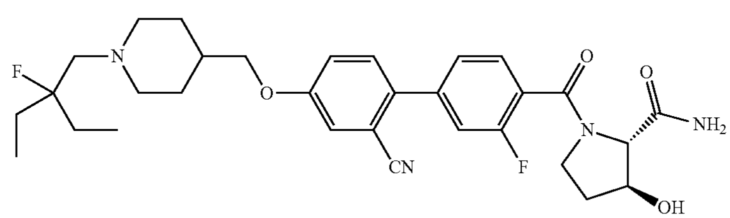 [SMILES: CCC(F)(CC)CN1CCC(COc2ccc(-c3ccc(C(=O)N4CC[C@H](O)[C@H]4C(N)=O)c(F)c3)c(C#N)c2)CC1] |

TABLE 3

| Compound | Structure |
|---|---|
| 1235 | 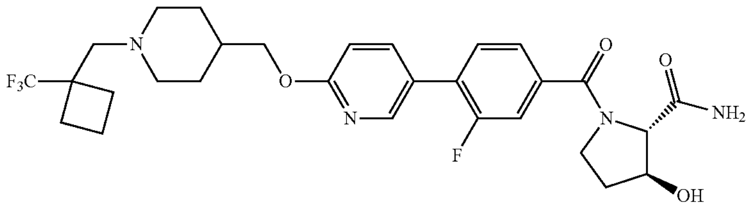 [SMILES: NC(=O)[C@@H]1[C@@H](O)CCN1C(=O)c1ccc(-c2ccc(OCC3CCN(CC4(C(F)(F)F)CCC4)CC3)nc2)c(F)c1] |
| 1238 | 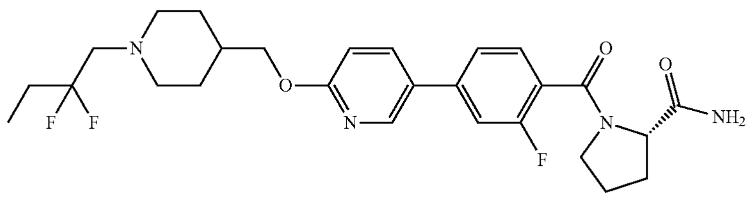 [SMILES: CCC(F)(F)CN1CCC(COc2ccc(-c3ccc(C(=O)N4CCC[C@H]4C(N)=O)c(F)c3)cn2)CC1] |
| 1239 | 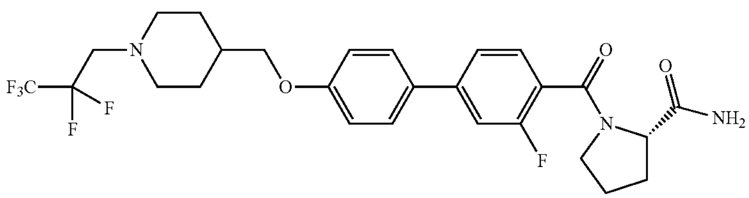 [SMILES: NC(=O)[C@@H]1CCCN1C(=O)c1ccc(-c2ccc(OCC3CCN(CC(F)(F)C(F)(F)F)CC3)cc2)cc1F] |
| 1240 | 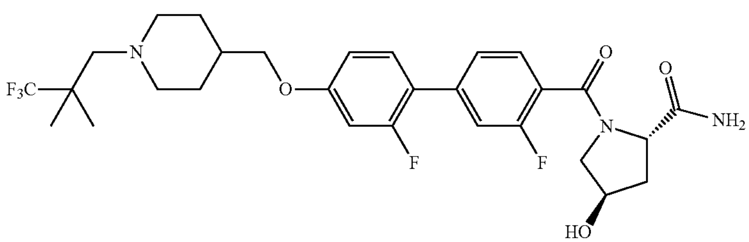 [SMILES: CC(C)(CN1CCC(COc2ccc(-c3ccc(C(=O)N4C[C@H](O)C[C@H]4C(N)=O)c(F)c3)c(F)c2)CC1)C(F)(F)F] |
| 1241 | 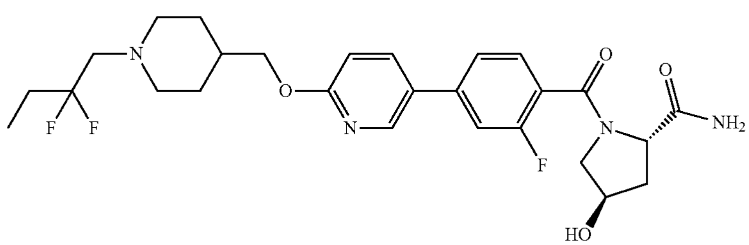 [SMILES: CCC(F)(F)CN1CCC(COc2ccc(-c3ccc(C(=O)N4C[C@H](O)C[C@H]4C(N)=O)c(F)c3)cn2)CC1] |
| 1244 | 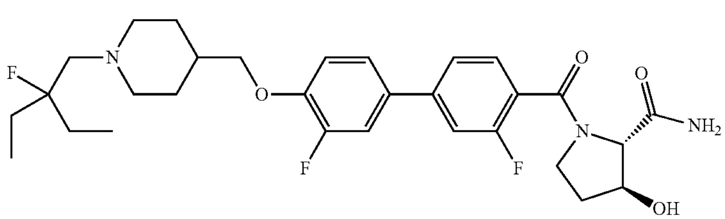 [SMILES: CCC(F)(CC)CN1CCC(COc2ccc(-c3ccc(C(=O)N4CC[C@H](O)[C@H]4C(N)=O)c(F)c3)cc2F)CC1] |
| 1245 | 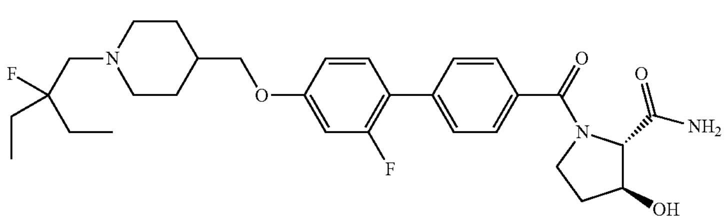 [SMILES: CCC(F)(CC)CN1CCC(COc2ccc(-c3ccc(C(=O)N4CC[C@H](O)[C@H]4C(N)=O)cc3)c(F)c2)CC1] |

TABLE 3-continued
| Compound | Structure |
|---|---|
| 1249 | 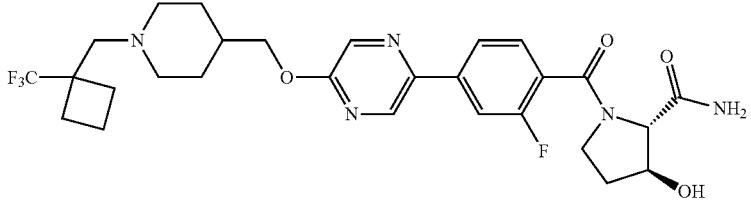 [SMILES: NC(=O)[C@@H]1[C@@H](O)CCN1C(=O)c1ccc(-c2cnc(OCC3CCN(CC4(C(F)(F)F)CCC4)CC3)cn2)cc1F] |
| 1253 | 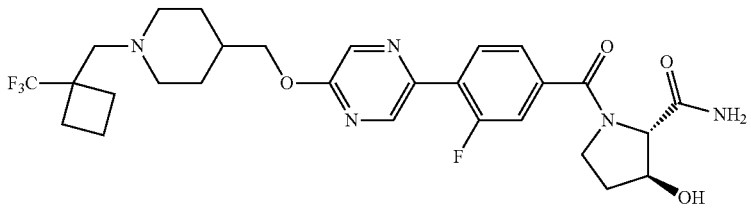 |
TABLE 4
| Compound | Structure |
|---|---|
| 1255 | 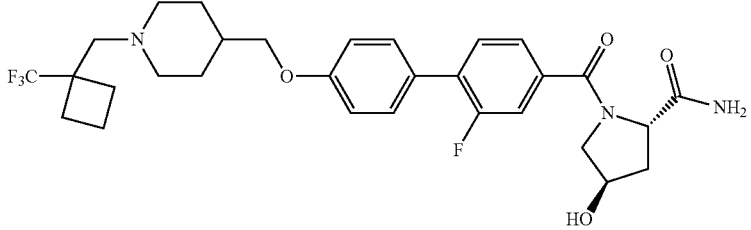 |
| 1256 | 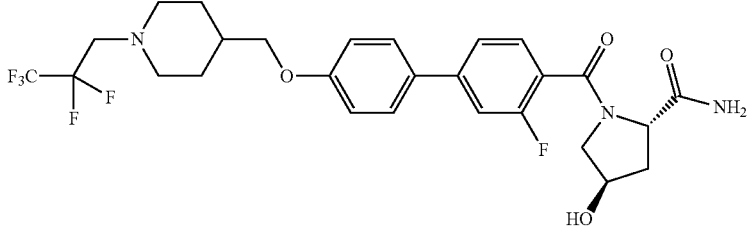 |
| 1257 | 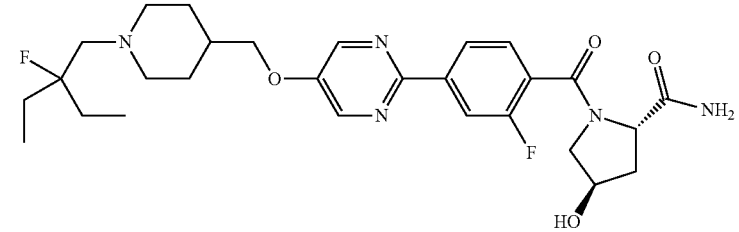 |
| 1258 | 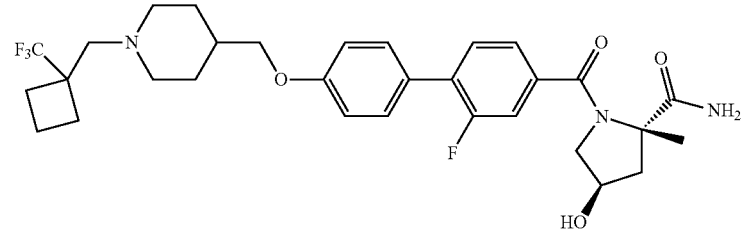 [SMILES: C[C@@]1(C(N)=O)C[C@@H](O)CN1C(=O)c1ccc(-c2ccc(OCC3CCN(CC4(C(F)(F)F)CCC4)CC3)cc2)c(F)c1] |

TABLE 4-continued

| Compound | Structure |
| --- | --- |
| 1259 | 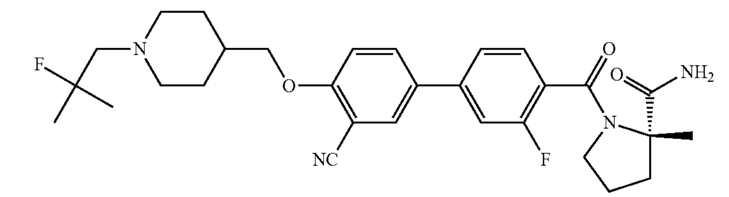 [SMILES: CC(C)(F)CN1CCC(COc2ccc(-c3ccc(C(=O)N4CCC[C@@]4(C)C(N)=O)c(F)c3)cc2C#N)CC1] |
| 1261 | 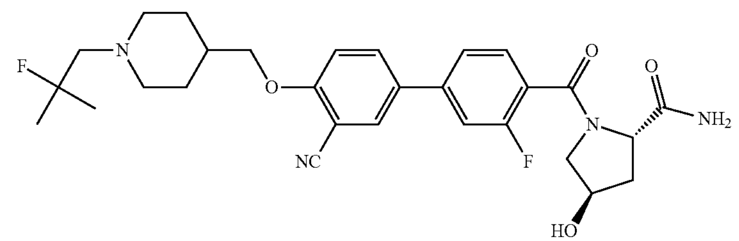 [SMILES: CC(C)(F)CN1CCC(COc2ccc(-c3ccc(C(=O)N4C[C@H](O)C[C@H]4C(N)=O)c(F)c3)cc2C#N)CC1] |
| 1262 | 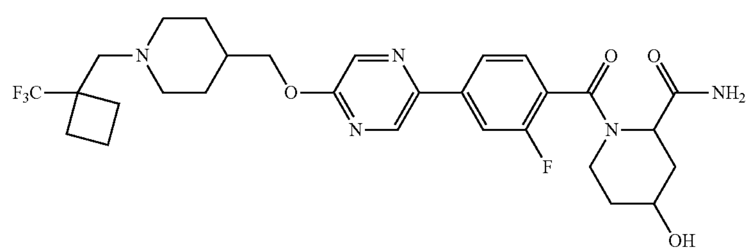 [SMILES: NC(=O)C1CC(O)CCN1C(=O)c1ccc(-c2cnc(OCC3CCN(CC4(C(F)(F)F)CCC4)CC3)cn2)cc1F] |
| 1263 | 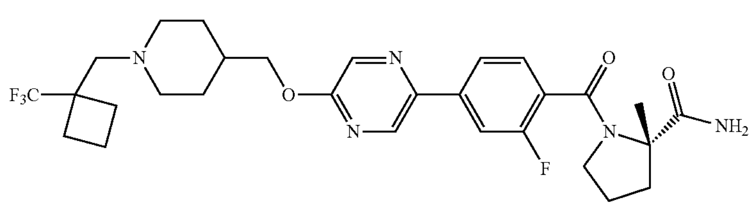 |
| 1264 | 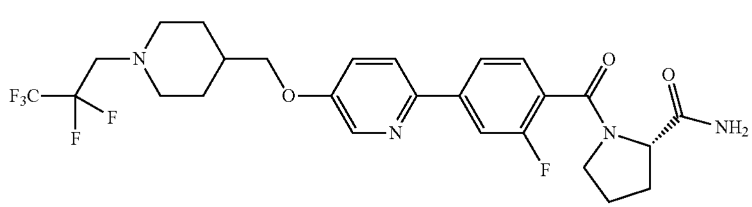 |

TABLE 5

| Compound | Structure |
| --- | --- |
| 1265 | 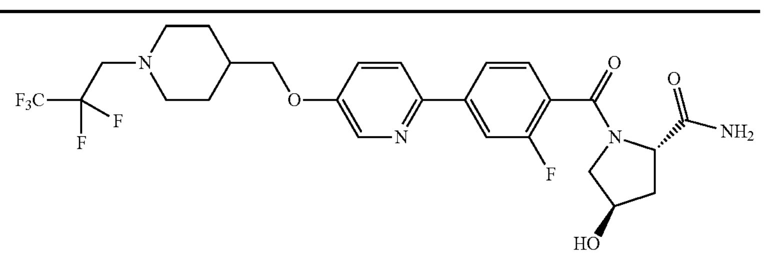 |

TABLE 5-continued

| Compound | Structure |
|---|---|
| 1266 | 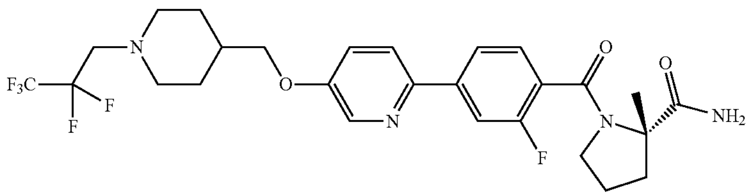 [SMILES: C[C@@]1(C(N)=O)CCCN1C(=O)c1ccc(-c2ccc(OCC3CCN(CC(F)(F)C(F)(F)F)CC3)cn2)cc1F] |
| 1267 | 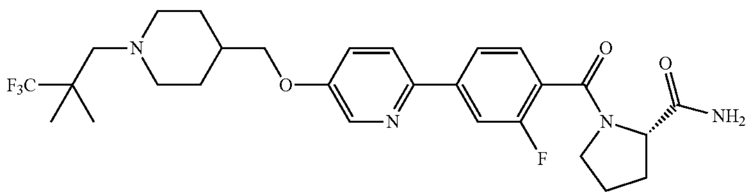 [SMILES: CC(C)(CN1CCC(COc2ccc(-c3ccc(C(=O)N4CCC[C@H]4C(N)=O)c(F)c3)nc2)CC1)C(F)(F)F] |
| 1268 | 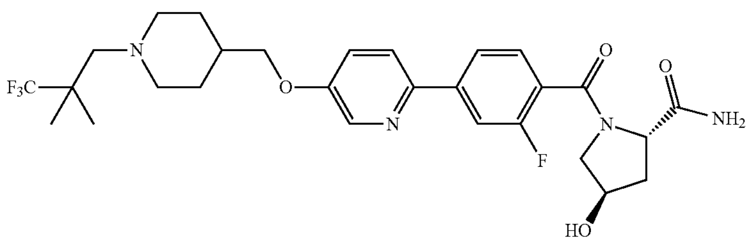 [SMILES: CC(C)(CN1CCC(COc2ccc(-c3ccc(C(=O)N4C[C@H](O)C[C@H]4C(N)=O)c(F)c3)nc2)CC1)C(F)(F)F] |
| 1269 | 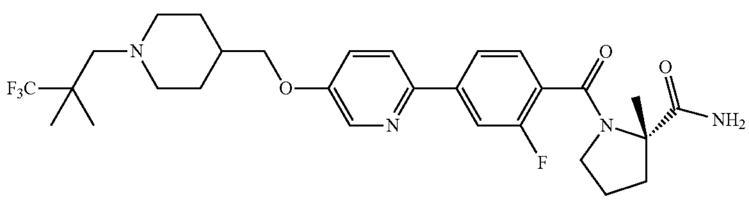 [SMILES: CC(C)(CN1CCC(COc2ccc(-c3ccc(C(=O)N4CCC[C@@]4(C)C(N)=O)c(F)c3)nc2)CC1)C(F)(F)F] |
| 1271 | 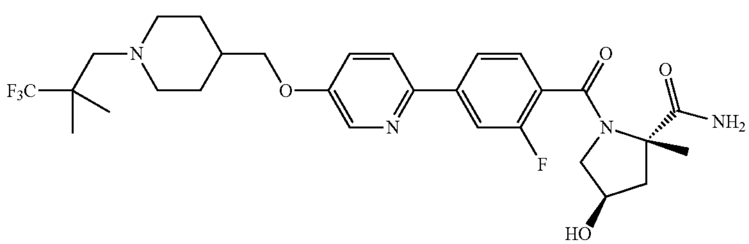 [SMILES: CC(C)(CN1CCC(COc2ccc(-c3ccc(C(=O)N4C[C@H](O)C[C@@]4(C)C(N)=O)c(F)c3)nc2)CC1)C(F)(F)F] |
| 1272 | 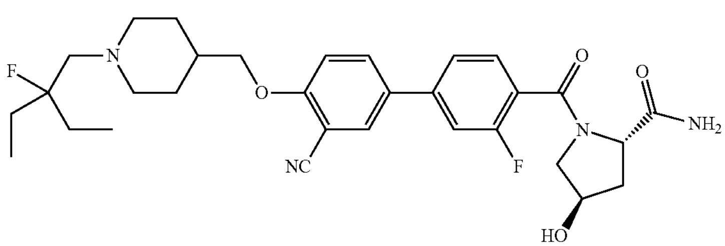 [SMILES: CCC(F)(CC)CN1CCC(COc2ccc(-c3ccc(C(=O)N4C[C@H](O)C[C@H]4C(N)=O)c(F)c3)cc2C#N)CC1] |
| 1276 | 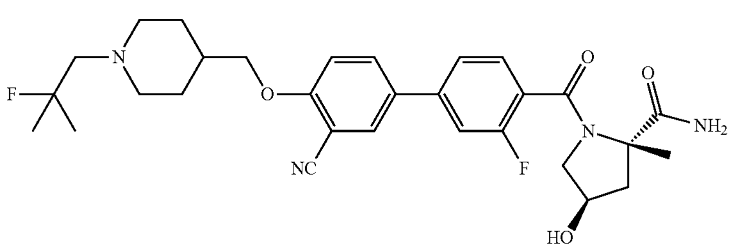 [SMILES: CC(C)(F)CN1CCC(COc2ccc(-c3ccc(C(=O)N4C[C@H](O)C[C@@]4(C)C(N)=O)c(F)c3)cc2C#N)CC1] |

TABLE 6

| Compound | Structure |
|---|---|
| 1277 | 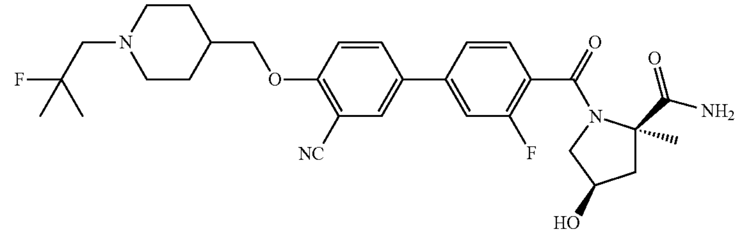 [SMILES: CC(C)(F)CN1CCC(COc2ccc(-c3ccc(C(=O)N4C[C@H](O)C[C@]4(C)C(N)=O)c(F)c3)cc2C#N)CC1] |
| 1278 | 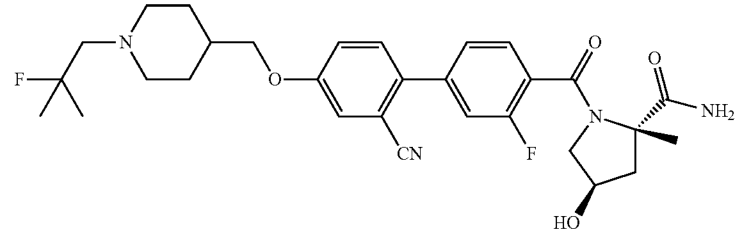 [SMILES: CC(C)(F)CN1CCC(COc2ccc(-c3ccc(C(=O)N4C[C@H](O)C[C@@]4(C)C(N)=O)c(F)c3)c(C#N)c2)CC1] |
| 1279 | 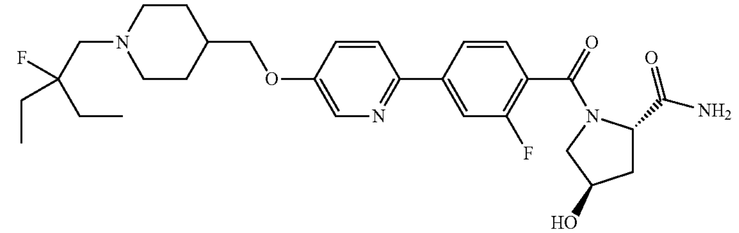 [SMILES: CCC(F)(CC)CN1CCC(COc2ccc(-c3ccc(C(=O)N4C[C@H](O)C[C@H]4C(N)=O)c(F)c3)nc2)CC1] |
| 1280 | 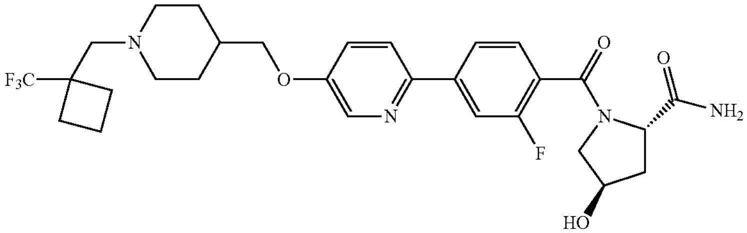 |
| 1281 | 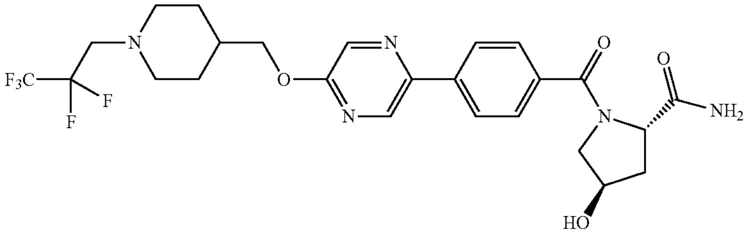 [SMILES: NC(=O)[C@@H]1C[C@@H](O)CN1C(=O)c1ccc(-c2cnc(OCC3CCN(CC(F)(F)C(F)(F)F)CC3)cn2)cc1] |
| 1286 | 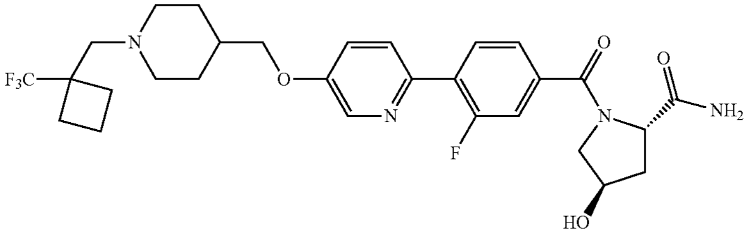 |

TABLE 6-continued

| Compound | Structure |
|---|---|
| 1287 | 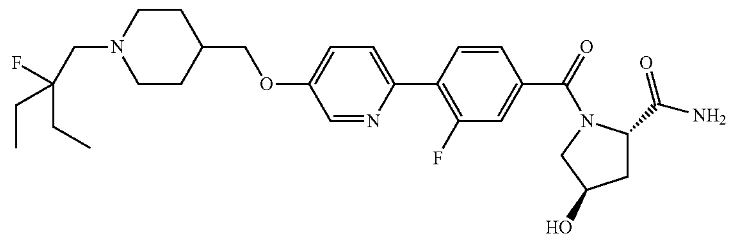 [SMILES: CCC(F)(CC)CN1CCC(COc2ccc(-c3ccc(C(=O)N4C[C@H](O)C[C@H]4C(N)=O)cc3F)nc2)CC1] |
| 1288 | 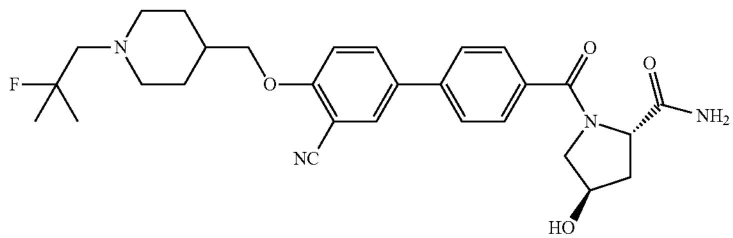 [SMILES: CC(C)(F)CN1CCC(COc2ccc(-c3ccc(C(=O)N4C[C@H](O)C[C@H]4C(N)=O)cc3)cc2C#N)CC1] |

TABLE 7

| Compound | Structure |
|---|---|
| 1290 | 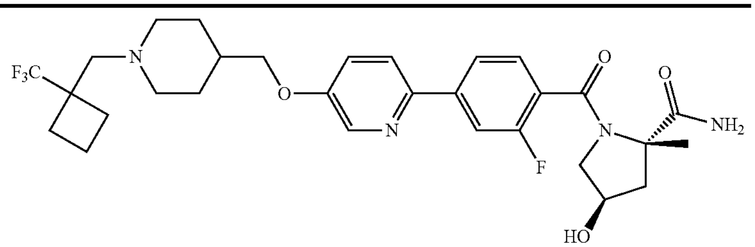 |
| 1291 | 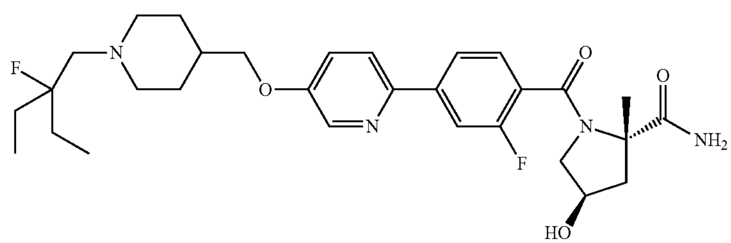 [SMILES: CCC(F)(CC)CN1CCC(COc2ccc(-c3ccc(C(=O)N4C[C@H](O)C[C@@]4(C)C(N)=O)c(F)c3)nc2)CC1] |
| 1292 | 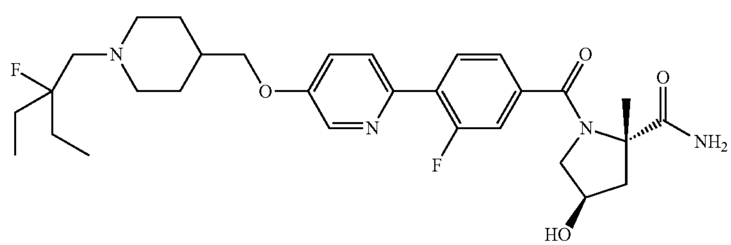 [SMILES: CCC(F)(CC)CN1CCC(COc2ccc(-c3ccc(C(=O)N4C[C@H](O)C[C@@]4(C)C(N)=O)cc3F)nc2)CC1] |
| 1294 | 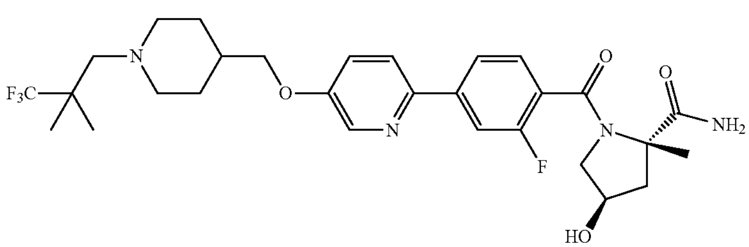 [SMILES: CC(C)(CN1CCC(COc2ccc(-c3ccc(C(=O)N4C[C@H](O)C[C@@]4(C)C(N)=O)c(F)c3)nc2)CC1)C(F)(F)F] |

TABLE 7-continued

| Compound | Structure |
|---|---|
| 1295 | 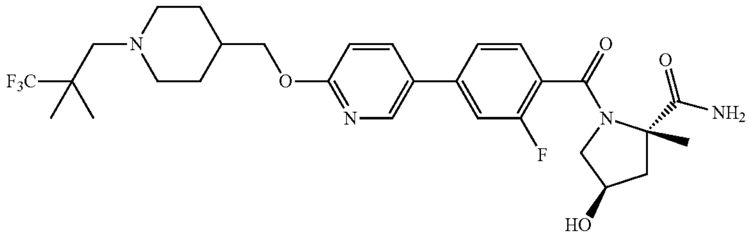 [SMILES: CC(C)(CN1CCC(COc2ccc(-c3ccc(C(=O)N4C[C@H](O)C[C@@]4(C)C(N)=O)c(F)c3)cn2)CC1)C(F)(F)F] |
| 1297 | 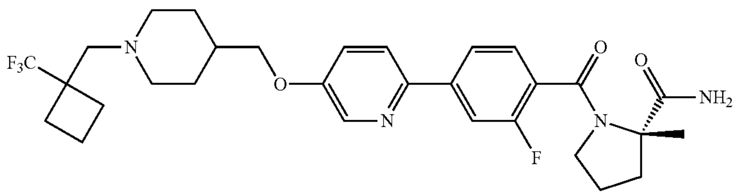 [SMILES: C[C@@]1(C(N)=O)CCCN1C(=O)c1ccc(-c2ccc(OCC3CCN(CC4(C(F)(F)F)CCC4)CC3)cn2)cc1F] |
| 1299 | 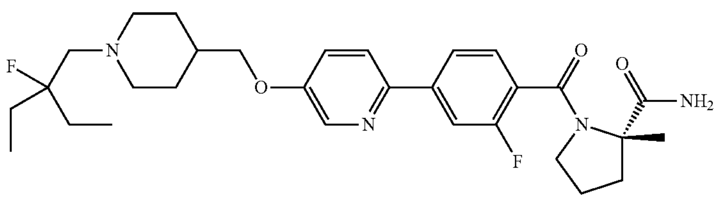 [SMILES: CCC(F)(CC)CN1CCC(COc2ccc(-c3ccc(C(=O)N4CCC[C@@]4(C)C(N)=O)c(F)c3)nc2)CC1] |
| 1300 | 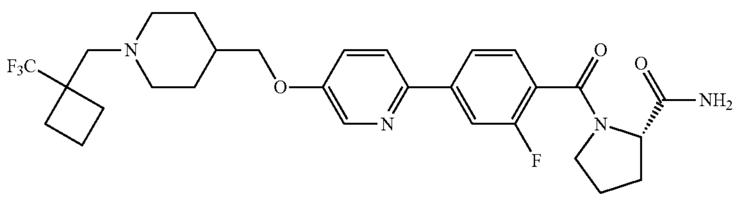 [SMILES: NC(=O)[C@@H]1CCCN1C(=O)c1ccc(-c2ccc(OCC3CCN(CC4(C(F)(F)F)CCC4)CC3)cn2)cc1F] |

TABLE 8

| Compound | Structure |
|---|---|
| 1301 | 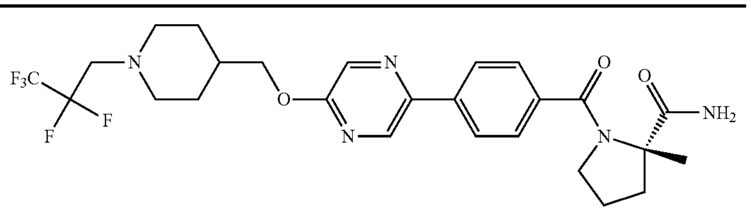 |
| 1305 | 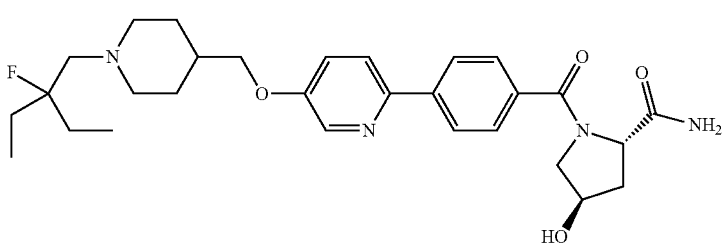 [SMILES: CCC(F)(CC)CN1CCC(COc2ccc(-c3ccc(C(=O)N4C[C@H](O)C[C@H]4C(N)=O)cc3)nc2)CC1] |

TABLE 8-continued

| Compound | Structure |
|---|---|
| 1306 | 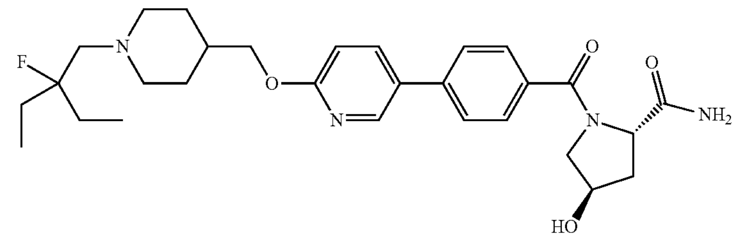 [SMILES: CCC(F)(CC)CN1CCC(COc2ccc(-c3ccc(C(=O)N4C[C@H](O)C[C@H]4C(N)=O)cc3)cn2)CC1] |
| 1307 | 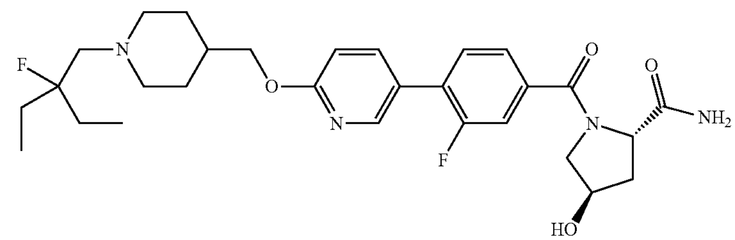 |
| 1308 | 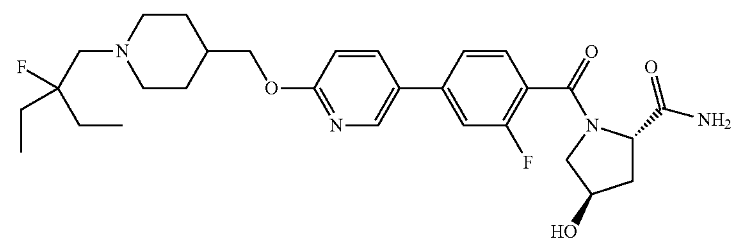 [SMILES: CCC(F)(CC)CN1CCC(COc2ccc(-c3ccc(C(=O)N4C[C@H](O)C[C@H]4C(N)=O)c(F)c3)cn2)CC1] |
| 1309 | 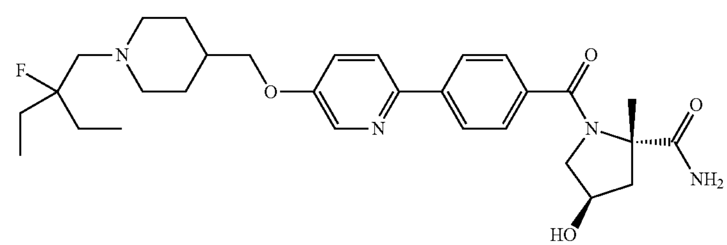 [SMILES: CCC(F)(CC)CN1CCC(COc2ccc(-c3ccc(C(=O)N4C[C@H](O)C[C@@]4(C)C(N)=O)cc3)nc2)CC1] |
| 1311 | 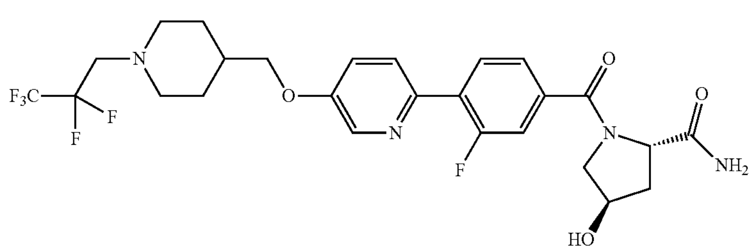 [SMILES: NC(=O)[C@@H]1C[C@@H](O)CN1C(=O)c1ccc(-c2ccc(OCC3CCN(CC(F)(F)C(F)(F)F)CC3)cn2)c(F)c1] |
| 1312 | 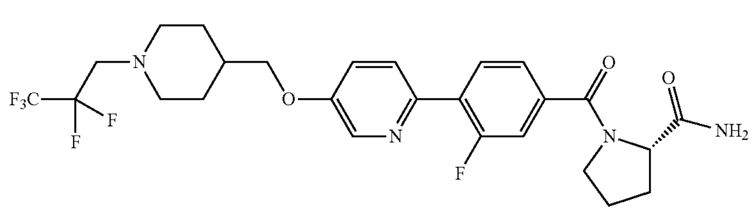 [SMILES: NC(=O)[C@@H]1CCCN1C(=O)c1ccc(-c2ccc(OCC3CCN(CC(F)(F)C(F)(F)F)CC3)cn2)c(F)c1] |

TABLE 9

| Compound | Structure |
|---|---|
| 1313 | 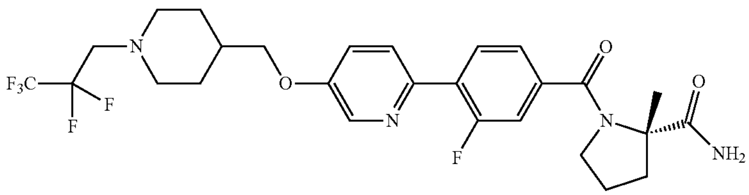 [SMILES: C[C@@]1(C(N)=O)CCCN1C(=O)c1ccc(-c2ccc(OCC3CCN(CC(F)(F)C(F)(F)F)CC3)cn2)c(F)c1] |
| 1314 | 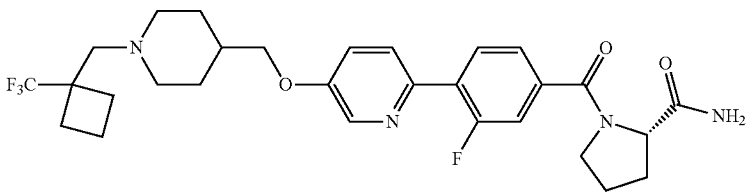 [SMILES: NC(=O)[C@@H]1CCCN1C(=O)c1ccc(-c2ccc(OCC3CCN(CC4(C(F)(F)F)CCC4)CC3)cn2)c(F)c1] |
| 1315 | 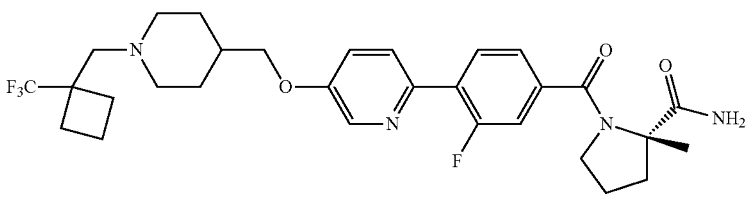 [SMILES: C[C@@]1(C(N)=O)CCCN1C(=O)c1ccc(-c2ccc(OCC3CCN(CC4(C(F)(F)F)CCC4)CC3)cn2)c(F)c1] |
| 1316 | 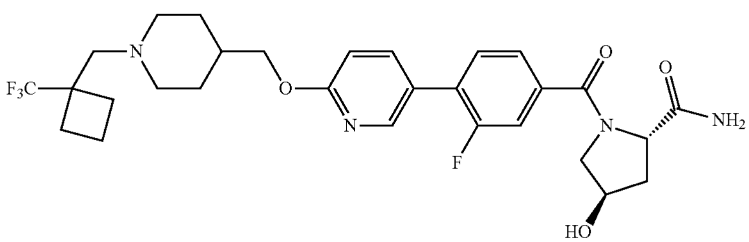 |
| 1317 | 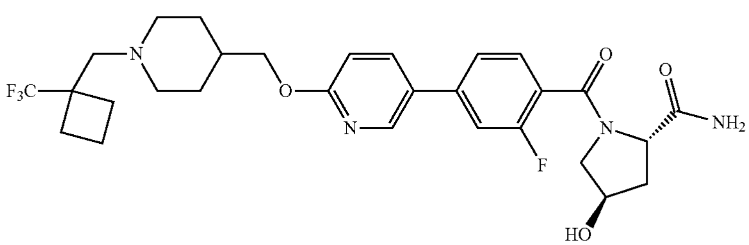 [SMILES: NC(=O)[C@@H]1C[C@@H](O)CN1C(=O)c1ccc(-c2ccc(OCC3CCN(CC4(C(F)(F)F)CCC4)CC3)nc2)cc1F] |
| 1318 | 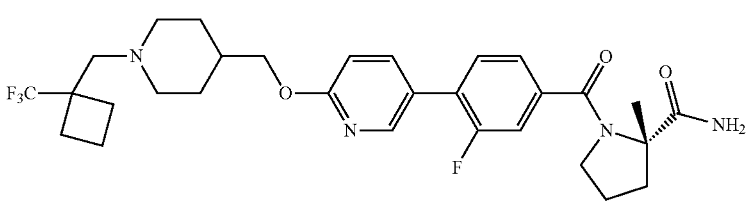 [SMILES: C[C@@]1(C(N)=O)CCCN1C(=O)c1ccc(-c2ccc(OCC3CCN(CC4(C(F)(F)F)CCC4)CC3)nc2)c(F)c1] |
| 1319 | 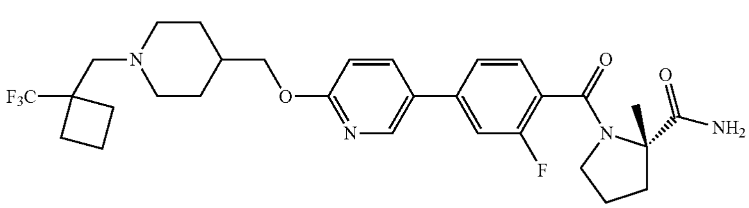 [SMILES: C[C@@]1(C(N)=O)CCCN1C(=O)c1ccc(-c2ccc(OCC3CCN(CC4(C(F)(F)F)CCC4)CC3)nc2)cc1F] |

TABLE 9-continued

| Compound | Structure |
|---|---|
| 1320 | 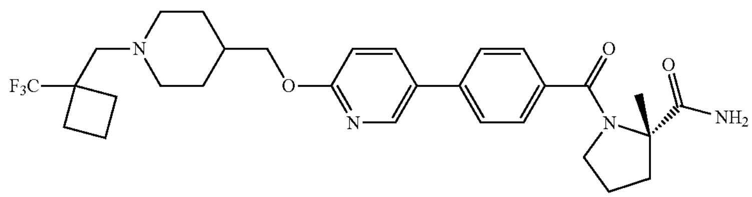 [SMILES: C[C@@]1(C(N)=O)CCCN1C(=O)c1ccc(-c2ccc(OCC3CCN(CC4(C(F)(F)F)CCC4)CC3)nc2)cc1] |

TABLE 10

| Compound | Structure |
|---|---|
| 1321 | 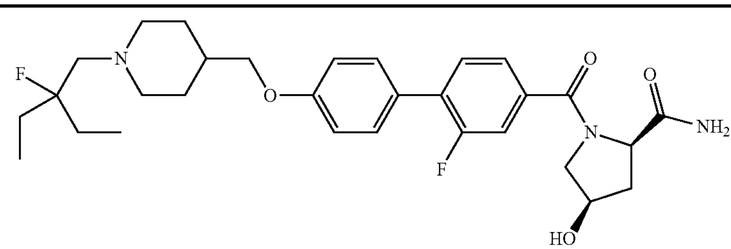 |
| 1322 | 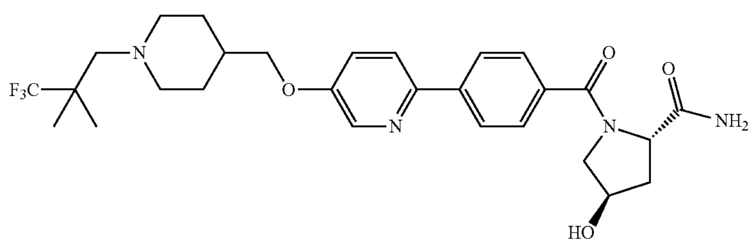 [SMILES: CC(C)(CN1CCC(COc2ccc(-c3ccc(C(=O)N4C[C@H](O)C[C@H]4C(N)=O)cc3)nc2)CC1)C(F)(F)F] |
| 1323 | 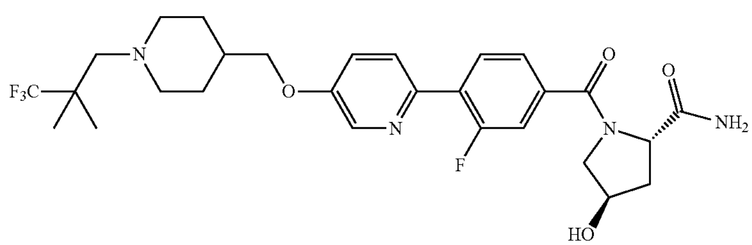 [SMILES: CC(C)(CN1CCC(COc2ccc(-c3ccc(C(=O)N4C[C@H](O)C[C@H]4C(N)=O)cc3F)nc2)CC1)C(F)(F)F] |
| 1325 | 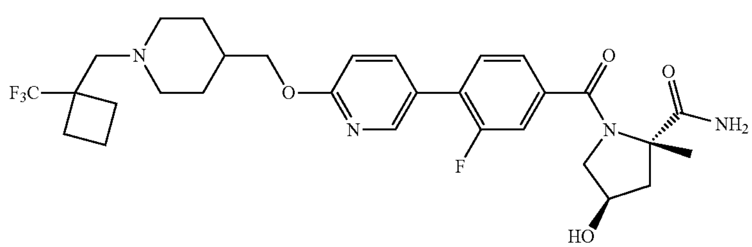 [SMILES: C[C@@]1(C(N)=O)C[C@@H](O)CN1C(=O)c1ccc(-c2ccc(OCC3CCN(CC4(C(F)(F)F)CCC4)CC3)nc2)c(F)c1] |
| 1326 | 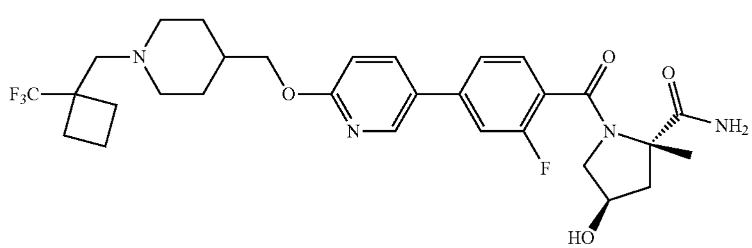 [SMILES: C[C@@]1(C(N)=O)C[C@@H](O)CN1C(=O)c1ccc(-c2ccc(OCC3CCN(CC4(C(F)(F)F)CCC4)CC3)nc2)cc1F] |

TABLE 10-continued

| Compound | Structure |
|---|---|
| 1327 | 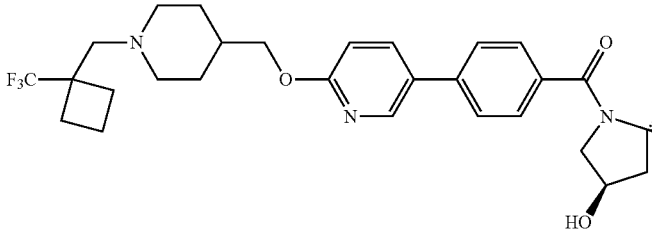 |
| 1328 | 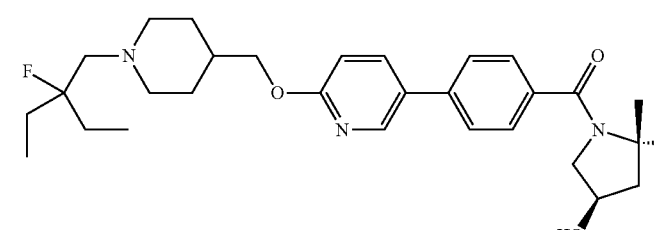 |
| 1329 | 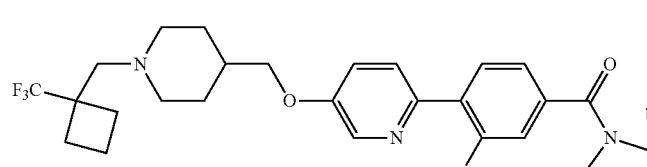 |

Protocol of Experiment: Activity Test of the Compound of the Present Invention

Using the commercial product as a control group, the treatment activities of the compounds of formula 1 according to the present invention for type II diabetes were tested, and the safety of the compound of formula 1 was also tested.

Experimental Example 1. Activity Test for the GPR 119 Receptor (in Vitro)

1. Human GPR119 Receptor Cell

As a human GPR119 receptor expression cell for this test, the cell line "GeneBLAzer™ T-Rex GPR 119 CHO-K1 DA cells" that is commercially available from Invitrogen, was used. The cell was incubated in the DMEM media containing 1% dialyzed fetal bovine serum etc. The cell incubator was kept at constant temperature and constant humidity of 37° C., 5% $CO_2$.

2. Activity Test for Human GPR119 Receptor

The human GPR119 receptor expressing cell was used to this test. Each of test compounds was added to be final concentrations of 0.1, 1, 10 µM in 96 well and tested in duplicate. A fixed amount of cell was added to each well of 96 well separately, and then treated with the test compound for 5 hours. After treatment of color development agent for 2 hours, the fluorescence value was determined with plate reader. To the luminous wavelength of control well, which was not treated with the sample, but in which only a vehicle (i.e., cell) was contained, the ratio of the luminous wavelength of test well, which was treated with the sample, was calculated, and then converted to obtain $EC_{50}$ value.

3. Statistical Processing

All the results were expressed as mean±SD, and each test groups and the control group were compared using student's t-test to adjudge the effects of each test groups.

4. Result of Activity Test for Human GPR119

TABLE 11

Result of activity test for human GPR119

| Compound | hGPR119 $EC_{50}$ (µM) |
|---|---|
| 1199 | 0.012 |
| 1200 | 0.0008 |
| 1205 | 0.002 |
| 1206 | 0.009 |
| 1207 | 0.00007 |
| 1208 | 0.003 |
| 1209 | 0.00009 |
| 1210 | 0.0002 |
| 1211 | 0.00008 |
| 1220 | 0.0001 |
| 1238 | 0.0009 |
| 1239 | 0.0001 |
| 1240 | 0.0001 |
| 1244 | 0.0003 |
| 1245 | 0.001 |
| 1249 | 0.0001 |
| 1253 | 0.0002 |
| 1255 | 0.002 |
| 1256 | 0.0004 |
| 1257 | 0.010 |
| 1258 | 0.001 |
| 1259 | 0.005 |
| 1262 | 0.0008 |
| 1263 | 0.00004 |
| 1264 | 0.00009 |
| 1265 | 0.00005 |

TABLE 11-continued

Result of activity test for human GPR119

| Compound | hGPR119 EC$_{50}$ (μM) |
|---|---|
| 1267 | 0.00009 |
| 1268 | 0.00007 |
| 1269 | 0.00009 |
| 1271 | 0.065 |
| 1276 | 0.024 |
| 1279 | 0.013 |
| 1280 | 0.038 |
| 1286 | 0.003 |
| 1287 | 0.02 |
| 1290 | 0.006 |
| 1291 | 0.013 |
| 1292 | 0.012 |
| 1294 | 0.019 |
| 1295 | 0.018 |
| 1297 | 0.004 |
| 1299 | 0.009 |
| 1309 | 0.047 |
| 1316 | 0.065 |
| 1317 | 0.060 |
| 1321 | 0.053 |
| 1322 | 0.006 |
| 1323 | 0.004 |
| 1325 | 0.014 |
| 1326 | 0.05 |
| 1327 | 0.065 |
| 1329 | 0.01 |

In Table 11, "EC$_{50}$" shows the extent that human GPR119 receptor is activated by test compounds of each concentration. The lower value of EC$_{50}$ means the more excellent activity. The compounds 1200, 1205, 1207, 1208, 1209, 1210, 1211, 1220, 1238, 1240, 1244, 1245, 1249, 1253, 1255, 1256, 1262, 1263, 1264, 1265, 1267, 1268, 1269, 1279, 1280, 1286, 1290, 1291, 1292, 1294, 1295, 1297, 1299, 1322, 1323, 1325 and 1329 show the excellent activity.

Experimental Example 2. Animal Test of Activity for the GPR 119 Receptor in Normal Mouse (In Vivo)

1. Method of Glucose Tolerance Test

Male C57/6J Jms mice of 6-7 weeks of age were fasted for 16 hours before the start of glucose tolerance test. The experimental animal groups consist of: a vehicle group (10% EtOH, 20% HPBCD in saline); and test groups administered with each compounds (10 mg/kg).

Before compound administration, that is, at 0 hour, whole blood glucose level was determined using a Glucometer (ACCU-CHEK, Roche). At 30 minutes after compound administration, whole blood glucose level was determined once again, and 20% glucose (2 g/kg/10 mL) was administered orally. Whole blood glucose level was determined at 20, 40, 60, 80, and 120 minutes after 20% glucose administration. Whole blood glucose level vs. Time was graphicalized. Area under the curve (AUC) of whole blood glucose level was obtained using GraphPad Prism 4.0. The effect of glucose tolerance was adjudged with the corrected area under the curve (cAUC), on which the base value of glucose area under the curve was excluded.

2. Result of Glucose Tolerance Test

In Table 12, "Decrease % of AUC" shows the extent that whole blood glucose level is decreased by the test compounds administrated after oral administration of glucose into normal mouse. The higher value of decrease % of AUC means the more excellent drop effect in blood glucose level. Some of the compounds of the present invention show more than 30% of the excellent drop effect in blood glucose level. The compounds 1199, 1205, 1207, 1208 and 1240 show the very excellent drop effect in blood glucose level with 31%, 37%, 32% 38% and 35% respectively.

TABLE 12

Result of glucose tolerance test at 10 mg/kg of dose

| | Decrease % of AUC at 10 mg/kg |
|---|---|
| MBX-2982 | 20~30% |
| GSK-1292263 | 10~20% |
| Compound 1199 | 31% |
| Compound 1205 | 36.7% |
| Compound 1207 | 41.9% |
| Compound 1208 | 38% |
| Compound 1240 | 35% |

TABLE 13

Result of glucose tolerance test at 2.5 and 5 mg/kg of lower dose

| | Decrease % of AUC at 2.5 mg/kg | Decrease % of AUC at 5 mg/kg |
|---|---|---|
| MBX-2982 | 9.5% | 18.5% |
| Compound 1207 | 31.3% | 45.1% |
| Compound 1279 | 20.8% | 30.2% |
| Compound 1291 | 15.7% | 38.0% |

3. Secretion Capacity Test of Glucagon-Like Peptide-1 (GLP-1)

Male C57/6J Jms mice of 6-7 weeks of age were fasted for 16 hours before the start of the test of secretion capacity test of GLP-1. The experimental animal groups consist of: a vehicle group (100% DI water); and test groups administered with each compounds (10 mg/kg). Blood samples were taken from the orbital vein of the test animals. Plasma GLP-1 level was determined using a GLP-1 ELISA kit (Total GLP-1 ELISA, ALPCO). With the base of 30 minutes before the compound administration, each blood samples were taken at 30, 60, 120 and 210 minutes after the compound administration. 30% Glucose solution (3 g/kg/10 mL) was administered orally at 5 minutes before each blood-collecting. From the collected blood, only plasma was taken using a centrifuge (12000 rpm, 15 minutes), and stored at −80° C. before analysis. Plasma GLP-1 level vs. Time was graphicalized. Area under the curve (AUC) of plasma GLP-1 level was obtained using GraphPad Prism 4.0. All the results were expressed as mean±SD, and each test groups and the control group were compared using one-way ANOVA test (Dunnett's test, *p<0.05, p<0.01, *p<0.001) to adjudge the effects of each test groups.

4. Result of Secretion Capacity Test of Glucagon-Like Peptide-1 (GLP-1)

In Table 14, the change of plasma GLP-1 level in normal mice administered orally with each test compounds was shown with area under the curve (AUC). The higher value of AUC value means the more excellent capacity of GLP-1 secretion.

TABLE 14

Result of GLP-1 secretion capacity test at 10 mg/kg of dose

| | GLP-1 secretion (%) at 10 mg/kg of dose |
|---|---|
| Vehicle (water) | 100% |
| MBX-2982 | 114% |
| Compound 1207 | 223% |

TABLE 14-continued

| Result of GLP-1 secretion capacity test at 10 mg/kg of dose | |
|---|---|
| | GLP-1 secretion (%) at 10 mg/kg of dose |
| Compound 1279 | 324% |
| Compound 1291 | 347% |

Experimental Example 3. Solubility Test of GPR 119 Agonist Compounds

1. Method of Solubility Test

Each test compounds were dissolved in 5% DMSO aqueous solution as a solvent at several concentrations. When a laser was irradiated to the solution, the particles, which are not dissolved in the solvent, scatter the light. The level of the scattered light is dependent to the number of the particles, so the solubility of the test compound in the solution can be determined using the relationship. As the test equipment, Nephelostar was used.

2. Result of Solubility Test

In each solutions of several pH, the solubilities of the compounds according to the present invention were compared with that of MBX-2982. As a result, it was confirmed that, in all of the test pH, the solubilities of the compounds according to the present invention are excellent.

TABLE 15

| | Solubility (microgram/mL) | | | |
|---|---|---|---|---|
| | pH 2 | pH 4 | pH 6 | pH 8 |
| MBX-2982 | >208 | 133 | 61 | 39 |
| Compound 1205 | >271 | >271 | 157 | 55 |
| Compound 1207 | >257 | >257 | >257 | >257 |
| Compound 1268 | >283 | >283 | >283 | 54 |
| Compound 1279 | >272 | >272 | >272 | 133 |
| Compound 1286 | >289 | >289 | >289 | 108 |
| Compound 1290 | >296 | >296 | >296 | 102 |
| Compound 1291 | >279 | >279 | >279 | 166 |
| Compound 1292 | >279 | >279 | >279 | >279 |
| Compound 1294 | >290 | >290 | 203 | 52 |
| Compound 1322 | >274 | >274 | >274 | 89 |
| Compound 1323 | >283 | >283 | 355 | 88 |
| Compound 1325 | >296 | >296 | >296 | 114 |
| Compound 1329 | >296 | >296 | >296 | 112 |

The invention claimed is:

1. A amide derivative of the following formula 1, stereoisomers thereof or pharmaceutically acceptable salts thereof:

[Formula 1]

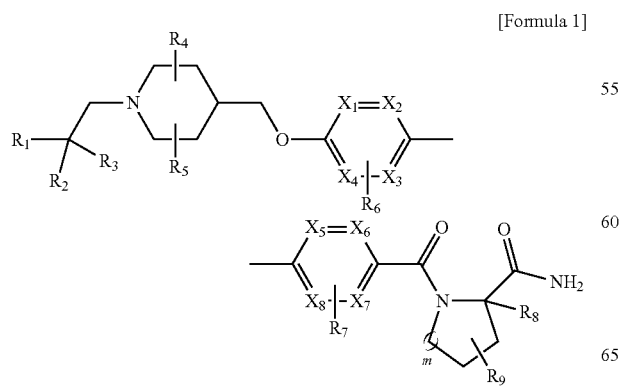

wherein $X_1$, $X_2$, $X_3$, $X_4$, $X_5$, $X_6$, $X_7$ and $X_8$ are each independently C or N;

$R_1$ is —F or —$C_{1-3}$perfluorinated alkyl;

$R_2$ and $R_3$ are each independently selected from the group consisting of halogen, —$C_{1-5}$alkyl and $C_{3-6}$cycloalkyl, wherein —$C_{1-5}$alkyl and $C_{3-6}$cycloalkyl may be each independently non-substituted, or substituted with halogen, —CN, —$OC_{1-5}$alkyl or —$C_{1-5}$alkyl, or $R_2$ and $R_3$, taken together with the carbon atom to which they are attached, may form $C_{3-6}$cycloalkyl (wherein $C_{3-6}$cycloalkyl may be non-substituted, or substituted with halogen, —$OC_{1-5}$alkyl or —$C_{1-5}$alkyl);

$R_4$ and $R_5$ are each independently H, halogen or —$C_{1-5}$alkyl;

$R_6$ and $R_7$ are each independently H, halogen, —$C_{1-5}$alkyl or CN;

$R_8$ is H, —$C_{1-5}$alkyl or —$C_{1-5}$alkylOCH$_3$—;

$R_9$ is H, halogen or OH—; and m is 1 or 2.

2. The amide derivative, stereoisomers thereof or pharmaceutically acceptable salts thereof according to claim 1, wherein $R_1$ is —F or —$C_{1-3}$perfluorinated alkyl;

$R_2$ and $R_3$ are each independently selected from the group consisting of halogen and —$C_{1-5}$alkyl, or $R_2$ and $R_3$, taken together with the carbon atom to which they are attached, may form $C_{3-6}$ cycloalkyl (wherein $C_{3-6}$ cycloalkyl may be non-substituted, or substituted with halogen, —$OC_{1-5}$alkyl or —$C_{1-5}$alkyl);

$R_4$ and $R_5$ are each independently H;

$R_6$ and $R_7$ are each independently H, halogen or CN;

$R_8$ is H or —$C_{1-5}$alkyl;

$R_9$ is H or OH; and m is 1.

3. The amide derivative, stereoisomers thereof or pharmaceutically acceptable salts thereof according to claim 1, wherein

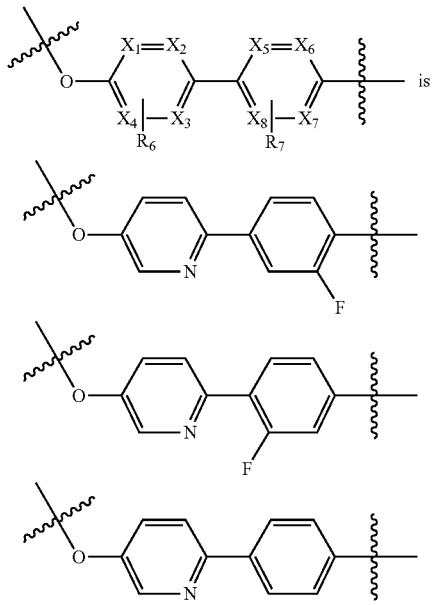

-continued

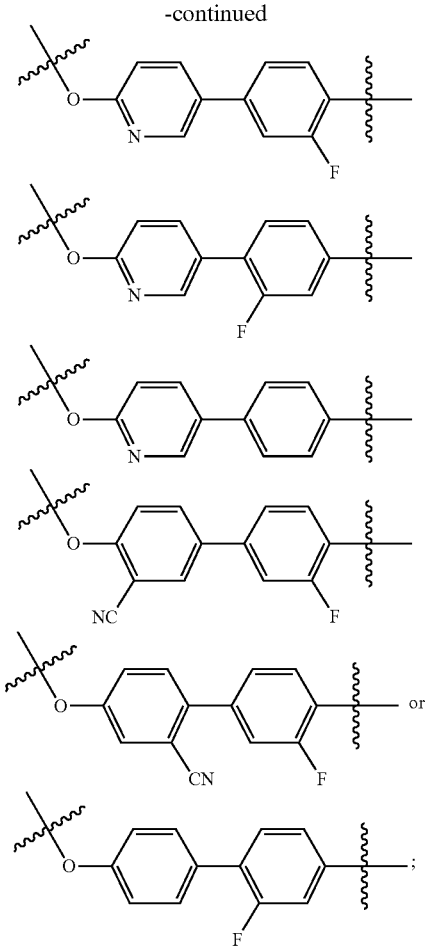

R₁ is —F or —$C_{1-3}$perfluorinated alkyl;
R₂ and R₃ are each independently selected from the group consisting of halogen and —$C_{1-5}$alkyl,
or R₂ and R₃, taken together with the carbon atom to which they are attached, may form $C_{3-6}$ cycloalkyl (wherein $C_{3-6}$ cycloalkyl may be non-substituted, or substituted with halogen, —$OC_{1-5}$alkyl or —$C_{1-5}$ alkyl);
R₄ and R₅ are each independently H;
R₈ is H or —$C_{1-5}$alkyl;
R₉ is H or OH; and
m is 1.

4. The amide derivative, stereoisomers thereof or pharmaceutically acceptable salts thereof according to claim 1, wherein
(S)-1-(2'-cyano-3-fluoro-4'-((1-(2-fluoro-2-methylpropyl)piperidin-4-yl)methoxy)biphenylcarbonyl)-2-methylpyrrolidin-2-carboxamide;
(2S,4R)-1-(2'-cyano-3-fluoro-4'-((1-(2-fluoro-2-methylpropyl)piperidin-4-yl)methoxy)biphenylcarbonyl)-4-hydroxypyrrolidin-2-carboxamide;
(2S,4S)-1-(2'-cyano-3-fluoro-4'-((1-(2-fluoro-2-methylpropyl)piperidin-4-yl)methoxy)biphenylcarbonyl)-4-fluoropyrrolidin-2-carboxamide;
(2S,4S)-4-fluoro-1-(4'-((1-((1-(trifluoromethyl)cyclobutyl)methyl)piperidin-4-yl)methoxy)biphenylcarbonyl)pyrrolidin-2-carboxamide;
(2S,4R)-4-hydroxy-1-(4'-((1-((1-(trifluoromethyl)cyclobutyl)methyl)piperidin-4-yl)methoxy)biphenylcarbonyl)pyrrolidin-2-carboxamide;
(2S,4R)-1-(2-fluoro-4-(5-((1-((1-(trifluoromethyl)cyclobutyl)methyl)piperidin-4-yl)methoxy)pyrazin-2-yl)benzoyl)-4-hydroxypyrrolidin-2-carboxamide;
(2S,4R)-1-(4'-((1-(2-ethyl-2-fluorobutyl)piperidin-4-yl)methoxy)biphenylcarbonyl)-4-hydroxypyrrolidin-2-carboxamide;
(2S,4R)-1-(4'-((1-(2-ethyl-2-fluorobutyl)piperidin-4-yl)methoxy)-2-fluorobiphenylcarbonyl)-4-hydroxypyrrolidin-2-carboxamide;
(S)-1-(2-fluoro-4-(5-((1-(2-fluoro-2-methylpropyl)piperidin-4-yl)methoxy)pyrimidin-2-yl)benzoyl)-2-methylpyrrolidin-2-carboxamide;
(S)-1-(2-fluoro-4-(5-((1-(2-fluoro-2-methylpropyl)piperidin-4-yl)methoxy)pyridin-2-yl)benzoyl)-2-methylpyrrolidin-2-carboxamide;
(2S,4R)-1-(2-fluoro-4-(6-((1-(3,3,3-trifluoro-2,2-dimethylpropyl)piperidin-4-yl)methoxy)pyridin-3-yl)benzoyl)-4-hydroxypyrrolidin-2-carboxamide;
(2S,4S)-4-fluoro-1-(4-(5-((1-((1-(trifluoromethyl)cyclobutyl)methyl)piperidin-4-yl)methoxy)pyrazin-2-yl)benzoyl)pyrrolidin-2-carboxamide;
(2S,4S)-1-(4'-((1-(2-ethyl-2-fluorobutyl)piperidin-4-yl)methoxy)-2-fluorobiphenylcarbonyl)-4-fluoropyrrolidin-2-carboxamide;
(2S,4S)-1-(4'-((1-(2-ethyl-2-fluorobutyl)piperidin-4-yl)methoxy)-3-fluorobiphenylcarbonyl)-4-fluoropyrrolidin-2-carboxamide;
(2S,3S)-1-(2-fluoro-4'-((1-((1-(trifluoromethyl)cyclobutyl)methyl)piperidin-4-yl)methoxy)biphenylcarbonyl)-3-hydroxypyrrolidin-2-carboxamide;
(2S,3S)-1-(2'-cyano-4'-((1-(2-ethyl-2-fluorobutyl)piperidin-4-yl)methoxy)-3-fluorobiphenylcarbonyl)-3-hydroxypyrrolidin-2-carboxamide;
(2S,3S)-1-(3-fluoro-4-(6-((1-((1-(trifluoromethyl)cyclobutyl)methyl)piperidin-4-yl)methoxy)pyridin-3-yl)benzoyl)-3-hydroxypyrrolidin-2-carboxamide;
(S)-1-(4-(6-((1-(2,2-difluorobutyl)piperidin-4-yl)methoxy)pyridin-3-yl)-2-fluorobenzoyl)pyrrolidin-2-carboxamide;
(S)-1-(3-fluoro-4'-((1-(2,2,3,3,3-pentafluoropropyl)piperidin-4-yl)methoxy)biphenylcarbonyl)pyrrolidin-2-carboxamide;
(2S,4R)-1-(2',3-difluoro-4'-((1-(3,3,3-trifluoro-2,2-dimethylpropyl)piperidin-4-yl)methoxy)biphenylcarbonyl)-4-hydroxypyrrolidin-2-carboxamide;
(2S,4R)-1-(4-(6-((1-(2,2-difluorobutyl)piperidin-4-yl)methoxy)pyridin-3-yl)-2-fluorobenzoyl)-4-hydroxypyrrolidin-2-carboxamide;
(2S,3S)-1-(4'-((1-(2-ethyl-2-fluorobutyl)piperidin-4-yl)methoxy)-3,3'-difluorobiphenylcarbonyl)-3-hydroxypyrrolidin-2-carboxamide;
(2S,3S)-1-(4'-((1-(2-ethyl-2-fluorobutyl)piperidin-4-yl)methoxy)-2'-fluorobiphenylcarbonyl)-3-hydroxypyrrolidin-2-carboxamide;
(2S,3S)-1-(2-fluoro-4-(5-((1-((1-(trifluoromethyl)cyclobutyl)methyl)piperidin-4-yl)methoxy)pyrazin-2-yl)benzoyl)-3-hydroxypyrrolidin-2-carboxamide;
(2S,3S)-1-(3-fluoro-4-(5-((1-((1-(trifluoromethyl)cyclobutyl)methyl)piperidin-4-yl)methoxy)pyrazin-2-yl)benzoyl)-3-hydroxypyrrolidin-2-carboxamide;
(2S,4R)-1-(2-fluoro-4'-((1-((1-trifluoromethyl)cyclobutyl)methyl)piperidin-4-yl)methoxy)biphenylcarbonyl)-4-hydroxypyrrolidin-2-carboxamide;
(2S,4R)-1-(3-fluoro-4'-((1-(2,2, 3,3,3-pentafluoropropyl)piperidin-4-yl)methoxy)biphenylcarbonyl)-4-hydroxypyrrolidin-2-carboxamide;

(2S,4R)-1-(4-(5-((1-(2-ethyl-2-fluorobutyl)piperidin-4-yl)methoxy)pyrimidin-2-yl)-2-fluorobenzoyl)-4-hydroxypyrrolidin-2-carboxamide;
(2S,4R)-1-(2-fluoro-4'-((1-((1-(trifluoromethyl)cyclobutyl)methyl)piperidin-4-yl)methoxy)biphenylcarbonyl)-4-hydroxy-2-methylpyrrolidin-2-carboxamide;
(S)-1-(3'-cyano-3-fluoro-4'-((1-(2-fluoro-2-methylpropyl)piperidin-4-yl)methoxy)biphenylcarbonyl)-2-methylpyrrolidin-2-carboxamide;
(2S,4R)-1-(3'-cyano-3-fluoro-4'-((1-(2-fluoro-2-methylpropyl)piperidin-4-yl)methoxy)biphenylcarbonyl)-4-hydroxypyrrolidin-2-carboxamide;
1-(2-fluoro-4-(5-((1-((1-(trifluoromethyl)cyclobutyl)methyl)piperidin-4-yl)methoxy)pyrazin-2-yl)benzoyl)-4-hydroxypiperidin-2-carboxamide;
(S)-1-(2-fluoro-4-(5-((1-((1-(trifluoromethyl)cyclobutyl)methyl)piperidin-4-yl)methoxy)pyrazin-2-yl)benzoyl)-2-methylpyrrolidin-2-carboxamide;
(S)-1-(2-fluoro-4-(5-((1-(2,2,3,3,3-pentafluoropropyl)piperidin-4-yl)methoxy)pyridin-2-yl)benzoyl)pyrrolidin-2-carboxamide;
(2S,4R)-1-(2-fluoro-4-(5-((1-(2,2,3,3,3-pentafluoropropyl)piperidin-4-yl)methoxy)pyridin-2-yl)benzoyl)-4-hydroxypyrrolidin-2-carboxamide;
(S)-1-(2-fluoro-4-(5-((1-(2,2,3,3,3-pentafluoropropyl)piperidin-4-yl)methoxy)pyridin-2-yl)benzoyl)-2-methylpyrrolidin-2-carboxamide;
(S)-1-(2-fluoro-4-(5-((1-(3,3,3-trifluoro-2,2-dimethylpropyl)piperidin-4-yl)methoxy)pyridin-2-yl)benzoyl)pyrrolidin-2-carboxamide;
(2S,4R)-1-(2-fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxamide;
(S)-1-(2-fluoro-4-(5-((1-(3,3,3-trifluoro-2,2-dimethylpropyl)piperidin-4-yl)methoxy)pyridin-2-yl)benzoyl)-2-methylpyrrolidin-2-carboxamide;
(2S,4R)-1-(2-fluoro-4-(5-((1-(2-fluoro-2-methylpropyl)piperidin-4-yl)methoxy)pyridin-2-yl)benzoyl)-4-hydroxy-2-methylpyrrolidin-2-carboxamide;
(2S,4R)-1-(3'-cyano-4'-((1-(2-ethyl-2-fluorobutyl)piperidin-4-yl)methoxy)-3-fluorobiphenylcarbonyl)-4-hydroxypyrrolidin-2-carboxamide;
(2S,4R)-1-(3'-cyano-3-fluoro-4'-((1-(2-fluoro-2-methylpropyl)piperidin-4-yl)methoxy)biphenylcarbonyl)-4-hydroxy-2-methylpyrrolidin-2-carboxamide;
(2R,4R)-1-(3'-cyano-3-fluoro-4'-((1-(2-fluoro-2-methylpropyl)piperidin-4-yl)methoxy)biphenylcarbonyl)-4-hydroxy-2-methylpyrrolidin-2-carboxamide;
(2S,4R)-1-(2'-cyano-3-fluoro-4'-((1-(2-fluoro-2-methylpropyl)piperidin-4-yl)methoxy)biphenylcarbonyl)-4-hydroxy-2-methylpyrrolidin-2-carboxamide;
(2S,4R)-1-(4-(5-((1-(2-ethyl-2-fluorobutyl)piperidin-4-yl)methoxy)pyridin-2-yl)-2-fluorobenzoyl)-4-hydroxypyrrolidin-2-carboxamide;
(2S,4R)-1-(2-fluoro-4-(5-((1-((1-(trifluoromethyl)cyclobutyl)methyl)piperidin-4-yl)methoxy)pyridin-2-yl)benzoyl)-4-hydroxypyrrolidin-2-carboxamide;
(2S,4R)-4-hydroxy-1-(4-(5-((1-(2,2,3,3,3-pentafluoropropyl)piperidin-4-yl)methoxy)pyrazin-2-yl)benzoyl)pyrrolidin-2-carboxamide;
(2S,4R)-1-(3-fluoro-4-(5-((1-((1-(trifluoromethyl)cyclobutyl)methyl)piperidin-4-yl)methoxy)pyridin-2-yl)benzoyl)-4-hydroxypyrrolidin-2-carboxamide;
(2S,4R)-1-(4-(5-((1-(2-ethyl-2-fluorobutyl)piperidin-4-yl)methoxy)pyridin-2-yl)-3-fluorobenzoyl)-4-hydroxypyrrolidin-2-carboxamide;
(2S,4R)-1-(3'-cyano-4'-((1-(2-fluoro-2-methylpropyl)piperidin-4-yl)methoxy)biphenylcarbonyl)-4-hydroxypyrrolidin-2-carboxamide;
(2S,4R)-1-(2-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxamide;
(2S,4R)-1-(4-(5-((1-(2-ethyl-2-fluorobutyl)piperidin-4-yl)methoxy)pyridin-2-yl)-2-fluorobenzoyl)-4-hydroxy-2-methylpyrrolidin-2-carboxamide;
(2S,4R)-1-(4-(5-((1-(2-ethyl-2-fluorobutyl)piperidin-4-yl)methoxy)pyridin-2-yl)-3-fluorobenzoyl)-4-hydroxy-2-methylpyrrolidin-2-carboxamide;
(2S,4R)-1-(2-fluoro-4-(5-((1-(3,3,3-trifluoro-2,2-dimethylpropyl)piperidin-4-yl)methoxy)pyridin-2-yl)benzoyl)-4-hydroxy-2-methylpyrrolidin-2-carboxamide;
(2S,4R)-1-(2-fluoro-4-(6-((1-(3,3,3-trifluoro-2,2-dimethylpropyl)piperidin-4-yl)methoxy)pyridin-3-yl)benzoyl)-4-hydroxy-2-methylpyrrolidin-2-carboxamide;
(S)-1-(2-fluoro-4-(5-((1-((1-(trifluoromethyl)cyclobutyl)methyl)piperidin-4-yl)methoxy)pyridin-2-yl)benzoyl)-2-methylpyrrolidin-2-carboxamide;
(S)-1-(4-(5-((1-(2-ethyl-2-fluorobutyl)piperidin-4-yl)methoxy)pyridin-2-yl)-2-fluorobenzoyl)-2-methylpyrrolidin-2-carboxamide;
(S)-1-(2-fluoro-4-(5-((1-((1-(trifluoromethyl)cyclobutyl)methyl)piperidin-4-yl)methoxy)pyridin-2-yl)benzoyl)pyrrolidin-2-carboxamide;
(S)-2-methyl-1-(4-(5-((1-(2,2,3,3,3-pentafluoropropyl)piperidin-4-yl)methoxy)pyrazin-2-yl)benzoyl)pyrrolidin-2-carboxamide;
(2S,4R)-1-(4-(5-((1-(2-ethyl-2-fluorobutyl)piperidin-4-yl)methoxy)pyridin-2-yl)benzoyl)-4-hydroxypyrrolidin-2-carboxamide;
(2S,4R)-1-(4-(6-((1-(2-ethyl-2-fluorobutyl)piperidin-4-yl)methoxy)pyridin-3-yl)benzoyl)-4-hydroxypyrrolidin-2-carboxamide;
(2S,4R)-1-(4-(6-((1-(2-ethyl-2-fluorobutyl)piperidin-4-yl)methoxy)pyridin-3-yl)-3-fluorobenzoyl)-4-hydroxypyrrolidin-2-carboxamide;
(2S,4R)-1-(4-(6-((1-(2-ethyl-2-fluorobutyl)piperidin-4-yl)methoxy)pyridin-3-yl)-2-fluorobenzoyl)-4-hydroxypyrrolidin-2-carboxamide;
(2S,4R)-1-(4-(5-((1-(2-ethyl-2-fluorobutyl)piperidin-4-yl)methoxy)pyridin-2-yl)benzoyl)-4-hydroxy-2-methylpyrrolidin-2-carboxamide;
(2S,4R)-1-(3-fluoro-4-(5-((1-(2,2,3,3,3-pentafluoropropyl)piperidin-4-yl)methoxy)pyridin-2-yl)benzoyl)-4-hydroxypyrrolidin-2-carboxamide;
(S)-1-(3-fluoro-4-(5-((1-(2,2,3,3,3-pentafluoropropyl)piperidin-4-yl)methoxy)pyridin-2-yl)benzoyl)pyrrolidin-2-carboxamide;
(S)-1-(3-fluoro-4-(5-((1-(2,2,3,3,3-pentafluoropropyl)piperidin-4-yl)methoxy)pyridin-2-yl)benzoyl)-2-methylpyrrolidin-2-carboxamide;
(S)-1-(3-fluoro-4-(5-((1-((1-(trifluoromethyl)cyclobutyl)methyl)piperidin-4-yl)methoxy)pyridin-2-yl)benzoyl)pyrrolidin-2-carboxamide;
(S)-1-(3-fluoro-4-(5-((1-((1-(trifluoromethyl)cyclobutyl)methyl)piperidin-4-yl)methoxy)pyridin-2-yl)benzoyl)-2-methylpyrrolidin-2-carboxamide;
(2S,4R)-1-(3-fluoro-4-(6-((1-((1-(trifluoromethyl)cyclobutyl)methyl)piperidin-4-yl)methoxy)pyridin-3-yl)benzoyl)-4-hydroxypyrrolidin-2-carboxamide;
(2S,4R)-1-(2-fluoro-4-(6-((1-((1-(trifluoromethyl)cyclobutyl)methyl)piperidin-4-yl)methoxy)pyridin-3-yl)benzoyl)-4-hydroxypyrrolidin-2-carboxamide;

(S)-1-(3-fluoro-4-(6-((1-((1-(trifluoromethyl)cyclobutyl)methyl)piperidin-4-yl)methoxy)pyridin-3-yl)benzoyl)-2-methylpyrrolidin-2-carboxamide;

(S)-1-(2-fluoro-4-(6-((1-((1-(trifluoromethyl)cyclobutyl)methyl)piperidin-4-yl)methoxy)pyridin-3-yl)benzoyl)-2-methylpyrrolidin-2-carboxamide;

(S)-2-methyl-1-(4-(6-((1-((1-(trifluoromethyl)cyclobutyl)methyl)piperidin-4-yl)methoxy)pyridin-3-yl)benzoyl)pyrrolidin-2-carboxamide;

(2R,4R)-1-(4'-((1-(2-ethyl-2-fluorobutyl)piperidin-4-yl)methoxy)-2-fluorobiphenylcarbonyl)-4-hydroxypyrrolidin-2-carboxamide;

(2S,4R)-4-hydroxy-1-(4-(5-((1-(3,3,3-trifluoro-2,2-dimethylpropyl)piperidin-4-yl)methoxy)pyridin-2-yl)benzoyl)pyrrolidin-2-carboxamide;

(2S,4R)-1-(3-fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxamide;

(2S,4R)-1-(3-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxamide;

(2S,4R)-1-(2-fluoro-4-(6-((1-((1-(trifluoromethyl)cyclobutyl)methyl)piperidin-4-yl)methoxy)pyridin-3-yl)benzoyl)-4-hydroxy-2-methylpyrrolidin-2-carboxamide;

(2S,4R)-4-hydroxy-2-methyl-1-(4-(6-((1-((1-(trifluoromethyl)cyclobutyl)methyl)piperidin-4-yl)methoxy)pyridin-3-yl)benzoyl)pyrrolidin-2-carboxamide;

(2S,4R)-1-(4-(6-((1-(2-ethyl-2-fluorobutyl)piperidin-4-yl)methoxy)pyridin-3-yl)benzoyl)-4-hydroxy-2-methylpyrrolidin-2-carboxamide; and (2S,4R)-1-(3-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxamide.

5. The amide derivative, stereoisomers thereof, pharmaceutically acceptable salts thereof according to claim 4, wherein the amide derivative is selected from the group consisting of:

(2S,4R)-1-(4'-((1-(2-ethyl-2-fluorobutyl)piperidin-4-yl)methoxy)-2-fluorobiphenylcarbonyl)-4-hydroxypyrrolidin-2-carboxamide;

(S)-1-(2-fluoro-4-(5-((1-(2-fluoro-2-methylpropyl)piperidin-4-yl)methoxy)pyridin-2-yl)benzoyl)-2-methylpyrrolidin-2-carboxamide;

(2S,4R)-1-(4-(5-((1-(2-ethyl-2-fluorobutyl)piperidin-4-yl)methoxy)pyridin-2-yl)-2-fluorobenzoyl)-4-hydroxypyrrolidin-2-carboxamide;

(2S,4R)-1-(2-fluoro-4-(5-((1-((1-(trifluoromethyl)cyclobutyl)methyl)piperidin-4-yl)methoxy)pyridin-2-yl)benzoyl)-4-hydroxypyrrolidin-2-carboxamide;

(2S,4R)-1-(2-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxamide;

(2S,4R)-1-(4-(5-((1-(2-ethyl-2-fluorobutyl)piperidin-4-yl)methoxy)pyridin-2-yl)-2-fluorobenzoyl)-4-hydroxy-2-methylpyrrolidin-2-carboxamide;

(2S,4R)-1-(3-fluoro-4-(5-((1-(3,3,3-trifluoro-2,2-dimethylpropyl)piperidin-4-yl)methoxy)pyridin-2-yl)benzoyl)-4-hydroxypyrrolidin-2-carboxamide; and (2S,4R)-1-(3-fluoro-4-(5-((1-((1-(trifluoromethyl)cyclobutyl)methyl)piperidin-4-yl)methoxy)pyridin-2-yl)benzoyl)-4-hydroxy-2-methylpyrrolidin-2-carboxamide.

6. A pharmaceutical composition comprising the amide derivative, stereoisomers thereof or pharmaceutically acceptable salts thereof according to claim 1; and pharmaceutically acceptable carriers.

7. The pharmaceutical composition according to claim 6, wherein the composition is used for treatment of a disease associated with GPR119 agonist, wherein said disease associated with GPR119 agonist is diabetes mellitus.

8. A pharmaceutical composition comprising the amide derivative, stereoisomers thereof or pharmaceutically acceptable salts thereof according to claim 2 and pharmaceutically acceptable carriers.

9. A pharmaceutical composition comprising the amide derivative, stereoisomers thereof or pharmaceutically acceptable salts thereof according to claim 3 and pharmaceutically acceptable carriers.

10. A pharmaceutical composition comprising the amide derivative, stereoisomers thereof or pharmaceutically acceptable salts thereof according to claim 4 and pharmaceutically acceptable carriers.

11. A pharmaceutical composition comprising the amide derivative, stereoisomers thereof or pharmaceutically acceptable salts thereof according to claim 5 and pharmaceutically acceptable carriers.

* * * * *